United States Patent
Boyle et al.

(10) Patent No.: US 8,318,751 B2
(45) Date of Patent: Nov. 27, 2012

(54) PYRIMIDINONE DERIVATIVES AND METHODS OF USE THEREOF

(75) Inventors: Craig D. Boyle, Branchburg, NJ (US); Samuel Chackalamannil, Califon, NJ (US); Claire M. Lankin, High Bridge, NJ (US); Unmesh G. Shah, Green Brook, NJ (US); Bernard R. Neustadt, West Orange, NJ (US); Hong Liu, Hillsborough, NJ (US); Andrew W. Stamford, Chatham Township, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 340 days.

(21) Appl. No.: 12/595,906

(22) PCT Filed: Apr. 17, 2008

(86) PCT No.: PCT/US2008/004938
§ 371 (c)(1),
(2), (4) Date: Jan. 13, 2010

(87) PCT Pub. No.: WO2008/130584
PCT Pub. Date: Oct. 30, 2008

(65) Prior Publication Data
US 2010/0113487 A1    May 6, 2010

Related U.S. Application Data

(60) Provisional application No. 60/925,465, filed on Apr. 20, 2007, provisional application No. 60/953,323, filed on Aug. 1, 2007.

(51) Int. Cl.
*A01N 43/90* (2006.01)
*A61K 31/519* (2006.01)
*C07D 471/00* (2006.01)

(52) U.S. Cl. .................. 514/264.1; 544/279

(58) Field of Classification Search ............... 514/264.1; 544/279
See application file for complete search history.

(56) References Cited

FOREIGN PATENT DOCUMENTS
WO    2008/038768    4/2008

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
West, Anthony R., Solid State Chemistry and Its Applications, Wiley, New York, 1988, 358.*
Zhang, et al., Design and Synthesis of Pyrimidinone and Pyrimidinedione Inhibitors of Dipeptidyl Peptidase IV, J. Med. Chem., 54, 510-524 (2011).*
Shah, GPR119 Agonists: A Promising New Approach for the Treatment of Type 2 Diabetes and Related Metabolic Disorders, Current Opinion in Drug Discovery & Development, 12(4), 519-532 (2009).*
Nakamura, "Preparation of bicyclic pyrimidine compounds . . . ", Chemical Abstracts, Database accession No. 2008:410717, XP002491158.
International Search Report, PCT/US2008/004938, (2008).
Shah, "GPR119 agonists: A promising new approach for the treatment of type 2 diabetes . . . ", Current Opin. in Drug Discovery & Develop. (2009), vol. 12, pp. 519-532.

* cited by examiner

*Primary Examiner* — Erich A Leeser
(74) *Attorney, Agent, or Firm* — Anna L. Cocuzzo; Jeffrey F. Bergman

(57) ABSTRACT

The present invention relates to Pyrimidinone Derivatives, compositions comprising a Pyrimidinone Derivative, and methods of using the Pyrimidinone Derivatives for treating or preventing obesity, diabetes, a metabolic disease, a cardiovascular disease or a disorder related to the activity of GPR119 in a patient.

42 Claims, No Drawings

PYRIMIDINONE DERIVATIVES AND METHODS OF USE THEREOF

CROSS REFERENCE TO RELATED APPLICATIONS

This application is the national stage application under 35 U.S.C. 371 of International Patent Application No.: PCT/US2008/004938, filed in the U.S. Receiving Office on Apr. 17, 2008, which claims the benefit of U.S. Provisional Application No. 60/925,465, filed Apr. 20, 2007 and U.S. Provisional Application No. 60/953,323, filed Aug. 1, 2007. Each of the aforementioned PCT and Provisional applications is incorporated by reference in its entirety as if fully set forth herein.

FIELD OF THE INVENTION

The present invention relates to Pyrimidinone Derivatives, compositions comprising a Pyrimidinone Derivative, and methods of using the Pyrimidinone Derivatives for treating or preventing obesity, diabetes, a metabolic disorder, a cardiovascular disease or a disorder related to the activity of G protein-coupled receptor 119 ("GPR119") in a patient.

BACKGROUND OF THE INVENTION

Although a number of receptor classes exist in humans, by far the most abundant and therapeutically relevant is represented by the G protein-coupled receptor (GPCR or GPCRs) class. It is estimated that there are some 100,000 genes within the human genome, and of these, approximately 2% or 2,000 genes, are estimated to code for GPCRs. Receptors, including GPCRs, for which the endogenous ligand has been identified are referred to as "known" receptors, while receptors for which the endogenous ligand has not been identified are referred to as "orphan" receptors. GPCRs represent an important area for the development of pharmaceutical products, as evidenced by the fact that pharmaceutical products have been developed from approximately 20 of the 100 known GPCRs. This distinction is not merely semantic, particularly in the case of GPCRs. Thus, the orphan GPCRs are to the pharmaceutical industry what gold was to California in the late 19th century—an opportunity to drive growth, expansion, enhancement and development.

GPCRs share a common structural motif. All these receptors have seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when an endogenous ligand binds with the receptor (often referred to as "activation" of the receptor), there is a change in the conformation of the intracellular region that allows for coupling between the intracellular region and an intracellular "G-protein." It has been reported that GPCRs are "promiscuous" with respect to G proteins, i.e., that a GPCR can interact with more than one G protein. See, Kenakin, T., Life Sciences 43:1095 (1988). Although other G proteins exist, currently, Gq, Gs, Gi, and Go are G proteins that have been identified. Endogenous ligand-activated GPCR coupling with the G-protein begins a signaling cascade process (referred to as "signal transduction"). Under normal conditions, signal transduction ultimately results in cellular activation or cellular inhibition. It is thought that the IC-3 loop as well as the carboxy terminus of the receptor interact with the G protein.

Under physiological conditions, GPCRs exist in the cell membrane in equilibrium between two different conformations: an "inactive" state and an "active" state. A receptor in an inactive state is unable to link to the intracellular signaling transduction pathway to produce a biological response. Changing the receptor conformation to the active state allows linkage to the transduction pathway (via the G-protein) and produces a biological response. A receptor can be stabilized in an active state by an endogenous ligand or a compound such as a drug.

Modulation of G-protein coupled receptors has been well-studied for controlling various metabolic disorders. Small molecule modulators of the receptor GPR119, a G-protein coupled-receptor described in, for example, GenBank (see, e.g., accession numbers XM.sub.-066873 and AY288416), have been shown to be useful for treating or preventing certain metabolic disorders. GPR119 is a G protein-coupled receptor that is selectively expressed on pancreatic beta cells. GPR119 activation leads to elevation of a level of intracellular cAMP, consistent with GPR119 being coupled to Gs. Agonists to GPR119 stimulate glucose-dependent insulin secretion in vitro and lower an elevated blood glucose level in vivo. See, e.g., International Publication Nos. WO 04/065380 and WO 04/076413, and European Patent Application No. EP 1338651, the disclosure of each of which is herein incorporated by reference in its entirety.

U.S. Pat. No. 7,132,426 discloses pyrazolo[3,4-d]pyrimidine ethers and related compounds as modulators of the GPR119 receptor that are useful for the treatment of various metabolic-related disorders such as type I diabetes, type II diabetes, inadequate glucose tolerance, insulin resistance, hyperglycemia, hyperlipidemia, hypertriglyceridemia, hypercholesterolemia, dyslipidemia or syndrome X. The compounds are also reported as being useful for controlling weight gain, controlling food intake, and inducing satiety in mammals. The promising nature of these GPR119 modulators indicates a need in the art for additional small molecule GPR119 modulators with improved efficacy and safety profiles. This invention addresses that need.

SUMMARY OF THE INVENTION

In one aspect, the present invention provides compounds of Formula (I):

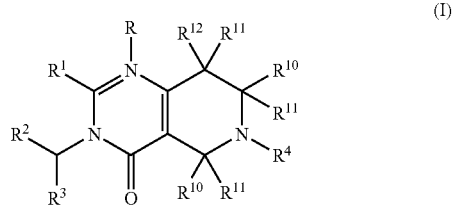

and pharmaceutically acceptable salts, solvates, esters and prodrugs thereof, wherein:

R is absent or R is oxygen, such that when R is oxygen, this is understood to represent the N-oxide form of the nitrogen atom to which R is attached;

$R^1$ is —H, alkyl, haloalkyl, —N($R^9$)$_2$, —S$R^9$, —S(O)$_q$N($R^6$)$_2$, —S(O)$_p$$R^7$, —O$R^9$, -(alkylene)$_n$-aryl, -(alkylene)$_n$-cycloalkyl, -(alkylene)$_n$-cycloalkenyl, -(alkylene)$_n$-heterocycloalkyl, -(alkylene)$_n$-heteroaryl, -(alkylene)$_n$-heterocycloalkenyl, —C(O)-aryl, —C(O)-alkyl, -alkylene-O-aryl, -alkylene-O-alkyl or —C(O)NH$_2$, wherein any aryl, cycloalkyl, cycloalkenyl, heterocycloalkyl, heterocycloalkenyl or heteroaryl group can be optionally substituted with up to 3 substituents, which can be the same or different, and are selected from alkyl, haloalkyl, hydroxyalkyl, aryl, halo, —OH, —O-haloalkyl, —O-alkyl, -alkylene-O-alkyl, —S(O)$_p$ $R^7$, —CN, —N($R^6$)$_2$, —C(O)$R^5$, —C(O)O$R^5$, —C(O)N($R^6$)$_2$, —NHC(O)$R^5$, —NHS(O)$_q$$R^7$ and —S(O)$_q$N($R^6$)$_2$;

$R^2$ is alkyl, haloalkyl, -(alkylene)$_n$-aryl, -(alkylene)$_n$-cycloalkyl, -(alkylene)$_n$-cycloalkenyl, -(alkylene)$_n$-heterocycloalkyl, -(alkylene)$_n$-heteroaryl, -(alkylene)$_n$-heterocycloalkenyl, —C(O)-aryl, —C(O)-alkyl, -alkylene-O-haloalkyl, -alkylene-O-aryl, -alkylene-O-alkyl, —C(O)O$R^5$, or —C(O)N($R^6$)$_2$, wherein any aryl, cycloalkyl, cycloalkenyl, heterocycloalkyl, heterocycloalkenyl or heteroaryl group can be optionally substituted with up to 3 substituents, which can be the same or different, and are selected from alkyl, haloalkyl, hydroxyalkyl, aryl, halo, —OH, —O-haloalkyl, —O-alkyl, -alkylene-O-alkyl, —S(O)$_p$$R^7$, —CN, —N($R^6$)$_2$, —C(O)$R^5$, —C(O)O$R^5$, —C(O)N($R^6$)$_2$, —NHC(O)$R^5$, —NHS(O)$_q$$R^7$ and —S(O)$_q$N($R^6$)$_2$, or $R^2$ and $R^3$ and the carbon atom to which they are both attached, combine to form an aryl, cycloalkyl, cycloalkenyl, heterocycloalkyl, heterocycloalkenyl or heteroaryl group, wherein any of these groups is unsubstituted or substituted with up to 3 substituents, which can be the same or different, and which are selected from alkyl, haloalkyl, hydroxyalkyl, halo, —OH, —O-haloalkyl, —O-alkyl, —O-aryl, -alkylene-O-alkyl, —CN, —N($R^6$)$_2$, —C(O)$R^5$, —C(O)O$R^5$, —C(O)N($R^6$)$_2$, —NHC(O)$R^5$, —NHS(O)$_q$$R^7$, —S(O)$_p$$R^7$ and —S(O)$_q$N($R^6$)$_2$;

$R^3$ is alkyl, -(alkylene)$_n$-aryl, -(alkylene)$_n$-cycloalkyl, -(alkylene)$_n$-cycloalkenyl, -(alkylene)$_n$-heterocycloalkyl, -(alkylene)$_n$-heteroaryl, -(alkylene)$_n$-heterocycloalkenyl, —C(O)-aryl, —C(O)-alkyl, -alkylene-O-aryl, -alkylene-O-alkyl, —C(O)O$R^5$, or —C(O)N($R^6$)$_2$, wherein any aryl, cycloalkyl, cycloalkenyl, heterocycloalkyl, heterocycloalkenyl or heteroaryl group can be optionally substituted with up to 3 substituents, which can be the same or different, and are selected from alkyl, haloalkyl, hydroxyalkyl, aryl, halo, —OH, —O-haloalkyl, —O-alkyl, -alkylene-O-alkyl, —S(O)$_p$ $R^7$, —CN, —N($R^6$)$_2$, —C(O)$R^5$, —C(O)O$R^5$, —C(O)N($R^6$)$_2$, —NHC(O)$R^5$, —NHS(O)$_q$$R^7$ and —S(O)$_q$N($R^6$)$_2$, or $R^2$ and $R^3$ and the carbon atom to which they are both attached, combine to form an aryl, cycloalkyl, cycloalkenyl, heterocycloalkyl, heterocycloalkenyl or heteroaryl group, wherein any of these groups is unsubstituted or substituted with up to 3 substituents, which can be the same or different, and which are selected from alkyl, haloalkyl, hydroxyalkyl, halo, —OH, —O-haloalkyl, —O-alkyl, —O-aryl, -alkylene-O-alkyl, —CN, —N($R^6$)$_2$, —C(O)$R^5$, —C(O)O$R^5$, —C(O)N($R^6$)$_2$, —NHC(O)$R^5$, —NHS(O)$_q$$R^7$, —S(O)$_p$$R^7$ and —S(O)$_q$N($R^6$)$_2$;

$R^4$ is H, alkyl, —C(O)$R^5$, —S(O)$_q$$R^7$, -alkylene-O-alkyl, -alkylene-O-aryl, -alkylene-S-alkyl, -alkylene-S-aryl, -alkylene-NH-alkyl, -alkylene-NH-aryl, -alkylene-NC(O)O-alkyl, —C(O)O$R^5$, —C(O)N($R^6$)$_2$, —C(O)NH—O$R^8$, -(alkylene)$_n$-aryl, -(alkylene)$_n$-cycloalkyl, -(alkylene)$_n$-cycloalkenyl, -(alkylene)$_n$-heterocycloalkyl, -(alkylene)$_n$-heterocycloalkenyl or -(alkylene)$_n$-heteroaryl, wherein any aryl, cycloalkyl, cycloalkenyl, heterocycloalkyl, heterocycloalkenyl or heteroaryl group that is part of an $R^4$ group can be unsubstituted or substituted with up to 3 substituents, which can be the same or different, and are selected from: alkyl, aryl, heterocycloalkyl, heteroaryl, -alkylene-O-alkylene-Si(alkyl)$_3$, —NH$_2$, —NH-alkyl, —N(alkyl)$_2$, —OH, -hydroxyalkyl, -alkynylene-aryl, —S(O)$_p$$R^7$, —O-alkyl, —O-aryl, —C(O)O-alkyl, —C(O)O-haloalkyl, halo, —NO$_2$, —CN, heteroaryl, haloalkyl, —O-haloalkyl, —S-haloalkyl, —S(O)-haloalkyl and -(alkynylene)$_n$-aryl, and wherein a cycloalkyl group that is part of an $R^4$ group can be fused with a benzene ring, and wherein an alkylene group can be optionally substituted with a group selected from: alkyl, cycloalkyl, aryl, heterocycloalkyl or heteroaryl;

$R^5$ is alkyl, alkenyl, alkynyl, haloalkyl, -alkylene-O-aryl, -alkylene-S-aryl, -alkylene-N($R^8$)C(O)O-alkyl, -(alkylene)$_n$-aryl, -(alkylene)$_n$-cycloalkyl, -(alkylene)$_n$-cycloalkenyl, -(alkylene)$_n$-heterocycloalkyl, -(alkylene)$_n$-heterocycloalkenyl or -(alkylene)$_n$-heteroaryl, wherein any aryl, cycloalkyl, cycloalkenyl, heterocycloalkyl, heterocycloalkenyl or heteroaryl group can be unsubstituted or substituted with up to 4 substituents, which can be the same or different, and are selected from alkyl, haloalkyl, hydroxyalkyl, halo, —OH, —O-haloalkyl, —O-alkyl, —O-aryl, —S-haloalkyl, -alkylene-O-alkyl, —CN, —N($R^9$)$_2$, —C(O)H, —C(O)$R^9$, —C(O)O$R^9$, —C(O)N($R^9$)$_2$, —NHC(O)$R^9$, —NHS(O)$_q$$R^9$, —S(O)$_p$$R^9$ and —S(O)$_q$N($R^9$)$_2$;

each occurrence of $R^6$ is independently H, alkyl, -(alkylene)$_n$-aryl, -(alkylene)$_n$-cycloalkyl, -(alkylene)$_n$-cycloalkenyl, -(alkylene)$_n$-heterocycloalkyl, -(alkylene)$_n$-heterocycloalkenyl or -(alkylene)$_n$-heteroaryl, wherein any of the above groups, excluding H, can be unsubstituted or substituted with from 1 to 3 substituents, which can be the same or different, and which are selected from alkyl, haloalkyl, hydroxyalkyl, halo, —OH, —O-haloalkyl, —O-alkyl, —O-aryl, -alkylene-O-alkyl, —CN, —N($R^9$)$_2$, —C(O)H, —C(O)$R^9$, —C(O)O$R^9$, —C(O)N($R^9$)$_2$, —NHC(O)$R^9$, —NHS(O)$_q$$R^9$, —S(O)$_p$$R^9$ and —S(O)$_q$N($R^9$)$_2$;

each occurrence of $R^7$ is independently alkyl, aryl, heterocycloalkyl, heteroaryl or cycloalkyl, any of which can be unsubstituted or substituted with from 1 to 3 substituents, which can be the same or different, and which are selected from alkyl, haloalkyl, hydroxyalkyl, halo, —OH, —O-haloalkyl, —O-alkyl, —O-aryl, -alkylene-O-alkyl, —CN, —N($R^9$)$_2$, —C(O)H, —C(O)$R^9$, —C(O)O$R^9$, —C(O)N($R^9$)$_2$, —NHC(O)$R^9$, —NHS(O)$_q$$R^9$, —S(O)$_p$$R^9$ and —S(O)$_q$ N($R^9$)$_2$;

each occurrence of $R^8$ is independently H or alkyl;

each occurrence of $R^9$ is independently H, alkyl, -(alkylene)$_n$-aryl, heterocycloalkyl, heteroaryl or cycloalkyl;

each occurrence of $R^{10}$ is independently H, alkyl, -(alkylene)$_n$-aryl, heterocycloalkyl, heteroaryl or cycloalkyl;

each occurrence of $R^{11}$ is independently H, alkyl, -(alkylene)$_n$-aryl, heterocycloalkyl, heteroaryl or cycloalkyl, or any $R^{10}$ and $R^{11}$, together with the carbon atoms to which they are attached, can join to form a 3- to 7-membered fused or spirocyclic ring, or a 4- to 7-membered bridged ring;

$R^{12}$ is H, alkyl, -(alkylene)$_n$-aryl, heterocycloalkyl, heteroaryl, cycloalkyl, alkoxy or hydroxyalkyl;

each occurrence of n is independently 0 or 1;

each occurrence of p is independently 0, 1 or 2; and each occurrence of q is independently 1 or 2, such that the compound of formula (I) is not a compound having the formula (II):

(II)

wherein $R^i$ and $R^{ii}$ are denoted using an "X" as set forth below in Tables A-D, and $R^i$ and $R^{ii}$ are defined below in Tables E and F, respectively.

TABLE A

| | $R^i$ | | | | | | | | | |
|---|---|---|---|---|---|---|---|---|---|---|
| $R^{ii}$ | 1 | 2 | 3 | 4 | 5 | 6 | 7 | 8 | 9 | 10 |
| 1 | X | X | X | X | X | X | X | X | X | X |
| 2 | X | X | X | X | X | X | X | X | X | X |
| 3 | X | X | X | X | X | X | X | X | X | X |
| 4 | X | X | X | X | X | X | X | X | X | X |
| 5 | X | X | X | X | X | X | X | X | X | X |
| 6 | X | X | X | X | X | X | X | X | X | X |
| 7 | X | X | X | X | X | X | X | X | X | X |
| 8 | X | X | X | X | X | X | X | X | X | X |
| 9 | X | X | X | X | X | X | X | X | X | X |
| 10 | X | X | X | X | X | X | X | X | X | X |
| 11 | X | X | X | X | X | X | X | X | X | X |
| 12 | X | X | X | X | X | X | X | X | X | X |
| 13 | X | X | X | X | X | X | X | X | X | X |
| 14 | X | X | X | X | X | X | X | X | X | X |
| 15 | X | X | X | X | X | X | X | X | X | X |
| 16 | X | X | X | X | X | X | X | X | X | X |
| 17 | X | X | X | X | X | X | X | X | X | X |
| 18 | X | X | X | X | X | X | X | X | X | X |
| 19 | X | X | X | X | X | X | X | X | X | X |
| 20 | X | X | X | X | X | X | X | X | X | X |
| 21 | X | X | X | X | X | X | X | X | X | X |
| 22 | X | X | X | X | X | X | X | X | X | X |
| 23 | X | X | X | X | X | X | X | X | X | X |
| 24 | X | X | X | X | X | X | X | X | X | X |
| 25 | X | X | X | X | X | X | X | X | X | X |
| 26 | X | X | X | X | X | X | X | X | X | X |
| 27 | X | X | X | X | X | X | X | X | X | X |
| 28 | X | X | X | X | X | X | X | X | X | X |
| 29 | X | X | X | X | X | X | X | X | X | X |
| 30 | X | X | X | X | X | X | X | X | X | X |
| 31 | X | X | X | X | X | X | X | X | X | X |
| 32 | X | X | X | X | X | X | X | X | X | X |
| 33 | X | X | X | X | X | X | X | X | X | X |
| 34 | X | X | X | X | X | X | X | X | X | X |
| 35 | X | X | X | X | X | X | X | X | X | X |
| 36 | X | X | X | X | X | X | X | X | X | X |
| 37 | X | X | X | X | X | X | X | X | X | X |
| 38 | X | X | X | X | X | X | X | X | X | X |
| 39 | X | X | X | X | X | X | X | X | X | X |
| 40 | X | X | X | X | X | X | X | X | X | X |
| 41 | X | X | X | X | X | X | X | X | X | X |
| 42 | X | X | X | X | X | | X | X | X | X |
| 43 | X | X | X | X | X | | | | | |
| 44 | X | X | X | X | | X | X | X | X | X |
| 45 | X | X | X | X | X | X | | | X | |
| 46 | X | X | X | X | X | X | X | X | X | X |
| 47 | X | X | X | X | X | X | X | X | X | X |
| 48 | X | X | X | X | X | X | X | X | X | X |
| 49 | X | X | X | X | X | X | X | X | X | X |
| 50 | X | X | X | X | X | X | X | X | X | X |
| 51 | X | X | X | X | X | X | X | X | X | X |
| 52 | X | X | X | X | X | X | X | X | X | X |
| 53 | X | X | X | X | X | X | X | X | X | X |
| 54 | X | X | X | X | X | X | X | X | X | X |
| 55 | X | X | X | X | X | X | X | X | X | X |
| 56 | X | X | X | X | X | X | X | X | X | X |
| 57 | X | X | | X | X | X | X | X | X | X |
| 58 | X | X | X | X | | X | X | X | X | X |
| 59 | X | X | X | X | | X | X | X | X | X |
| 60 | X | X | X | X | X | X | X | X | X | X |

TABLE A-continued

| | $R^i$ | | | | | | | | | |
|---|---|---|---|---|---|---|---|---|---|---|
| $R^{ii}$ | 1 | 2 | 3 | 4 | 5 | 6 | 7 | 8 | 9 | 10 |
| 61 | X | X | X | X | | X | X | X | X | X |
| 62 | X | X | X | X | X | X | X | X | X | X |
| 63 | X | X | | X | | X | X | X | X | X |
| 64 | X | X | X | X | X | X | X | X | X | X |
| 65 | X | X | | X | X | X | X | X | X | X |
| 66 | X | X | | X | | X | X | X | X | X |
| 67 | X | X | | X | | X | X | X | X | X |
| 68 | X | X | | X | | X | X | X | X | X |
| 69 | X | X | | X | | X | X | X | X | X |
| 70 | X | X | | X | | X | X | X | X | X |
| 71 | X | X | X | X | X | X | X | X | X | X |
| 72 | X | X | X | X | | X | X | X | X | X |
| 73 | X | X | X | X | X | X | X | X | X | X |
| 74 | X | X | X | X | | X | X | X | X | X |
| 75 | X | X | X | X | | X | X | X | X | X |
| 76 | X | X | X | X | | X | X | X | X | X |
| 77 | X | X | X | X | | X | X | X | X | X |
| 78 | X | X | X | X | | X | X | X | X | X |
| 79 | X | X | X | X | | X | X | X | X | X |
| 80 | X | X | X | X | | X | X | X | X | X |
| 81 | | X | X | X | X | | | | | |
| 82 | | X | X | X | X | | | | | |
| 83 | | X | X | X | X | | | | | |
| 84 | | X | X | X | X | X | X | X | | X |
| 85 | | X | X | X | X | | | | | |
| 86 | | X | X | X | X | X | X | X | X | X |
| 87 | | X | X | X | X | | | | | |
| 88 | | X | X | X | X | | | | | |
| 89 | X | X | | X | | X | X | | X | X |
| 90 | X | X | | X | | X | X | X | X | X |
| 91 | X | X | | X | | X | X | X | X | X |
| 92 | X | X | | X | | X | X | X | X | X |
| 93 | X | X | X | X | | X | X | X | X | X |
| 94 | X | X | | X | | X | X | X | X | X |
| 95 | X | X | | X | | X | X | | X | X |
| 96 | X | X | | X | | X | X | X | X | X |
| 97 | X | X | X | X | | X | X | X | X | X |
| 98 | X | X | | X | | X | X | X | X | X |
| 99 | X | X | X | X | | X | X | X | X | X |
| 100 | X | X | X | X | | X | X | X | X | X |
| 101 | X | X | X | X | | X | X | X | X | X |
| 102 | X | X | X | X | | X | X | X | X | X |
| 103 | X | X | X | X | | X | X | X | X | X |
| 104 | X | X | X | X | | X | X | X | X | X |
| 105 | X | X | X | X | | X | X | X | X | X |
| 106 | X | X | X | X | | X | X | X | X | X |
| 107 | X | X | X | X | | X | X | X | X | X |
| 108 | X | X | X | X | | X | X | X | X | X |
| 109 | X | X | X | X | | X | X | X | X | X |
| 110 | X | X | X | X | | X | X | X | X | X |
| 111 | X | X | X | X | | X | X | X | X | X |
| 112 | X | X | X | X | | X | X | | X | X |
| 113 | X | X | X | X | | X | X | X | X | X |
| 114 | X | X | X | X | | X | X | X | X | X |
| 115 | X | X | X | X | | X | X | X | X | X |
| 116 | X | X | X | X | | X | X | X | X | X |
| 117 | X | X | X | X | | X | X | X | X | X |
| 118 | X | X | X | X | | X | X | X | X | X |
| 119 | X | X | X | X | | X | X | X | X | X |
| 120 | X | X | X | X | | X | X | X | X | X |
| 121 | X | X | X | X | | X | X | X | X | X |
| 122 | X | X | X | X | | X | X | X | X | X |
| 123 | X | X | X | X | | X | X | X | X | X |
| 124 | X | X | X | X | | X | X | X | X | X |
| 125 | X | X | X | X | | X | X | X | X | X |
| 126 | X | X | X | X | | X | X | | X | X |
| 127 | X | X | X | X | | X | X | X | X | X |
| 128 | X | X | X | X | | X | X | X | X | X |
| 129 | X | X | X | X | | X | X | X | X | X |
| 130 | X | X | X | X | | X | X | X | X | X |
| 131 | X | X | X | X | | X | X | X | X | X |
| 132 | X | X | X | X | | X | X | X | X | X |
| 133 | X | X | X | X | X | X | X | X | X | X |
| 134 | X | X | X | X | | X | X | X | X | X |
| 135 | X | X | X | X | | X | X | X | X | X |
| 136 | X | X | X | X | | X | X | X | X | X |

TABLE A-continued

| $R^{ii}$ | \multicolumn{10}{c}{$R^{i}$} |
|---|---|---|---|---|---|---|---|---|---|---|
|  | 1 | 2 | 3 | 4 | 5 | 6 | 7 | 8 | 9 | 10 |
| 137 | X | X | X | X | X | X | X | X | X | X |
| 138 | X | X | X | X | X | X | X | X | X | X |
| 139 | X | X | X | X | X | X | X | X | X | X |
| 140 | X | X | X | X | X | X | X | X | X | X |
| 141 | X | X | X | X | X | X | X | X | X | X |
| 142 | X | X | X | X | X | X | X | X | X | X |
| 143 | X | X | X | X | X | X | X | X | X | X |
| 144 | X | X | X | X | X | X | X | X | X | X |
| 145 | X | X | X | X | X | X | X | X | X | X |
| 146 | X | X | X | X | X | X | X | X | X | X |
| 147 | X | X | X |   | X | X | X | X | X | X |
| 148 | X | X | X | X | X | X | X | X | X | X |
| 149 | X | X | X | X | X | X | X | X | X | X |
| 150 | X | X | X | X | X | X | X | X | X | X |
| 151 | X | X | X | X | X | X | X | X | X | X |
| 152 | X | X | X | X | X | X | X | X | X | X |
| 153 | X | X | X | X | X | X | X | X | X | X |
| 154 | X | X | X | X | X | X | X | X | X | X |
| 155 | X | X | X | X | X | X | X | X | X | X |
| 156 | X | X | X | X | X | X | X | X | X | X |
| 157 | X | X | X | X | X | X | X | X | X | X |
| 158 | X | X | X | X | X | X | X | X | X | X |
| 159 | X | X | X | X | X | X | X | X | X | X |
| 160 | X | X | X | X | X | X | X | X | X | X |
| 161 | X | X | X | X | X | X | X | X | X | X |
| 162 | X | X | X |   | X | X | X | X | X | X |
| 163 | X | X |   |   | X | X | X | X | X | X |
| 164 | X | X |   |   | X | X | X | X | X | X |
| 165 | X | X |   | X | X | X | X | X | X | X |
| 166 | X | X |   |   | X | X | X | X | X | X |
| 167 | X | X | X |   | X | X | X | X | X | X |
| 168 | X | X |   |   | X | X | X | X | X | X |
| 169 | X | X |   |   | X | X | X | X | X | X |
| 170 | X | X | X |   | X | X | X | X | X | X |
| 171 | X | X |   |   | X | X | X | X | X | X |
| 172 | X | X |   |   | X | X | X | X | X | X |
| 173 | X | X | X | X |   | X | X | X | X | X |
| 174 | X | X | X |   |   | X | X | X | X | X |
| 175 | X | X | X |   |   | X | X | X | X | X |
| 176 | X | X |   |   |   | X | X | X | X | X |
| 177 |   | X | X | X | X |   | X | X |   | X |
| 178 |   | X | X | X | X | X | X | X | X | X |
| 179 |   | X |   | X | X | X | X |   |   |   |
| 180 |   | X |   | X | X | X |   | X | X |   |
| 181 |   | X |   | X | X | X | X |   | X |   |
| 182 |   | X |   | X | X |   | X | X | X | X |
| 183 |   | X |   | X |   | X |   |   |   | X |
| 184 |   | X |   | X | X |   |   | X | X | X |
| 185 |   | X |   | X |   | X |   | X |   |   |
| 186 |   | X |   | X | X | X |   |   |   |   |
| 187 |   | X |   |   |   | X | X | X | X |   |
| 188 |   | X |   | X | X |   |   | X | X |   |
| 189 |   | X |   | X | X | X | X |   | X |   | X |
| 190 |   | X |   | X | X | X | X |   | X | X |
| 191 |   | X |   |   | X | X | X |   | X | X |
| 192 |   | X |   | X |   | X |   |   | X | X |
| 193 |   | X |   | X | X | X |   |   |   |   |
| 194 |   | X |   |   | X | X |   | X | X |   | X |
| 195 |   | X |   | X | X | X |   |   |   |   |
| 196 |   | X |   | X | X |   | X |   |   | X |   | X |
| 197 |   | X |   | X | X |   | X | X |   |   |
| 198 |   | X |   | X | X | X | X |   | X | X |
| 199 |   | X |   | X | X | X |   |   |   |   |
| 200 |   | X | X |   |   | X |   | X |   |   | X |
| 201 |   | X |   |   | X | X |   | X | X |   | X |
| 202 |   | X | X | X |   | X | X | X |   |   |
| 203 |   | X | X | X |   | X |   |   |   |   |
| 204 |   | X |   |   | X | X |   | X | X |   |
| 205 |   | X |   | X | X | X |   | X |   |   |
| 206 |   | X | X | X | X | X | X | X |   |   |
| 207 |   | X | X | X | X |   |   |   |   |   |
| 208 |   | X | X | X |   | X | X | X |   |   |
| 209 |   | X | X | X |   |   |   |   |   |   |
| 210 |   |   | X | X |   | X | X | X | X | X |
| 211 |   |   | X |   |   | X | X | X |   |   |
| 212 |   |   |   |   | X | X | X | X |   |   |
| 213 |   |   |   |   |   | X | X |   |   |   |
| 214 |   |   |   |   |   |   |   | X |   |   |
| 215 |   |   |   |   |   |   |   |   |   |   |
| 216 |   | X |   | X | X | X | X | X | X | X |
| 217 |   | X |   | X | X | X | X | X | X | X |
| 218 |   | X | X | X | X | X | X | X |   | X |
| 219 |   | X | X | X | X | X | X | X | X | X |
| 220 |   | X |   |   |   | X |   |   |   | X |
| 221 |   | X |   | X | X | X | X | X |   | X |
| 222 |   | X |   |   |   |   |   | X |   | X |
| 223 |   | X |   |   | X | X |   |   |   | X |
| 224 |   | X | X | X | X | X |   | X |   | X |
| 225 |   | X | X | X | X |   |   |   | X | X |
| 226 |   | X |   |   | X | X | X | X |   | X |
| 227 |   | X |   |   | X | X | X | X |   | X |
| 228 |   |   | X | X | X |   |   | X |   |   |
| 229 |   |   | X | X | X |   |   | X |   |   |
| 230 |   |   |   |   |   | X | X | X | X | X |
| 231 |   |   |   | X |   | X | X | X |   | X |
| 232 |   |   |   |   |   | X |   |   |   | X |
| 233 |   |   |   |   |   | X |   |   |   | X |
| 234 |   |   |   |   |   |   | X | X | X |   |
| 235 | X | X | X | X |   | X | X | X |   | X |
| 236 | X | X | X | X | X | X | X | X | X | X |
| 237 | X | X | X | X | X | X | X | X | X | X |
| 238 | X | X | X | X | X | X | X | X | X | X |
| 239 | X | X | X | X | X | X | X | X | X | X |
| 240 | X | X | X | X | X | X | X | X | X | X |
| 241 | X | X | X | X | X | X | X | X | X | X |
| 242 | X | X | X | X | X | X | X | X | X | X |
| 243 | X | X | X | X | X | X | X | X | X | X |
| 244 | X | X | X | X | X | X | X | X | X | X |
| 245 | X | X | X |   | X | X | X | X | X | X |
| 246 | X | X |   |   | X | X | X | X | X | X |
| 247 | X | X | X |   | X | X | X | X | X | X |
| 248 | X | X | X | X | X | X | X | X | X | X |
| 249 | X | X | X | X | X | X | X | X | X | X |
| 250 | X | X | X | X | X | X | X | X | X | X |
| 251 | X | X | X | X | X | X | X | X | X | X |
| 252 | X | X | X | X | X | X | X | X | X | X |
| 253 | X | X | X | X | X | X | X | X | X | X |
| 254 | X | X | X | X | X | X | X | X | X | X |
| 255 | X | X | X | X | X | X | X | X | X | X |
| 256 | X | X | X | X | X | X | X | X | X | X |
| 257 | X | X | X | X | X | X | X | X | X | X |
| 258 | X | X | X | X |   | X | X | X | X | X |
| 259 | X | X |   |   |   |   | X | X | X | X |
| 260 | X | X | X | X | X |   | X | X | X | X |
| 261 | X | X | X |   | X |   |   | X |   | X |
| 262 | X | X |   |   |   | X | X |   | X | X |
| 263 | X | X | X | X |   | X |   |   | X | X |
| 264 | X | X |   |   | X | X |   | X | X | X |
| 265 | X | X | X | X | X | X | X |   | X | X |
| 266 | X | X | X | X |   | X | X | X | X | X |
| 267 | X | X | X | X | X | X | X |   | X | X |
| 268 | X | X | X | X | X | X | X |   | X | X |
| 269 |   | X | X | X | X | X | X | X | X | X |
| 270 |   | X | X | X | X | X | X | X | X | X |
| 271 |   | X | X | X | X | X |   |   | X | X |
| 272 |   | X |   |   | X |   |   | X | X | X |
| 273 |   | X | X | X |   | X | X | X | X | X |
| 274 |   | X | X | X | X | X | X | X | X | X |
| 275 |   | X | X | X | X | X | X | X | X | X |
| 276 |   | X | X | X | X | X | X | X | X | X |
| 277 | X | X | X |   | X | X | X | X | X | X |
| 278 |   |   | X | X | X | X | X | X | X | X |

TABLE B

| R$^{ii}$ | 11 | 12 | 13 | 14 | 15 | 16 | 17 | 18 | 19 | 20 |
|---|---|---|---|---|---|---|---|---|---|---|
| 1 | X | X | X | X | X | X | X | X | X | X |
| 2 | X | X | X | X | X | X | X | X | X | X |
| 3 | X | X | X | X | X | X | X | X | X | X |
| 4 | X | X | X | X | X | X | X | X | X | X |
| 5 | X | X | X | X |   | X | X | X | X | X |
| 6 | X | X | X | X | X | X | X | X | X | X |
| 7 | X | X | X | X | X | X | X | X | X | X |
| 8 | X | X | X | X | X | X | X | X | X | X |
| 9 | X | X | X | X | X | X | X | X | X | X |
| 10 | X | X | X | X | X | X | X | X | X | X |
| 11 | X | X | X | X | X | X | X | X | X | X |
| 12 | X | X | X | X | X | X | X | X | X | X |
| 13 | X | X | X | X | X | X | X |   | X | X |
| 14 | X | X | X | X |   |   | X |   | X |   |
| 15 | X | X | X | X | X |   | X | X | X | X |
| 16 | X | X | X | X | X | X | X | X | X | X |
| 17 | X | X | X | X | X | X | X | X | X | X |
| 18 | X | X | X | X | X | X | X | X | X | X |
| 19 | X | X | X | X | X | X | X | X | X | X |
| 20 | X | X | X | X | X | X | X | X | X | X |
| 21 | X | X | X | X | X | X | X | X | X | X |
| 22 | X | X | X | X | X | X | X | X | X | X |
| 23 | X | X | X | X | X | X | X | X | X | X |
| 24 | X | X | X | X | X | X | X | X | X | X |
| 25 | X | X | X | X | X | X | X | X | X | X |
| 26 | X | X | X | X | X | X | X | X | X | X |
| 27 | X | X | X | X | X | X | X | X | X | X |
| 28 | X | X | X | X | X | X | X | X | X | X |
| 29 | X | X | X | X | X | X | X | X | X | X |
| 30 | X | X | X | X | X | X | X | X | X | X |
| 31 | X | X | X | X | X | X | X | X | X | X |
| 32 | X | X | X | X | X | X | X | X | X | X |
| 33 | X | X | X | X | X | X | X | X | X | X |
| 34 | X | X | X | X | X | X | X | X | X | X |
| 35 | X | X | X | X | X | X | X | X | X | X |
| 36 | X | X | X | X | X | X | X | X | X | X |
| 37 | X | X | X | X | X | X | X | X | X | X |
| 38 | X | X | X | X | X | X | X | X | X | X |
| 39 | X | X | X | X | X | X | X | X | X | X |
| 40 | X | X | X | X | X | X | X | X | X | X |
| 41 | X | X | X | X | X | X | X | X | X | X |
| 42 | X | X | X | X |   | X | X | X | X | X |
| 43 | X | X |   |   | X | X |   | X |   | X |
| 44 | X |   | X | X | X | X | X | X | X | X |
| 45 |   | X |   |   | X | X | X | X | X | X |
| 46 | X |   | X | X | X | X | X | X | X | X |
| 47 | X | X | X | X |   | X | X | X | X | X |
| 48 |   | X |   | X | X | X |   |   |   | X |
| 49 | X | X | X | X |   | X | X | X | X | X |
| 50 | X | X | X | X | X | X | X | X | X | X |
| 51 | X | X | X | X | X | X | X | X | X | X |
| 52 | X | X | X | X |   | X | X | X | X | X |
| 53 | X |   | X | X | X | X |   | X | X |   |
| 54 | X | X | X | X | X |   | X | X | X |   |
| 55 | X | X | X | X | X | X |   | X | X | X |
| 56 | X | X | X | X | X | X | X | X | X | X |
| 57 | X | X | X | X | X | X | X | X | X | X |
| 58 | X | X | X | X | X | X | X | X | X | X |
| 59 | X | X | X | X | X | X | X | X | X | X |
| 60 | X | X | X | X | X | X | X | X | X | X |
| 61 | X | X | X | X | X | X | X | X | X | X |
| 62 | X | X | X | X | X | X | X | X | X | X |
| 63 | X | X | X | X | X | X | X | X | X | X |
| 64 | X | X | X | X | X |   | X | X | X | X |
| 65 | X | X | X | X | X |   | X | X | X |   |
| 66 | X | X | X | X | X |   | X | X | X |   |
| 67 | X | X | X | X | X |   | X | X | X |   |
| 68 | X | X | X | X | X |   | X |   | X | X |
| 69 | X | X | X | X | X |   | X | X | X |   |
| 70 | X | X | X | X | X |   | X | X | X |   |
| 71 | X | X | X | X | X | X | X | X | X | X |
| 72 | X | X | X | X | X |   | X | X | X | X |
| 73 | X | X | X | X | X |   | X | X | X | X |
| 74 | X | X | X | X | X | X | X | X | X | X |
| 75 | X | X | X | X | X | X | X | X | X | X |
| 76 | X | X | X | X | X | X | X | X | X | X |
| 77 | X | X | X | X | X | X | X | X | X | X |
| 78 | X | X | X | X | X | X | X | X | X | X |
| 79 | X | X | X | X | X | X | X | X | X | X |
| 80 | X | X | X | X | X | X | X | X | X | X |
| 81 |   |   |   |   |   | X |   |   |   | X |
| 82 |   |   |   |   |   | X |   |   | X | X |
| 83 |   |   | X |   |   | X | X | X | X | X |
| 84 | X | X | X | X |   | X |   |   |   | X |
| 85 |   |   |   |   | X |   |   |   |   | X |
| 86 | X |   | X | X | X | X |   | X | X |   |
| 87 |   |   |   | X | X |   |   |   |   | X |
| 88 |   |   |   |   |   | X |   |   |   | X |
| 89 | X | X | X | X |   | X | X |   | X | X |
| 90 | X | X | X | X | X | X | X | X | X | X |
| 91 | X | X | X | X | X | X | X | X | X | X |
| 92 | X | X | X | X | X | X | X | X | X | X |
| 93 | X | X | X | X | X | X | X | X | X | X |
| 94 | X | X | X | X | X | X | X | X | X | X |
| 95 | X | X | X | X | X | X | X | X |   | X |
| 96 | X | X | X | X | X | X | X | X | X | X |
| 97 | X | X | X | X | X | X | X | X | X |   |
| 98 | X | X | X | X | X | X | X | X |   |   |
| 99 | X | X | X | X | X | X | X | X | X |   |
| 100 | X | X | X | X | X | X | X | X | X | X |
| 101 | X | X | X | X | X | X | X | X | X | X |
| 102 | X | X | X | X | X | X | X | X | X | X |
| 103 | X | X | X | X | X | X | X | X | X | X |
| 104 | X | X | X | X | X | X | X | X | X | X |
| 105 | X | X | X | X | X | X | X | X | X | X |
| 106 | X | X | X | X | X | X | X | X | X | X |
| 107 | X | X | X | X | X | X | X | X | X | X |
| 108 | X | X | X | X | X | X | X | X | X | X |
| 109 | X | X | X | X | X | X | X | X | X | X |
| 110 | X | X | X | X | X | X | X | X | X | X |
| 111 | X |   | X | X | X | X | X | X | X | X |
| 112 | X | X | X | X | X | X | X |   | X | X |
| 113 | X | X | X | X | X | X | X | X | X | X |
| 114 | X | X | X | X | X | X | X | X | X | X |
| 115 | X | X | X | X | X | X | X | X | X | X |
| 116 | X | X | X | X | X | X | X | X | X | X |
| 117 | X | X | X | X | X | X | X | X | X | X |
| 118 | X | X | X | X | X | X | X | X | X | X |
| 119 | X | X | X | X | X | X | X | X | X | X |
| 120 | X | X | X | X | X | X | X | X | X | X |
| 121 | X | X | X | X | X | X | X | X | X | X |
| 122 | X | X | X | X | X | X | X | X | X | X |
| 123 | X | X | X | X | X | X | X | X | X | X |
| 124 | X | X | X | X | X | X |   |   | X |   |
| 125 | X |   |   | X | X | X | X | X | X | X |
| 126 | X | X |   | X | X | X | X | X | X | X |
| 127 | X |   | X | X | X | X | X | X | X | X |
| 128 | X |   | X | X | X | X | X | X | X | X |
| 129 | X |   | X | X | X | X | X |   | X |   |
| 130 | X |   | X | X | X | X | X |   |   |   |
| 131 | X |   | X | X | X | X |   | X | X | X |
| 132 | X |   | X | X | X | X | X | X | X | X |
| 133 | X | X | X | X | X | X | X | X | X | X |
| 134 | X | X | X | X | X | X | X | X | X | X |
| 135 | X | X | X | X | X | X | X | X | X | X |
| 136 | X | X | X | X | X | X | X | X | X | X |
| 137 | X | X | X | X | X | X | X | X | X | X |
| 138 | X | X | X | X | X | X | X | X | X | X |
| 139 | X | X | X | X | X | X | X | X | X | X |
| 140 | X | X | X | X | X | X | X | X | X | X |
| 141 | X | X | X | X | X | X | X | X | X | X |
| 142 | X | X | X | X | X | X | X | X | X | X |
| 143 | X | X | X | X | X | X | X | X | X | X |
| 144 | X | X | X | X | X | X | X | X | X | X |
| 145 | X | X | X | X | X | X | X | X | X | X |
| 146 | X | X | X | X | X | X | X | X | X | X |
| 147 | X | X | X | X | X | X | X | X | X | X |
| 148 | X | X | X | X | X | X | X | X | X | X |
| 149 | X | X | X | X | X | X | X | X | X | X |
| 150 | X | X | X | X | X | X | X | X | X | X |
| 151 | X | X | X | X | X | X | X | X | X | X |
| 152 | X | X | X | X | X | X | X | X | X | X |

TABLE B-continued

| $R^{ii}$ | 11 | 12 | 13 | 14 | 15 | 16 | 17 | 18 | 19 | 20 |
|---|---|---|---|---|---|---|---|---|---|---|
| 153 | X | X | X | X | X | X | X | X | X | X |
| 154 | X | X | X | X | X | X | X | X | X | X |
| 155 | X | X | X | X | X | X | X | X | X | X |
| 156 | X | X | X | X | X | X | X | X | X | X |
| 157 | X | X | X | X | X | X | X | X | X | X |
| 158 | X | X | X | X | X | X | X | X | X | X |
| 159 | X | X | X | X | X | X | X | X | X | X |
| 160 | X | X | X | X | X | X | X | X | X | X |
| 161 | X | X | X | X | X | X | X | X | X | X |
| 162 | X | X | X | X | X | X | X | X | X | X |
| 163 | X | X | X | X | X | X | X | X | X | X |
| 164 | X | X | X | X | X | X | X | X | X | X |
| 165 | X | X | X | X | X | X | X | X | X | X |
| 166 | X | X | X | X | X | X | X | X | X | X |
| 167 | X | X | X | X | X | X | X | X | X | X |
| 168 | X | X | X | X | X | X | X | X | X | X |
| 169 | X | X | X | X | X | X | X | X | X | X |
| 170 | X | X | X | X | X | X | X | X | X | X |
| 171 | X | X | X | X | X | X | X | X | X | X |
| 172 | X | X | X | X | X | X | X | X | X | X |
| 173 | X | X | X | X | X | X | X | X | X | X |
| 174 | X | X | X | X | X | X | X | X | X | X |
| 175 | X | X | X | X | X | X | X | X | X | X |
| 176 | X | X | X | X | X | X | X | X | X | X |
| 177 | X |  | X |  |  |  |  | X | X | X |
| 178 | X |  | X | X |  |  | X | X | X | X |
| 179 | X | X | X |  |  |  | X | X | X | X |
| 180 |  | X |  | X | X |  |  | X |  | X |
| 181 |  | X | X | X |  | X |  | X | X | X |
| 182 | X |  | X | X | X |  | X | X | X | X |
| 183 |  |  | X |  |  |  |  | X | X | X |
| 184 | X | X |  | X | X |  |  | X | X | X |
| 185 |  |  |  |  |  |  |  |  |  |  |
| 186 |  | X |  |  |  |  |  | X |  |  |
| 187 |  |  | X | X |  | X | X | X | X | X |
| 188 |  |  | X |  |  |  |  | X | X |  |
| 189 |  | X | X |  |  | X | X | X | X | X |
| 190 | X |  |  |  |  |  |  | X | X | X |
| 191 | X | X | X | X |  |  | X | X | X | X |
| 192 | X | X |  |  |  |  |  |  | X |  |
| 193 | X | X | X | X |  |  | X | X | X | X |
| 194 | X |  | X | X |  |  |  | X | X | X |
| 195 |  | X |  |  | X |  |  |  |  | X |
| 196 | X | X | X | X | X |  |  | X | X | X |
| 197 |  | X | X | X | X | X | X | X | X | X |
| 198 | X | X | X | X | X |  | X | X | X | X |
| 199 |  | X |  | X |  | X |  | X | X | X |
| 200 | X |  | X |  |  |  |  | X | X | X |
| 201 | X | X |  | X | X | X | X | X | X | X |
| 202 |  | X |  | X |  |  | X | X | X | X |
| 203 | X |  |  |  |  |  |  | X | X | X |
| 204 | X | X |  | X | X |  | X | X | X |  |
| 205 |  | X |  | X | X | X |  | X | X | X |
| 206 | X | X | X | X | X |  |  | X | X | X |
| 207 | X |  |  |  |  |  | X | X | X | X |
| 208 |  | X |  | X | X | X |  | X | X | X |
| 209 | X |  |  |  |  |  |  | X | X | X |
| 210 | X | X | X | X | X |  | X | X | X | X |
| 211 |  |  |  |  |  | X |  | X | X | X |
| 212 | X | X |  | X | X | X | X | X | X | X |
| 213 |  |  | X | X | X | X |  | X | X | X |
| 214 |  | X |  |  | X |  |  | X |  | X |
| 215 |  |  | X |  |  |  |  |  |  | X |
| 216 | X | X | X | X |  | X | X | X | X | X |
| 217 |  | X | X | X | X | X | X | X | X | X |
| 218 | X | X | X | X | X | X | X | X | X | X |
| 219 | X | X | X | X | X | X |  | X | X | X |
| 220 |  | X | X | X | X | X |  | X |  | X |
| 221 | X |  | X | X |  |  |  | X |  | X |
| 222 | X | X | X |  |  |  |  | X |  |  |
| 223 |  |  | X |  | X |  | X | X | X | X |
| 224 |  |  | X |  |  | X | X | X | X | X |
| 225 | X |  | X |  | X |  |  | X | X | X |
| 226 | X |  | X | X |  |  | X | X | X | X |
| 227 | X | X | X | X | X | X |  | X | X | X |
| 228 | X |  | X |  | X |  |  | X | X |  |
| 229 |  |  |  | X |  |  |  |  |  |  |
| 230 | X |  | X | X | X | X | X | X | X | X |
| 231 |  | X | X | X | X | X |  | X | X | X |
| 232 |  |  | X | X | X |  |  | X |  |  |
| 233 |  | X | X | X |  |  | X | X | X | X |
| 234 |  | X | X | X | X |  | X | X | X | X |
| 235 | X | X |  | X | X | X | X | X | X | X |
| 236 | X | X | X | X | X | X | X | X | X | X |
| 237 | X | X | X | X | X | X | X | X | X | X |
| 238 | X |  | X | X | X | X | X | X | X | X |
| 239 | X | X | X | X | X | X | X | X | X | X |
| 240 | X | X | X | X | X | X | X | X | X | X |
| 241 | X | X | X | X | X | X | X | X | X | X |
| 242 | X | X |  | X | X | X | X | X | X | X |
| 243 | X | X | X | X | X | X | X | X | X | X |
| 244 | X | X | X | X | X | X | X | X | X | X |
| 245 | X | X | X | X | X | X | X | X | X | X |
| 246 | X |  | X | X | X |  | X |  | X | X |
| 247 | X | X | X | X | X | X | X | X | X | X |
| 248 | X | X | X | X | X | X | X | X | X | X |
| 249 | X | X | X | X |  | X | X | X | X | X |
| 250 | X | X |  | X | X | X | X | X | X | X |
| 251 | X | X | X | X | X | X | X | X | X | X |
| 252 | X | X | X | X | X | X | X | X | X | X |
| 253 |  |  | X |  | X | X | X | X | X | X |
| 254 | X | X | X | X | X | X | X | X | X | X |
| 255 | X | X | X | X | X | X | X | X | X | X |
| 256 | X | X | X |  | X | X | X | X | X | X |
| 257 | X | X | X |  | X |  | X | X | X |  |
| 258 | X | X |  | X | X | X | X | X | X | X |
| 259 | X | X | X | X | X | X | X | X | X | X |
| 260 | X | X | X | X | X | X | X | X | X | X |
| 261 |  | X | X | X | X | X | X | X |  |  |
| 262 |  | X | X | X | X | X | X | X | X | X |
| 263 | X | X |  | X | X | X | X | X | X | X |
| 264 | X | X | X | X |  | X | X | X | X | X |
| 265 | X | X | X | X | X |  | X | X | X | X |
| 266 | X | X | X |  | X | X | X | X | X | X |
| 267 | X | X |  | X | X | X | X | X | X | X |
| 268 | X | X |  | X | X | X | X | X | X | X |
| 269 | X | X | X | X | X | X | X | X | X | X |
| 270 | X | X | X | X | X |  | X | X | X | X |
| 271 |  | X | X | X |  |  | X | X |  | X |
| 272 | X |  | X |  |  | X |  | X |  |  |
| 273 | X | X | X | X |  | X | X | X | X | X |
| 274 |  | X |  | X |  | X | X | X | X | X |
| 275 | X | X | X | X | X | X | X | X | X | X |
| 276 | X | X | X | X | X |  | X | X | X | X |
| 277 | X | X | X | X |  | X | X | X | X | X |
| 278 |  | X | X | X |  | X | X | X | X | X |

TABLE C

| $R^{ii}$ | 21 | 22 | 23 | 24 | 25 | 26 | 27 | 28 | 29 | 30 |
|---|---|---|---|---|---|---|---|---|---|---|
| 1 | X |  | X | X | X | X | X | X | X | X |
| 2 | X | X | X | X | X | X | X | X | X | X |
| 3 | X |  | X | X | X | X | X | X | X | X |
| 4 | X | X | X | X | X | X | X | X | X | X |
| 5 | X | X | X |  | X | X | X | X | X | X |
| 6 | X | X |  |  | X | X | X | X | X | X |
| 7 | X | X | X | X | X | X | X | X | X | X |
| 8 | X | X | X | X | X | X | X | X | X | X |
| 9 | X | X | X | X | X | X | X | X | X | X |
| 10 | X | X | X | X | X | X | X | X | X | X |
| 11 | X | X | X | X | X |  | X | X | X | X |
| 12 | X | X | X |  | X |  | X | X | X | X |
| 13 | X |  | X | X | X | X | X | X | X | X |
| 14 | X | X | X | X | X | X | X | X | X | X |
| 15 | X |  | X | X | X | X | X | X | X | X |
| 16 | X | X | X |  | X | X | X | X | X | X |

TABLE C-continued

| $R^{ii}$ | 21 | 22 | 23 | 24 | 25 | 26 | 27 | 28 | 29 | 30 |
|---|---|---|---|---|---|---|---|---|---|---|
| 17 | X | X | X | X | X | X | X | X | X | X |
| 18 | X | X | X | X | X | X | X | X | X | X |
| 19 | X | X | X | X | X | X | X | X | X | X |
| 20 | X | X | X | X | X | X | X | X | X | X |
| 21 | X | X | X | X | X | X | X | X | X | X |
| 22 | X | X | X | X | X | X | X | X | X | X |
| 23 | X | X | X | X | X | X | X | X | X | X |
| 24 | X | X | X | X | X | X | X | X | X | X |
| 25 | X | X | X | X | X | X | X | X | X | X |
| 26 | X | X | X | X | X | X | X | X | X | X |
| 27 | X | X | X | X | X | X |  | X | X | X |
| 28 | X | X | X | X | X | X |  | X | X | X |
| 29 | X | X | X | X | X | X | X | X | X | X |
| 30 | X | X | X | X | X | X | X | X | X | X |
| 31 | X | X | X | X | X | X | X | X | X | X |
| 32 | X | X | X | X | X | X | X | X | X | X |
| 33 | X | X | X | X | X | X | X | X | X | X |
| 34 | X | X | X | X | X | X | X | X | X | X |
| 35 | X | X | X | X | X | X | X | X | X | X |
| 36 | X | X | X | X | X | X | X | X | X | X |
| 37 | X | X | X | X | X | X | X | X | X | X |
| 38 | X | X | X | X | X | X | X | X | X | X |
| 39 | X | X | X | X | X | X | X | X | X | X |
| 40 | X | X | X | X | X | X | X | X | X | X |
| 41 | X | X | X | X | X | X | X | X | X | X |
| 42 | X | X | X | X | X | X | X | X | X | X |
| 43 | X | X | X | X | X | X | X | X | X | X |
| 44 | X | X | X | X | X | X | X | X | X | X |
| 45 | X | X | X | X | X |  |  | X | X | X |
| 46 | X | X | X | X | X | X | X | X | X | X |
| 47 | X | X | X | X | X | X | X | X | X | X |
| 48 | X | X | X | X |  | X | X |  |  | X |
| 49 | X | X | X | X | X | X | X | X |  | X |
| 50 | X | X | X | X | X | X | X | X |  | X |
| 51 | X | X | X | X | X | X | X | X | X | X |
| 52 | X | X | X | X |  | X | X | X | X | X |
| 53 | X | X | X |  | X | X | X | X | X | X |
| 54 | X | X | X |  | X | X | X | X | X | X |
| 55 | X | X | X | X | X | X |  | X | X | X |
| 56 | X | X | X | X | X |  |  | X | X | X |
| 57 | X | X | X | X | X | X | X | X | X | X |
| 58 | X | X | X | X | X |  |  | X | X | X |
| 59 | X | X | X | X | X | X |  | X | X | X |
| 60 | X | X | X | X | X | X | X | X | X | X |
| 61 | X | X | X | X | X |  |  | X | X | X |
| 62 | X | X | X | X | X | X | X | X | X | X |
| 63 |  | X | X | X | X | X | X | X | X | X |
| 64 |  | X | X | X | X | X | X | X | X | X |
| 65 |  | X | X |  | X | X | X | X | X | X |
| 66 |  | X | X |  | X |  |  | X | X | X |
| 67 |  | X | X |  |  |  |  | X | X | X |
| 68 | X | X | X | X |  | X |  | X | X | X |
| 69 |  | X | X |  | X |  |  | X | X | X |
| 70 |  | X | X |  | X |  |  | X | X | X |
| 71 | X | X | X | X | X |  |  | X | X | X |
| 72 |  | X | X | X | X |  |  | X | X | X |
| 73 | X | X | X | X | X | X | X | X | X | X |
| 74 | X | X | X | X | X | X | X | X | X | X |
| 75 | X | X | X | X | X | X | X | X | X | X |
| 76 | X | X | X | X | X | X | X | X | X | X |
| 77 | X | X | X | X | X | X | X | X | X | X |
| 78 | X | X | X | X | X | X | X | X | X | X |
| 79 | X | X | X | X | X | X | X | X | X | X |
| 80 | X | X | X | X | X | X |  | X | X | X |
| 81 | X |  |  | X |  | X |  |  |  | X |
| 82 | X |  |  | X | X | X |  |  |  | X |
| 83 | X |  | X |  | X |  |  | X | X | X |
| 84 | X |  |  | X |  | X | X |  |  | X |
| 85 | X |  |  | X |  | X |  | X |  | X |
| 86 | X | X | X | X | X | X |  |  | X | X |
| 87 | X |  |  | X |  | X |  |  |  | X |
| 88 | X | X | X |  |  | X |  | X |  | X |
| 89 |  | X |  | X | X | X |  |  | X | X |
| 90 | X | X | X | X | X | X | X |  | X | X |
| 91 | X | X | X | X | X | X | X |  | X | X |
| 92 | X | X | X | X | X | X | X |  | X | X |
| 93 | X | X | X | X | X | X | X |  | X | X |
| 94 | X | X | X | X | X | X | X |  | X | X |
| 95 | X | X | X | X | X | X | X |  | X | X |
| 96 | X | X | X | X | X | X | X |  | X | X |
| 97 | X | X | X | X | X | X | X | X | X | X |
| 98 |  | X |  | X | X | X | X | X | X | X |
| 99 | X | X | X | X | X | X | X | X | X | X |
| 100 | X | X | X | X | X | X | X | X | X | X |
| 101 | X | X | X | X | X | X | X | X | X | X |
| 102 | X | X | X | X | X | X | X | X | X | X |
| 103 | X | X | X | X | X | X | X | X | X | X |
| 104 | X | X | X | X | X | X | X | X | X | X |
| 105 | X | X | X | X | X | X | X | X | X | X |
| 106 | X | X | X | X | X | X | X | X | X | X |
| 107 | X | X | X | X | X | X | X | X | X | X |
| 108 | X | X | X | X | X | X | X | X | X | X |
| 109 | X | X | X | X | X | X | X | X | X | X |
| 110 | X | X | X |  | X | X | X | X | X | X |
| 111 |  | X |  |  | X | X | X | X | X | X |
| 112 | X |  | X | X | X | X | X | X | X | X |
| 113 | X |  | X | X | X | X | X | X | X | X |
| 114 | X |  | X | X | X | X | X | X | X | X |
| 115 | X |  | X | X | X | X | X | X | X | X |
| 116 | X |  | X | X | X | X | X | X | X | X |
| 117 | X |  | X | X | X | X | X | X | X | X |
| 118 | X |  | X | X | X | X | X | X | X | X |
| 119 | X |  | X | X | X | X | X | X | X | X |
| 120 | X |  | X | X | X | X | X | X | X | X |
| 121 | X |  | X | X | X | X | X | X | X | X |
| 122 | X |  | X | X | X | X | X | X | X | X |
| 123 | X | X | X | X | X | X | X | X | X | X |
| 124 |  | X |  | X | X | X | X | X | X | X |
| 125 |  | X |  | X | X | X | X | X | X | X |
| 126 | X |  | X |  | X | X | X | X | X | X |
| 127 | X | X | X |  | X | X | X | X | X | X |
| 128 | X | X | X | X | X | X | X | X | X | X |
| 129 | X |  |  | X | X | X | X | X | X | X |
| 130 |  |  |  | X | X | X | X | X | X | X |
| 131 | X |  | X | X | X | X | X | X | X | X |
| 132 | X | X | X | X | X | X | X | X | X | X |
| 133 | X | X | X | X | X | X | X | X | X | X |
| 134 | X | X | X | X | X | X | X | X | X | X |
| 135 | X | X | X | X | X | X | X | X | X | X |
| 136 | X | X | X | X | X | X | X | X | X | X |
| 137 | X | X | X | X | X | X | X | X | X | X |
| 138 | X | X | X | X | X | X | X | X | X | X |
| 139 | X | X | X | X | X | X | X | X | X | X |
| 140 | X | X | X | X | X | X | X | X | X | X |
| 141 | X | X | X | X | X | X | X | X | X | X |
| 142 | X | X | X | X | X | X | X | X | X | X |
| 143 | X | X | X | X | X | X | X | X | X | X |
| 144 | X | X | X | X | X | X | X | X | X | X |
| 145 | X | X | X | X | X | X | X | X | X | X |
| 146 | X | X | X | X | X | X | X | X | X | X |
| 147 | X | X | X | X | X | X | X | X | X | X |
| 148 | X | X | X | X | X | X | X | X | X | X |
| 149 | X | X | X | X | X | X | X | X | X | X |
| 150 | X | X | X | X | X | X | X | X | X | X |
| 151 | X | X | X | X | X | X | X | X | X | X |
| 152 | X | X | X | X | X | X | X | X | X | X |
| 153 | X | X | X | X | X | X | X | X | X | X |
| 154 | X | X | X | X | X | X | X | X | X | X |
| 155 | X | X | X | X | X | X | X | X | X | X |
| 156 | X | X | X | X | X | X | X | X | X | X |
| 157 | X | X | X | X | X | X | X | X | X | X |
| 158 | X | X | X | X | X | X | X | X | X | X |
| 159 | X | X | X | X | X | X | X | X | X | X |
| 160 | X | X | X | X | X | X | X | X | X | X |
| 161 | X | X | X | X | X | X | X | X | X | X |
| 162 | X | X | X | X | X | X | X | X | X | X |
| 163 | X | X | X | X | X | X | X | X | X | X |
| 164 | X | X | X | X | X | X | X | X | X | X |
| 165 | X | X | X | X | X | X | X | X | X | X |
| 166 | X | X | X | X | X | X | X | X | X | X |
| 167 | X | X | X | X | X | X | X | X | X | X |
| 168 | X | X | X | X | X | X | X | X | X | X |

TABLE C-continued

| $R^{ii}$ | 21 | 22 | 23 | 24 | 25 | 26 | 27 | 28 | 29 | 30 |
|---|---|---|---|---|---|---|---|---|---|---|
| 169 | X | X | X | X | X | X | X | X | X | X |
| 170 | X | X | X | X | X | X | X | X | X | X |
| 171 | X | X | X | X | X | X | X | X | X | X |
| 172 | X | X | X | X | X | X | X | X | X | X |
| 173 | X | X | X | X | X | X | X | X | X | X |
| 174 | X | X | X | X | X | X | X | X | X | X |
| 175 | X | X | X | X | X | X | X | X | X | X |
| 176 | X | X | X | X | X | X | X | X | X | X |
| 177 | X | X | X | X |   | X | X | X | X | X |
| 178 | X | X | X | X |   |   | X | X | X |   |
| 179 | X | X | X | X | X |   |   | X |   |   |
| 180 |   |   |   |   | X |   |   |   |   |   |
| 181 |   |   |   |   | X |   | X | X |   |   |
| 182 |   | X | X | X | X | X | X | X |   |   |
| 183 |   |   |   |   | X |   | X | X |   |   |
| 184 | X | X | X | X | X | X | X | X |   |   |
| 185 |   |   |   |   |   |   |   |   |   |   |
| 186 |   |   |   |   |   |   |   |   |   |   |
| 187 |   |   |   |   |   |   | X | X |   |   |
| 188 |   |   |   | X | X | X |   |   |   |   |
| 189 | X | X | X | X | X |   |   | X | X |   |
| 190 | X | X | X | X | X | X | X | X |   |   |
| 191 | X | X | X | X |   |   | X |   |   |   |
| 192 |   |   |   |   | X |   |   |   |   |   |
| 193 | X | X | X |   | X |   |   | X |   |   |
| 194 | X | X | X |   |   |   | X |   |   |   |
| 195 |   | X |   |   | X |   |   | X |   |   |
| 196 | X | X | X | X |   |   | X | X |   |   |
| 197 |   |   |   |   | X |   | X | X |   |   |
| 198 | X | X | X | X |   |   |   | X |   |   |
| 199 | X |   | X |   | X |   |   | X |   |   |
| 200 | X | X | X | X |   |   |   |   |   |   |
| 201 | X | X | X | X |   |   | X | X |   |   |
| 202 |   | X | X | X |   |   |   |   |   |   |
| 203 |   |   |   |   |   |   | X | X |   |   |
| 204 |   |   |   | X | X | X |   |   |   |   |
| 205 |   | X |   |   | X |   |   |   |   |   |
| 206 | X | X | X | X | X | X | X | X |   |   |
| 207 |   | X |   |   | X |   | X | X |   |   |
| 208 | X | X | X | X | X | X | X | X |   |   |
| 209 | X |   | X |   | X |   |   |   |   |   |
| 210 | X | X | X | X | X | X | X |   |   |   |
| 211 |   | X |   |   | X | X |   | X |   |   |
| 212 | X | X |   | X | X |   |   | X |   |   |
| 213 |   |   |   |   | X | X |   |   |   |   |
| 214 |   |   |   |   |   |   | X | X |   |   |
| 215 |   |   |   |   |   |   |   |   |   |   |
| 216 | X | X | X | X | X | X | X | X | X | X |
| 217 | X | X | X | X | X | X | X | X | X | X |
| 218 | X | X | X | X | X | X | X | X | X | X |
| 219 | X | X | X | X | X |   | X | X | X | X |
| 220 | X | X | X |   | X |   | X | X | X | X |
| 221 | X | X |   |   | X |   | X | X | X | X |
| 222 |   | X |   |   |   |   |   | X |   |   |
| 223 | X |   |   |   |   |   | X | X |   | X |
| 224 | X | X | X | X | X | X | X | X | X | X |
| 225 |   | X |   |   |   |   | X | X |   | X |
| 226 | X | X |   | X |   | X | X | X | X | X |
| 227 | X | X | X | X | X |   | X | X | X | X |
| 228 | X | X |   | X | X | X | X | X |   | X |
| 229 |   | X |   |   |   |   |   |   |   |   |
| 230 | X | X | X |   | X |   | X | X | X | X |
| 231 | X | X | X | X |   |   | X | X | X | X |
| 232 | X | X | X |   |   |   | X |   |   | X |
| 233 | X |   |   | X |   | X | X | X |   | X |
| 234 |   | X | X | X | X | X |   |   |   | X |
| 235 | X | X |   |   |   | X |   | X | X | X |
| 236 | X | X |   |   |   | X | X | X | X | X |
| 237 | X | X |   |   |   | X | X | X | X | X |
| 238 | X | X |   |   |   | X | X | X | X | X |
| 239 | X | X |   |   |   | X | X | X | X | X |
| 240 | X | X |   |   |   | X | X | X | X | X |
| 241 | X | X |   |   |   | X | X | X | X | X |
| 242 | X | X |   |   |   | X | X | X | X | X |
| 243 | X | X |   |   |   | X | X | X | X | X |
| 244 | X |   |   |   |   | X | X | X | X | X |
| 245 | X | X |   |   | X | X | X | X | X | X |
| 246 | X |   |   |   | X |   | X | X | X | X |
| 247 | X | X |   |   | X | X | X | X | X | X |
| 248 | X | X |   |   | X | X | X | X | X | X |
| 249 | X | X |   |   | X | X | X | X | X | X |
| 250 | X | X |   |   | X | X | X | X | X | X |
| 251 | X | X |   |   | X | X | X | X | X | X |
| 252 | X | X |   |   | X | X | X | X | X | X |
| 253 | X | X |   |   | X | X | X | X | X | X |
| 254 | X | X |   |   | X | X | X | X | X | X |
| 255 | X | X |   |   | X | X | X | X | X | X |
| 256 | X | X |   |   | X | X | X | X | X | X |
| 257 | X | X |   |   | X | X | X | X | X | X |
| 258 | X | X |   |   | X | X | X | X | X | X |
| 259 | X | X |   |   | X | X | X | X | X | X |
| 260 | X | X |   |   |   |   |   | X | X | X |
| 261 |   |   |   |   | X | X | X | X |   | X |
| 262 | X | X |   |   | X | X | X | X |   | X |
| 263 | X | X |   |   | X | X |   | X | X | X |
| 264 | X | X |   |   | X | X | X | X | X | X |
| 265 | X |   |   |   | X | X | X | X | X | X |
| 266 | X |   |   |   | X | X | X | X | X | X |
| 267 | X |   |   |   | X |   | X | X | X | X |
| 268 | X | X |   |   | X | X | X | X | X | X |
| 269 | X | X |   |   | X | X | X | X | X | X |
| 270 | X | X |   |   | X | X | X | X | X | X |
| 271 |   | X |   |   |   |   | X | X | X | X |
| 272 | X |   |   |   | X | X |   | X |   | X |
| 273 | X | X |   |   | X | X | X | X | X | X |
| 274 | X |   |   |   | X | X |   | X | X | X |
| 275 | X | X |   |   | X | X | X | X | X | X |
| 276 | X | X |   |   | X | X | X | X | X | X |
| 277 | X | X |   |   | X | X | X | X | X | X |
| 278 |   | X |   |   | X | X | X | X | X | X |

TABLE D

| $R^{ii}$ | 31 | 32 | 33 | 34 | 35 | 36 | 37 | 38 | 39 | 40 |
|---|---|---|---|---|---|---|---|---|---|---|
| 1 | X | X | X | X | X |   |   |   |   |   |
| 2 | X | X | X | X | X |   |   |   |   |   |
| 3 | X | X | X | X | X |   |   |   |   |   |
| 4 | X | X | X | X | X |   |   |   |   |   |
| 5 | X | X | X | X | X |   |   |   |   |   |
| 6 | X | X | X | X | X |   |   |   |   |   |
| 7 | X | X | X | X | X |   |   |   |   |   |
| 8 | X | X | X | X | X |   |   |   |   |   |
| 9 | X | X | X | X | X |   |   |   |   |   |
| 10 | X | X | X | X | X |   |   |   |   |   |
| 11 | X | X | X | X | X |   |   |   |   |   |
| 12 | X | X | X | X | X |   |   |   |   |   |
| 13 | X | X | X | X | X |   |   |   |   |   |
| 14 | X | X | X | X | X |   |   |   |   |   |
| 15 | X | X | X | X | X |   |   |   |   |   |
| 16 | X | X | X | X | X |   |   |   |   |   |
| 17 | X | X | X | X | X |   |   |   |   |   |
| 18 | X | X | X | X | X |   |   |   |   |   |
| 19 | X | X | X | X | X |   |   |   |   |   |
| 20 | X | X | X | X | X |   |   |   |   |   |
| 21 | X | X | X | X | X |   |   |   |   |   |
| 22 | X | X | X | X | X |   |   |   |   |   |
| 23 | X | X | X | X | X |   |   |   |   |   |
| 24 | X | X | X | X | X |   |   |   |   |   |
| 25 | X | X | X | X | X |   |   |   |   |   |
| 26 | X | X | X | X | X |   |   |   |   |   |
| 27 | X | X | X | X | X |   |   |   |   |   |
| 28 | X | X | X | X | X |   |   |   |   |   |
| 29 | X | X | X | X | X |   |   |   |   |   |
| 30 | X | X | X | X | X |   |   |   |   |   |
| 31 | X | X | X | X | X |   |   |   |   |   |
| 32 | X | X | X | X | X |   |   |   |   |   |

TABLE D-continued

| $R^{ii}$ | 31 | 32 | 33 | 34 | 35 | 36 | 37 | 38 | 39 | 40 |
|---|---|---|---|---|---|---|---|---|---|---|
| 33 | X | X | X | X | X | | | | | |
| 34 | X | X | X | X | X | | | | | |
| 35 | X | X | X | X | X | | | | | |
| 36 | X | X | X | X | X | | | | | |
| 37 | X | X | X | X | X | | | | | |
| 38 | X | X | X | X | X | | | | | |
| 39 | X | X | X | X | X | | | | | |
| 40 | X | X | X | X | X | | | | | |
| 41 | X | X | X | X | X | | | | | |
| 42 | X | X | X | X | X | | | | | |
| 43 | X | X | X | X | X | | | | | |
| 44 | X | X | X | X | X | | | | | |
| 45 | X | X | X | X | X | | | | | |
| 46 | X | X | X | X | X | | | | | |
| 47 | X | X | X | X | X | | | | | |
| 48 | X | | | | | | | | | |
| 49 | | X | X | X | X | | | | | |
| 50 | X | X | X | X | X | | | | | |
| 51 | X | X | X | X | X | | | | | |
| 52 | X | X | X | X | X | | | | | |
| 53 | | | X | | | | | | | |
| 54 | | | X | | | | | | | |
| 55 | X | X | X | X | X | | | | | |
| 56 | X | X | X | X | X | | | | | |
| 57 | X | X | X | X | X | | | | | |
| 58 | X | X | X | X | X | | | | | |
| 59 | X | X | X | X | X | | | | | |
| 60 | X | X | X | X | X | | | | | |
| 61 | X | X | X | X | X | | | | | |
| 62 | X | X | X | X | X | | | | | |
| 63 | X | X | X | X | X | | | | | |
| 64 | | | | | | | | | | |
| 65 | | X | X | | X | | | | | |
| 66 | | | | | | | | | | |
| 67 | | | | | | | | | | |
| 68 | X | X | X | X | X | | | | | |
| 69 | | | | | | | | | | |
| 70 | X | | | X | | | | | | |
| 71 | X | X | X | X | X | | | | | |
| 72 | X | | | | | | | | | |
| 73 | X | X | | X | X | | | | | |
| 74 | X | | X | X | X | | | | | |
| 75 | X | X | X | | | | | | | |
| 76 | X | X | | X | X | | | | | |
| 77 | X | X | X | | | | | | | |
| 78 | X | X | X | X | | | | | | |
| 79 | X | X | X | X | | | | | | |
| 80 | X | X | X | X | X | | | | | |
| 81 | X | X | X | X | X | | | | | |
| 82 | X | X | X | X | X | | | | | |
| 83 | X | X | X | X | X | | | | | |
| 84 | X | X | X | X | X | | | | | |
| 85 | X | X | X | X | X | | | | | |
| 86 | X | X | X | X | X | | | | | |
| 87 | X | X | X | X | X | | | | | |
| 88 | X | X | X | X | X | | | | | |
| 89 | X | X | X | X | X | X | X | X | X | |
| 90 | X | X | X | X | X | X | X | X | X | |
| 91 | X | X | X | X | X | X | X | X | X | |
| 92 | X | X | X | X | X | X | X | X | X | |
| 93 | X | | X | X | X | X | X | X | X | |
| 94 | | X | X | X | X | X | X | X | X | |
| 95 | X | | X | X | X | X | X | X | X | |
| 96 | | X | X | X | X | X | X | X | X | |
| 97 | | X | X | X | X | X | X | X | X | |
| 98 | | X | X | X | X | X | X | X | X | |
| 99 | X | X | X | X | X | X | X | X | X | |
| 100 | X | X | X | X | X | X | X | X | X | |
| 101 | X | X | X | X | X | X | X | X | X | |
| 102 | X | X | X | X | X | X | X | X | X | |
| 103 | X | X | X | X | X | X | X | X | X | |
| 104 | X | X | X | X | X | X | X | X | X | |
| 105 | X | X | X | X | X | X | X | X | X | |
| 106 | X | X | X | X | X | X | X | X | X | |
| 107 | X | X | X | X | X | X | X | X | X | |
| 108 | X | X | X | X | X | X | X | X | X | |
| 109 | X | X | X | X | X | X | X | X | X | |
| 110 | X | X | X | X | X | X | X | X | X | |
| 111 | | X | X | X | X | X | X | X | X | |
| 112 | | X | X | X | X | X | X | X | X | |
| 113 | X | | | X | X | X | X | X | X | |
| 114 | X | | X | | X | X | X | X | X | |
| 115 | X | | X | | X | X | X | X | X | |
| 116 | X | | X | | X | X | X | X | X | |
| 117 | X | | X | | X | X | X | X | X | |
| 118 | X | | X | | X | X | X | X | X | |
| 119 | X | | X | | X | X | X | X | X | |
| 120 | X | | X | | X | X | X | X | X | |
| 121 | X | X | X | X | X | X | X | X | X | |
| 122 | X | X | X | X | X | X | X | X | X | |
| 123 | X | | X | X | X | X | X | X | X | |
| 124 | | X | X | X | X | X | X | X | X | |
| 125 | | X | X | X | X | X | X | X | | |
| 126 | X | X | X | X | X | X | X | X | | |
| 127 | X | X | X | X | X | X | X | X | | |
| 128 | X | X | X | X | X | X | X | X | | |
| 129 | X | X | X | X | X | X | X | X | | |
| 130 | | X | X | X | X | X | X | X | | |
| 131 | X | X | X | X | X | X | X | X | | |
| 132 | X | X | X | X | X | X | X | X | | |
| 133 | X | X | X | X | X | X | X | X | X | |
| 134 | X | X | X | X | X | X | X | X | X | |
| 135 | X | X | X | X | X | X | X | X | X | |
| 136 | X | X | X | X | X | X | X | X | X | |
| 137 | X | X | X | X | X | X | X | X | X | |
| 138 | X | X | X | X | X | X | X | X | X | |
| 139 | X | X | X | X | X | X | X | X | X | |
| 140 | X | X | X | X | X | X | X | X | X | |
| 141 | X | X | X | X | X | X | X | X | X | |
| 142 | X | X | X | X | X | X | X | X | X | |
| 143 | X | X | X | X | X | X | X | X | X | |
| 144 | X | X | X | X | X | X | X | X | X | |
| 145 | X | X | X | X | X | X | X | X | X | |
| 146 | X | X | X | X | X | X | X | X | X | |
| 147 | X | X | X | X | X | X | X | X | X | |
| 148 | X | X | X | X | X | X | X | X | X | |
| 149 | X | X | X | X | X | X | X | X | X | |
| 150 | X | X | X | X | X | X | X | X | X | |
| 151 | X | X | X | X | X | X | X | X | X | |
| 152 | X | X | X | X | X | X | X | X | X | |
| 153 | X | X | X | X | X | X | X | X | X | |
| 154 | X | X | X | X | X | X | X | X | X | |
| 155 | X | X | X | X | X | X | X | X | X | |
| 156 | X | X | X | X | X | X | X | X | X | |
| 157 | X | X | X | X | X | X | X | X | X | |
| 158 | X | X | X | X | X | X | X | X | X | |
| 159 | X | X | X | X | X | X | X | X | X | |
| 160 | X | X | X | X | X | X | X | X | X | |
| 161 | X | X | X | X | X | X | X | X | X | |
| 162 | X | X | X | X | X | X | X | X | X | |
| 163 | X | X | X | X | X | X | X | X | X | |
| 164 | X | X | X | X | X | X | X | X | X | |
| 165 | X | X | X | X | X | X | X | X | X | |
| 166 | X | X | X | X | X | X | X | X | X | |
| 167 | X | X | X | X | X | X | X | X | X | |
| 168 | X | X | X | X | X | X | X | X | X | |
| 169 | X | X | X | X | X | X | X | X | X | |
| 170 | X | X | X | X | X | X | X | X | X | |
| 171 | X | X | X | X | X | X | X | X | X | |
| 172 | X | X | X | X | X | X | X | X | X | |
| 173 | X | X | X | X | X | X | X | X | X | |
| 174 | X | X | X | X | X | X | X | X | X | |
| 175 | X | X | X | X | X | X | X | X | X | |
| 176 | X | X | X | X | X | X | X | X | X | |
| 177 | | | X | X | X | | | X | | |
| 178 | | | X | X | X | | | X | X | |
| 179 | | | X | X | X | X | | X | X | X |
| 180 | | | | | | X | | | | |
| 181 | | X | X | X | X | X | X | | | X |
| 182 | | X | X | X | X | X | X | X | | |
| 183 | | | X | | X | | X | | | |
| 184 | | | | | X | X | | | | X |

TABLE D-continued

| $R^{ii}$ | 31 | 32 | 33 | 34 | 35 | 36 | 37 | 38 | 39 | 40 |
|---|---|---|---|---|---|---|---|---|---|---|
| 185 | | | | | | X | | | | |
| 186 | | | | | | X | | | | |
| 187 | | | X | X | X | X | | | | |
| 188 | | | X | | | X | | X | | |
| 189 | | | X | X | X | X | X | X | X | |
| 190 | | | X | | | X | | | | |
| 191 | | | X | X | X | | X | X | X | |
| 192 | | | | | | X | X | | | |
| 193 | | | X | | | X | | X | | |
| 194 | | | X | | | X | X | X | X | |
| 195 | | | | | | X | | | | X |
| 196 | | | X | X | | X | X | X | X | |
| 197 | | | X | X | X | X | X | X | X | |
| 198 | | X | X | X | | X | X | X | X | |
| 199 | | X | X | X | X | X | X | X | X | |
| 200 | | X | | X | | | X | | | |
| 201 | | X | X | | X | X | X | X | | |
| 202 | | X | | | | X | X | | | |
| 203 | | X | X | | | | X | X | | |
| 204 | | X | X | | | X | X | | | |
| 205 | | X | | | X | X | | X | X | |
| 206 | | X | X | X | X | X | X | X | X | X |
| 207 | | | X | | X | | | | | |
| 208 | | X | X | X | X | X | | X | X | |
| 209 | | | | | | X | X | X | | |
| 210 | | | X | X | X | X | X | | X | |
| 211 | | X | X | | | X | X | | | |
| 212 | | | | X | X | X | | | | |
| 213 | | | | X | X | X | | | | |
| 214 | | | | X | | X | | | | |
| 215 | | | | | | | | | | |
| 216 | X | X | | X | X | X | X | X | X | |
| 217 | X | X | X | | X | X | X | X | X | |
| 218 | X | X | X | X | | X | X | X | X | |
| 219 | X | X | X | X | | X | | X | X | |
| 220 | X | X | X | X | | X | | X | X | |
| 221 | X | X | X | X | | X | X | X | X | |
| 222 | | | | | | X | | X | | X |
| 223 | | X | | | | | | | X | |
| 224 | X | X | | | X | | X | X | X | |
| 225 | | X | | | | | | | | |
| 226 | X | X | X | | X | | | X | X | |
| 227 | X | | | | | X | X | X | X | |
| 228 | X | X | | | X | X | X | X | X | X |
| 229 | | | | | | | | | X | |
| 230 | X | X | X | | | X | X | X | X | |
| 231 | X | X | X | X | X | X | | X | X | |
| 232 | X | X | | | | | X | X | X | |
| 233 | X | X | | | | | X | X | X | |
| 234 | | X | | | X | | X | | | |
| 235 | X | X | X | X | | X | | X | X | |
| 236 | X | X | X | X | | X | | X | X | |
| 237 | X | X | X | | X | X | X | X | X | |
| 238 | X | X | | X | X | X | X | X | X | |
| 239 | X | X | X | X | | X | X | X | X | |
| 240 | X | X | X | X | | X | X | X | X | |
| 241 | X | X | X | X | | X | X | X | X | |
| 242 | X | X | X | X | | X | X | X | X | |
| 243 | X | X | X | X | | X | X | X | X | |
| 244 | X | X | X | X | | X | X | X | X | |
| 245 | X | X | X | X | | X | X | X | X | |
| 246 | X | X | X | X | | X | X | X | X | |
| 247 | X | X | X | X | X | X | X | X | X | |
| 248 | X | X | X | X | X | X | X | X | X | |
| 249 | X | X | X | X | X | X | X | X | X | |
| 250 | X | X | X | X | X | X | X | X | X | |
| 251 | X | X | X | X | X | X | X | X | X | |
| 252 | X | X | X | X | X | X | X | X | X | |
| 253 | X | X | X | X | X | X | X | X | X | |
| 254 | X | X | X | X | X | X | X | X | X | |
| 255 | X | X | X | X | X | X | X | X | X | |
| 256 | X | X | X | X | X | X | X | X | X | |
| 257 | X | X | X | X | X | X | X | X | X | |
| 258 | X | X | X | X | X | X | X | X | X | |
| 259 | X | X | X | X | X | X | X | X | X | |
| 260 | X | X | X | X | X | X | X | X | X | |
| 261 | X | X | X | X | X | X | X | X | X | |
| 262 | X | | X | X | X | X | | | X | |
| 263 | X | X | X | X | X | X | X | X | X | |
| 264 | X | X | X | X | X | X | X | X | X | |
| 265 | X | | X | X | X | X | X | X | X | |
| 266 | X | | X | X | X | X | X | X | X | |
| 267 | X | | X | X | X | X | X | X | X | |
| 268 | X | X | X | X | X | X | X | X | X | |
| 269 | X | X | X | X | | X | X | X | X | |
| 270 | X | X | | X | | X | X | X | X | |
| 271 | X | X | X | X | | X | X | X | | |
| 272 | X | | X | X | X | X | | X | X | |
| 273 | X | X | X | X | X | X | X | X | X | |
| 274 | X | | X | X | X | | X | X | X | |
| 275 | X | X | X | X | X | | X | X | X | |
| 276 | X | X | X | X | X | X | X | X | X | |
| 277 | X | | X | X | X | X | X | X | X | |
| 278 | X | | | X | | | X | X | | |

TABLE E $R^i$ Groups

1. Z–CH₃ (methyl, shown as Z with line)

2. Z–CH₂CH₃ (ethyl)

3. Z–CH₂–C(=O)–NH₂ (acetamide)

4. Z–CH₂CH₂–O–CH₃ (methoxyethyl)

5. Z–CH₂–cyclobutyl

6. Z–CH₂–CH(CH₂CH₃)₂ (2-ethylbutyl)

7. Z–CH₂CH₂–phenyl (phenethyl)

8. Z–CH₂–(2-methylphenyl) (o-methylbenzyl)

TABLE E-continued
R<sup>i</sup> Groups
9
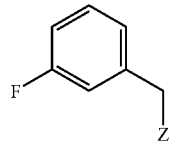
10
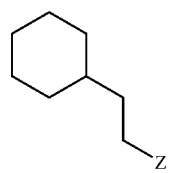
11
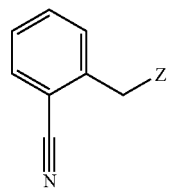
12
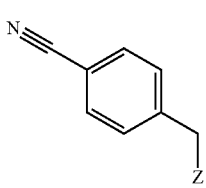
13
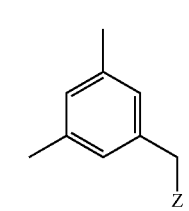
14
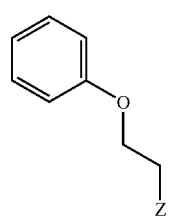
15
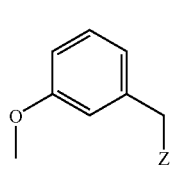
TABLE E-continued
R<sup>i</sup> Groups
16
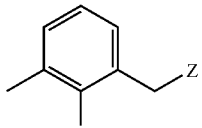
17
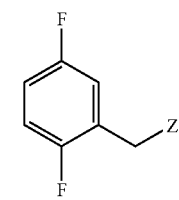
18
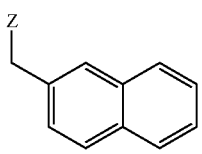
19
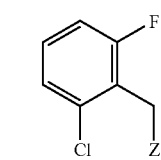
20
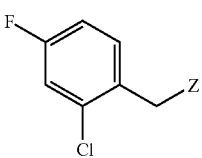
21
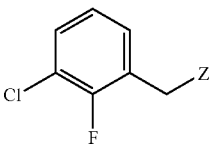
22
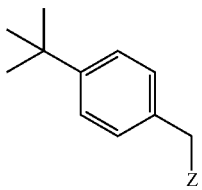
23
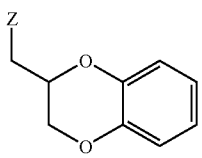

TABLE E-continued
R<sup>i</sup> Groups
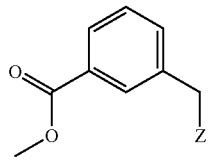
25
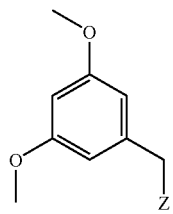
26
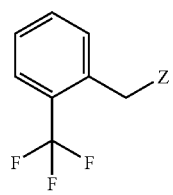
27
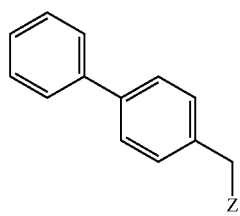
28
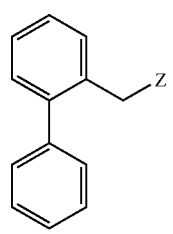
29
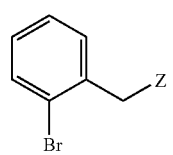
30
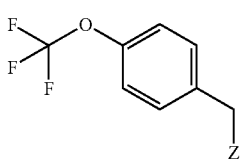
31
TABLE E-continued
R<sup>i</sup> Groups
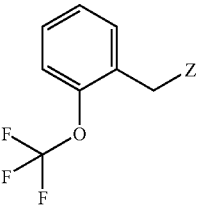
32
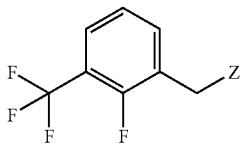
33
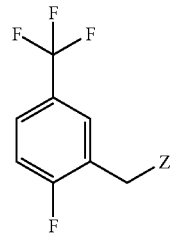
34
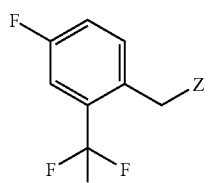
35
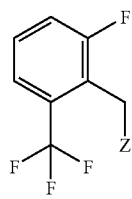
36
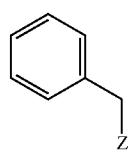
37
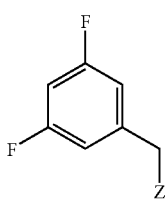
38

TABLE E-continued
R<sup>i</sup> Groups
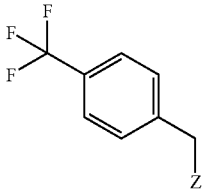
wherein Z designates the point of attachment of group R<sup>i</sup> to the nitrogen atom to which group R<sup>i</sup> is attached.
TABLE F
R<sup>ii</sup> Groups
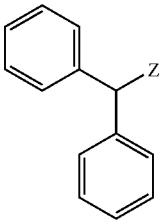
TABLE F-continued
R<sup>ii</sup> Groups
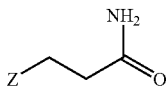

TABLE F-continued
R^ii Groups
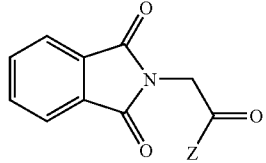
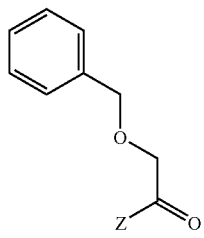
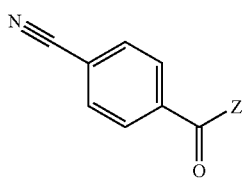
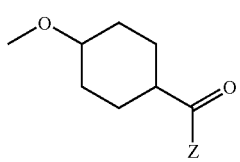
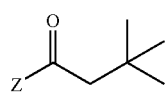
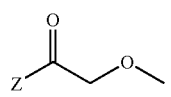
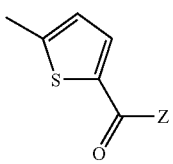
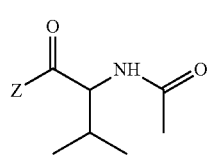
TABLE F-continued
R^ii Groups
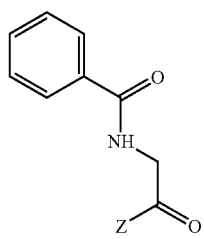
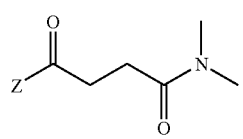
Chiral
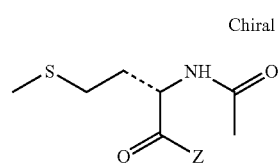
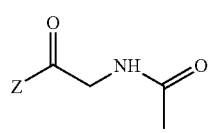
Chiral
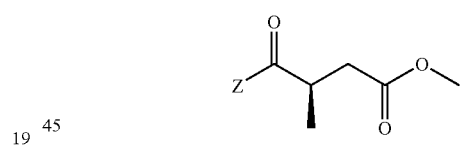
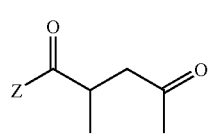
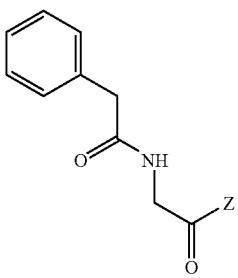

TABLE F-continued
R^ii Groups
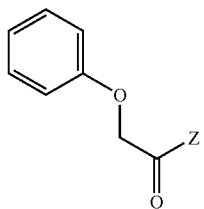
29
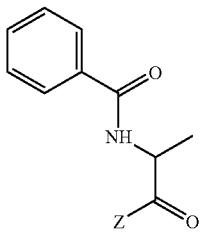
30
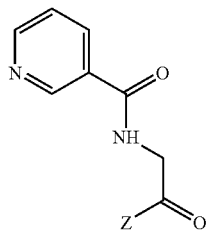
31
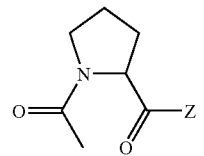
32
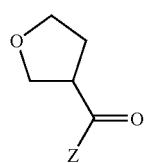
33
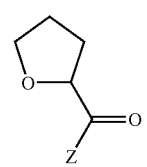
34
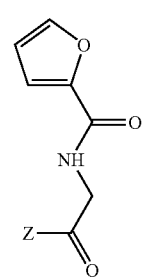
35
TABLE F-continued
R^ii Groups
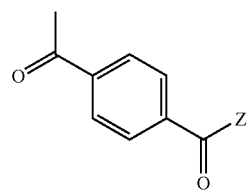
36
Chiral
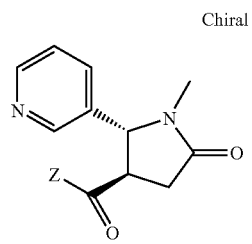
37
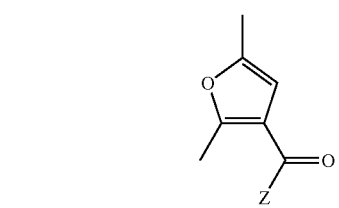
38
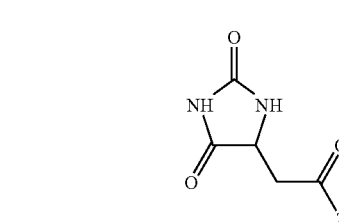
39
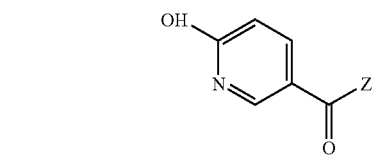
40
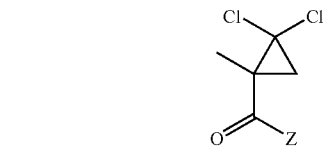
41
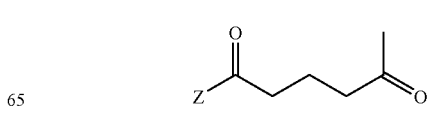
42

TABLE F-continued
R[ii] Groups
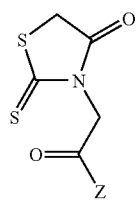
43
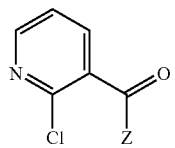
44
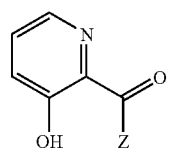
45
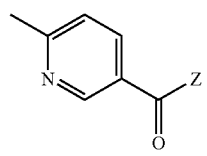
46
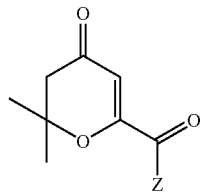
47
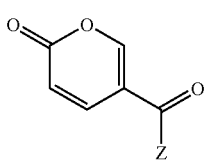
48
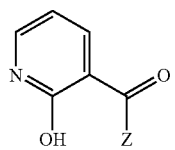
49
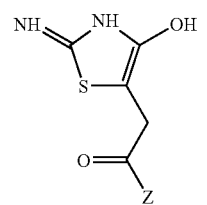
50
TABLE F-continued
R[ii] Groups
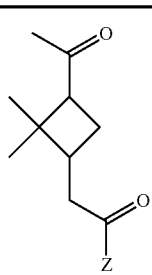
51
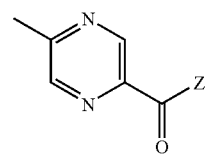
52
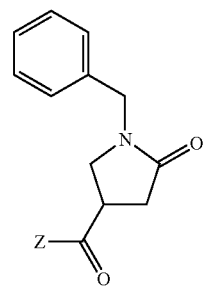
53
Chiral
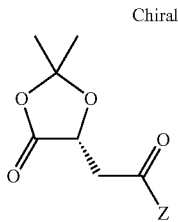
54
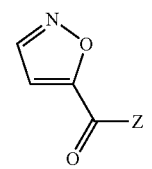
55
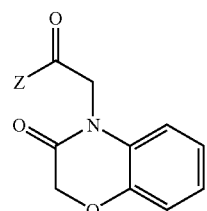
56

TABLE F-continued
R^ii Groups
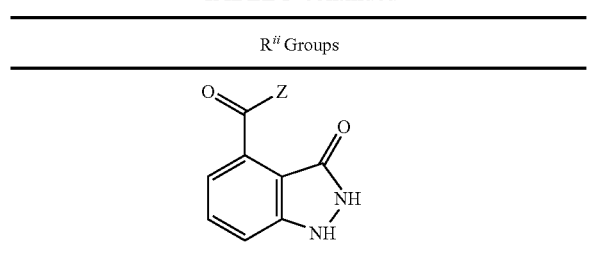
58
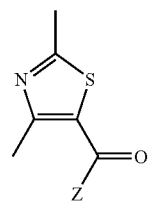
59
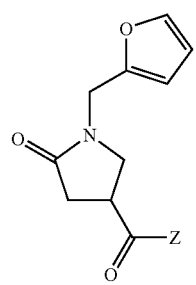
60
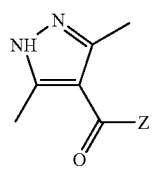
61
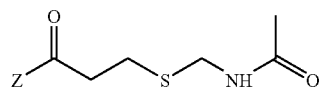
62
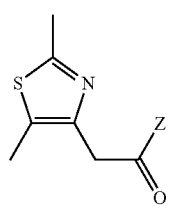
63
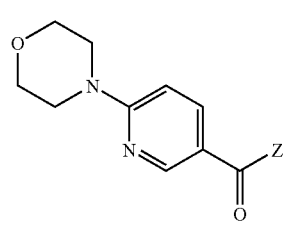
64
TABLE F-continued
R^ii Groups
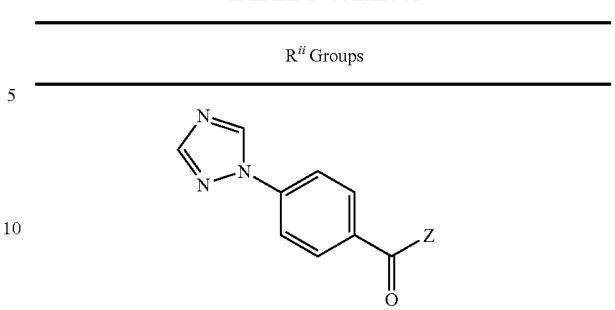
65
Chiral
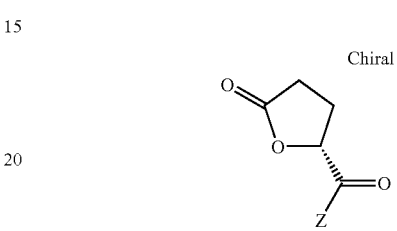
66
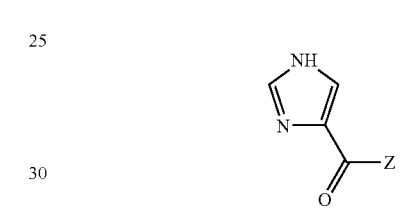
67
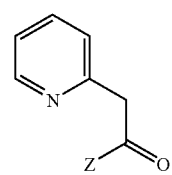
68
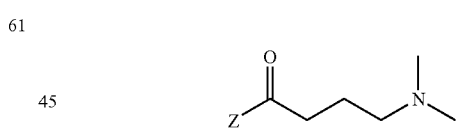
69
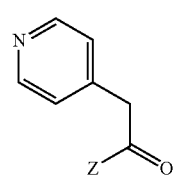
70
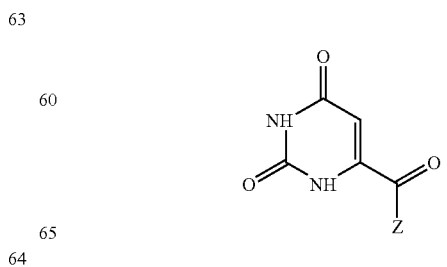
71

TABLE F-continued
$R^{ii}$ Groups
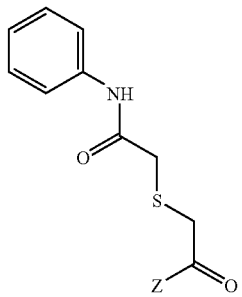
72
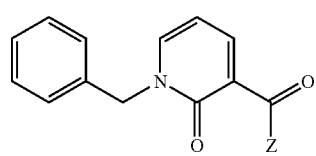
73
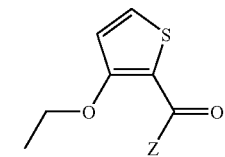
74
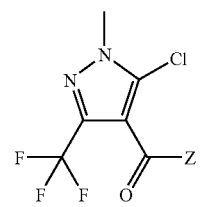
75
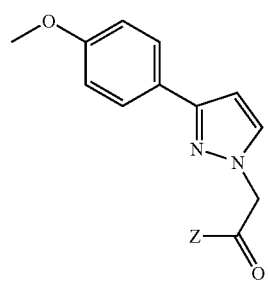
76
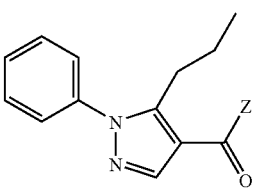
77
TABLE F-continued
$R^{ii}$ Groups
78
Chiral
79
80
81
82
83
84

TABLE F-continued
R(ii) Groups
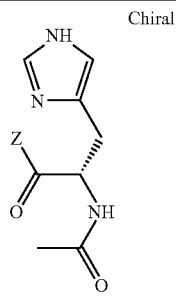
Chiral
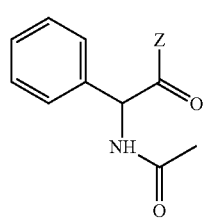
85
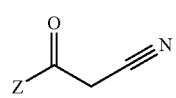
86
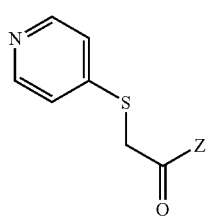
87
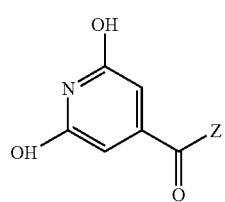
88
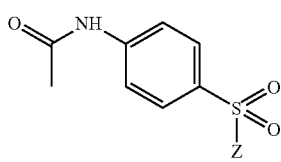
89
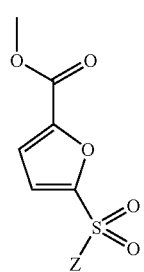
90
TABLE F-continued
R(ii) Groups
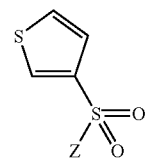
91
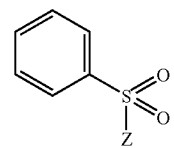
92
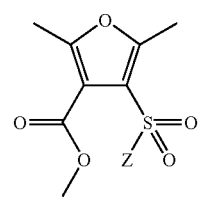
93
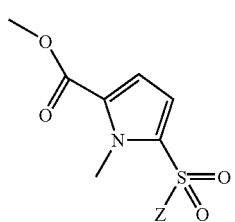
94
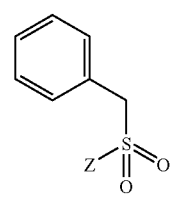
95
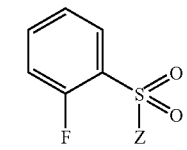
96
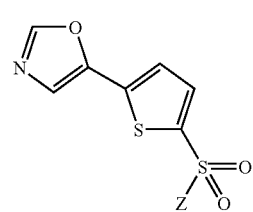
97

TABLE F-continued
R$^{ii}$ Groups
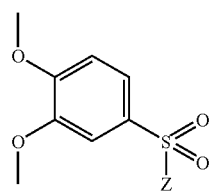
99
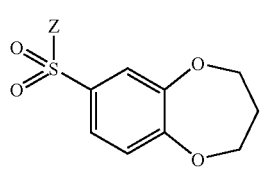
100
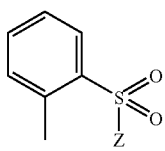
101
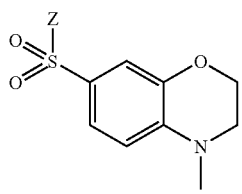
102
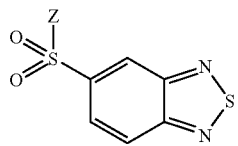
103
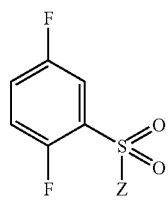
104
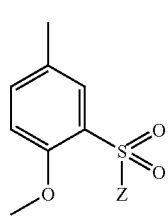
105
TABLE F-continued
R$^{ii}$ Groups
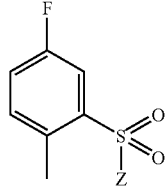
106
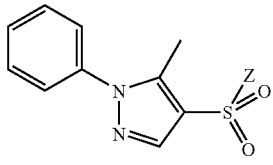
107
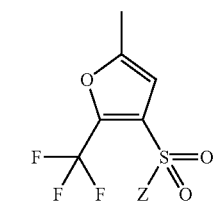
108
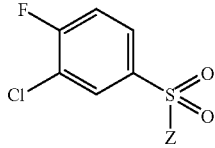
109
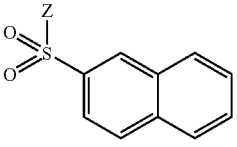
110
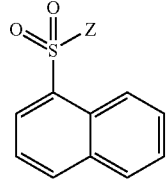
111
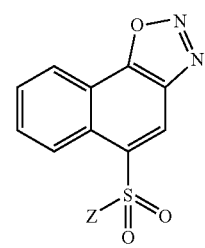
112

TABLE F-continued
R[ii] Groups
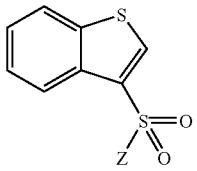
113
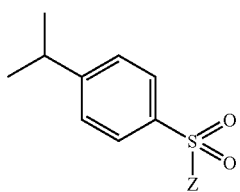
114
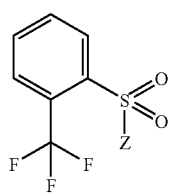
115
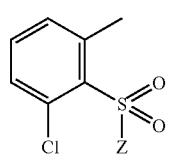
116
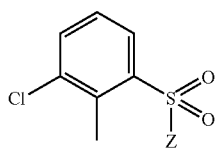
117
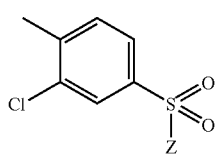
118
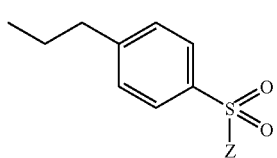
119
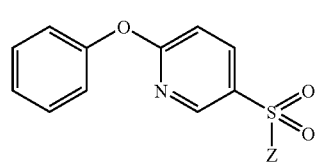
120
TABLE F-continued
R[ii] Groups
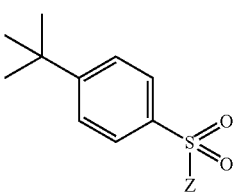
121
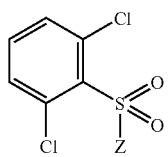
122
123
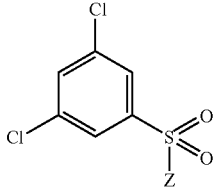
124
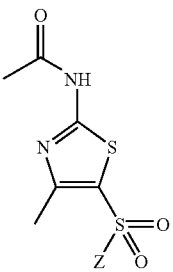
125
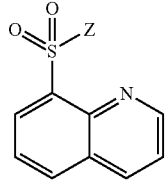
126
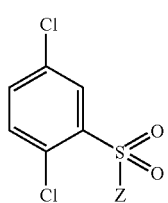
127

TABLE F-continued
R<sup>ii</sup> Groups
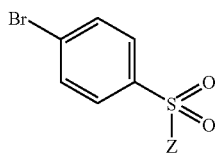
128
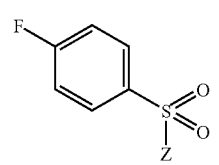
129
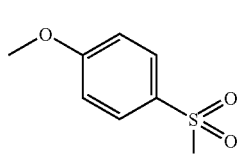
130
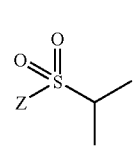
131
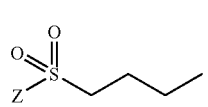
132
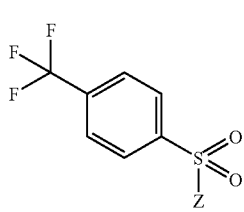
133
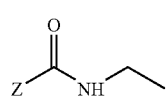
134
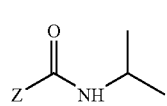
135
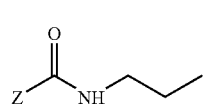
136
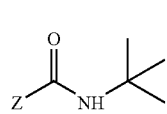
137
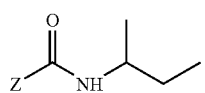
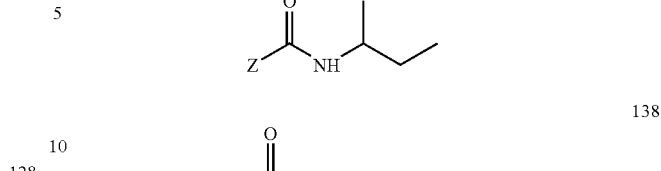
138
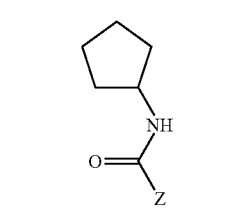
139
Chiral
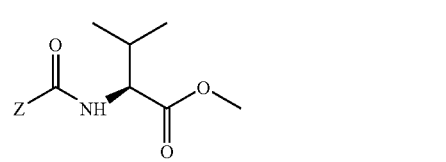
140
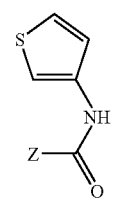
141
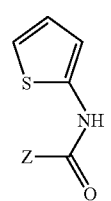
142
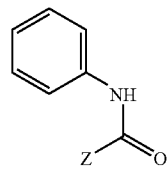
143
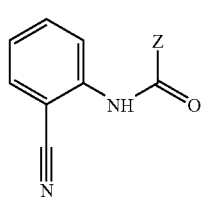
145

TABLE F-continued
R$^{ii}$ Groups
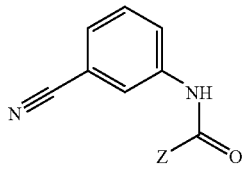<br>145
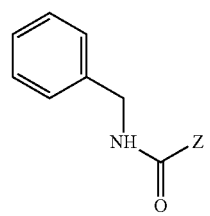<br>146
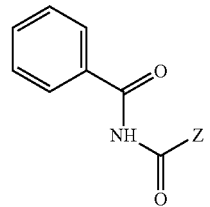<br>147
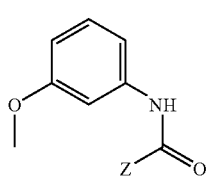<br>148
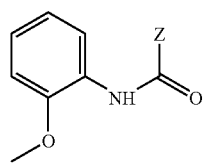<br>149
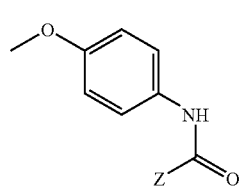<br>150
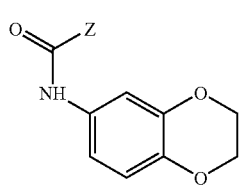<br>151
TABLE F-continued
R$^{ii}$ Groups
Chiral
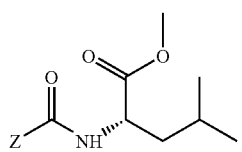<br>152
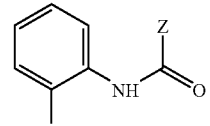<br>153
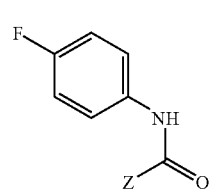<br>154
Chiral
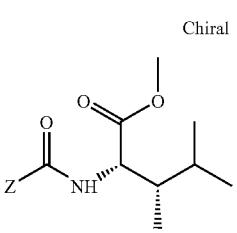<br>155
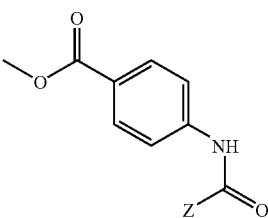<br>156
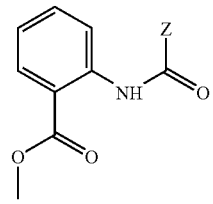<br>157
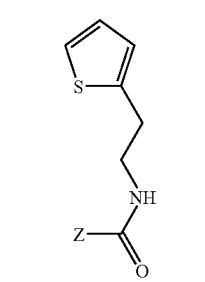<br>158

TABLE F-continued
R<sup>ii</sup> Groups
159
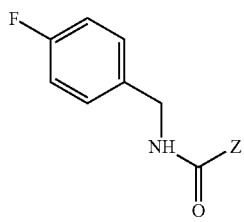
160
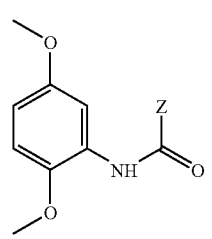
161
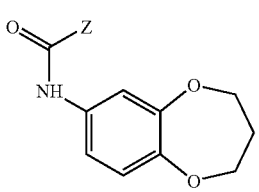
162
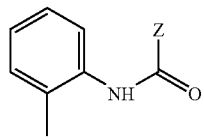
163
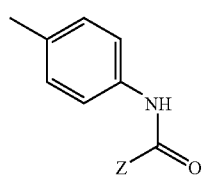
164
Chiral
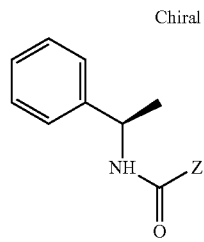
165
Chiral
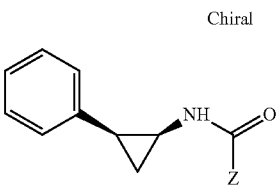
TABLE F-continued
R<sup>ii</sup> Groups
166
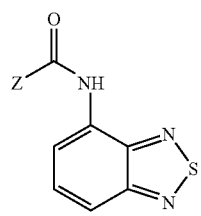
167
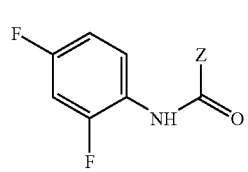
168
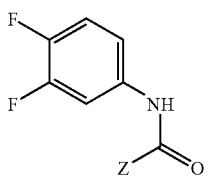
169
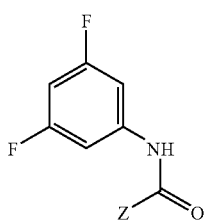
170
171
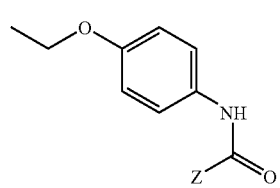
172
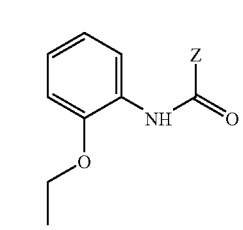
173

TABLE F-continued
R^ii Groups
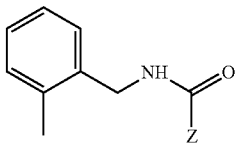
173
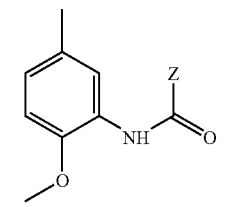
174
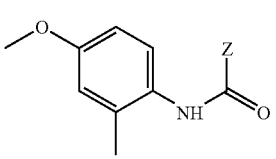
175
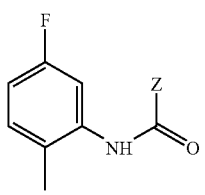
176
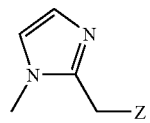
177
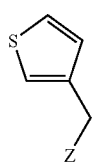
178
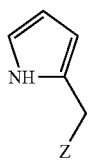
179
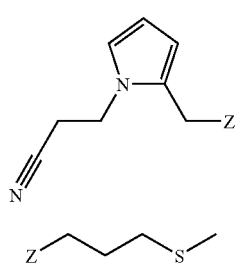
180
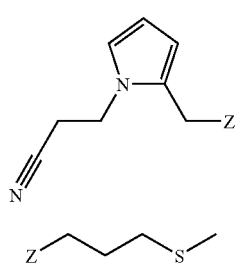
181
TABLE F-continued
R^ii Groups
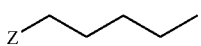
182
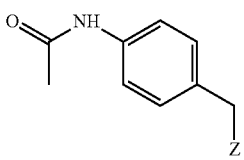
183
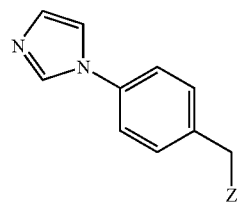
184
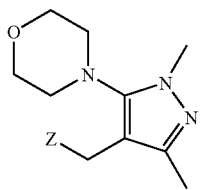
185
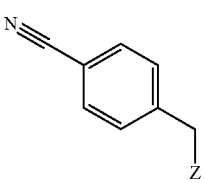
186
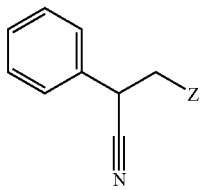
187
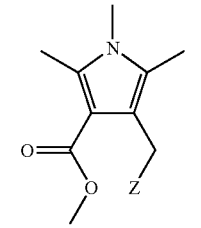
188

TABLE F-continued
R<sup>ii</sup> Groups
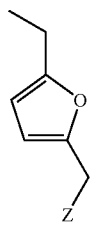
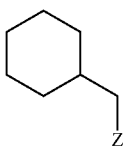
190
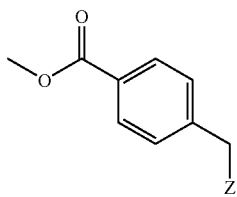
191
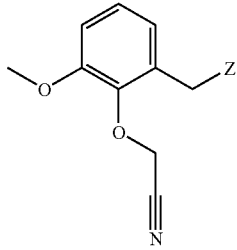
192
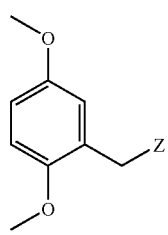
193
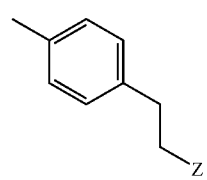
194
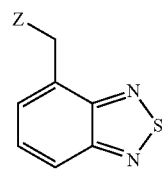
195
196
TABLE F-continued
R<sup>ii</sup> Groups
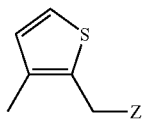
197
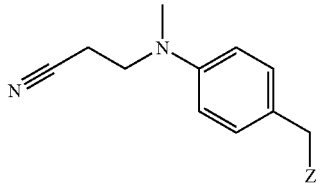
198
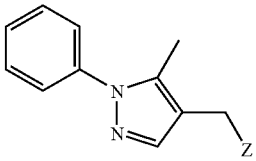
199
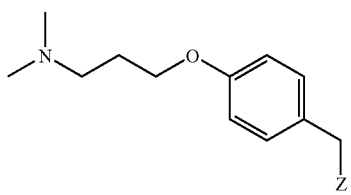
200
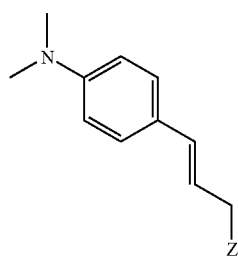
201
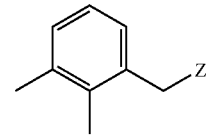
202
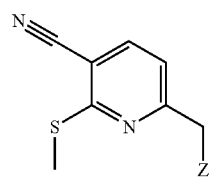
203

TABLE F-continued
R<sup>ii</sup> Groups
204
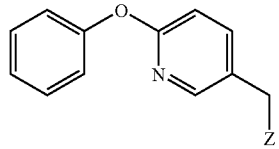
205
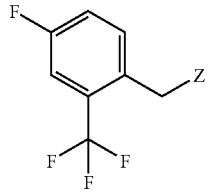
206
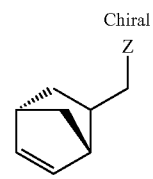
Chiral
207
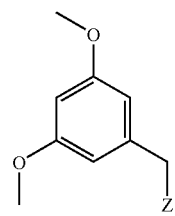
208
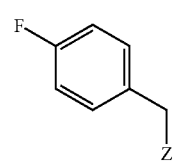
209
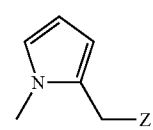
210
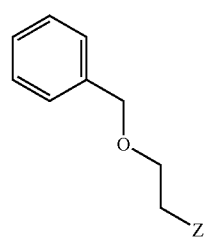
211
TABLE F-continued
R<sup>ii</sup> Groups
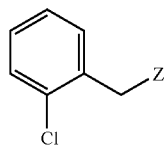
212
213
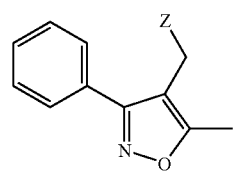
214
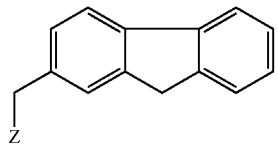
215
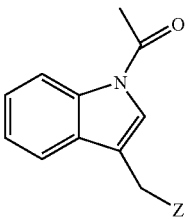
216
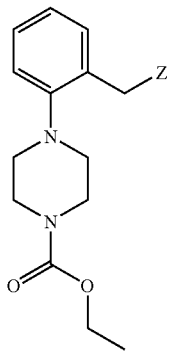
217

TABLE F-continued
R$^{ii}$ Groups
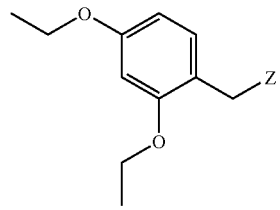
218
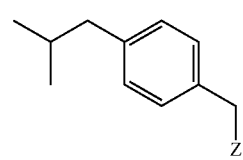
219
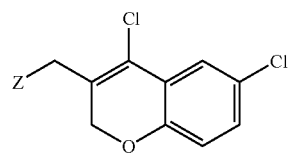
220
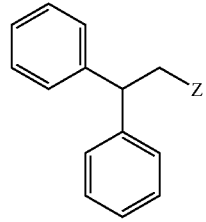
221
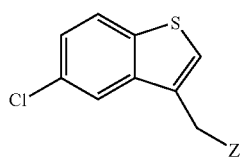
222
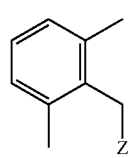
223
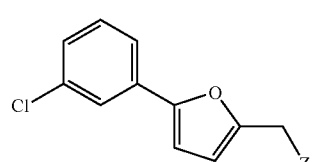
224
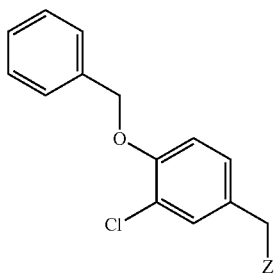
225
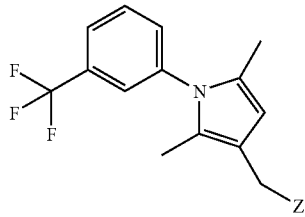
226
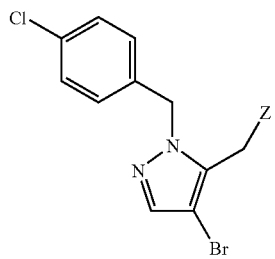
227
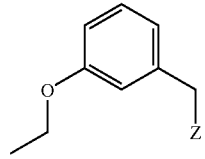
228
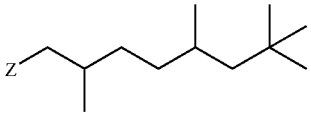
229
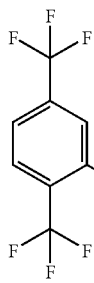
230

TABLE F-continued
R<sup>ii</sup> Groups
| | |
|---|---|
| 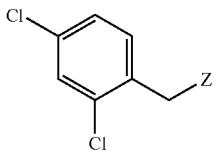 | 231 |
| 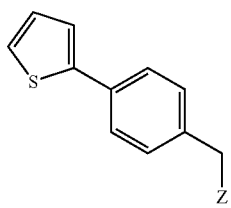 | 232 |
| 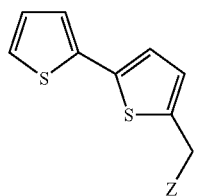 | 233 |
| 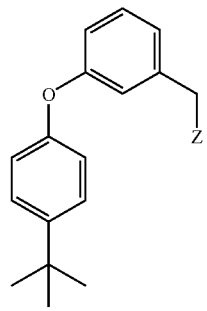 | 234 |
| 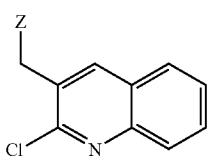 | 235 |
| 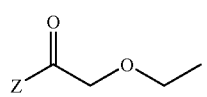 | 236 |
| 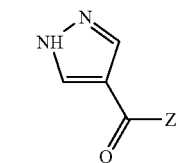 | 237 |
| 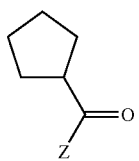 | 238 |
| 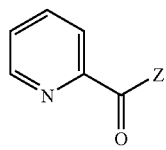 | 239 |
| 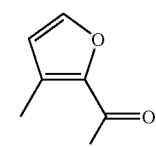 | 240 |
| 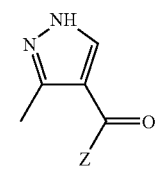 Chiral | 241 |
|  | 242 |
| 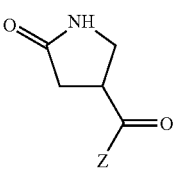 | 243 |
| 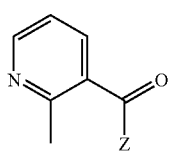 | 244 |
| 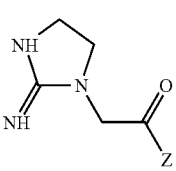 | 245 |

TABLE F-continued
R$^{ii}$ Groups
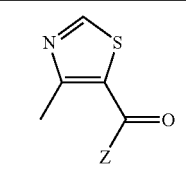
246
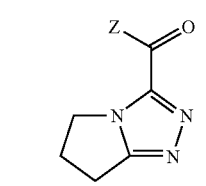
247
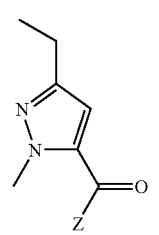
248
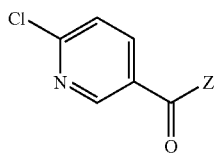
249
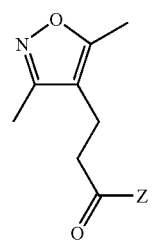
250
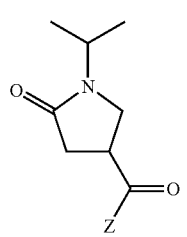
251
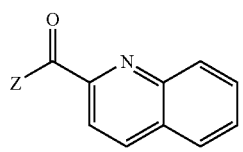
252
TABLE F-continued
R$^{ii}$ Groups
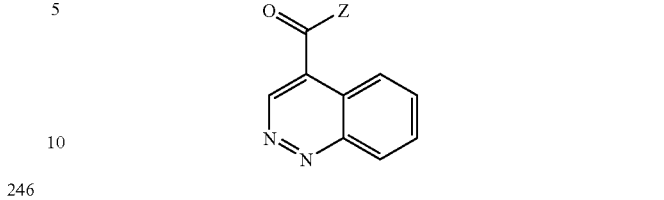
253
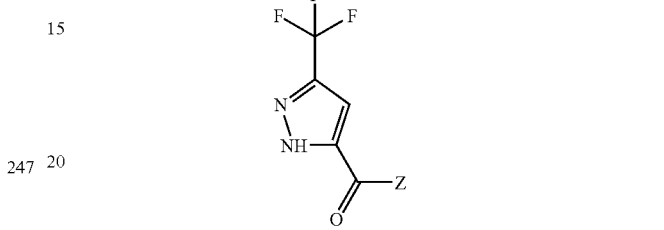
254
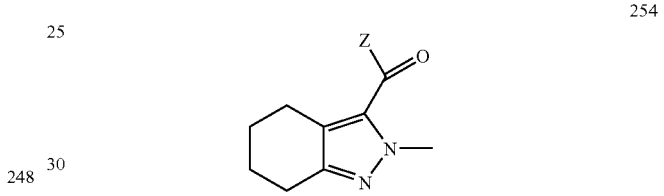
255
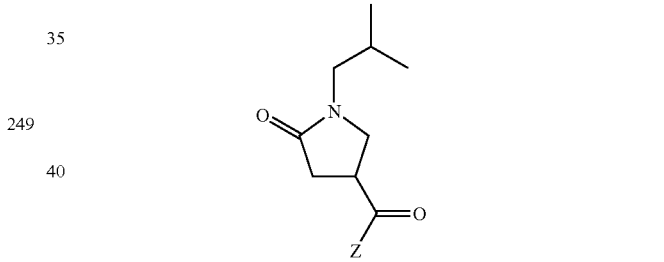
256
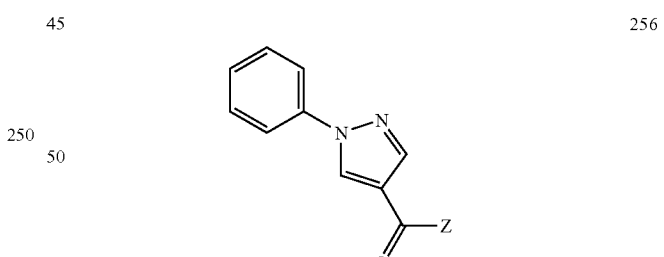
257
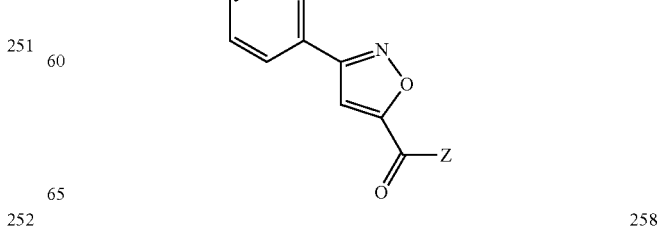
258

TABLE F-continued
R<sup>ii</sup> Groups
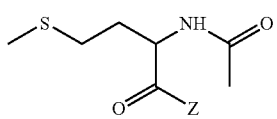 258
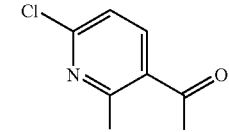 259
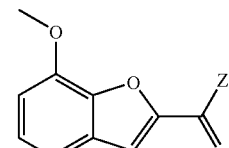 260
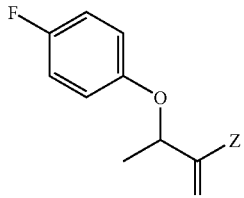 261
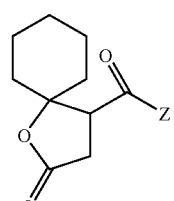 262
Chiral
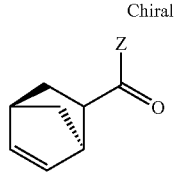 263
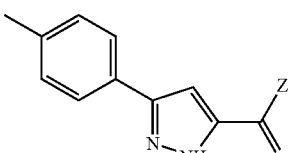 264
TABLE F-continued
R<sup>ii</sup> Groups
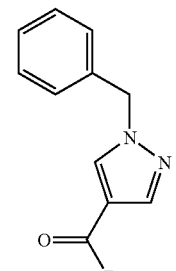 265
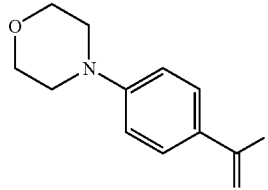 266
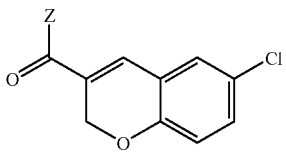 267
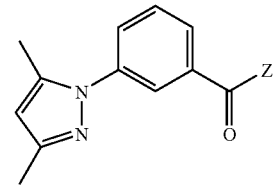 268
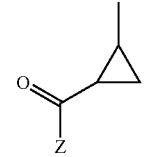 269
Chiral
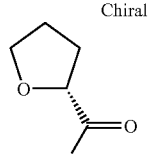 270
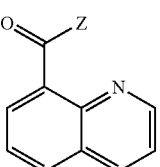 271

TABLE F-continued

R<sup>ii</sup> Groups

273

Chiral

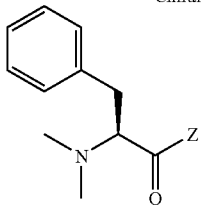

274

Chiral

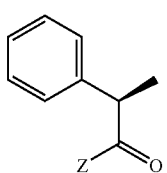

275

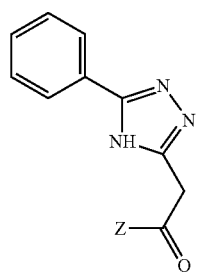

276

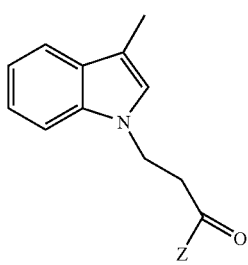

277

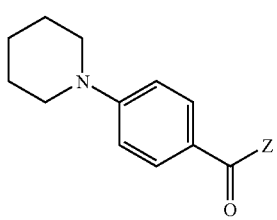

278

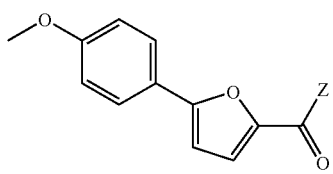

TABLE F-continued

R<sup>ii</sup> Groups

5

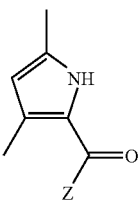

wherein Z designates the point of attachment of group $R^{ii}$ to the nitrogen atom to which group $R^{ii}$ is attached.

The compounds described by formula (I) and defined by an "X" in Tables A-D have the $R^i$ and $R^{ii}$ definitions as indicated by an "X" in the box formed by the intersection of the $R^{ii}$ column and the $R^i$ row, and are not within the scope of the present invention. The numbers in the top row of Tables A-D represent the $R^i$ groups defined in Table E. The numbers in the leftmost column in Tables A-D represent the $R^{ii}$ groups defined in Table F. The compounds described by formula (I) and denoted using an "X" in Tables A-D are specifically excluded from the scope of the present invention. The compounds represented by blank boxes in Tables A-D are not excluded from the scope of the present invention.

Any occurrence of the word "chiral" in Table F refers to the $R^2$ group situated directly below the word "chiral."

The compounds of formula (I) or pharmaceutically acceptable salts, solvates, esters or prodrugs thereof (referred to herein as the "Pyrimidinone Derivatives") can be useful for treating or preventing obesity, diabetes, metabolic syndrome, a cardiovascular disease or a disorder related to the activity of GPR119 (each being a "Condition") in a patient.

Also provided by the invention are methods for treating or preventing a Condition in a patient, comprising administering to the patient an effective amount of one or more Pyrimidinone Derivatives.

The present invention further provides pharmaceutical compositions comprising an effective amount of one or more Pyrimidinone Derivatives or a pharmaceutically acceptable salt, solvate, ester or prodrug thereof, and a pharmaceutically acceptable carrier. The compositions can be useful for treating or preventing a Condition in a patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

In an embodiment, the present invention provides Pyrimidinone Derivatives of Formula (I), pharmaceutical compositions comprising one or more Pyrimidinone Derivatives, and methods of using the Pyrimidinone Derivatives for treating pr preventing a Condition in a patient.

Definitions and Abbreviations

As used above, and throughout this disclosure, the following terms, unless otherwise indicated, shall be understood to have the following meanings:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "obesity" as used herein, refers to a patient being overweight and having a body mass index (BMI) of 25 or greater. In one embodiment, an obese patient has a BMI of about 25 or greater. In another embodiment, an obese patient has a BMI of between about 25 and about 30. In another embodiment, an obese patient has a BMI of between about 35 and about 40. In still another embodiment, an obese patient has a BMI greater than 40.

The term "obesity-related disorder" as used herein refers to: (i) disorders which result from a patient having a BMI of about 25 or greater; and (ii) eating disorders and other disorders associated with excessive food intake. Non-limiting examples of an obesity-related disorder include edema, shortness of breath, sleep apnea, skin disorders and high blood pressure.

The term "metabolic syndrome" as used herein, refers to a set of risk factors that make a patient more susceptible to cardiovascular disease and/or type 2 diabetes. As defined herein, a patient is considered to have metabolic syndrome if the patient has one or more of the following five risk factors:

1) central/abdominal obesity as measured by a waist circumference of greater than 40 inches in a male and greater than 35 inches in a female;
2) a fasting triglyceride level of greater than or equal to 150 mg/dL;
3) an HDL cholesterol level in a male of less than 40 mg/dL or in a female of less than 50 mg/dL;
4) blood pressure greater than or equal to 130/85 mm Hg; and
5) a fasting glucose level of greater than or equal to 110 mg/dL.

The term "effective amount" as used herein, refers to an amount of compound of formula (I) and/or an additional therapeutic agent, or a composition thereof that is effective in producing the desired therapeutic, ameliorative, inhibitory or preventative effect when administered to a patient suffering from a Condition. In the combination therapies of the present invention, an effective amount can refer to each individual agent or to the combination as a whole, wherein the amounts of all agents administered are together effective, but wherein the component agent of the combination may not be present individually in an effective amount.

The term "alkyl," as used herein, refers to an aliphatic hydrocarbon group which may be straight or branched and which contains from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is unsubstituted. In another embodiment, an alkyl group is linear. In another embodiment, an alkyl group is branched.

The term "alkenyl," as used herein, refers to an aliphatic hydrocarbon group containing at least one carbon-carbon double bond and which may be straight or branched and contains from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkyl, aryl, cycloalkyl, cyano, alkoxy and —S(alkyl). In one embodiment, an alkenyl group is unsubstituted.

The term "alkynyl," as used herein, refers to an aliphatic hydrocarbon group containing at least one carbon-carbon triple bond and which may be straight or branched and contains from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of alkyl, aryl and cycloalkyl. In one embodiment, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$— and —CH$_2$CH(CH$_3$)CH$_2$—. An alkylene group may be unsubstituted or substituted by one or more substituents which may be the same or different, each substituent being independently selected from the group consisting of halo, alkyl, aryl, cycloalkyl, cyano, alkoxy and —S(alkyl). In one embodiment, an alkylene group is unsubstituted. In another embodiment, an alkylene group has from 1 to about 6 carbon atoms. In another embodiment, an alkylene group is branched. In still another embodiment, an alkylene group is linear.

The term "alkenylene," as used herein, refers to an alkenyl group, as defined above, wherein one of the alkenyl group's hydrogen atoms has been replaced with a bond. Non-limiting examples of alkenylene groups include —CH═CH—, —CH$_2$CH═CH—, —CH$_2$CH═CHCH$_2$—, —CH═CHCH$_2$CH$_2$—, —CH$_2$CHCH═CH—, —CH(CH$_3$)CH═CH— and —CH═C(CH$_3$)CH$_2$—. In one embodiment, an alkenylene group has from 2 to about 6 carbon atoms. In another embodiment, an alkenylene group is branched. In another embodiment, an alkenylene group is linear.

The term "alkynylene," as used herein, refers to an alkynyl group, as defined above, wherein one of the alkynyl group's hydrogen atoms has been replaced with a bond. Non-limiting examples of alkynylene groups include —C≡C—, —CH$_2$C≡C—, —CH$_2$C≡CCH$_2$—, —C≡CCH$_2$CH$_2$—, —CH$_2$CHC≡C—, —CH(CH$_3$)C≡C— and —C≡CCH$_2$—. In one embodiment, an alkynylene group has from 2 to about 6 carbon atoms. In another embodiment, an alkynylene group is branched. In another embodiment, an alkynylene group is linear.

"Aryl" means an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. Non-limiting examples of aryl groups include phenyl and naphthyl. In one embodiment, an aryl group is unsubstituted. In another embodiment, an aryl group is phenyl.

The term "cycloalkyl," as used herein, refers to a non-aromatic mono- or multicyclic ring system comprising from about 3 to about 10 ring carbon atoms. In one embodiment, a cycloalkyl contains from about 3 to about 7 ring carbon atoms. In another embodiment, a cycloalkyl contains from about 5 to about 7 ring atoms. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted.

The term "cycloalkenyl," as used herein, refers to a non-aromatic mono- or multicyclic ring system comprising from about 3 to about 10 ring carbon atoms and containing at least one endocyclic double bond. In one embodiment, a cycloalkenyl contains from about 5 to about 10 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. In one embodiment, a cycloalkenyl group is unsubstituted. In another embodiment, a cycloalkenyl group is a 5-membered cycloalkenyl.

The term "5-membered cycloalkenyl," as used herein, refers to a cycloalkenyl group, as defined above, which has 5 ring carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which has been fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is unsubstituted. In another embodiment, a heteroaryl group is a 5-membered heteroaryl.

The term "5-membered heteroaryl," as used herein, refers to a heteroaryl group, as defined above, which has 5 ring atoms.

The term "heterocycloalkyl," as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. In one embodiment, a heterocycloalkyl group has from about 5 to about 10 ring atoms. In another embodiment, a heterocycloalkyl group has 5 or 6 ring atoms. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. A ring carbon atom of a heterocycloalkyl group may be functionalized as a carbonyl group. An illustrative example of such a heterocycloalkyl group is pyrrolidonyl:

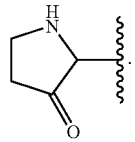

In one embodiment, a heterocycloalkyl group is unsubstituted. In another embodiment, a heterocycloalkyl group is a 5-membered heterocycloalkyl.

The term "5-membered heterocycloalkyl," as used herein, refers to a heterocycloalkyl group, as defined above, which has 5 ring atoms.

The term "heterocycloalkenyl," as used herein, refers to a heterocycloalkyl group, as defined above, wherein the heterocycloalkyl group contains from 3 to 10 ring atoms, and at least one endocyclic carbon-carbon or carbon-nitrogen double bond. In one embodiment, a heterocycloalkenyl group has from 5 to 10 ring atoms. In another embodiment, a heterocycloalkenyl group is monocyclic and has 5 or 6 ring atoms. A heterocycloalkenyl group can be optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like. A ring carbon atom of a heterocycloalkenyl group may be functionalized as a carbonyl group. An illustrative example of such a heterocycloalkenyl group is:

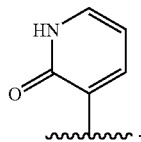

In one embodiment, a heterocycloalkenyl group is unsubstituted. In another embodiment, a heterocycloalkenyl group is a 5-membered heterocycloalkenyl.

The term "5-membered heterocycloalkenyl," as used herein, refers to a heterocycloalkenyl group, as defined above, which has 5 ring atoms.

It should also be noted that tautomeric forms such as, for example, the moieties:

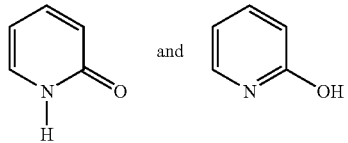

are considered equivalent in certain embodiments of this invention.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -alkylene-heteroaryl, -alkenylene-heteroaryl, -alkynylene-heteroaryl, hydroxy, hydroxyalkyl, haloalkyl, —O-alkyl, -alkylene-O-alkyl, —O-aryl, aralkoxy, acyl, aroyl, halo, nitro, cyano, carboxy, —C(O)O-alkyl, —C(O)O-aryl, —C(O)O-alkelene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)— and Y$_1$Y$_2$NSO$_2$—, wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

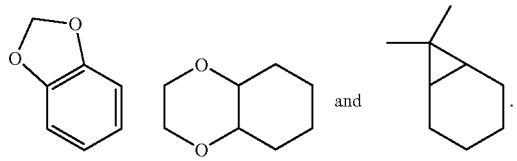

"Halo" means —F, —Cl, —Br or —I. In one embodiment, halo refers to —Cl or —Br.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "purified", "in purified form" or "in isolated and purified form" for a compound refers to the physical state of the compound after being isolated from a synthetic process (e.g. from a reaction mixture), or natural source or combination thereof. Thus, the term "purified", "in purified form" or "in isolated and purified form" for a compound refers to the physical state of the compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, R$^2$, etc.) occurs more than one time in any constituent or in Formula (I), its definition on each occurrence is independent of its definition at every other occurrence, unless otherwise noted.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a Pyrimidinone Derivative or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a Pyrimidinone Derivative or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a Pyrimidinone Derivative contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$) alkyl)$_2$ or glycosyl (the radical resulting from the removal of a hydroxyl group of the hemiacetal form of a carbohydrate), and the like.

If a Pyrimidinone Derivative incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$) alkyl, carboxy ($C_1$-$C_6$)alkyl, amino($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. "Hydrate" is a solvate wherein the solvent molecule is $H_2O$.

One or more compounds of the invention may optionally be converted to a solvate. Preparation of Solvates is Generally Known. Thus, for Example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Techours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The Pyrimidinone Derivatives can form salts which are also within the scope of this invention. Reference to a Pyrimidinone Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Pyrimidinone Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a Pyrimidinone Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (for example, methyl, ethyl, n-propyl, isopropyl, t-butyl, sec-butyl or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Also, some of the Pyrimidinone Derivatives may be atropisomers (e.g., substituted biaryls) and are considered as part of this invention. Enantiomers can also be separated by use of chiral HPLC column.

It is also possible that the Pyrimidinone Derivatives may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a Pyrimidinone Derivative incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled Pyrimidinone Derivatives (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled Pyrimidinone Derivatives can generally be prepared using synthetic chemical procedures analogous to those disclosed herein for making the Compounds of Formula (I), by substituting an appropriate isotopically labelled starting material or reagent for a non-isotopically labelled starting material or reagent.

Polymorphic forms of the Pyrimidinone Derivatives, and of the salts, solvates, hydrates, esters and prodrugs of the Pyrimidinone Derivatives, are intended to be included in the present invention.

The following abbreviations are used below and have the following meanings: Ac is acetyl, AcOH is acetic acid, Boc or BOC is —C(O)O-(t-butyl), n-BuLi is n-butyllithium, t-butyl is tertiary butyl, DAST is diethylaminosulfur trifluoride, dba is dibenzylidene acetone, DCE is dichloroethane, DCM is dichloromethane, DIAD is diisopropylazodicarboxylate, DIEA or META is diisopropylethylamine, DMEM is Dulbecco's modified eagle medium, DMF is N,N-dimethylformamide, DMSO is dimethylsulfoxide, dppf is 1,1'-bis(diphenylphosphino)ferrocene, EtOAc is ethyl acetate, EtOH is ethanol, $Et_3N$ is triethylamine, $EtNH_2$ is ethylamine, HOBt is 1-hydroxy-benzotriazole, i-Pr is isopropyl, LCMS is liquid chromatography mass spectrometry, LDA is lithiumdiisopropylamide, mCPBA is meta-chloroperoxybenzoic acid, MeOH is methanol, MP-TsOH is macroporous polystyrene sulfonic acid, NaOEt is sodium ethoxide, $Na(OAc)_3BH$ is sodium triacetoxyborohydride, NaOtBu is sodium t-butoxide, NMM is N-methylmorpholine, NMR is nuclear magnetic resonance, PCC is pyridinium chlorochromate, Pd/C is palladium on carbon, Ph is phenyl, PhMe is toluene, PS-EDC is polystyrene functionalized with EDC-1-(dimethylaminopropyl)-3-ethylcarbodiimide-available from Polymer Laboratories, PS-DIEA is polystyrene functionalized with disopropylethylamine, PS-NCO is polystyrene-based isocyanate resin, PS-trisamine is polystyrene-based trisamine resin, TBAF is tetra-n-butyl-ammonium fluoride, THF is tetrahydrofuran, and TLC is thin-layer chromatography.

The Pyrimidinone Derivatives of Formula (I)

The present invention provides Pyrimidinone Derivatives of Formula (I):

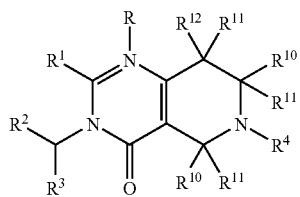

and pharmaceutically acceptable salts, solvates, esters and prodrugs thereof, wherein R, $R^1$, $R^2$, $R^3$, $R^4$, $R^{10}$, $R^{11}$ and $R^{12}$ are defined above for the compounds of formula (I).

In one embodiment, R is absent.
In another embodiment, R is oxygen.
In one embodiment, $R^1$ is —H.
In another embodiment, $R^1$ is alkyl.
In another embodiment, $R^1$ is —$N(R^9)_2$.
In still another embodiment, $R^1$ is —$OR^9$.
In yet another embodiment, $R^1$ is —$SR^9$.
In one embodiment, $R^1$ is —$NH_2$.
In another embodiment, $R^1$ is —NH-alkyl.
In another embodiment, $R^1$ is —$N(alkyl)_2$.
In still another embodiment, $R^1$ is —O-alkyl.
In a further embodiment, $R^1$ is —S-alkyl.
In another embodiment, $R^1$ is aryl.
In still another embodiment, $R^1$ is cycloalkyl.
In yet another embodiment, $R^1$ is cycloalkenyl.
In a further embodiment, $R^1$ is heterocycloalkyl.
In another embodiment, $R^1$ is heterocycloalkenyl.
In another embodiment, $R^1$ is heteroaryl.
In another embodiment, $R^1$ is -alkylene-aryl.
In still another embodiment, $R^1$ is -alkylene-cycloalkyl.
In yet another embodiment, $R^1$ is -alkylene-cycloalkenyl.
In a further embodiment, $R^1$ is -alkylene-heterocycloalkyl.
In another embodiment, $R^1$ is -alkylene-heterocycloalkenyl.
In another embodiment, $R^1$ is -alkylene-heteroaryl.
In still another embodiment, $R^1$ is haloalkyl.
In another embodiment, $R^1$ is fluoromethyl.
In another embodiment, $R^1$ is difluoromethyl.
In another embodiment, $R^1$ is trifluoromethyl.
In a further embodiment, $R^1$ is cyclopropyl.
In another embodiment, $R^1$ is alkenyl.
In another embodiment, $R^1$ is alkynyl.
In yet another embodiment, $R^1$ is propynyl.
In one embodiment, $R^1$ is methyl.
In another embodiment, $R^1$ is ethyl.
In another embodiment, $R^1$ is n-propyl.
In still another embodiment, $R^1$ isopropyl.
In a further embodiment, $R^1$ is benzyl.
In another embodiment, $R^1$ is phenyl.
In one embodiment, $R^2$ is aryl.
In another embodiment, $R^2$ is other than H.
In another embodiment, $R^2$ is heteroaryl.
In still another embodiment, $R^2$ is alkyl.
In another embodiment, $R^2$ is benzyl.
In yet another embodiment, $R^2$ is cycloalkyl.
In another embodiment, $R^2$ is cyclopropyl, cyclobutyl, cyclopentyl or cyclohexyl.
In another embodiment, $R^2$ is heterocycloalkyl.

In a further embodiment, $R^2$ is —C(O)-aryl.
In another embodiment, $R^2$ is -alkylene-aryl.
In another embodiment, $R^2$ is -alkylene-O-aryl.
In another embodiment, $R^2$ is -alkylene-O-alkyl.
In still another embodiment, $R^2$ is methyl.
In another embodiment, $R^2$ is phenyl.
In yet another embodiment, $R^2$ is 4-trifluoromethyl-phenyl.
In one embodiment, $R^2$ is 4-fluorophenyl.
In another embodiment, $R^2$ is 2-(4-fluorophenyl)ethyl.
In another embodiment, $R^2$ is pyridyl.
In still another embodiment, $R^2$ is 2-pyridyl.
In another embodiment, $R^2$ is —$C(O)NH_2$.
In another embodiment, $R^2$ is —$C(O)OR^5$.
In another embodiment, $R^2$ is —$C(O)N(R^9)_2$.
In still another embodiment, $R^2$ is trifluoromethyl.
In yet another embodiment, $R^2$ is cyclopropyl.
In still another embodiment, $R^2$ is cyclobutyl.
In another embodiment, $R^2$ is cyclopentyl.
In one embodiment, $R^2$ is cyclohexyl.
In another embodiment, $R^2$ is -alkylene-$N(R^9)_2$.
In another embodiment, $R^2$ is —$CH_2$—O-phenyl.
In one embodiment, $R^3$ is aryl.
In another embodiment, $R^3$ is heteroaryl.
In still another embodiment, $R^3$ is alkyl.
In another embodiment, $R^3$ is benzyl.
In yet another embodiment, $R^3$ is cycloalkyl.
In another embodiment, $R^3$ is cyclopropyl, cyclobutyl, cyclopentyl or cyclohexyl.
In another embodiment, $R^3$ is heterocycloalkyl.
In a further embodiment, $R^3$ is —C(O)-aryl.
In another embodiment, $R^3$ is -alkylene-aryl.
In another embodiment, $R^3$ is -alkylene-O-aryl.
In another embodiment, $R^3$ is -alkylene-O-alkyl.
In still another embodiment, $R^3$ is methyl.
In another embodiment, $R^3$ is phenyl.
In yet another embodiment, $R^3$ is 4-trifluoromethyl-phenyl.
In one embodiment, $R^3$ is 4-fluorophenyl.
In another embodiment, $R^3$ is 2-(4-fluorophenyl)ethyl.
In another embodiment, $R^3$ is pyridyl.
In still another embodiment, $R^3$ is 2-pyridyl.
In another embodiment, $R^3$ is —$C(O)NH_2$.
In another embodiment, $R^3$ is —$C(O)OR^5$.
In another embodiment, $R^3$ is —$C(O)N(R^9)_2$.
In still another embodiment, $R^3$ is trifluoromethyl.
In yet another embodiment, $R^3$ is cyclopropyl.
In still another embodiment, $R^3$ is cyclobutyl.
In another embodiment, $R^3$ is cyclopentyl.
In one embodiment, $R^3$ is cyclohexyl.
In another embodiment, $R^3$ is -alkylene-$N(R^9)_2$
In another embodiment, $R^3$ is —$CH_2$—O-phenyl.
In one embodiment, $R^4$ is H.
In another embodiment, $R^4$ is alkyl.
In another embodiment, $R^4$ is —$S(O)_qR^7$.
In another embodiment, $R^4$ is —$C(O)R^5$.
In still another embodiment, $R^4$ is -alkylene-O-alkyl.
In yet another embodiment, $R^4$ is -alkylene-O-aryl.
In another embodiment, $R^4$ is -alkylene-S-alkyl.
In another embodiment, $R^4$ is -alkylene-S-aryl.
In another embodiment, $R^4$ is -alkylene-NH-alkyl.
In yet another embodiment, $R^4$ is -alkylene-NH-aryl.
In a further embodiment, $R^4$ is $C(O)OR^5$.
In another embodiment, $R^4$ is —$C(O)N(R^6)_2$.
In another embodiment, $R^4$ is -alkylene-aryl.
In another embodiment, $R^4$ is -alkylene-cycloalkyl.
In still another embodiment, $R^4$ is -alkylene-cycloalkenyl.

In yet another embodiment, $R^4$ is -alkylene-heterocycloalkyl.

In a further embodiment, $R^4$ is -alkylene-heterocycloalkenyl.

In another embodiment, $R^4$ is -alkylene-heteroaryl.
In another embodiment, $R^4$ is aryl.
In another embodiment, $R^4$ is cycloalkyl.
In still another embodiment, $R^4$ is cycloalkenyl.
In yet another embodiment, $R^4$ is heterocycloalkyl.
In a further embodiment, $R^4$ is heterocycloalkenyl.
In another embodiment, $R^4$ is heteroaryl.
In another embodiment, $R^4$ is —CH(alkyl)-aryl.
In another embodiment, $R^4$ is —CH(alkyl)-cycloalkyl.
In still another embodiment, $R^4$ is —CH(alkyl)-cycloalkenyl.
In yet another embodiment, $R^4$ is —CH(alkyl)-heterocycloalkyl.
In a further embodiment, $R^4$ is —CH(alkyl)-heterocycloalkenyl.
In another embodiment, $R^4$ is —CH(alkyl)-heteroaryl.
In another embodiment, $R^4$ is —CH(CH$_3$)-aryl.
In another embodiment, $R^4$ is —CH(CH$_3$)-cycloalkyl.
In still another embodiment, $R^4$ is —CH(CH$_3$)-cycloalkenyl.
In yet another embodiment, $R^4$ is —CH(CH$_3$)-heterocycloalkyl.
In a further embodiment, $R^4$ is —CH(CH$_3$)-heterocycloalkenyl.
In another embodiment, $R^4$ is —CH(CH$_3$)-heteroaryl.
In another embodiment, $R^4$ is -alkylene-phenyl.
In another embodiment, $R^4$ is —CH(CH$_3$)-phenyl.
In still another embodiment, $R^4$ is —CH$_2$-aryl.
In another embodiment, $R^4$ is —CH$_2$-heteroaryl.
In still another embodiment, $R^4$ is phenyl.
In another embodiment, $R^4$ is benzyl.
In one embodiment, each occurrence of $R^{10}$ is H.
In another embodiment, each occurrence of $R^{11}$ is H.
In another embodiment, each occurrence of $R^{10}$ and $R^{11}$ is H.
In another embodiment, one occurrence of $R^{10}$ or $R^{11}$ is other than hydrogen.
In yet another embodiment, at least one occurrence of $R^{10}$ or $R^{11}$ is alkyl.
In still another embodiment, at least one occurrence of $R^{10}$ or $R^{11}$ is methyl.
In another embodiment, $R^4$ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^4$ is —CH(CH$_3$)-phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In still another embodiment, $R^4$ is:

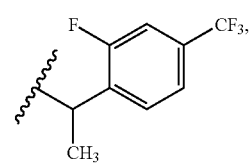
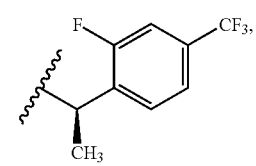
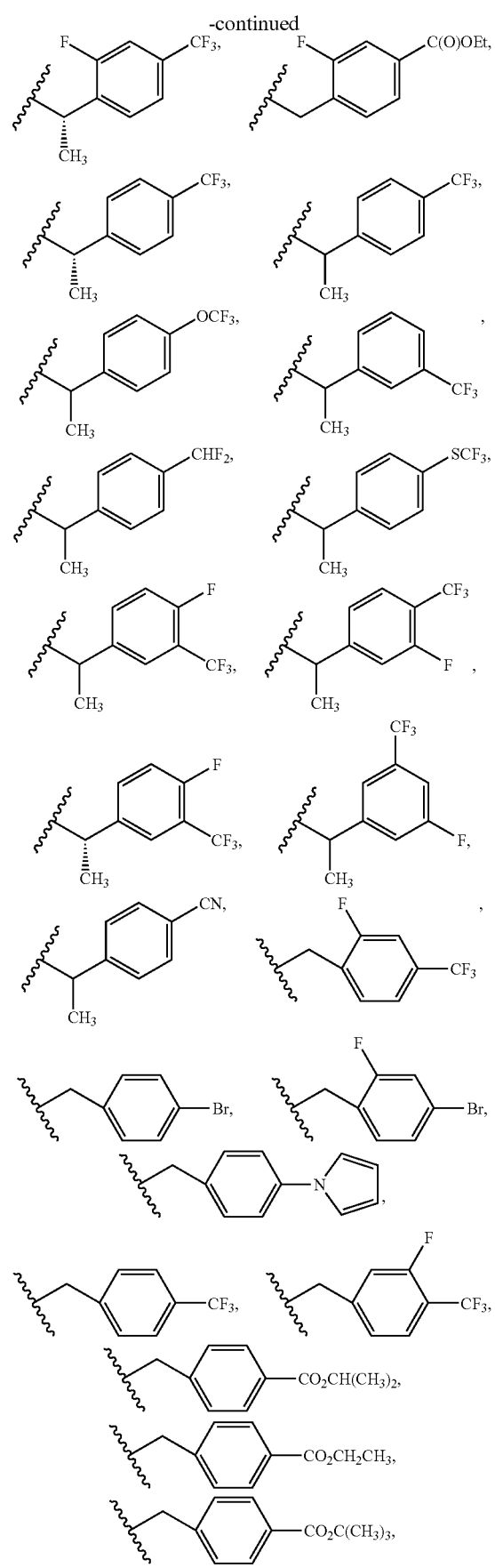

-continued

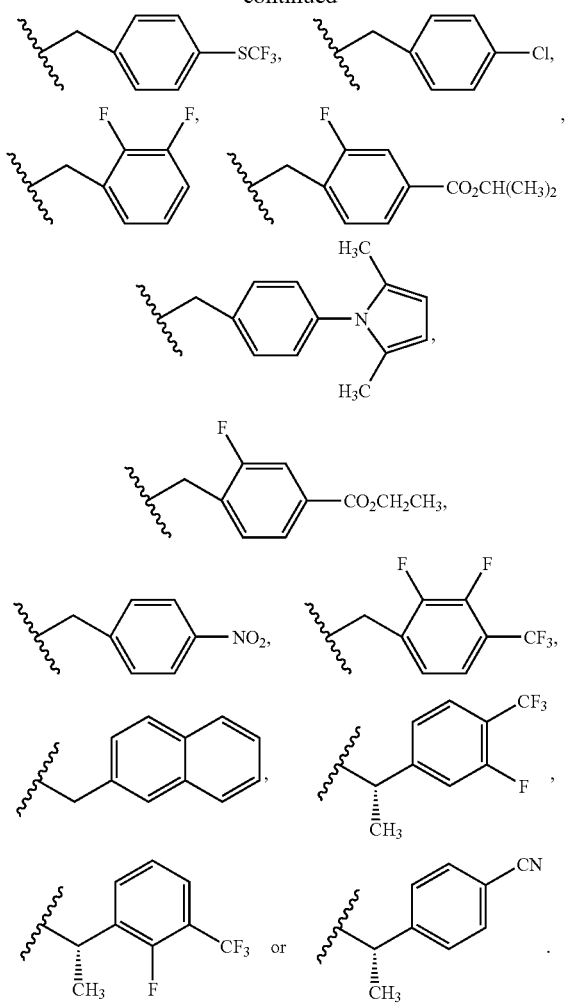

In yet another embodiment, $R^4$ is:

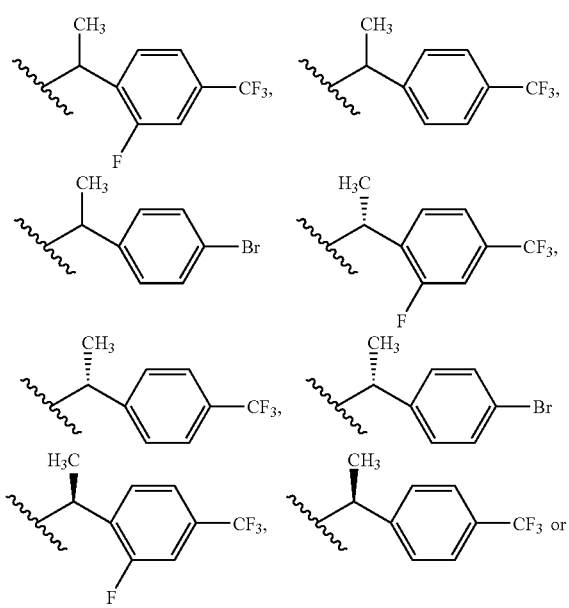

-continued

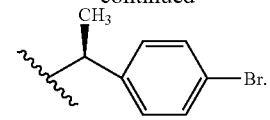

In one embodiment, $R^4$ is —$CH_2$-heteroaryl.
In another embodiment, $R^4$ is —$CH_2$-thienyl or —$CH_2$-benzthienyl.
In one embodiment, $R^4$ is —$CH(CH_3)$-heteroaryl.
In another embodiment, $R^4$ is:

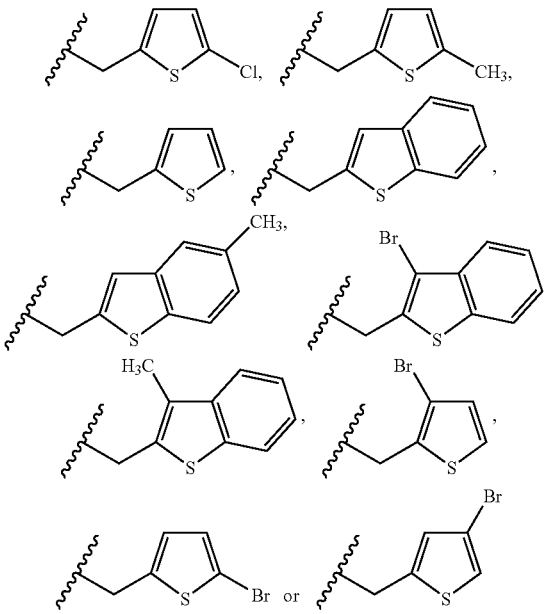

In one embodiment, one or more occurrences of n is 1.
In another embodiment, one or more occurrences of n is 0.
In another embodiment, one or more occurrences of p is 0.
In still another embodiment, one or more occurrences of p is 1.
In yet another embodiment, one or more occurrences of p is 2.
In one embodiment, one or more occurrences of q is 1.
In another embodiment, one or more occurrences of q is 2.
In another embodiment, $R^2$ and $R^3$ are each aryl.
In yet another embodiment, $R^2$ and $R^3$ are each heteroaryl.
In another embodiment, $R^2$ and $R^3$ are each phenyl.
In another embodiment, $R^2$ is aryl and $R^3$ is heteroaryl.
In still another embodiment, $R^2$ is phenyl and $R^3$ is heteroaryl.
In yet another embodiment, $R^2$ is phenyl and $R^3$ is pyridyl.
In a further embodiment, $R^2$ is phenyl and $R^3$ is 2-pyridyl.
In another embodiment, $R^2$ is phenyl and $R^3$ is 4-fluorophenyl.
In another embodiment, $R^2$ and $R^3$ are each 4-trifluoromethylphenyl.
In another embodiment, $R^2$ and $R^3$ are each 4-chlorophenyl.
In one embodiment, $R^2$ and $R^3$ are each 4-fluorophenyl.
In another embodiment, $R^2$ is aryl and $R^3$ is cycloalkyl.
In still another embodiment, $R^2$ is phenyl and $R^3$ is cycloalkyl.
In a further embodiment, $R^2$ is phenyl and $R^3$ is cyclopentyl.

In another embodiment, $R^2$ is phenyl and $R^3$ is cyclobutyl.

In another embodiment, $R^2$ is phenyl and $R^3$ is cyclopropyl.

In another embodiment, $R^2$ is phenyl and $R^3$ is cyclohexyl.

In yet another embodiment, $R^2$ is phenyl and $R^3$ is pyrimidinyl.

In still another embodiment, $R^2$ is phenyl and $R^3$ is thienyl.

In another embodiment, $R^1$ is alkyl, $R^2$ is aryl and $R^3$ is heteroaryl.

In still another embodiment, $R^1$ is alkyl, $R^2$ is phenyl and $R^3$ is heteroaryl.

In yet another embodiment, $R^1$ is alkyl, $R^2$ is phenyl and $R^3$ is pyridyl.

In another embodiment, $R^1$ is alkyl, $R^2$ is phenyl and $R^3$ is 2-pyridyl.

In another embodiment, $R^1$ is alkyl, $R^2$ is phenyl and $R^3$ is 4-fluorophenyl.

In a further embodiment, $R^1$ is alkyl, and $R^2$ and $R^3$ are each aryl.

In another embodiment, $R^1$ is alkyl, and $R^2$ and $R^3$ are each heteroaryl.

In yet another embodiment, $R^1$ is alkyl, and $R^2$ and $R^3$ are each phenyl.

In another embodiment, $R^1$ is alkyl, and $R^2$ and $R^3$ are each 4-trifluoromethylphenyl.

In a further embodiment, $R^1$ is alkyl, and $R^2$ and $R^3$ are each 4-chlorophenyl.

In one embodiment, $R^1$ is alkyl, and $R^2$ and $R^3$ are each 4-fluorophenyl.

In another embodiment, $R^1$ is methyl, $R^2$ is aryl and $R^3$ is heteroaryl.

In still another embodiment, $R^1$ is methyl, $R^2$ is phenyl and $R^3$ is heteroaryl.

In yet another embodiment, $R^1$ is methyl, $R^2$ is phenyl and $R^3$ is pyridyl.

In another embodiment, $R^1$ is methyl, $R^2$ is phenyl and $R^3$ is 2-pyridyl.

In another embodiment, $R^1$ is methyl, $R^2$ is phenyl and $R^3$ is 4-fluorophenyl.

In a further embodiment, $R^1$ is methyl and $R^2$ and $R^3$ are each aryl.

In another embodiment, $R^1$ is methyl and $R^2$ and $R^3$ are each heteroaryl.

In yet another embodiment, $R^1$ is alkyl and $R^2$ and $R^3$ are each phenyl.

In another embodiment, $R^1$ is methyl and $R^2$ and $R^3$ are each phenyl.

In another embodiment, $R^1$ is methyl and $R^2$ and $R^3$ are each 4-trifluoromethylphenyl.

In a further embodiment, $R^1$ is methyl and $R^2$ and $R^3$ are each 4-chlorophenyl.

In another embodiment, $R^1$ is methyl and $R^2$ and $R^3$ are each 4-fluorophenyl.

In another embodiment, $R^1$ is —$NH_2$, $R^2$ is aryl and $R^3$ is heteroaryl.

In still another embodiment, $R^1$ is —$NH_2$, $R^2$ is phenyl and $R^3$ is heteroaryl.

In yet another embodiment, $R^1$ is —$NH_2$, $R^2$ is phenyl and $R^3$ is pyridyl.

In another embodiment, $R^1$ is —$NH_2$, $R^2$ is phenyl and $R^3$ is 2-pyridyl.

In another embodiment, $R^1$ is —$NH_2$, $R^2$ is phenyl and $R^3$ is 4-fluorophenyl.

In a further embodiment, $R^1$ is —$NH_2$, and $R^2$ and $R^3$ are each aryl.

In another embodiment, $R^1$ is —$NH_2$, and $R^2$ and $R^3$ are each heteroaryl.

In yet another embodiment, $R^1$ is —$NH_2$, and $R^2$ and $R^3$ are each phenyl.

In another embodiment, $R^1$ is —$NH_2$, and $R^2$ and $R^3$ are each 4-trifluoromethylphenyl.

In a further embodiment, $R^1$ is —$NH_2$, and $R^2$ and $R^3$ are each 4-chlorophenyl.

In one embodiment, $R^1$ is —$NH_2$, and $R^2$ and $R^3$ are each 4-fluorophenyl.

In one embodiment, $R^1$ is alkyl; $R^2$ and $R^3$ are independently selected from phenyl, pyridyl and 4-fluorophenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —$NO_2$.

In another embodiment, $R^1$ is methyl or ethyl; $R^2$ and $R^3$ are independently selected from phenyl, pyridyl and 4-fluorophenyl; and $R^4$ is -alkylene-aryl, wherein the aryl ring of the alkylene-aryl group can be optionally substituted with up to 3 substituents, which may be the same or different, and are selected from: halo, haloalkyl, heteroaryl, —C(O)O-alkyl, —S-haloalkyl or —$NO_2$.

In another embodiment, $R^1$ is —$N(R^9)_2$; $R^2$ and $R^3$ are independently selected from phenyl, pyridyl and 4-fluorophenyl; and $R^4$ is -alkylene-aryl, wherein the aryl ring of the alkylene-aryl group can be optionally substituted with up to 3 substituents, which may be the same or different, and are selected from: halo, haloalkyl, heteroaryl, —C(O)O-alkyl, —S-haloalkyl or —$NO_2$.

In still another embodiment, $R^1$ is —$NH_2$; $R^2$ and $R^3$ are independently selected from phenyl, pyridyl and 4-fluorophenyl; and $R^4$ is -alkylene-aryl, wherein the aryl ring of the alkylene-aryl group can be optionally substituted with up to 3 substituents, which may be the same or different, and are selected from: halo, haloalkyl, heteroaryl, —C(O)O-alkyl, —S-haloalkyl or —$NO_2$.

In one embodiment, $R^1$ is alkyl; $R^2$ and $R^3$ are independently selected from phenyl, pyridyl and 4-fluorophenyl; and $R^4$ is -alkylene-heteroaryl, wherein the heteroaryl ring of the alkylene-heteroaryl group can be optionally substituted with up to 3 substituents, which may be the same or different, and are selected from alkyl and halo.

In another embodiment, $R^1$ is methyl or ethyl; $R^2$ and $R^3$ are independently selected from phenyl, pyridyl and 4-fluorophenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In another embodiment, $R^1$ is —$N(R^9)_2$; $R^2$ and $R^3$ are independently selected from phenyl, pyridyl and 4-fluorophenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In still another embodiment, $R^1$ is —$NH_2$; $R^2$ and $R^3$ are independently selected from phenyl, pyridyl and 4-fluorophenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In one embodiment, $R^1$ is alkyl; $R^2$ and $R^3$ are each phenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —$NO_2$.

In another embodiment, $R^1$ is methyl or ethyl; $R^2$ and $R^3$ are each phenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is —N(R$^9$)$_2$; $R^2$ and $R^3$ are each phenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In still another embodiment, $R^1$ is —NH$_2$; $R^2$ and $R^3$ are each phenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In one embodiment, $R^1$ is alkyl; $R^2$ and $R^3$ are each phenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In another embodiment, $R^1$ is methyl or ethyl; $R^2$ and $R^3$ are each phenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In another embodiment, $R^1$ is —N(R$^9$)$_2$; $R^2$ and $R^3$ are each phenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In still another embodiment, $R^1$ is —NH$_2$; $R^2$ and $R^3$ are each phenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In one embodiment, $R^1$ is alkyl; $R^2$ and $R^3$ are each 4-fluorophenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is methyl or ethyl; $R^2$ and $R^3$ are each 4-fluorophenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is —N(R$^9$)$_2$; $R^2$ and $R^3$ are each 4-fluorophenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In still another embodiment, $R^1$ is —NH$_2$; $R^2$ and $R^3$ are each 4-fluorophenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In one embodiment, $R^1$ is alkyl; $R^2$ and $R^3$ are each 4-fluorophenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In another embodiment, $R^1$ is methyl or ethyl; $R^2$ and $R^3$ are each 4-fluorophenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In another embodiment, $R^1$ is —N(R$^9$)$_2$; $R^2$ and $R^3$ are each 4-fluorophenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In still another embodiment, $R^1$ is —NH$_2$; $R^2$ and $R^3$ are each 4-fluorophenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In one embodiment, $R^1$ is alkyl; $R^2$ is phenyl; $R^3$ is 4-fluorophenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is methyl or ethyl; $R^2$ is phenyl; $R^3$ is 4-fluorophenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is —N(R$^9$)$_2$; $R^2$ is phenyl; $R^3$ is 4-fluorophenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In still another embodiment, $R^1$ is —NH$_2$; $R^2$ is phenyl; $R^3$ is 4-fluorophenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In one embodiment, $R^1$ is alkyl; $R^2$ is phenyl; $R^3$ is 4-fluorophenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In another embodiment, $R^1$ is methyl or ethyl; $R^2$ is phenyl; $R^3$ is 4-fluorophenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In another embodiment, $R^1$ is —N(R$^9$)$_2$; $R^2$ is phenyl; $R^3$ is 4-fluorophenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In still another embodiment, $R^1$ is —NH$_2$; $R^2$ is phenyl; $R^3$ is 4-fluorophenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In one embodiment, $R^1$ is alkyl; $R^2$ is pyridyl and $R^3$ is phenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is methyl or ethyl; $R^2$ is pyridyl and $R^3$ is phenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is —N($R^9$)$_2$; $R^2$ is pyridyl and $R^3$ is phenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In still another embodiment, $R^1$ is —NH$_2$; $R^2$ is pyridyl and $R^3$ is phenyl; and $R^4$ is -alkylene-aryl, wherein the aryl ring of the -alkylene-aryl group can be optionally substituted with up to 3 substituents, which may be the same or different, and are selected from: halo, haloalkyl, heteroaryl, —C(O)O-alkyl, —S-haloalkyl or —NO$_2$.

In one embodiment, $R^1$ is alkyl; $R^2$ is pyridyl and $R^3$ is phenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In another embodiment, $R^1$ is methyl or ethyl; $R^2$ is pyridyl and $R^3$ is phenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In another embodiment, $R^1$ is —N($R^9$)$_2$, $R^2$ is pyridyl and $R^3$ is phenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In still another embodiment, $R^1$ is —NH$_2$; $R^2$ is pyridyl and $R^3$ is phenyl; and $R^4$ is -alkylene-heteroaryl, wherein the heteroaryl ring of the -alkylene-heteroaryl group can be optionally substituted with up to 3 substituents, which may be the same or different, and are selected from alkyl and halo.

In one embodiment, $R^1$ is alkyl; $R^2$ and $R^3$ are independently selected from phenyl, pyridyl and 4-fluorophenyl; and $R^4$ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is methyl or ethyl; $R^2$ and $R^3$ are independently selected from phenyl, pyridyl and 4-fluorophenyl; and $R^4$ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is —NH$_2$; $R^2$ and $R^3$ are independently selected from phenyl, pyridyl and 4-fluorophenyl; and $R^4$ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In one embodiment, $R^1$ is alkyl; $R^2$ and $R^3$ are independently selected from phenyl, pyridyl and 4-fluorophenyl; and $R^4$ is —CH(CH$_3$)-phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is methyl or ethyl; $R^2$ and $R^3$ are independently selected from phenyl, pyridyl and 4-fluorophenyl; and $R^4$ is —CH(CH$_3$)-phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is —NH$_2$; $R^2$ and $R^3$ are independently selected from phenyl, pyridyl and 4-fluorophenyl; and $R^4$ is —CH(CH$_3$)-phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In one embodiment, $R^1$ is alkyl; $R^2$ and $R^3$ are independently selected from phenyl, pyridyl and 4-fluorophenyl; and $R^4$ is:

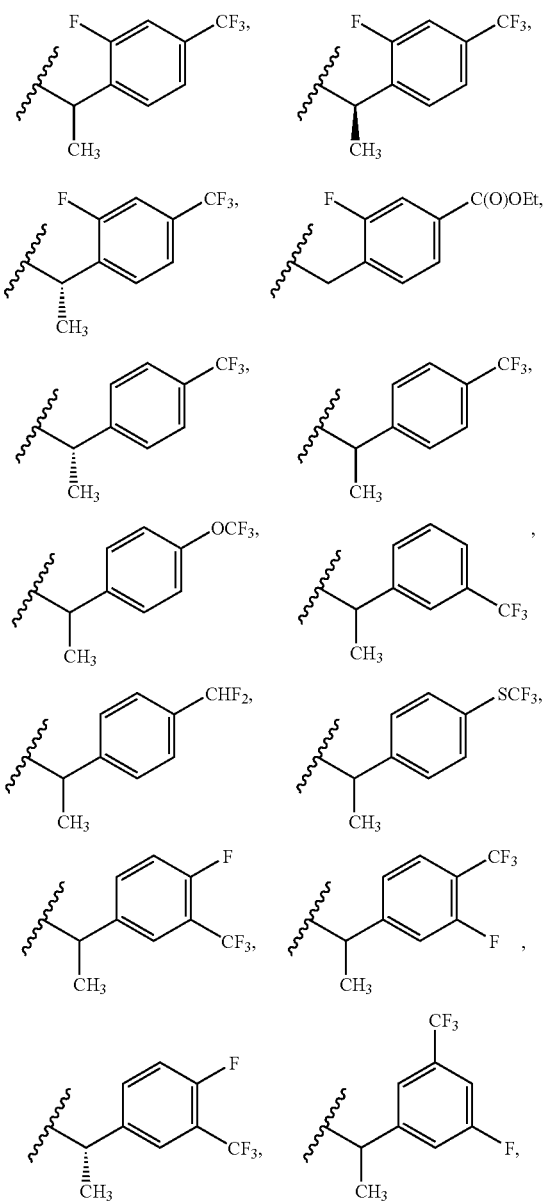

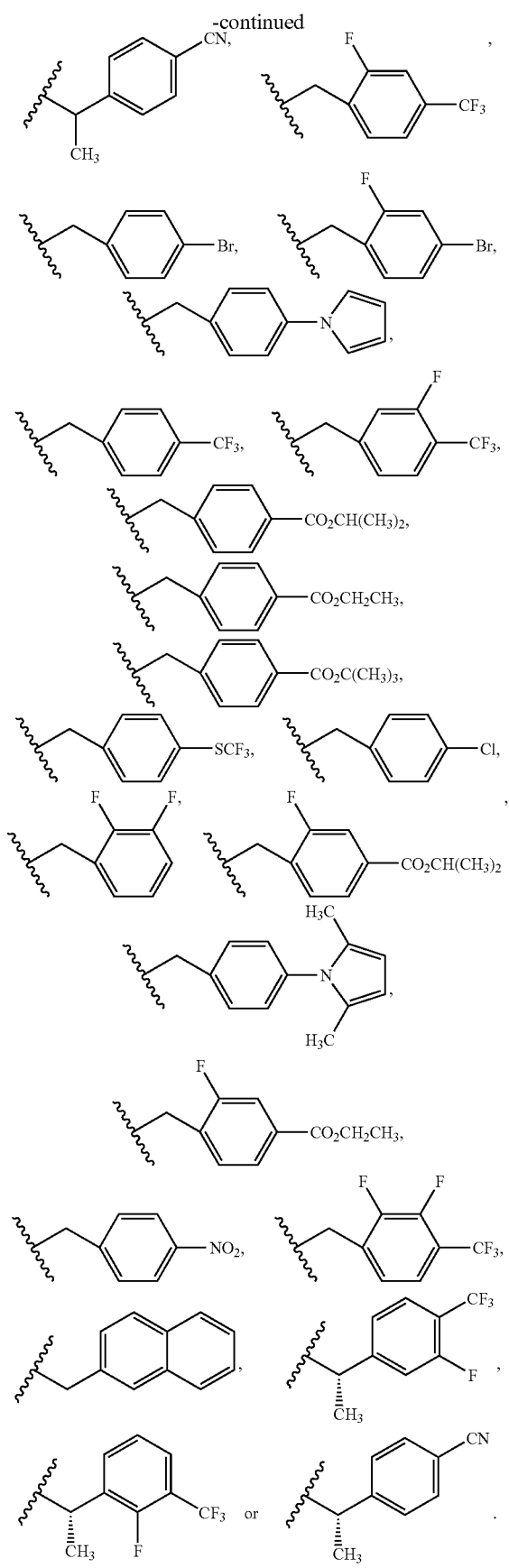
In another embodiment, $R^1$ is methyl or ethyl; $R^2$ and $R^3$ are independently selected from phenyl, pyridyl and 4-fluorophenyl; and $R^4$ is:
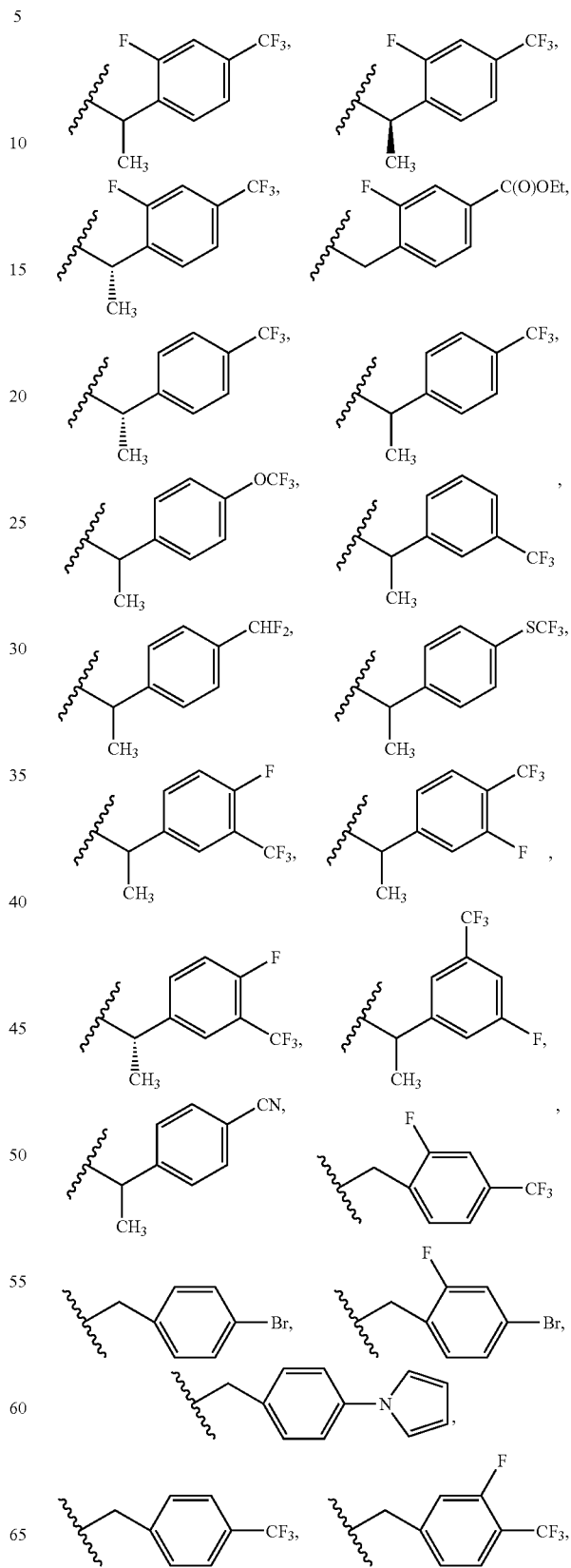

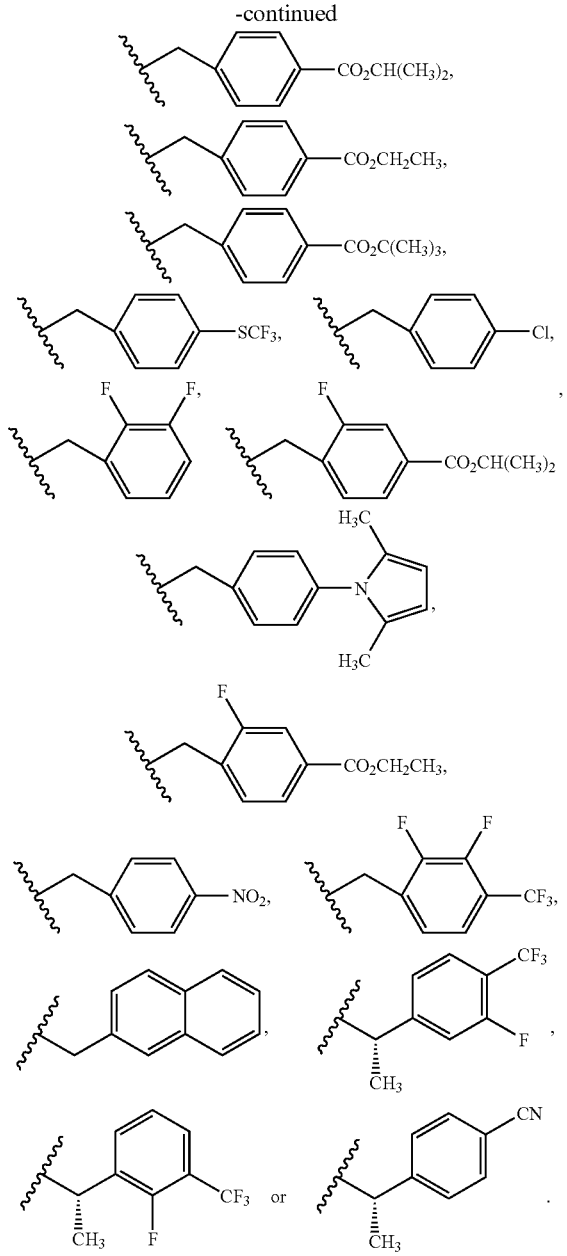
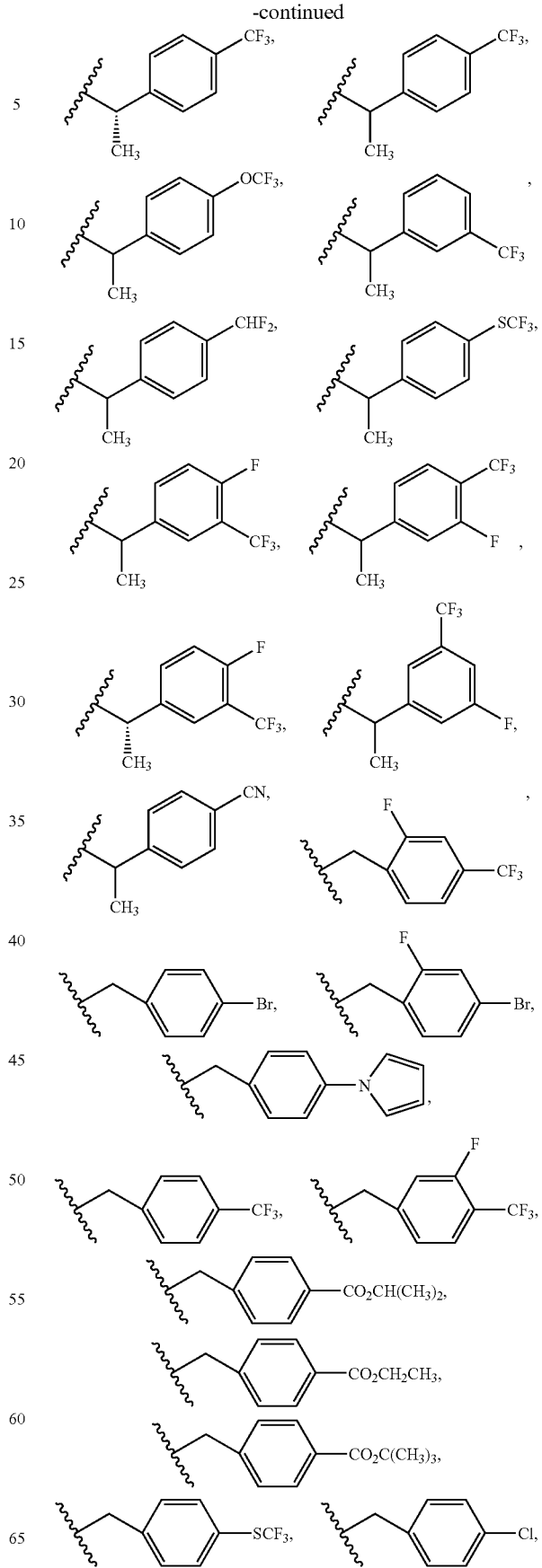
In another embodiment, $R^1$ is —$NH_2$; $R^2$ and $R^3$ are independently selected from phenyl, pyridyl and 4-fluorophenyl; and $R^4$ is:
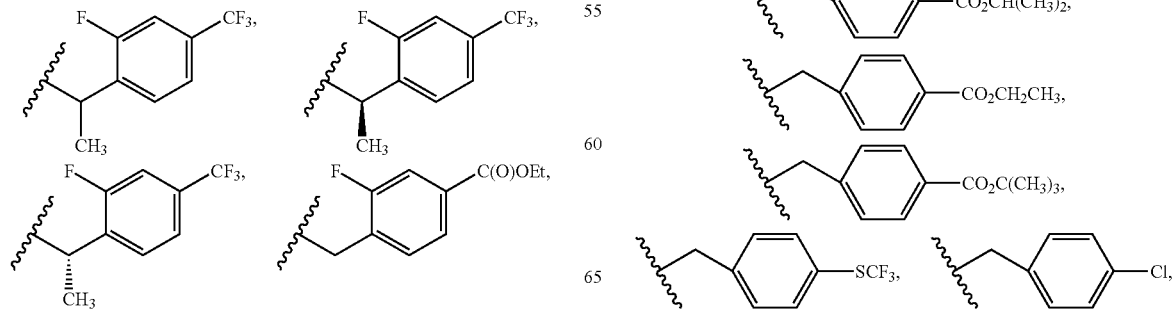

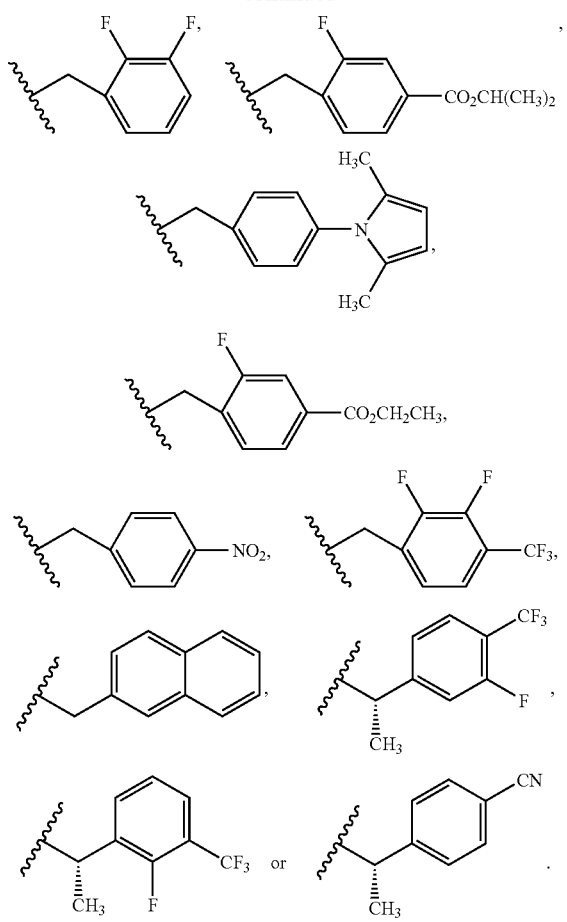
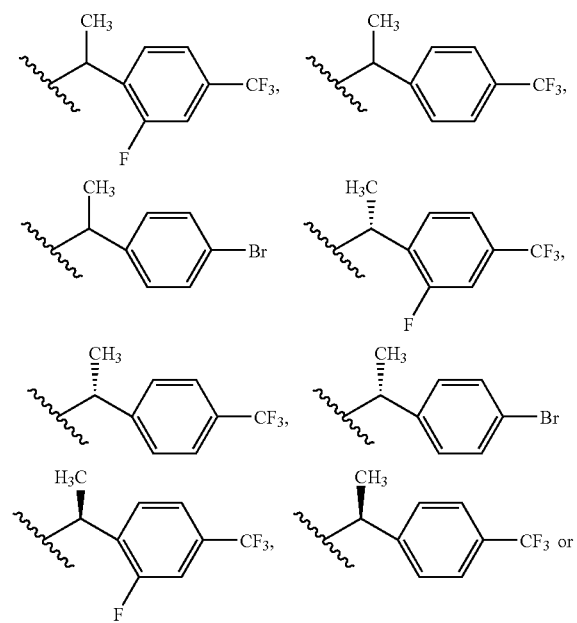
In one embodiment, R¹ is alkyl; R² and R³ are independently selected from phenyl, pyridyl and 4-fluorophenyl; and R⁴ is
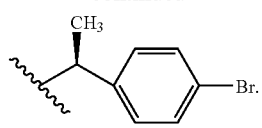
In another embodiment, R¹ is methyl or ethyl; R² and R³ are independently selected from phenyl, pyridyl and 4-fluorophenyl; and R⁴ is —
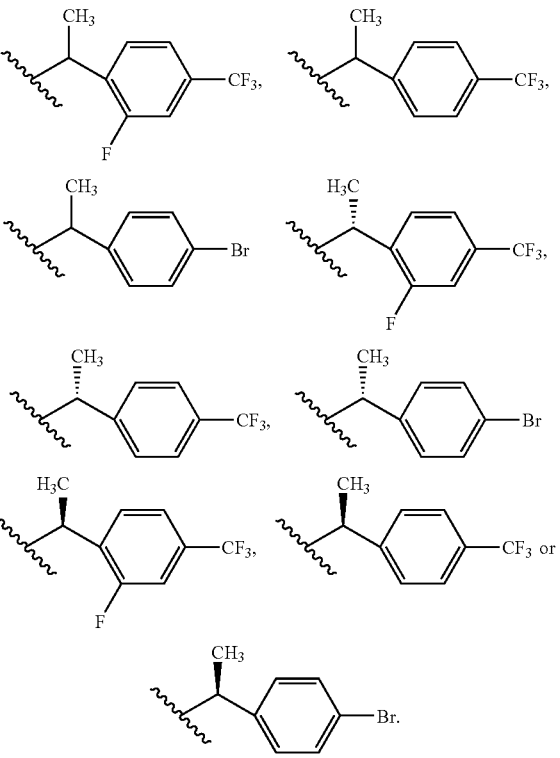
In another embodiment, R¹ is —NH₂; R² and R³ are independently selected from phenyl, pyridyl and 4-fluorophenyl; and R⁴ is

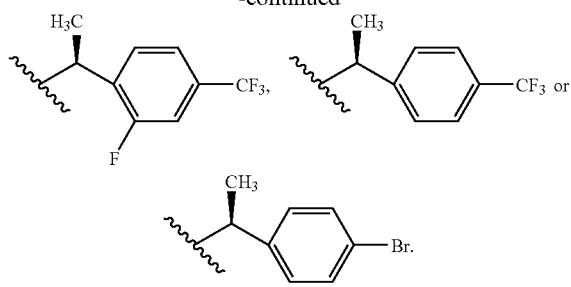

In one embodiment, $R^1$ is alkyl; $R^2$ and $R^3$ are independently selected from phenyl, pyridyl and 4-fluorophenyl; and $R^4$ is —CH$_2$-heteroaryl.

In another embodiment, $R^1$ is methyl or ethyl; $R^2$ and $R^3$ are independently selected from phenyl, pyridyl and 4-fluorophenyl; and $R^4$ is —CH$_2$-heteroaryl.

In another embodiment, $R^1$ is —NH$_2$; $R^2$ and $R^3$ are independently selected from phenyl, pyridyl and 4-fluorophenyl; and $R^4$ is —CH$_2$-heteroaryl.

In one embodiment, $R^1$ is alkyl; $R^2$ and $R^3$ are independently selected from phenyl, pyridyl and 4-fluorophenyl; and $R^4$ is —CH(CH$_3$)-heteroaryl.

In another embodiment, $R^1$ is methyl or ethyl; $R^2$ and $R^3$ are independently selected from phenyl, pyridyl and 4-fluorophenyl; and $R^4$ is —CH(CH$_3$)-heteroaryl.

In another embodiment, $R^1$ is —NH$_2$; $R^2$ and $R^3$ are independently selected from phenyl, pyridyl and 4-fluorophenyl; and $R^4$ is —CH(CH$_3$)-heteroaryl.

In one embodiment, $R^1$ is alkyl; $R^2$ and $R^3$ are independently selected from phenyl, pyridyl and 4-fluorophenyl; and $R^4$ is

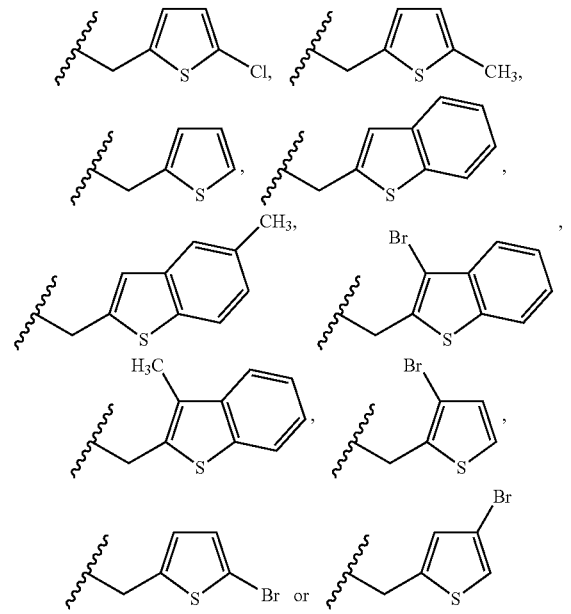

In another embodiment, $R^1$ is methyl or ethyl; $R^2$ and $R^3$ are independently selected from phenyl, pyridyl and 4-fluorophenyl; and $R^4$ is

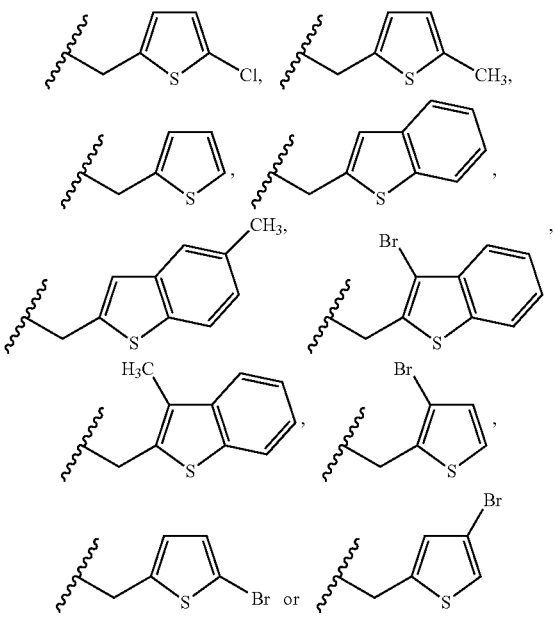

In another embodiment, $R^1$ is —NH$_2$; $R^2$ and $R^3$ are independently selected from phenyl, pyridyl and 4-fluorophenyl; and $R^4$ is

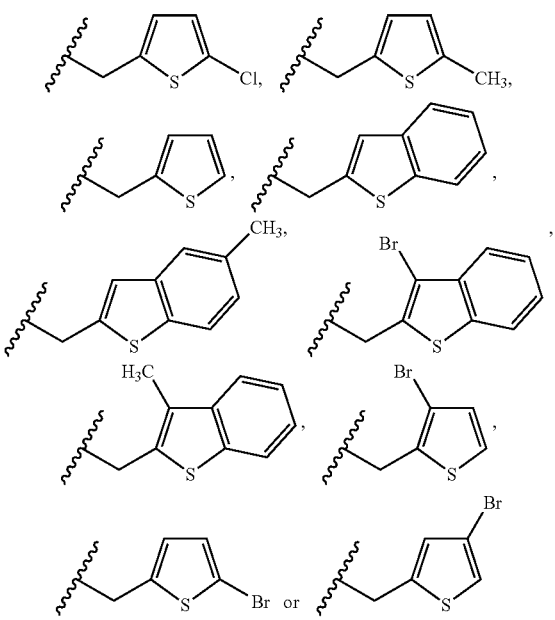

In one embodiment, $R^1$ is alkyl; $R^2$ and $R^3$ are each phenyl; and $R^4$ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is methyl or ethyl; $R^2$ and $R^3$ are each phenyl; and $R^4$ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is —$NH_2$; $R^2$ and $R^3$ are each phenyl; and $R^4$ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —$NO_2$.

In one embodiment, $R^1$ is alkyl; $R^2$ and $R^3$ are each phenyl; and $R^4$ is —CH($CH_3$)— phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —$NO_2$.

In another embodiment, $R^1$ is methyl or ethyl; $R^2$ and $R^3$ are each phenyl; and $R^4$ is —CH($CH_3$)-phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —$NO_2$.

In another embodiment, $R^1$ is —$NH_2$; $R^2$ and $R^3$ are each phenyl; and $R^4$ is —CH($CH_3$)— phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —$NO_2$.

In one embodiment, $R^1$ is alkyl; $R^2$ and $R^3$ are each phenyl; and $R^4$ is:

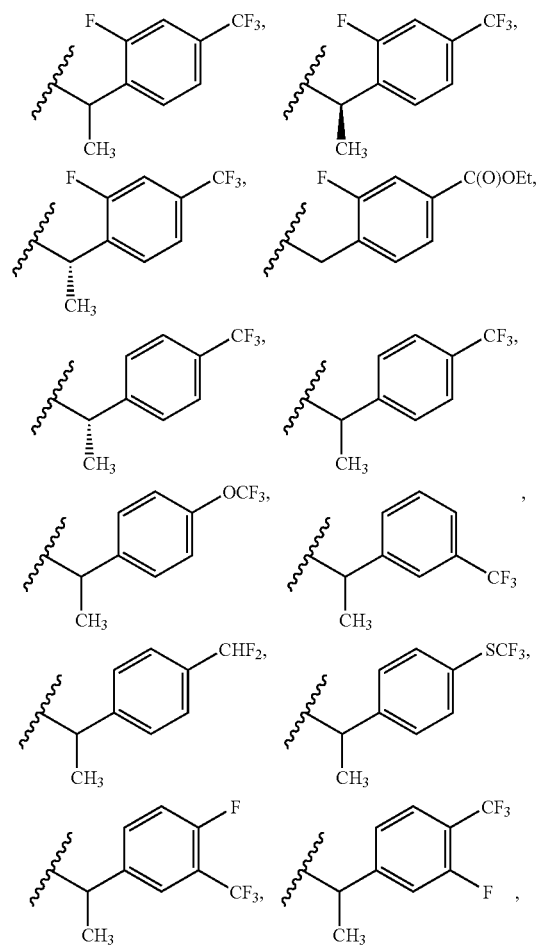

-continued

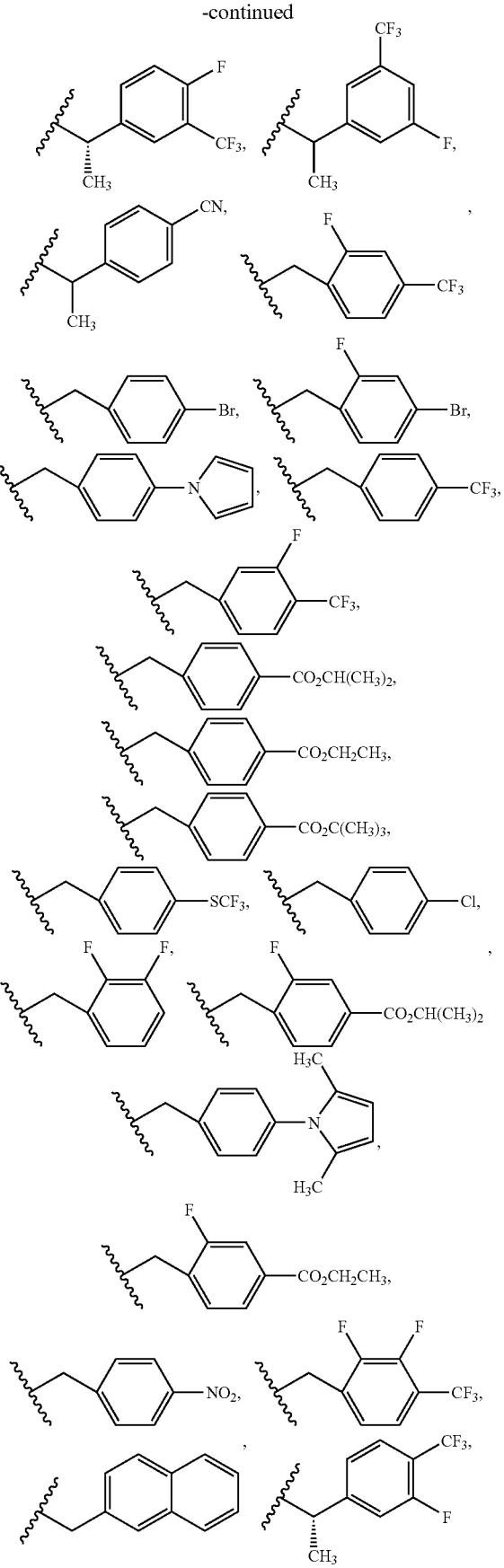

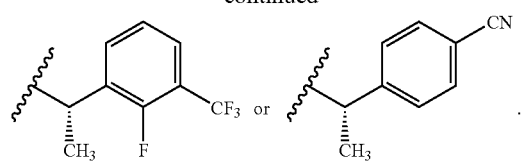
In another embodiment, $R^1$ is methyl or ethyl; $R^2$ and $R^3$ are each phenyl; and $R^4$ is:
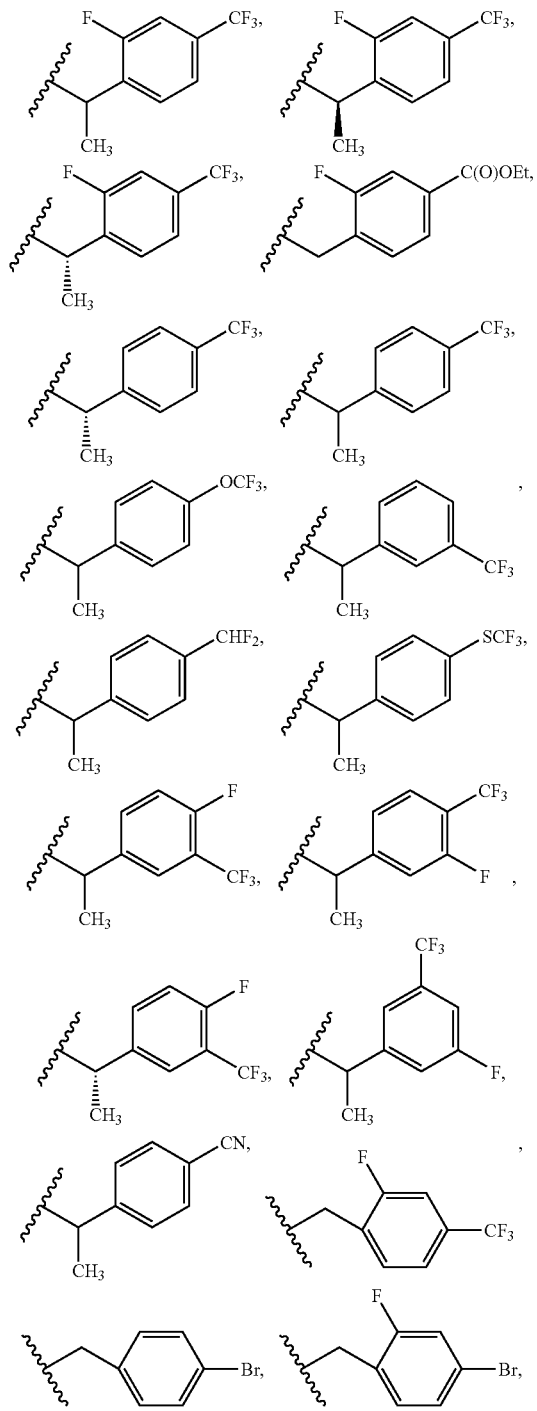
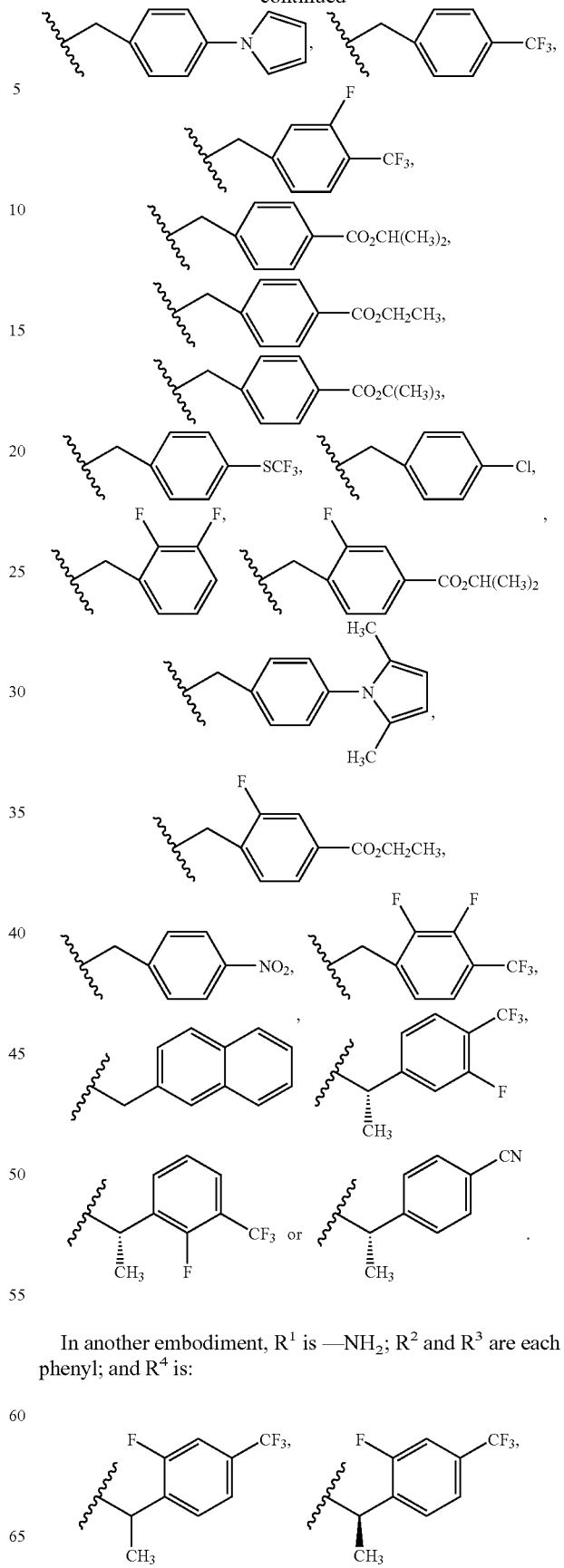
In another embodiment, $R^1$ is $—NH_2$; $R^2$ and $R^3$ are each phenyl; and $R^4$ is:

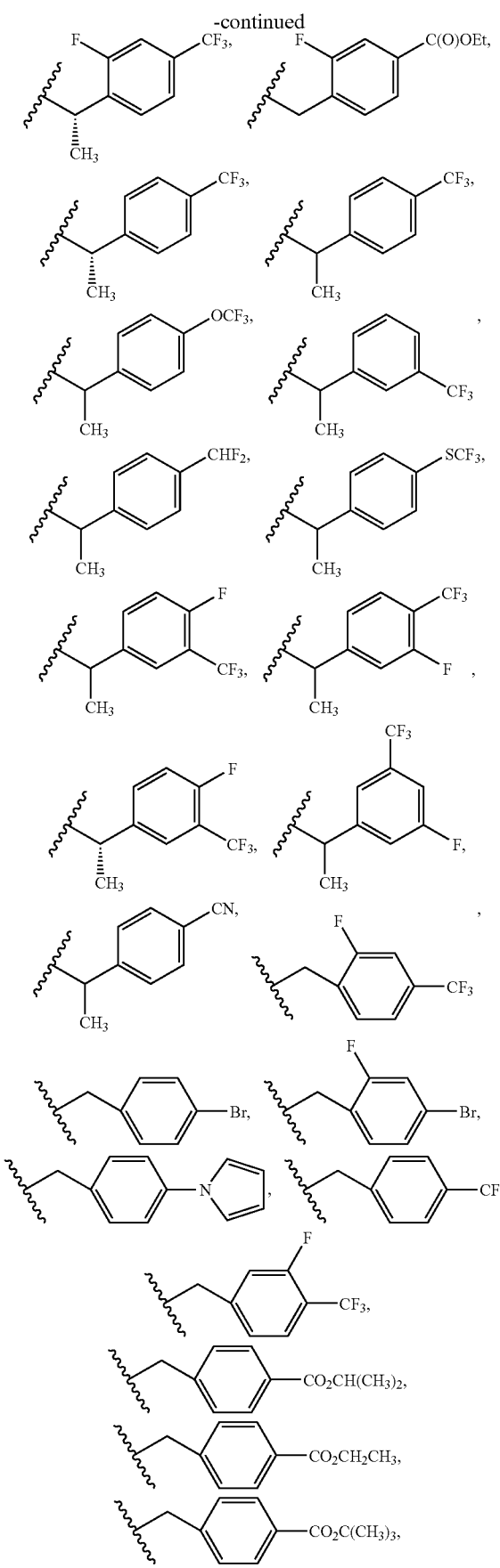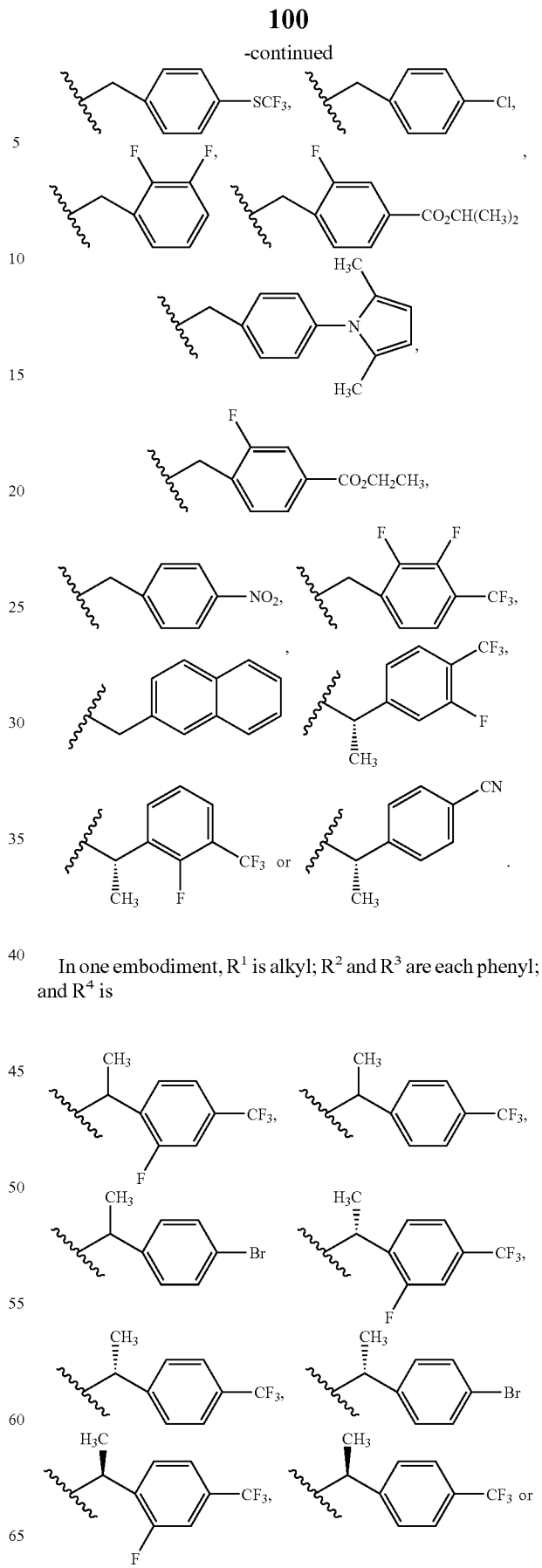
In one embodiment, $R^1$ is alkyl; $R^2$ and $R^3$ are each phenyl; and $R^4$ is

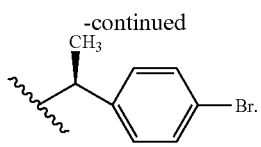

In another embodiment, R¹ is methyl or ethyl; R² and R³ are each phenyl; and R⁴ is

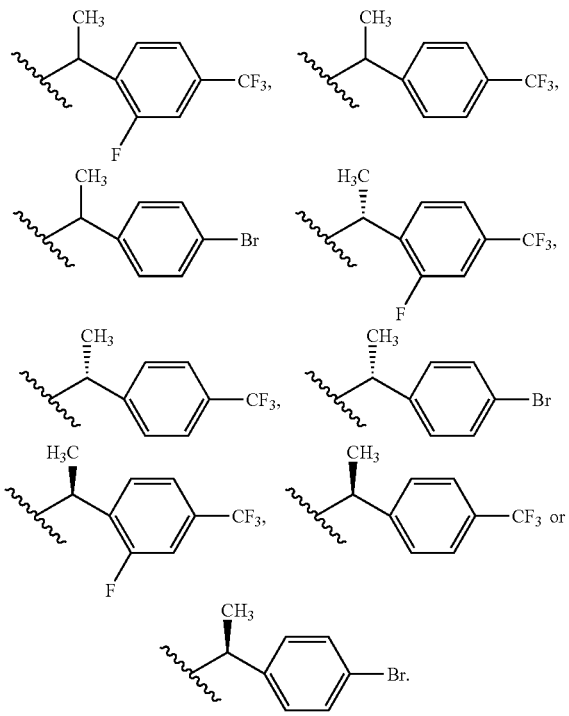

In another embodiment, R¹ is —NH₂; R² and R³ are each phenyl; and R⁴ is

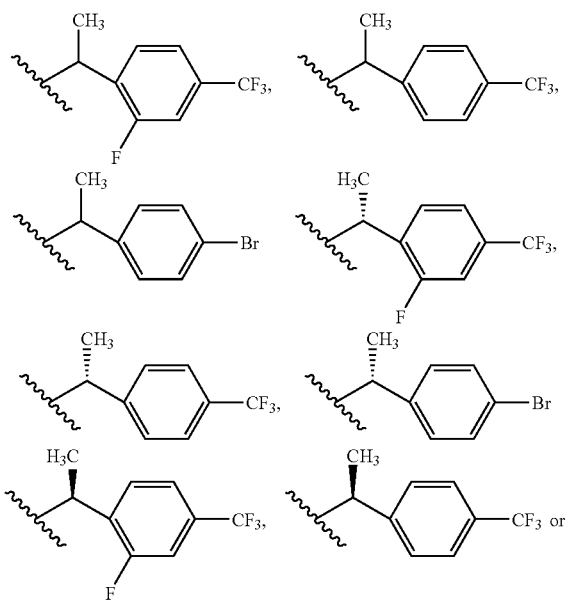

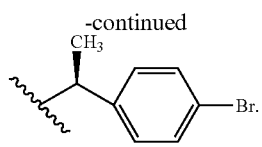

In one embodiment, R¹ is alkyl; R² and R³ are each phenyl; and R⁴ is —CH₂-heteroaryl.

In another embodiment, R¹ is methyl or ethyl; R² and R³ are each phenyl; and R⁴ is —CH₂-heteroaryl.

In another embodiment, R¹ is —NH₂; R² and R³ are each phenyl; and R⁴ is —CH₂-heteroaryl.

In one embodiment, R¹ is alkyl; R² and R³ are each phenyl; and R⁴ is —CH(CH₃)—heteroaryl.

In another embodiment, R¹ is methyl or ethyl; R² and R³ are each phenyl; and R⁴ is —CH(CH₃)-heteroaryl.

In another embodiment, R¹ is —NH₂; R² and R³ are each phenyl; and R⁴ is —CH(CH₃)—heteroaryl.

In one embodiment, R¹ is alkyl; R² and R³ are each phenyl; and R⁴ is

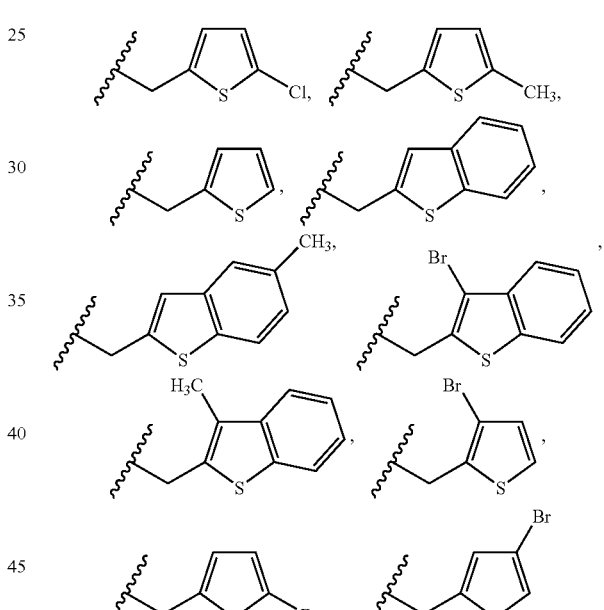

In another embodiment, R¹ is methyl or ethyl; R² and R³ are each phenyl; and R⁴ is

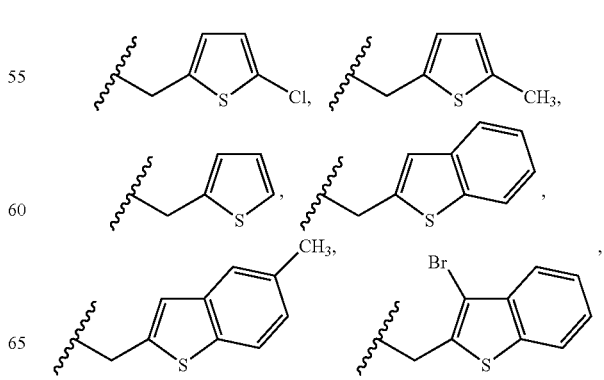

In another embodiment, R¹ is —NH₂; R² and R³ are each phenyl; and R⁴ is

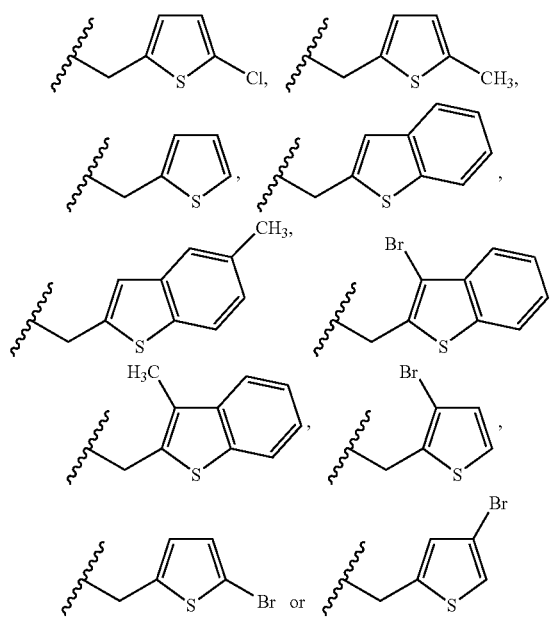

In one embodiment, R¹ is alkyl; R² and R³ are each 4-fluorophenyl; and R⁴ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO₂.

In another embodiment, R¹ is methyl or ethyl; R² and R³ are each 4-fluorophenyl; and R⁴ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO₂.

In another embodiment, R¹ is —NH₂; R² and R³ are each 4-fluorophenyl; and R⁴ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO₂.

In one embodiment, R¹ is alkyl; R² and R³ are each 4-fluorophenyl; and R⁴ is —CH(CH₃)-phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO₂.

In another embodiment, R¹ is methyl or ethyl; R² and R³ are each 4-fluorophenyl; and R⁴ is —CH(CH₃)-phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO₂.

In another embodiment, R¹ is —NH₂; R² and R³ are each 4-fluorophenyl; and R⁴ is —CH(CH₃)-phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO₂.

In one embodiment, R¹ is alkyl; R² and R³ are each 4-fluorophenyl; and R⁴ is:

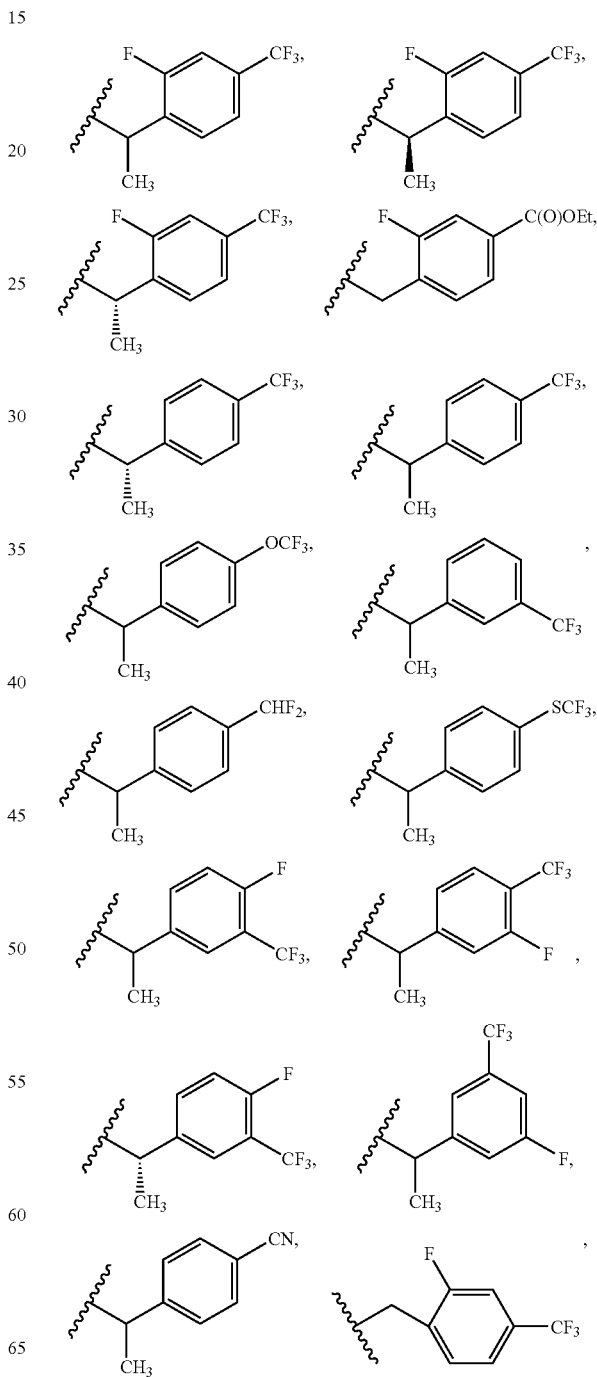

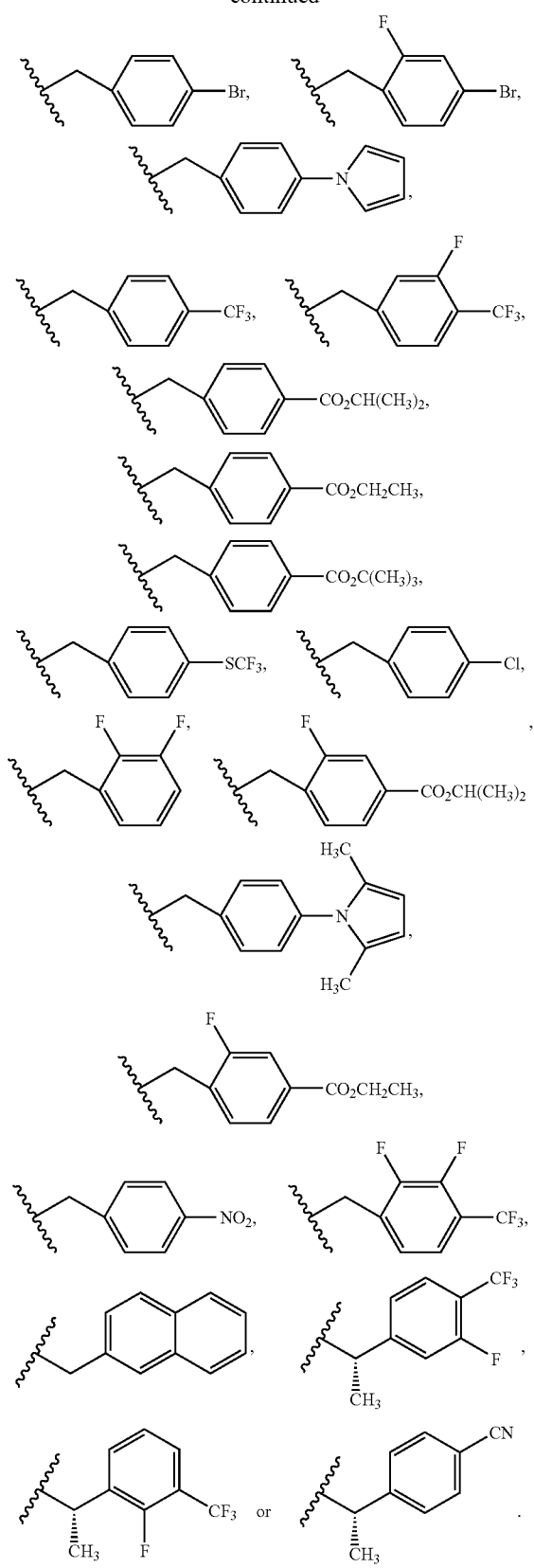
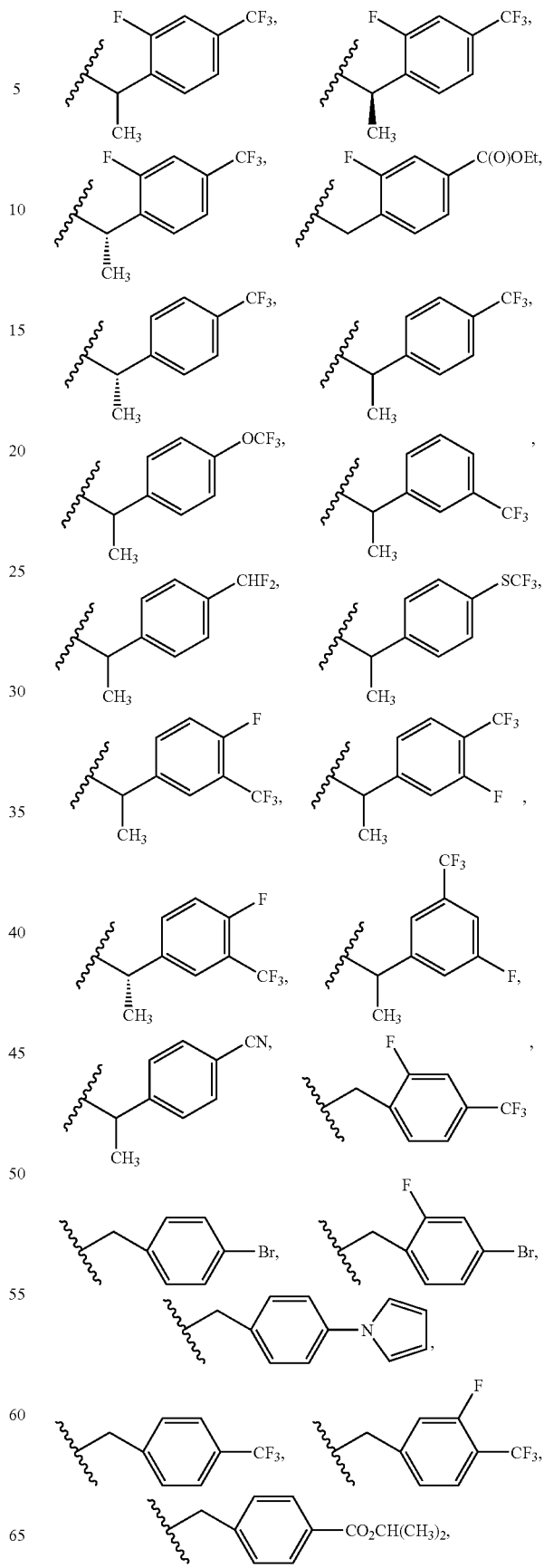
In another embodiment, $R^1$ is methyl or ethyl; $R^2$ and $R^3$ are each 4-fluorophenyl; and $R^4$ is:

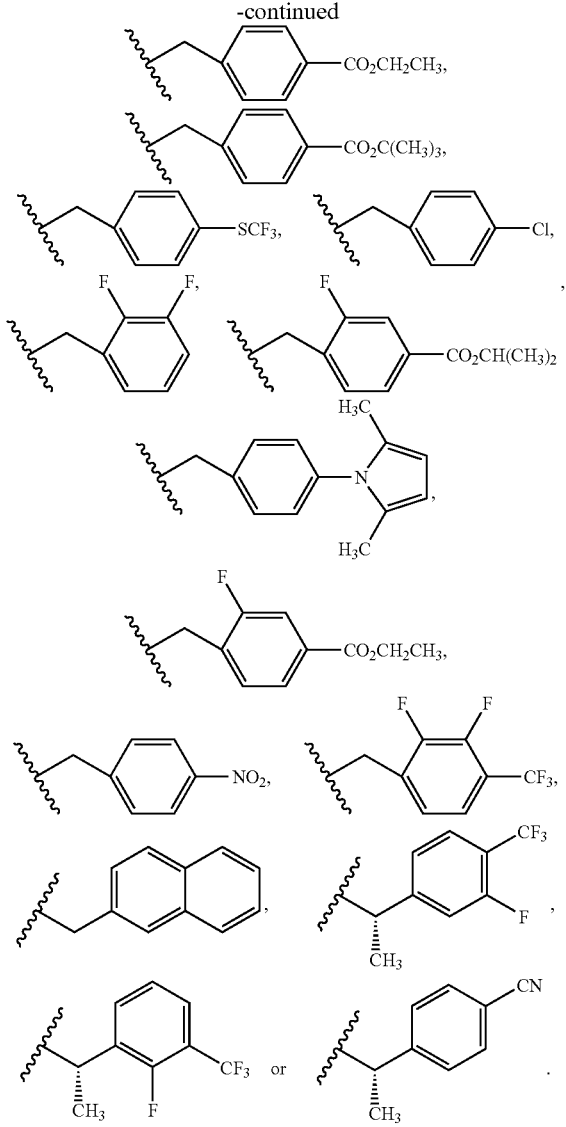
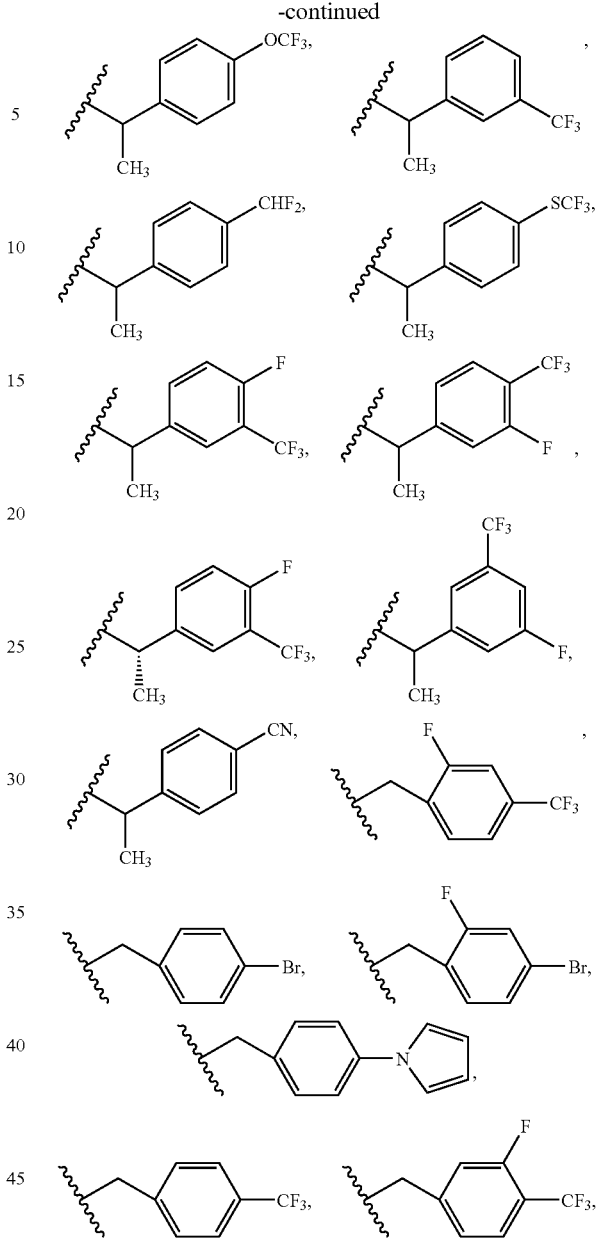
In another embodiment, $R^1$ is —$NH_2$; $R^2$ and $R^3$ are each 4-fluorophenyl; and $R^4$ is:
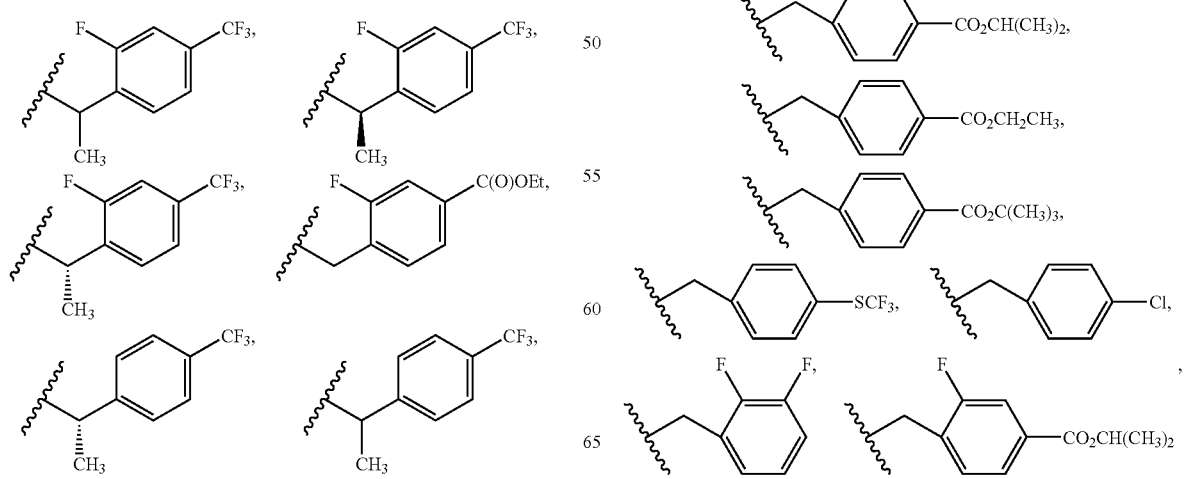

-continued

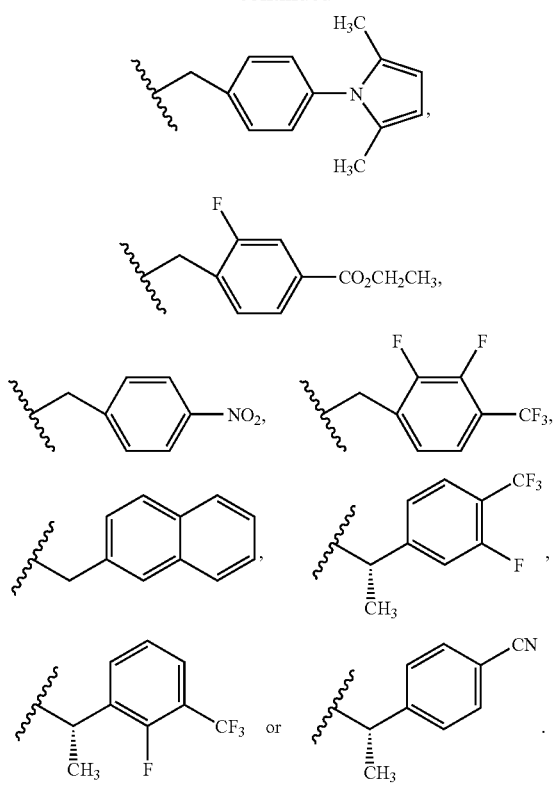

In one embodiment, $R^1$ is alkyl; $R^2$ and $R^3$ are each 4-fluorophenyl; and $R^4$ is In another embodiment, $R^1$ is methyl or ethyl; $R^2$ and $R^3$ are each 4-fluorophenyl; and $R^4$ is —

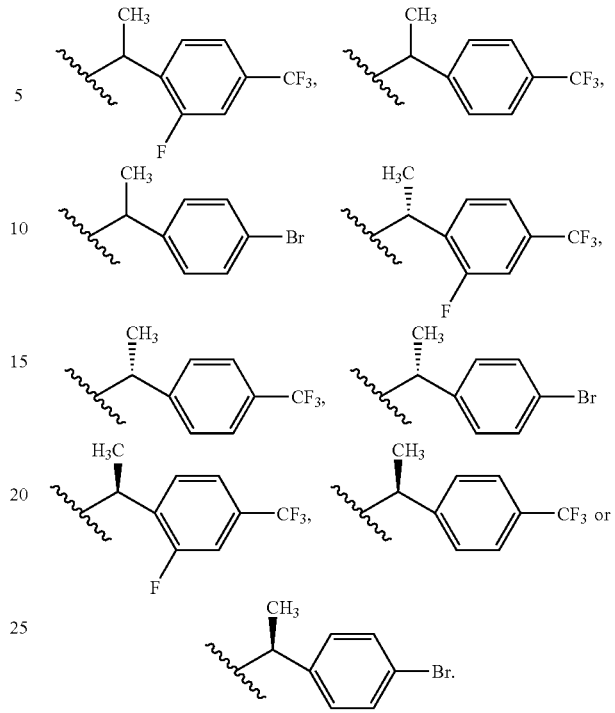

In another embodiment, $R^1$ is —$NH_2$; $R^2$ and $R^3$ are each 4-fluorophenyl; and $R^4$ is

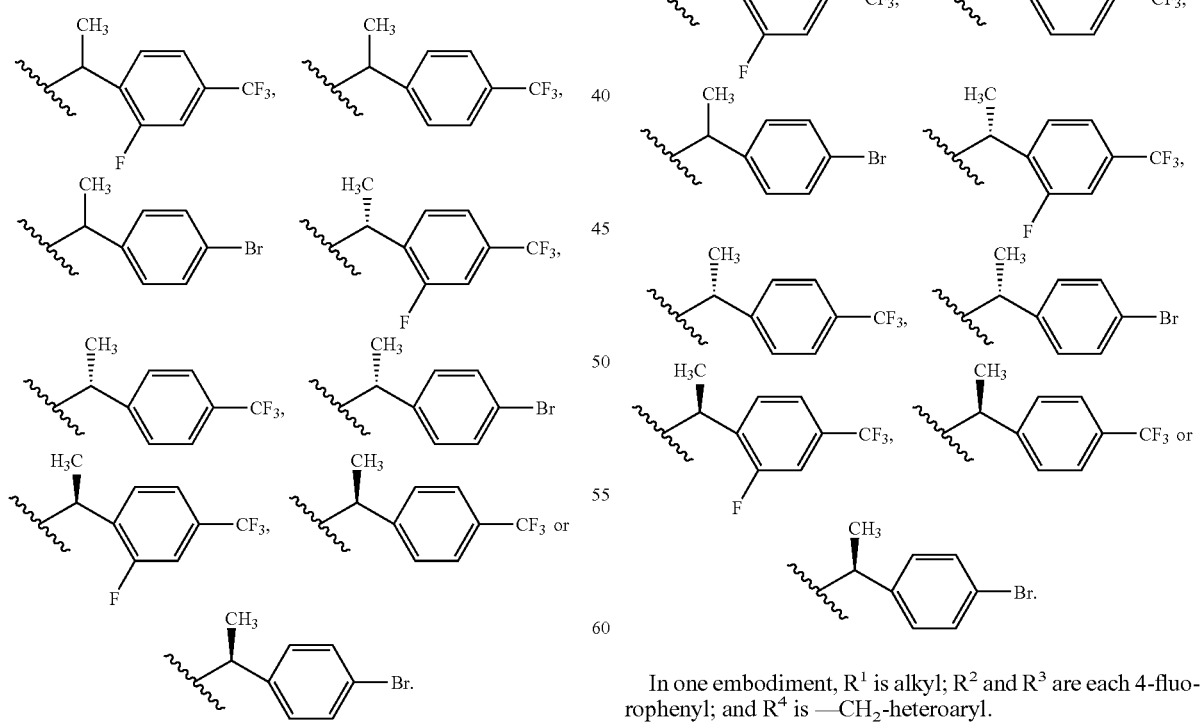

In one embodiment, $R^1$ is alkyl; $R^2$ and $R^3$ are each 4-fluorophenyl; and $R^4$ is —$CH_2$-heteroaryl.

In another embodiment, $R^1$ is methyl or ethyl; $R^2$ and $R^3$ are each 4-fluorophenyl; and $R^4$ is —$CH_2$-heteroaryl.

In another embodiment, $R^1$ is —$NH_2$; $R^2$ and $R^3$ are each 4-fluorophenyl; and $R^4$ is —$CH_2$-heteroaryl.

In one embodiment, $R^1$ is alkyl; $R^2$ and $R^3$ are each 4-fluorophenyl; and $R^4$ is —CH(CH$_3$)-heteroaryl.

In another embodiment, $R^1$ is methyl or ethyl; $R^2$ and $R^3$ are each 4-fluorophenyl; and $R^4$ is —CH(CH$_3$)-heteroaryl.

In another embodiment, $R^1$ is —NH$_2$; $R^2$ and $R^3$ are each 4-fluorophenyl; and $R^4$ is —CH(CH$_3$)-heteroaryl.

In one embodiment, $R^1$ is alkyl; $R^2$ and $R^3$ are each 4-fluorophenyl; and $R^4$ is

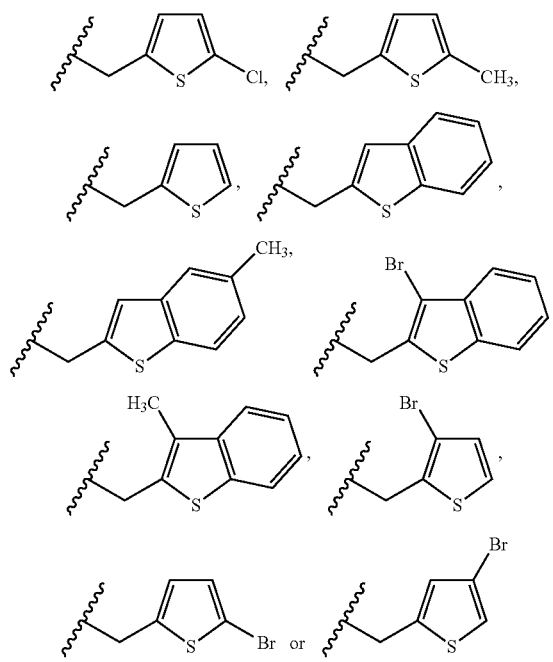

In another embodiment, $R^1$ is methyl or ethyl; $R^2$ and $R^3$ are each 4-fluorophenyl; and

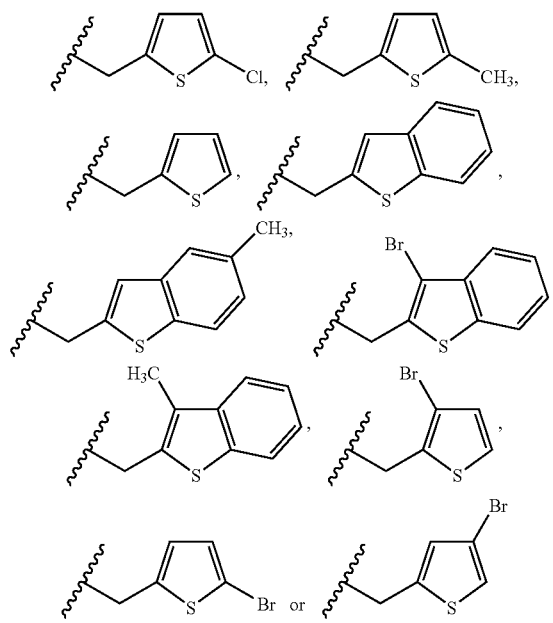

In another embodiment, $R^1$ is —NH$_2$; $R^2$ and $R^3$ are each 4-fluorophenyl; and $R^4$ is

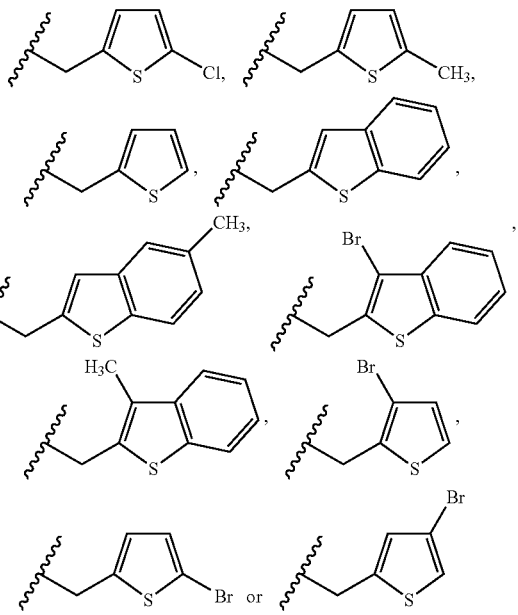

In one embodiment, $R^1$ is alkyl; $R^2$ is phenyl; $R^3$ is pyridyl; and $R^4$ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is methyl or ethyl; $R^2$ is phenyl; and $R^3$ is pyridyl; and $R^4$ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is —NH$_2$; $R^2$ is phenyl; $R^3$ is pyridyl; and $R^4$ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In one embodiment, $R^1$ is alkyl; $R^2$ is phenyl; $R^3$ is pyridyl; and $R^4$ is —CH(CH$_3$)—phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is methyl or ethyl; $R^2$ is phenyl; $R^3$ is pyridyl; and $R^4$ is —CH(CH$_3$)-phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is —NH$_2$; $R^2$ is phenyl; $R^3$ is pyridyl; and $R^4$ is —CH(CH$_3$)— phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In one embodiment, $R^1$ is alkyl; $R^2$ is phenyl; $R^3$ is pyridyl; and $R^4$ is:
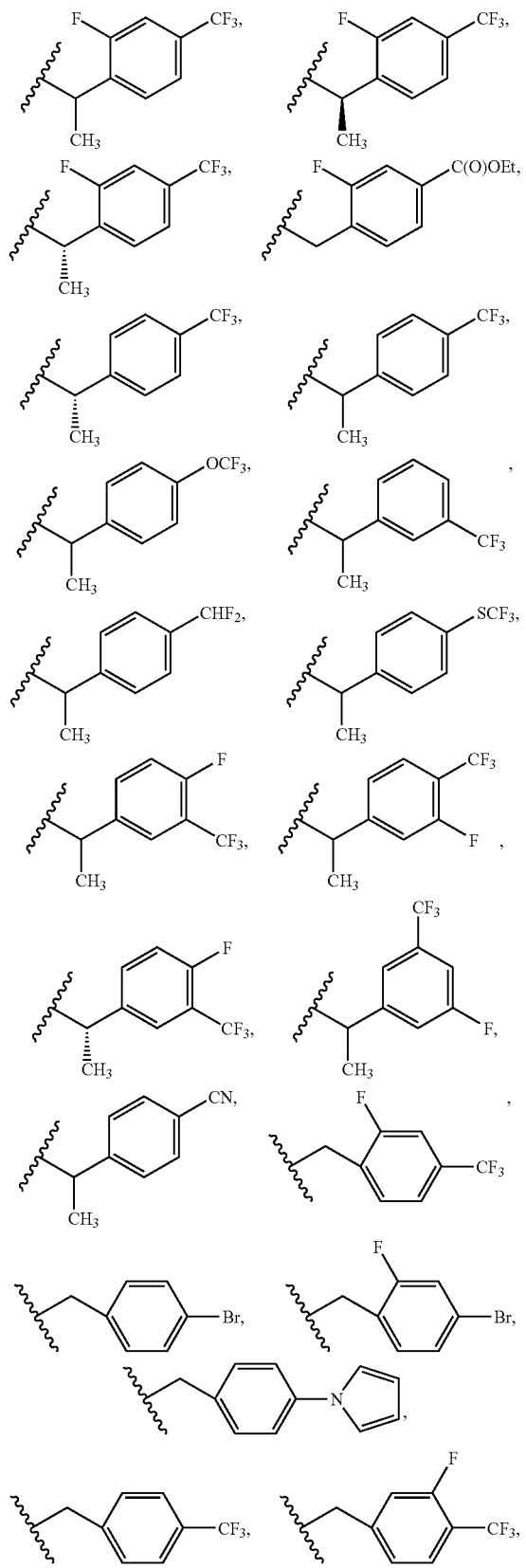
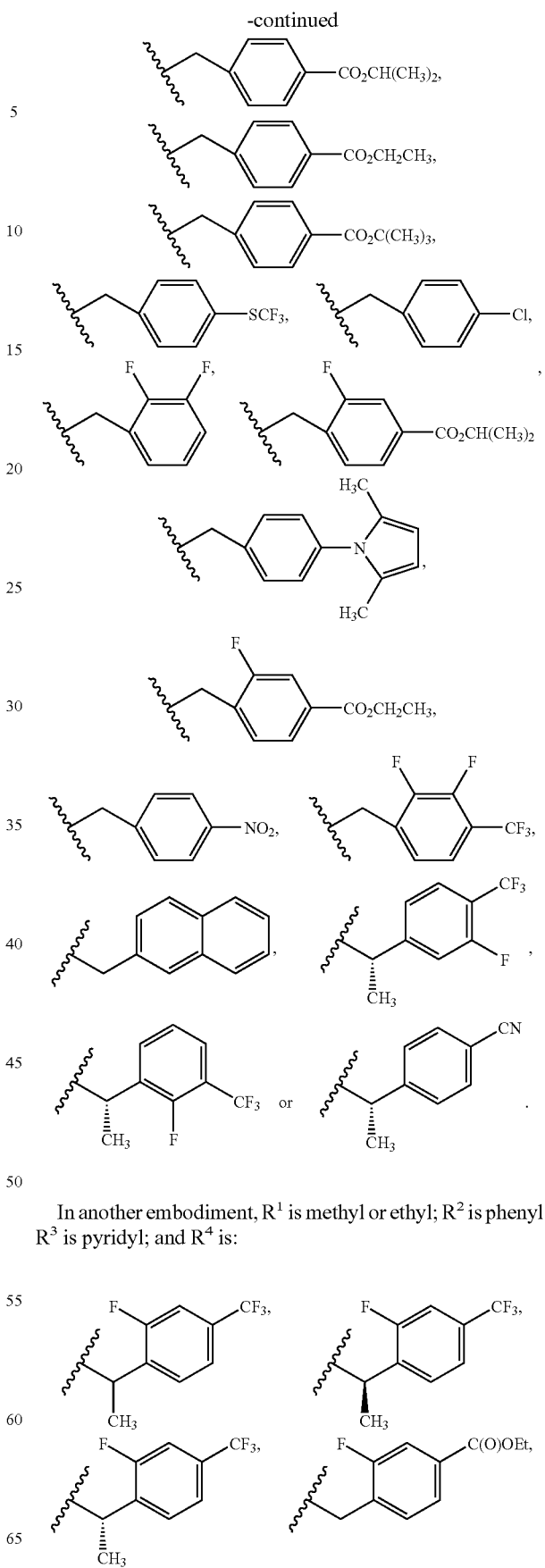
In another embodiment, $R^1$ is methyl or ethyl; $R^2$ is phenyl; $R^3$ is pyridyl; and $R^4$ is:

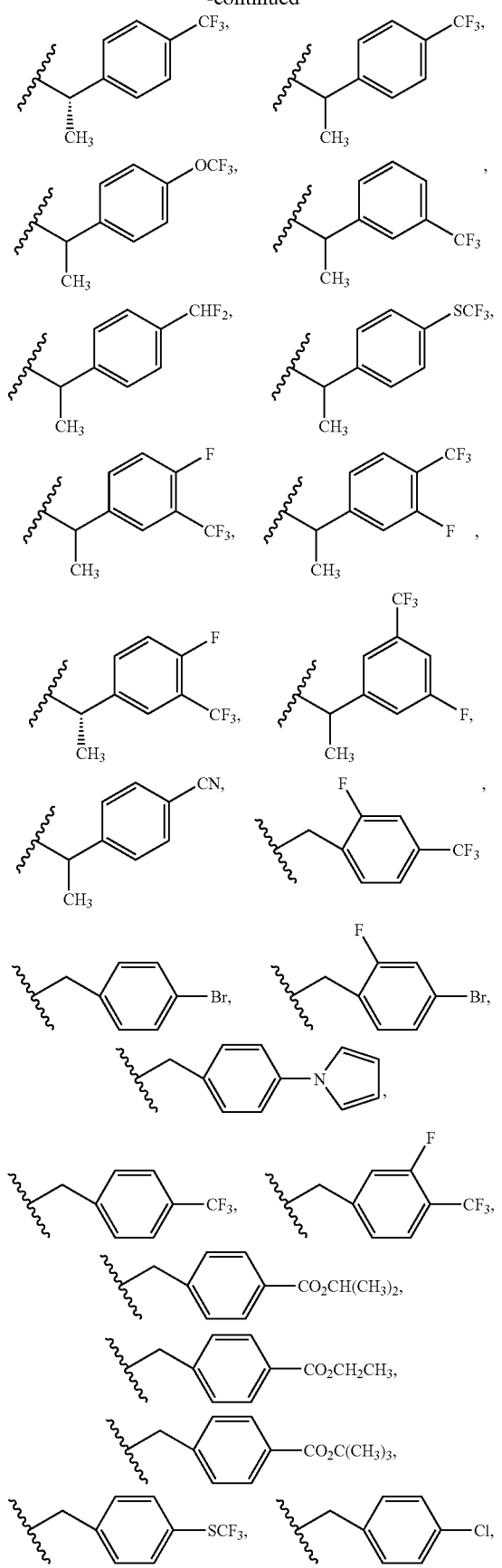
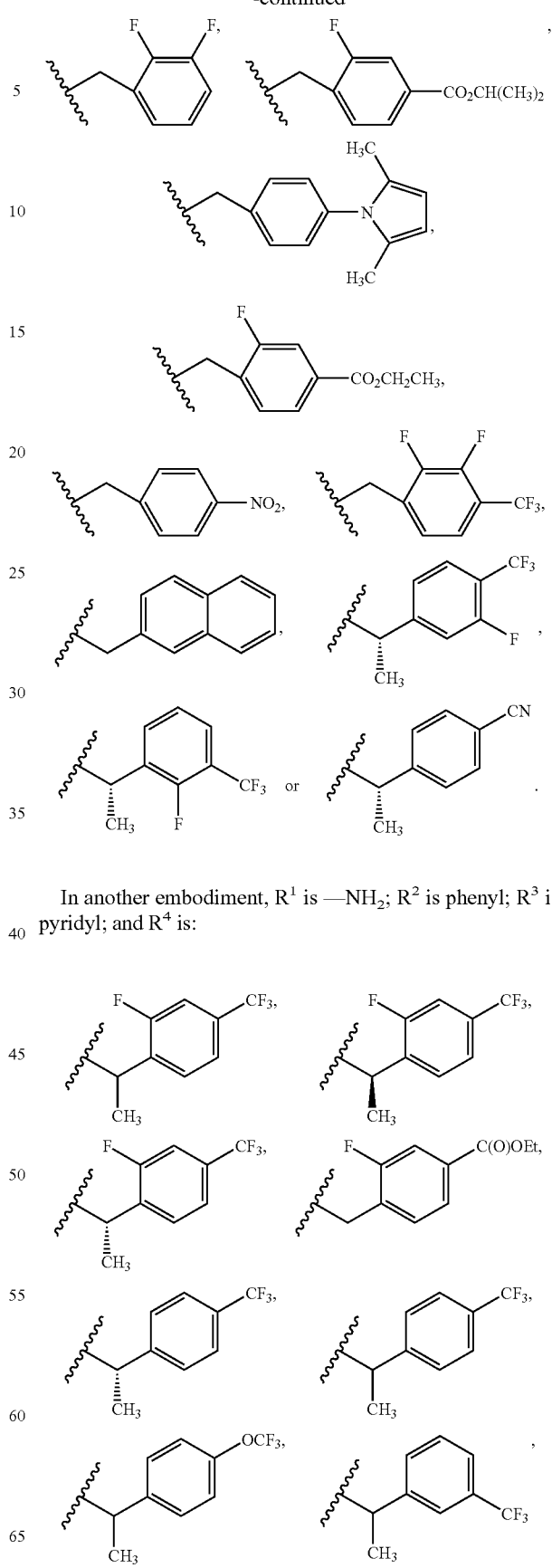
In another embodiment, $R^1$ is —$NH_2$; $R^2$ is phenyl; $R^3$ is pyridyl; and $R^4$ is:

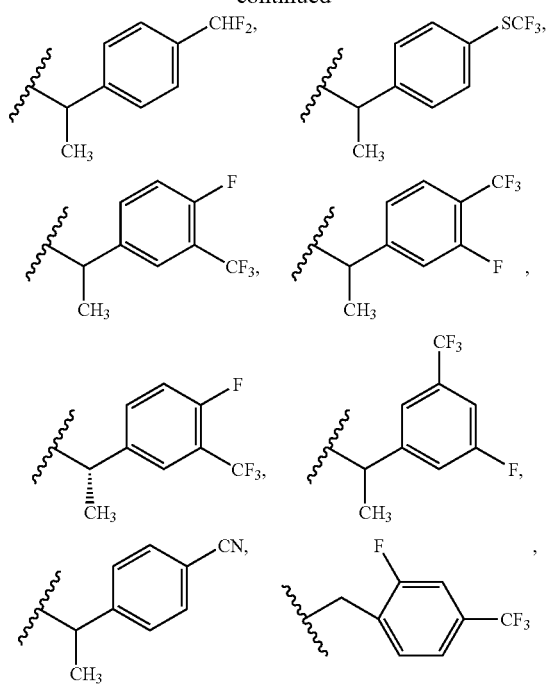
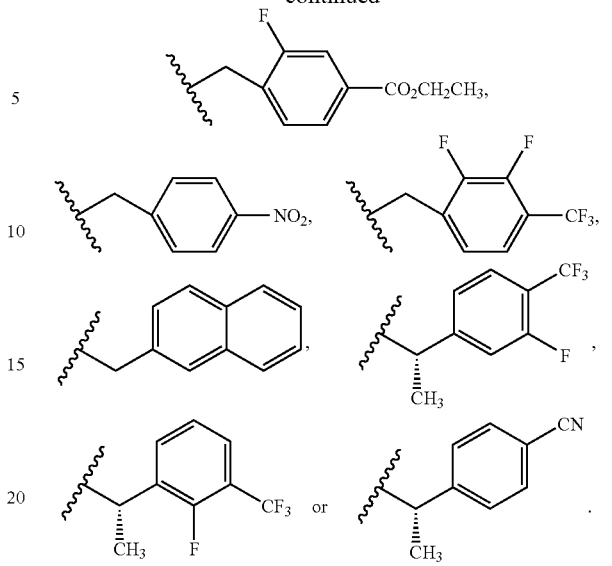
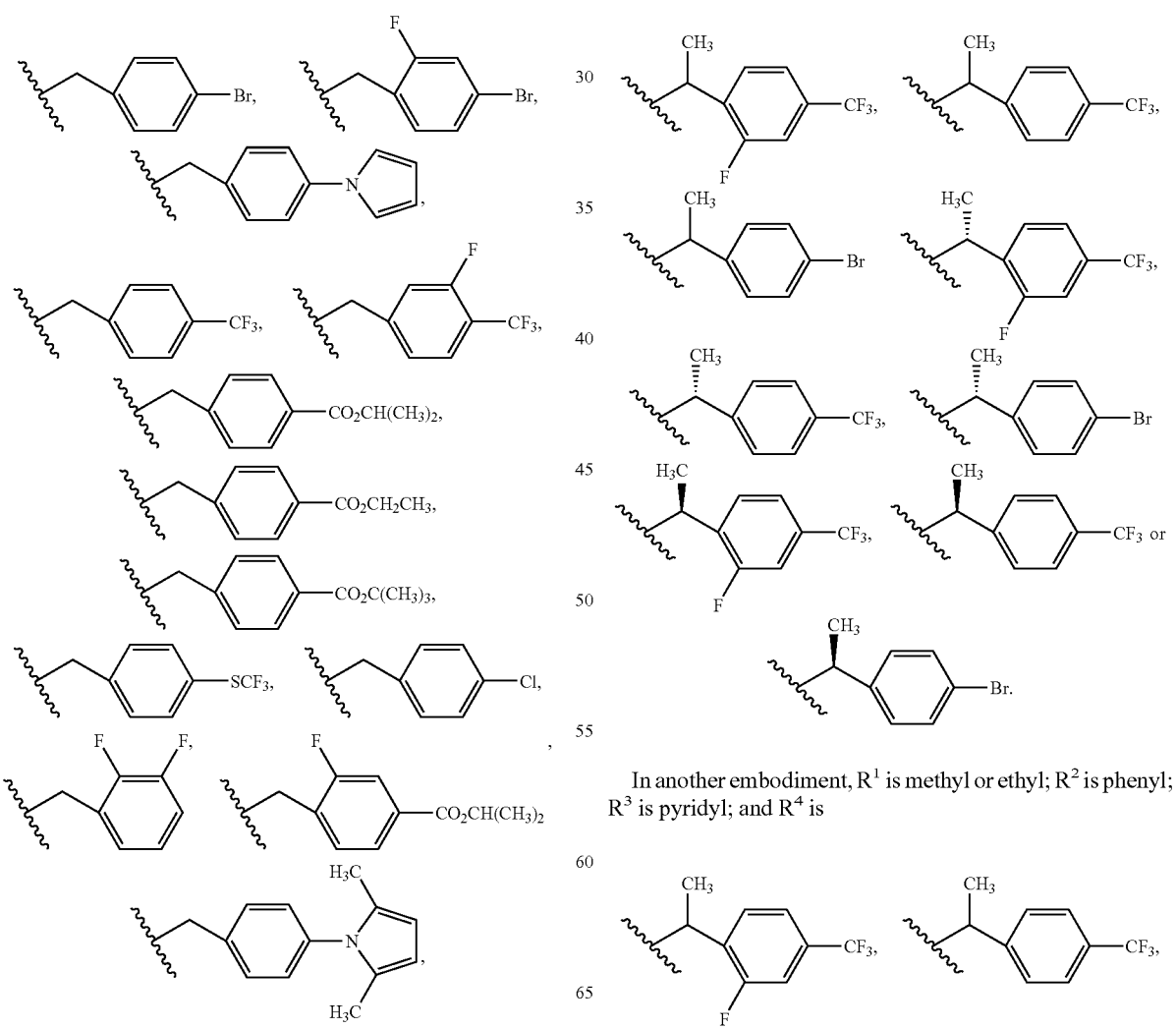
In one embodiment, $R^1$ is alkyl; $R^2$ is phenyl; $R^3$ is pyridyl; and $R^4$ is
In another embodiment, $R^1$ is methyl or ethyl; $R^2$ is phenyl; $R^3$ is pyridyl; and $R^4$ is

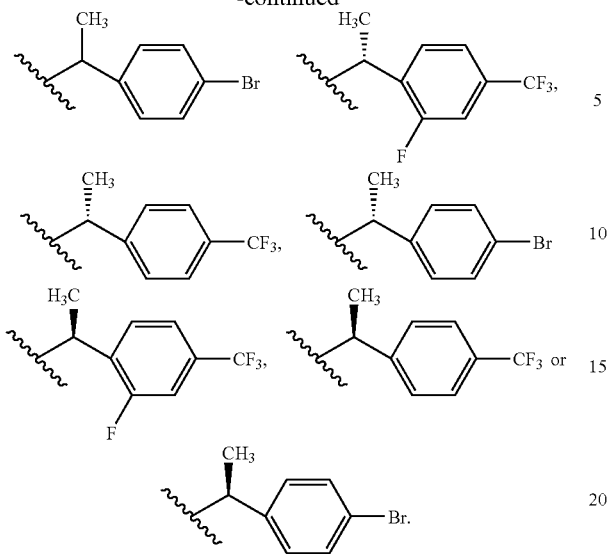

In another embodiment, R¹ is —NH₂; R² is phenyl; R³ is pyridyl; and R⁴ is

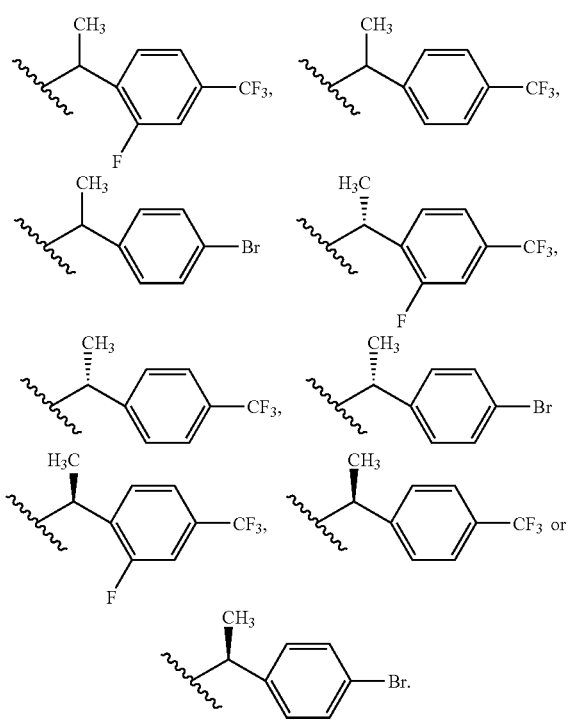

In one embodiment, R¹ is alkyl; R² is phenyl; R³ is pyridyl; and R⁴ is —CH₂-heteroaryl.
In another embodiment, R¹ is methyl or ethyl; R² is phenyl; R³ is pyridyl; and R⁴ is —CH₂-heteroaryl.
In another embodiment, R¹ is —NH₂; R² is phenyl; R³ is pyridyl; and R⁴ is —CH₂-heteroaryl.
In one embodiment, R¹ is alkyl; R² is phenyl; R³ is pyridyl; and R⁴ is —CH(CH₃)— heteroaryl.
In another embodiment, R¹ is methyl or ethyl; R² is phenyl; R³ is pyridyl; and R⁴ is —CH(CH₃)-heteroaryl.
In another embodiment, R¹ is —NH₂; R² is phenyl; R³ is pyridyl; and R⁴ is —CH(CH₃)-heteroaryl.

In one embodiment, R¹ is alkyl; R² is phenyl; R³ is pyridyl; and R⁴ is

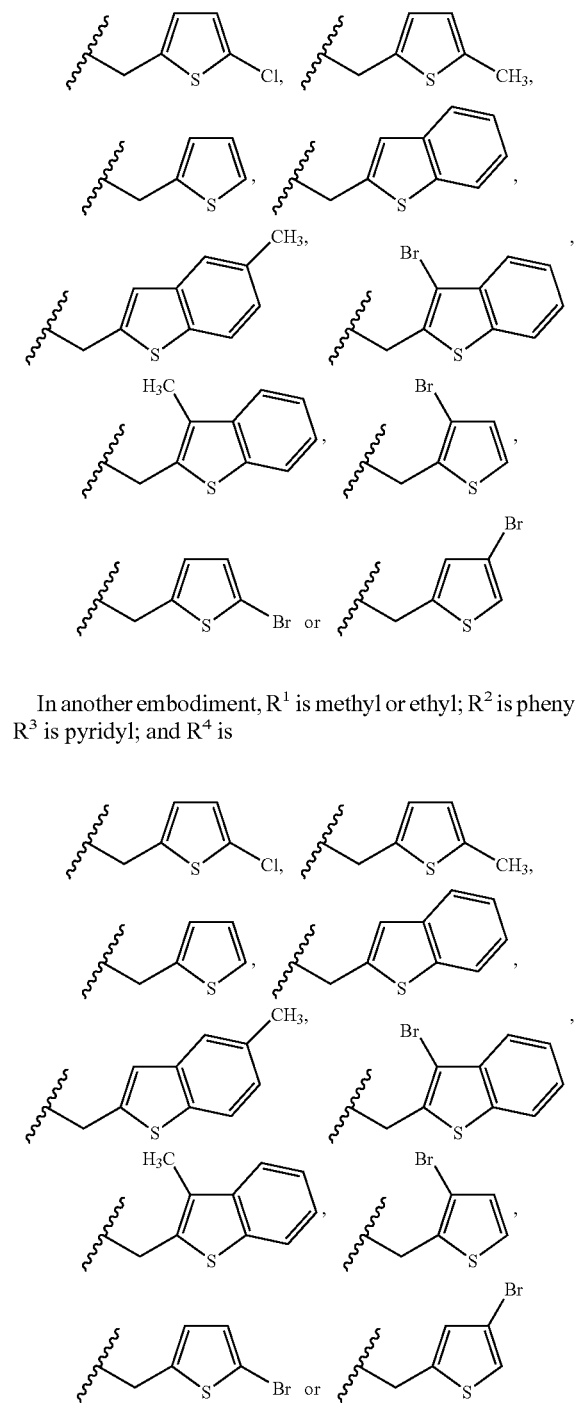

In another embodiment, R¹ is methyl or ethyl; R² is phenyl; R³ is pyridyl; and R⁴ is In another embodiment, R¹ is —NH₂; R² is phenyl; R³ is pyridyl; and R⁴ is

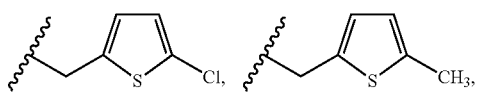

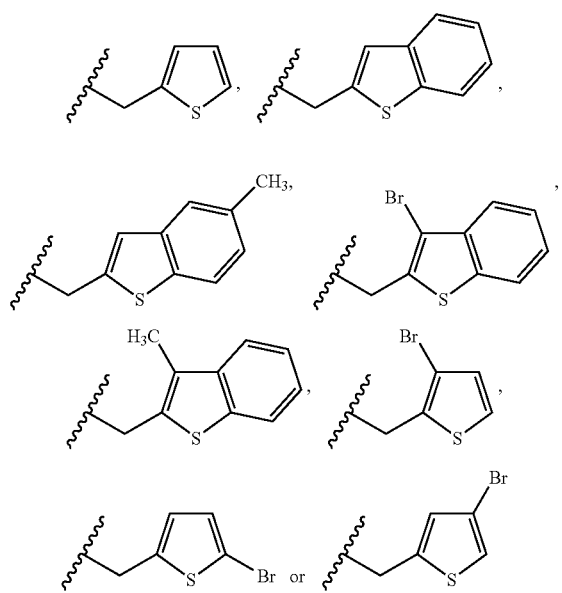

In one embodiment, $R^1$ is alkyl; $R^2$ is phenyl; $R^3$ is 4-fluorophenyl; and $R^4$ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is methyl or ethyl; $R^2$ is phenyl; and $R^3$ is 4-fluorophenyl; and $R^4$ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is —NH$_2$; $R^2$ is phenyl; $R^3$ is 4-fluorophenyl; and $R^4$ is -benzyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In one embodiment, $R^1$ is alkyl; $R^2$ is phenyl; $R^3$ is 4-fluorophenyl; and $R^4$ is —CH(CH$_3$)-phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is methyl or ethyl; $R^2$ is phenyl; $R^3$ is 4-fluorophenyl; and $R^4$ is —CH(CH$_3$)-phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In another embodiment, $R^1$ is —NH$_2$; $R^2$ is phenyl; $R^3$ is 4-fluorophenyl; and $R^4$ is —CH(CH$_3$)-phenyl, wherein the phenyl ring of the benzyl group can be optionally substituted with up to 3 substituents, which may be the same or different, and are selected from: halo, haloalkyl, heteroaryl, —C(O)O-alkyl, —S-haloalkyl or —NO$_2$.

In one embodiment, $R^1$ is alkyl; $R^2$ is phenyl; $R^3$ is 4-fluorophenyl; and $R^4$ is:

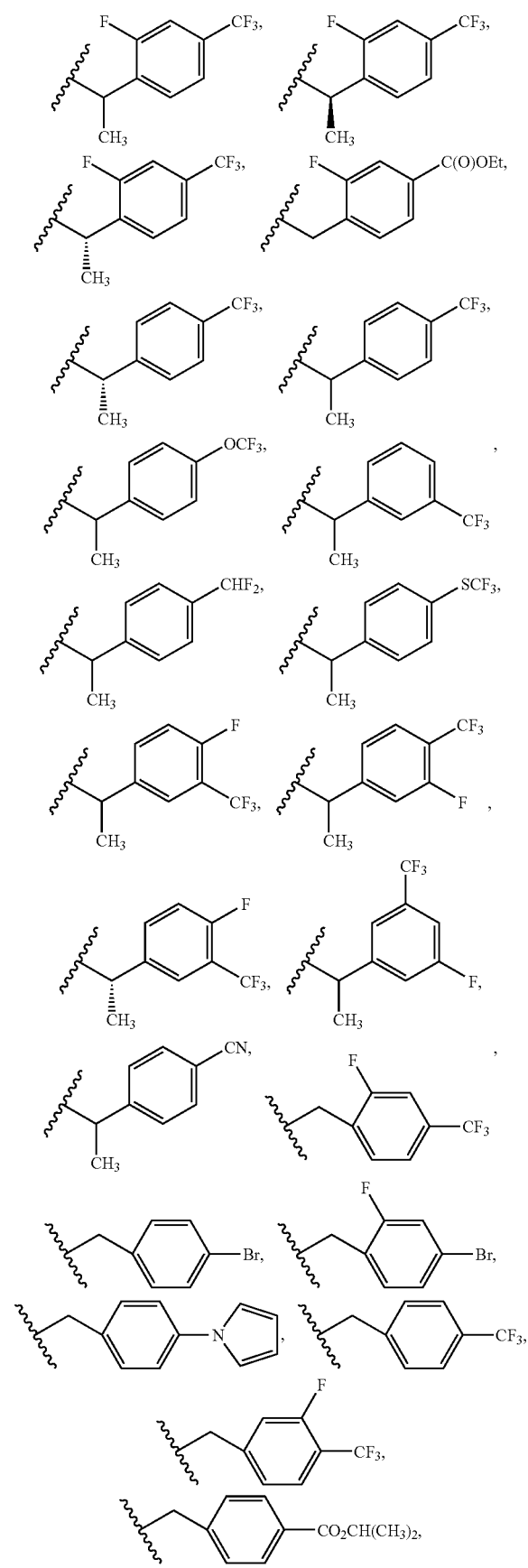

-continued
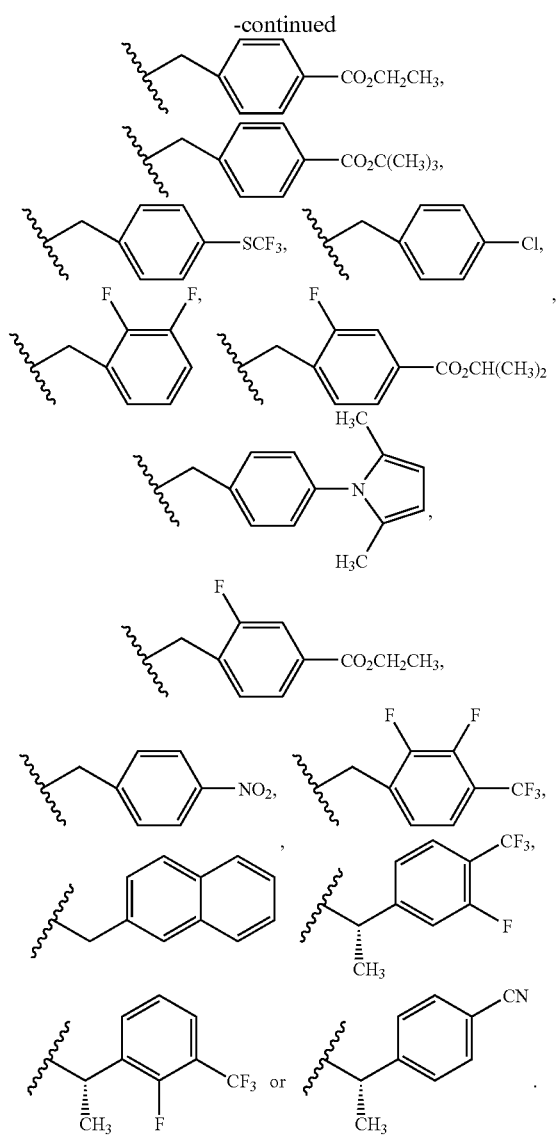
In another embodiment, $R^1$ is methyl or ethyl; $R^2$ is phenyl; $R^3$ is 4-fluorophenyl; and $R^4$ is:
-continued
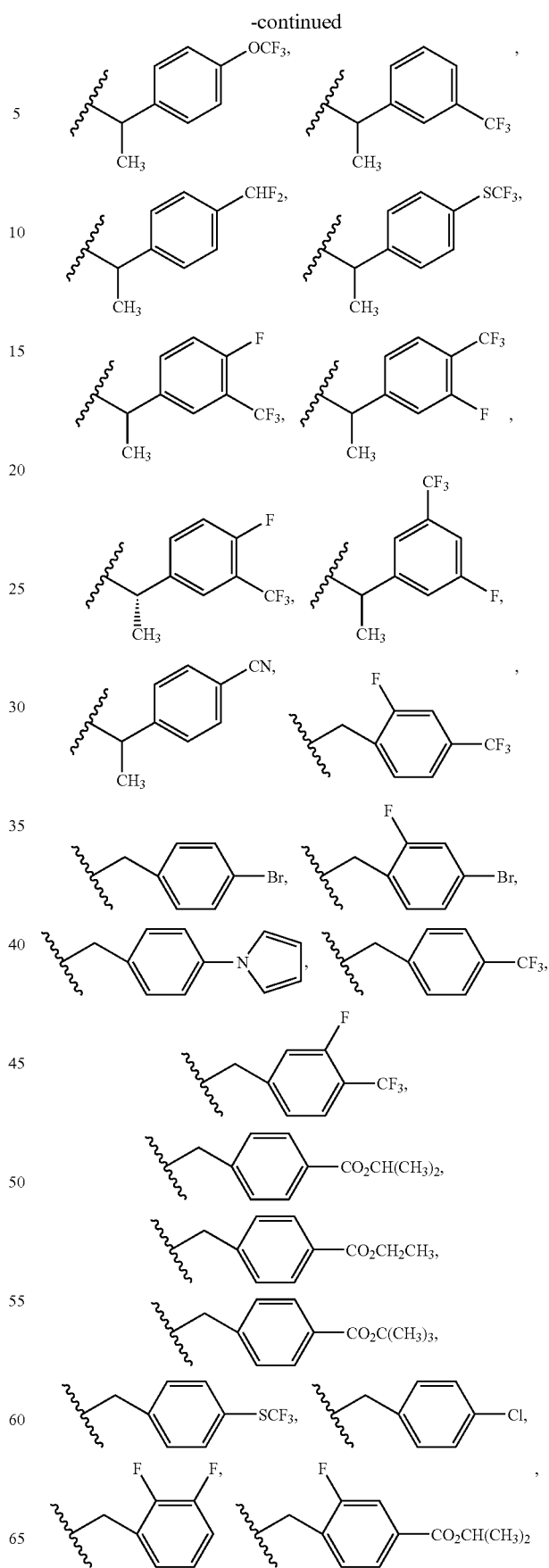

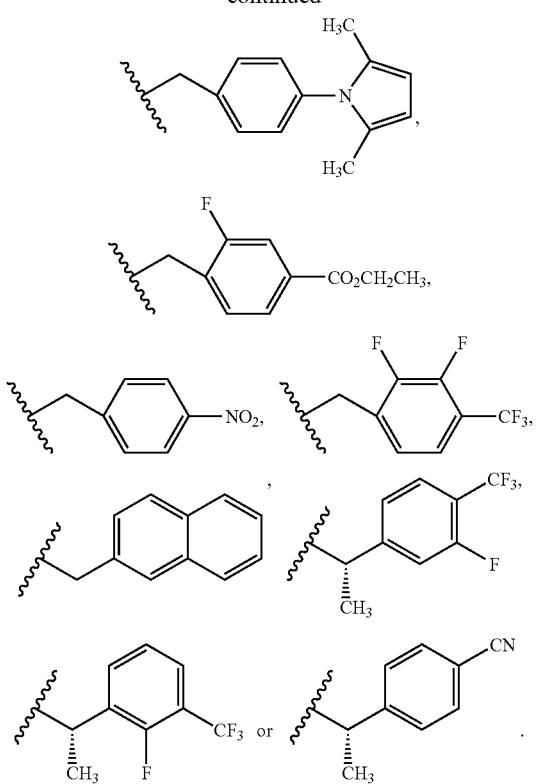
In another embodiment, $R^1$ is —NH$_2$; $R^2$ is phenyl; $R^3$ is 4-fluorophenyl; and $R^4$ is:
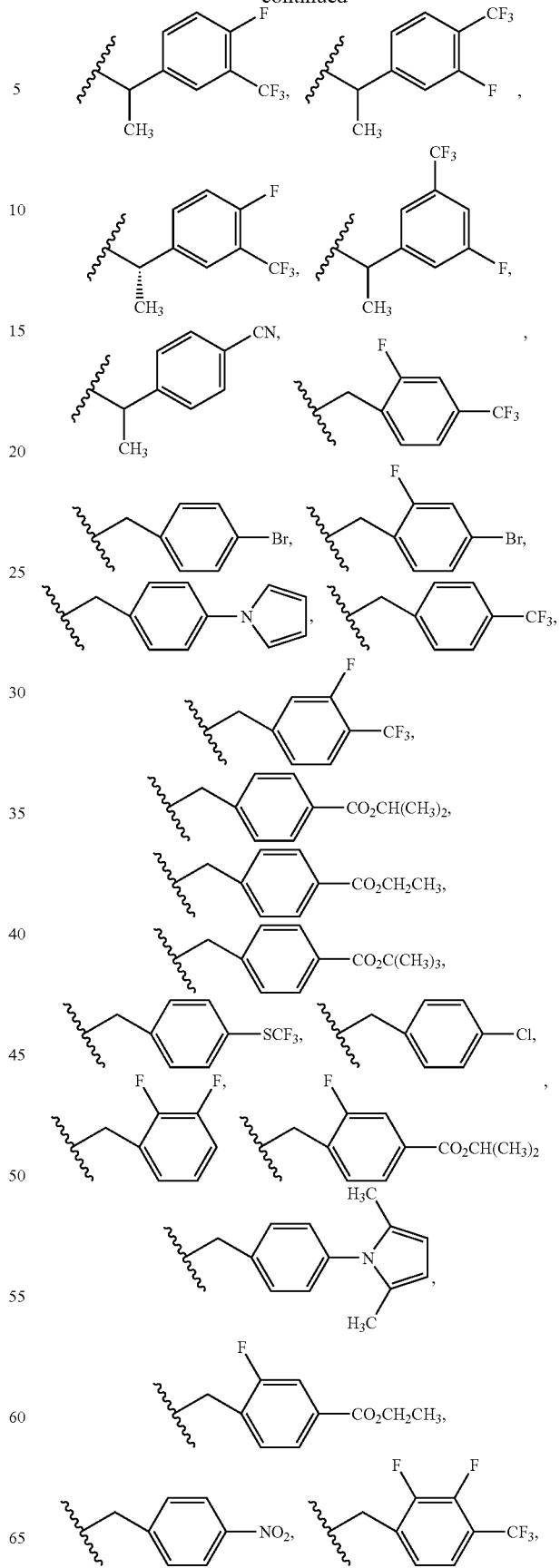

-continued

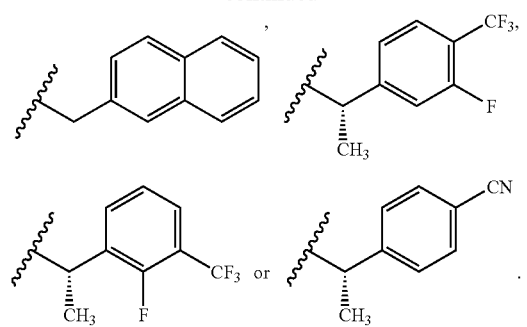

In one embodiment, $R^1$ is alkyl; $R^2$ is phenyl; $R^3$ is 4-fluorophenyl; and $R^4$ is

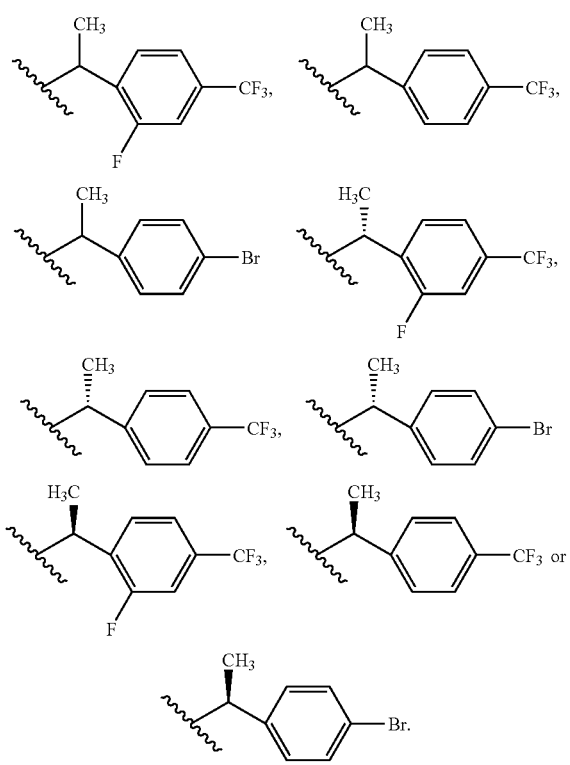

In another embodiment, $R^1$ is methyl or ethyl; $R^2$ is phenyl; $R^3$ is 4-fluorophenyl; and $R^4$ is

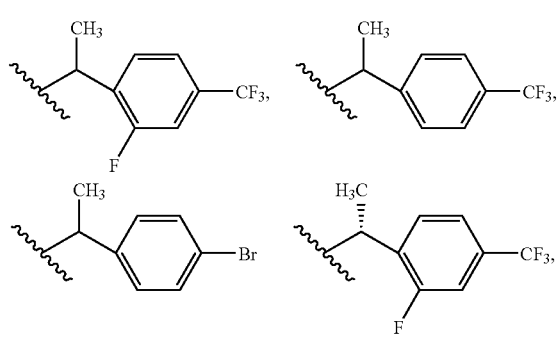

-continued

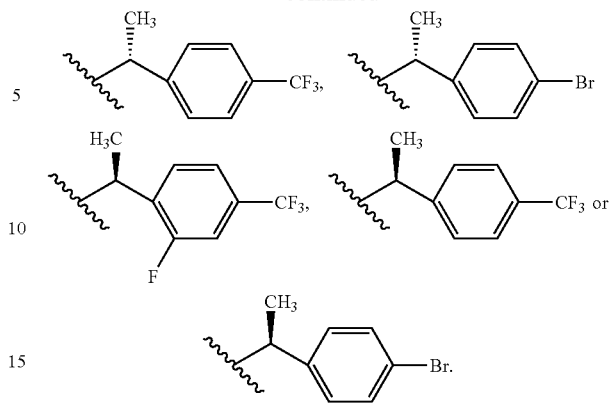

In another embodiment, $R^1$ is —$NH_2$; $R^2$ is phenyl; $R^3$ is 4-fluorophenyl; and $R^4$ is

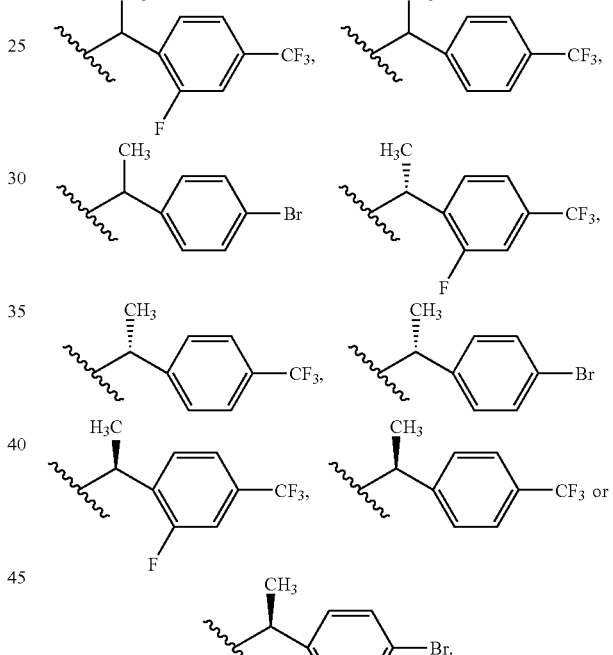

In one embodiment, $R^1$ is alkyl; $R^2$ is phenyl; $R^3$ is 4-fluorophenyl; and $R^4$ is —$CH_2$-heteroaryl.

In another embodiment, $R^1$ is methyl or ethyl; $R^2$ is phenyl; $R^3$ is 4-fluorophenyl; and $R^4$ is —$CH_2$-heteroaryl.

In another embodiment, $R^1$ is —$NH_2$; $R^2$ is phenyl; $R^3$ is 4-fluorophenyl; and $R^4$ is —$CH_2$-heteroaryl.

In one embodiment, $R^1$ is alkyl; $R^2$ is phenyl; $R^3$ is 4-fluorophenyl; and $R^4$ is —$CH(CH_3)$-heteroaryl.

In another embodiment, $R^1$ is methyl or ethyl; $R^2$ is phenyl; $R^3$ is 4-fluorophenyl; and $R^4$ is —$CH(CH_3)$-heteroaryl.

In another embodiment, $R^1$ is —$NH_2$; $R^2$ is phenyl; $R^3$ is 4-fluorophenyl; and $R^4$ is —$CH(CH_3)$-heteroaryl.

In one embodiment, $R^1$ is alkyl; $R^2$ is phenyl; $R^3$ is 4-fluorophenyl; and $R^4$ is

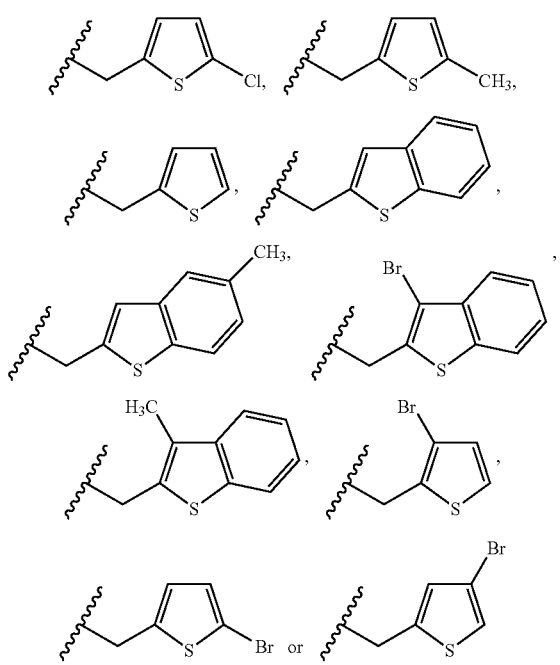

In another embodiment, $R^1$ is methyl or ethyl; $R^2$ is phenyl; $R^3$ is 4-fluorophenyl; and $R^4$ is

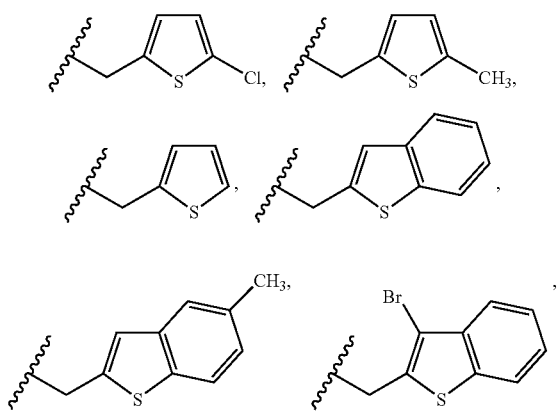

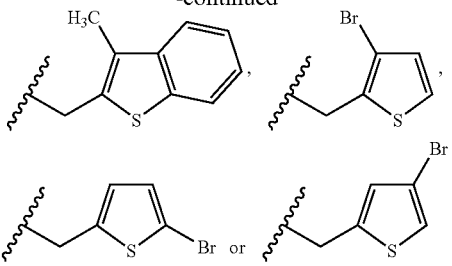

In another embodiment, $R^1$ is —$NH_2$; $R^2$ is phenyl; $R^3$ is 4-fluorophenyl; and $R^4$ is

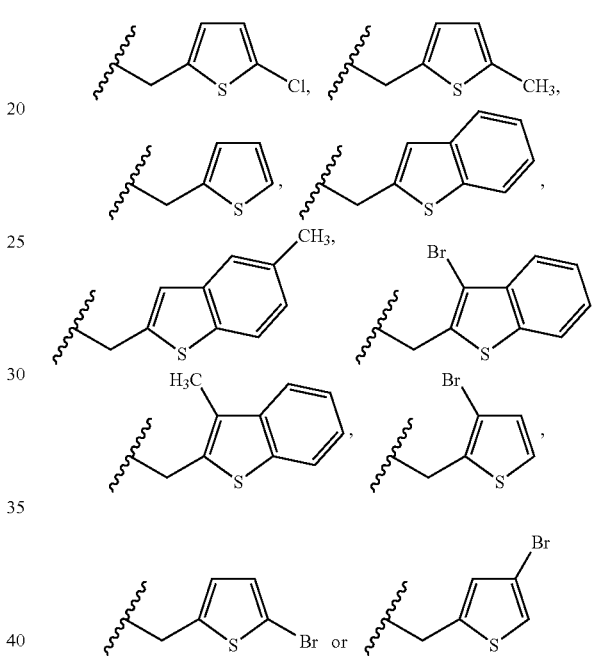

In one embodiment, for the compounds of formula (I), variables R, $R^1$, $R^2$, $R^3$, $R^4$, $R^{10}$, $R^{11}$ and $R^{12}$ are selected independently of each other.

In one embodiment, a compound of formula (I) is in purified form.

Non-limiting examples of the Pyrimidinone Derivatives of formula (I) include compounds 1-352 as depicted below:

| No. | Structure |
|---|---|
| 1 | 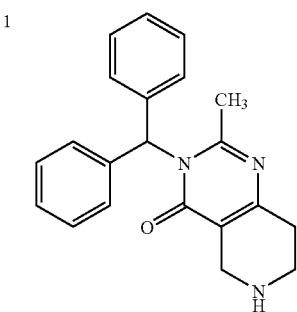 |

| No. | Structure |
|---|---|
| 2 | 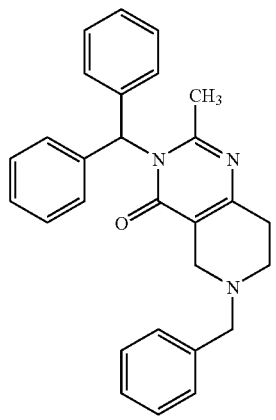 |
| 3 | 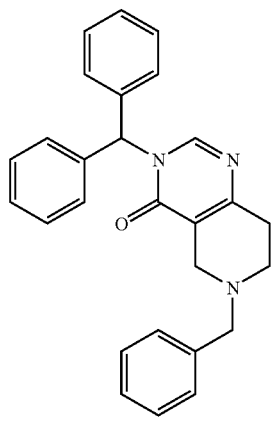 |
| 4 | 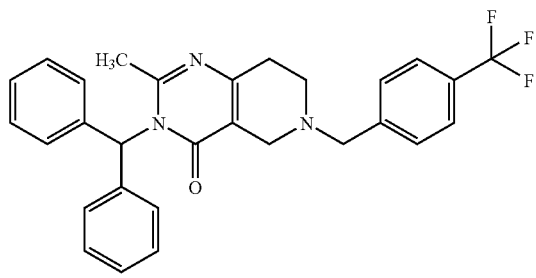 |
| 5 | 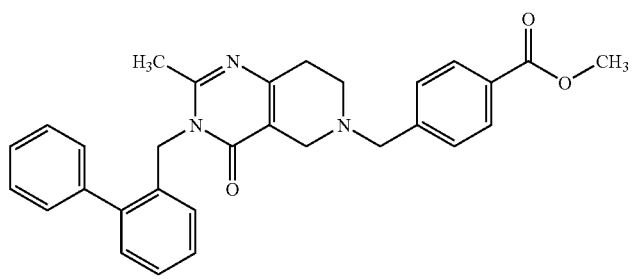 |

-continued
| No. | Structure |
|---|---|
| 6 | 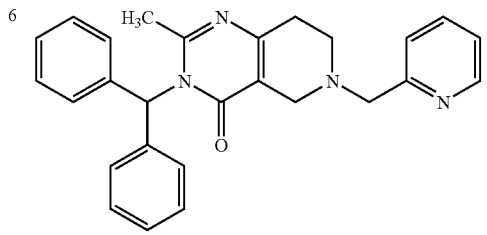 |
| 7 | 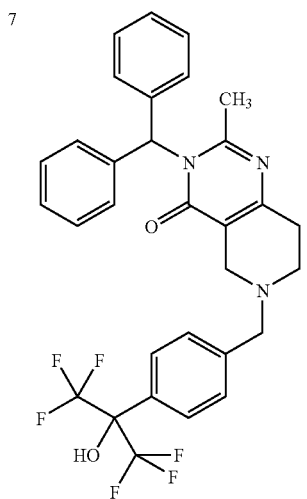 |
| 8 | 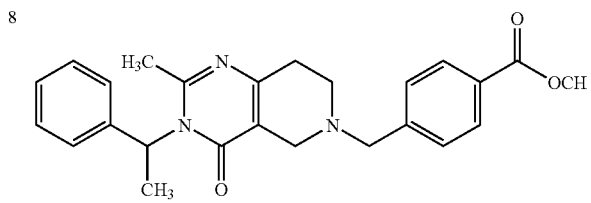 |
| 9 | 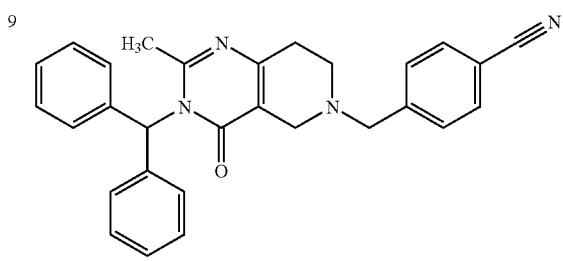 |
| 10 | 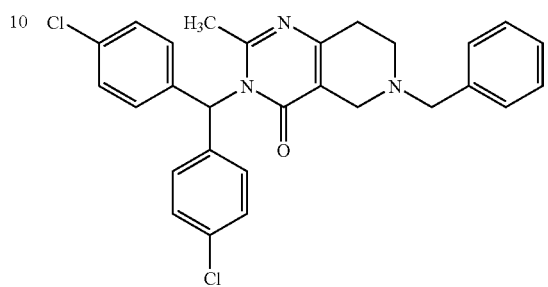 |

| No. | Structure |
|---|---|
| 11 | 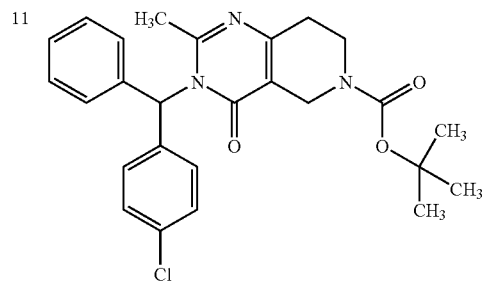 |
| 12 | 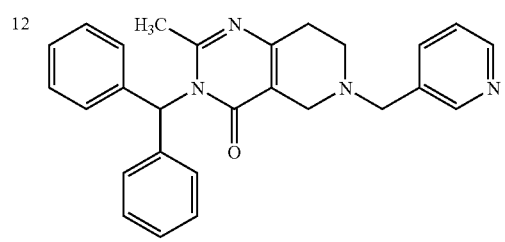 |
| 13 | 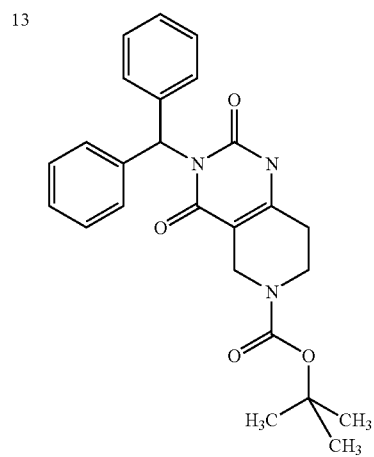 |
| 14 | 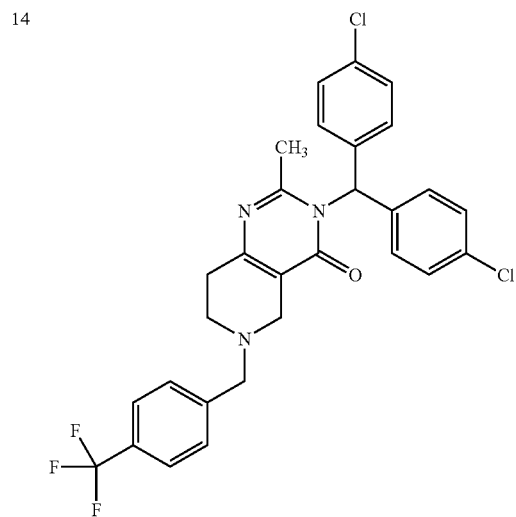 |

-continued
| No. | Structure |
|-----|-----------|
| 15 | 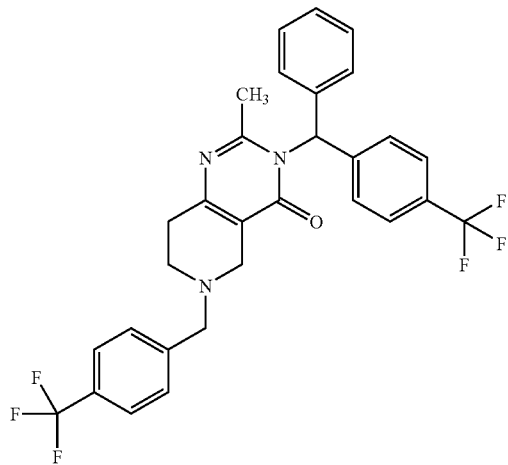 |
| 16 | 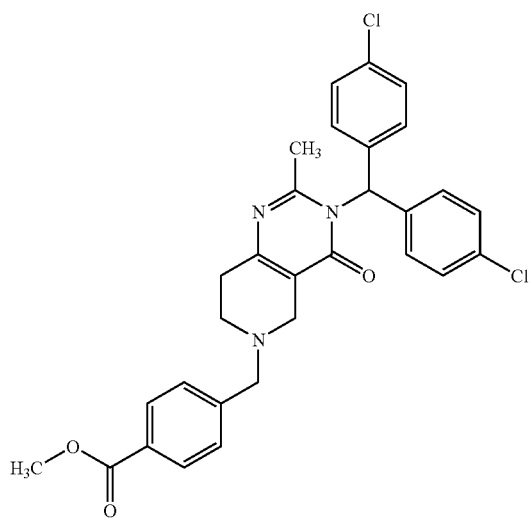 |
| 17 | 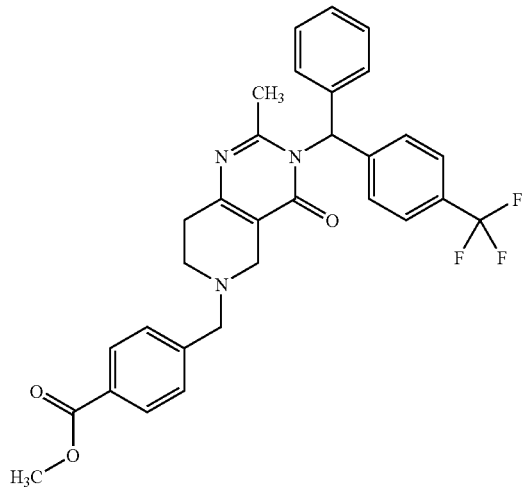 |

-continued
| No. | Structure |
|---|---|
| 18 | 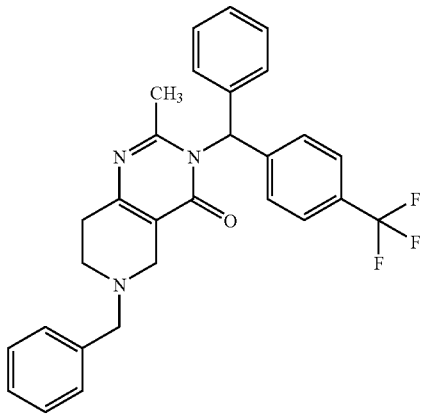 |
| 19 | 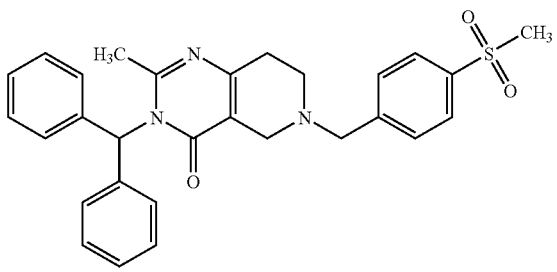 |
| 20 | 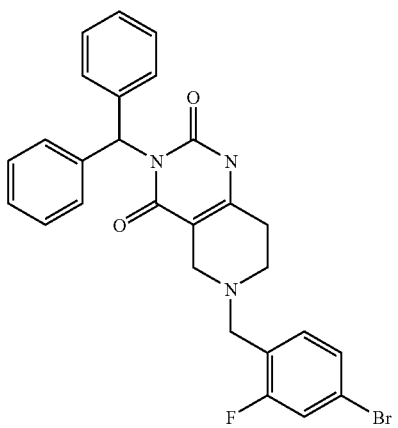 |
| 21 | 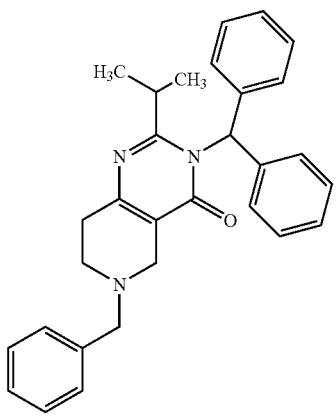 |

-continued
| No. | Structure |
|---|---|
| 22 | 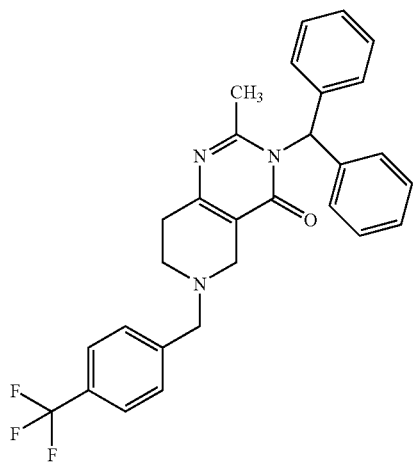 |
| 23 | 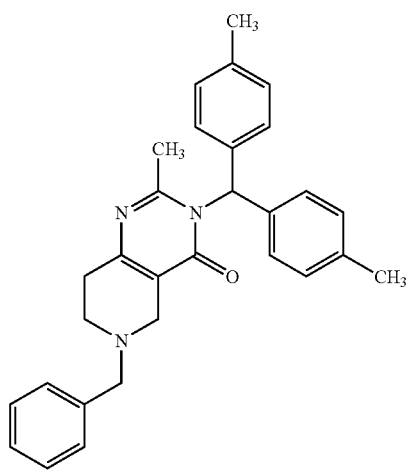 |
| 24 | 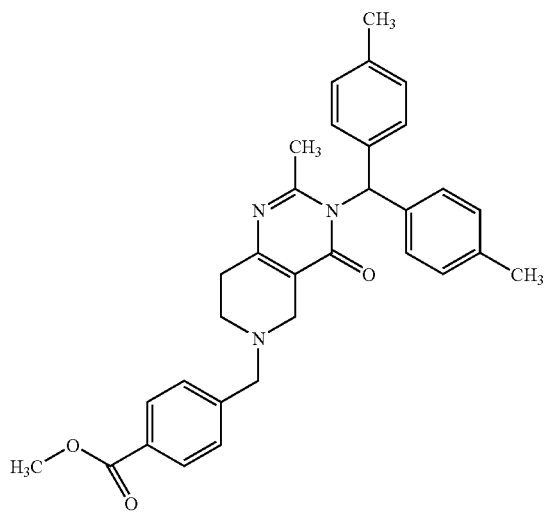 |

-continued
| No. | Structure |
|---|---|
| 25 | 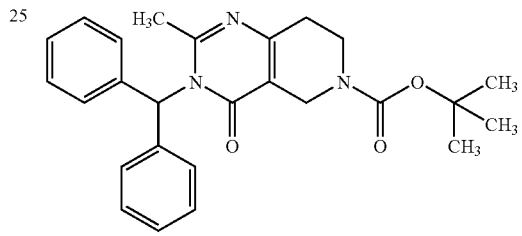 |
| 26 | 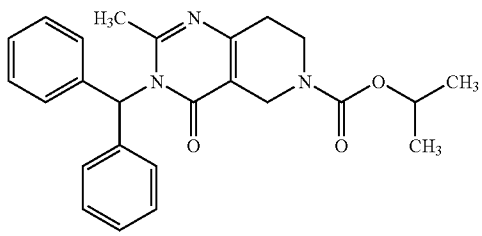 |
| 27 | 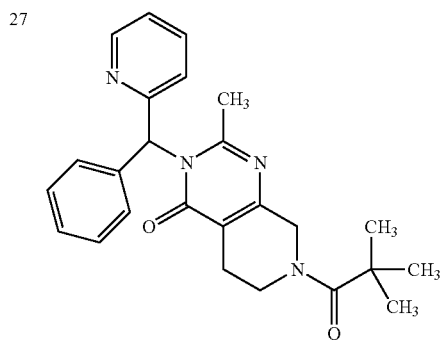 |
| 28 | 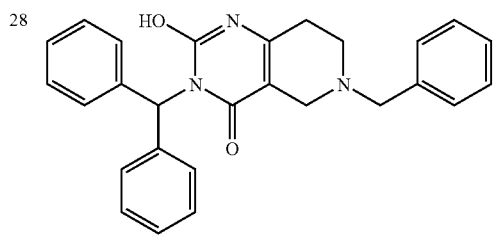 |
| 29 | 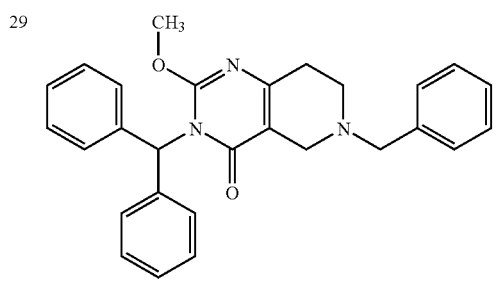 |

| No. | Structure |
|---|---|
| 30 | 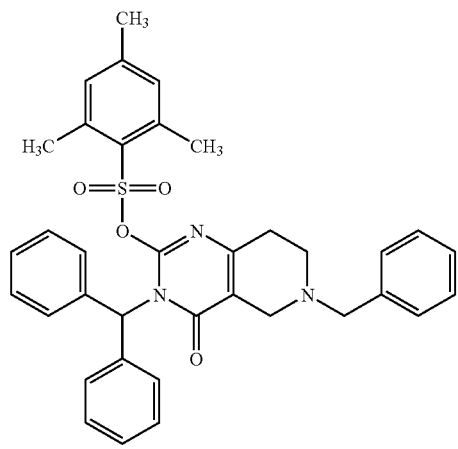 |
| 31 | 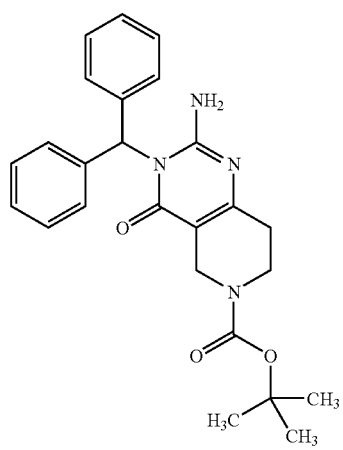 |
| 32 | 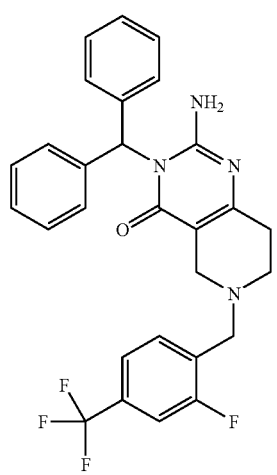 |

-continued
| No. | Structure |
|---|---|
| 33 | 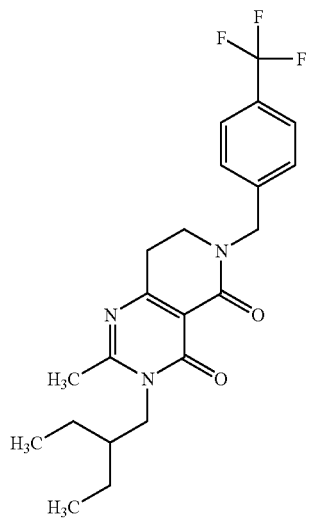 |
| 34 | 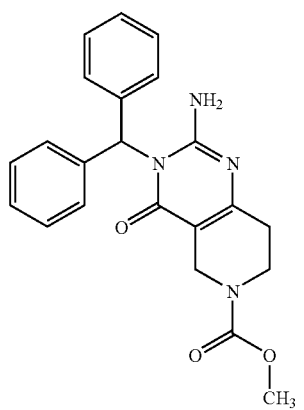 |
| 35 | 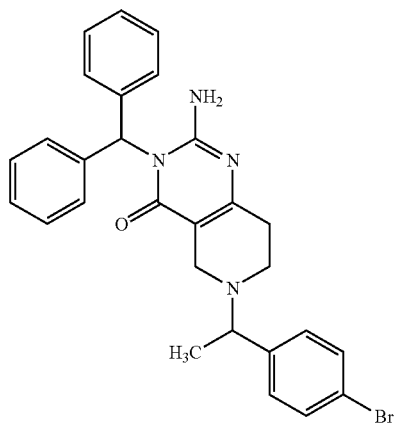 |

-continued
| No. | Structure |
|---|---|
| 36 | 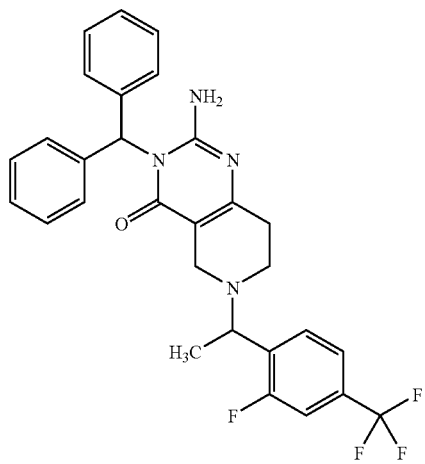 |
| 37 | 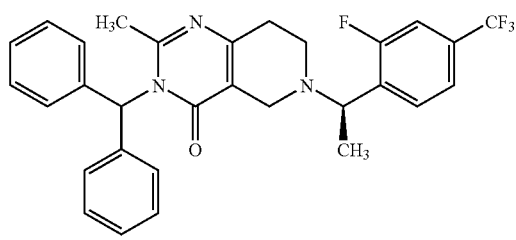<br>Enantiomer 1 |
| 38 | 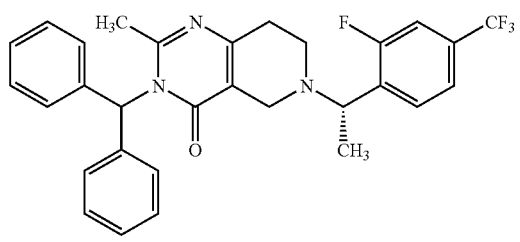<br>Enantiomer 2 |
| 39 | 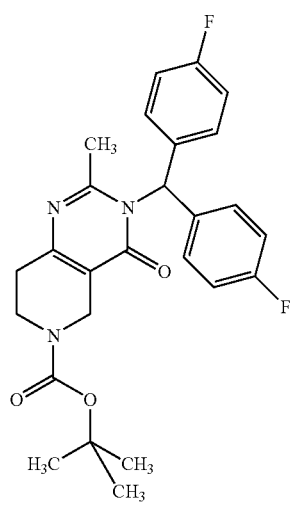 |

-continued
| No. | Structure |
|---|---|
| 40 | 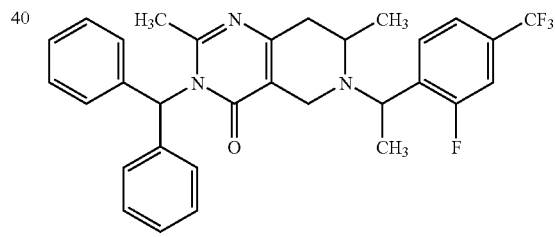
Isomer 1 |
| 41 | 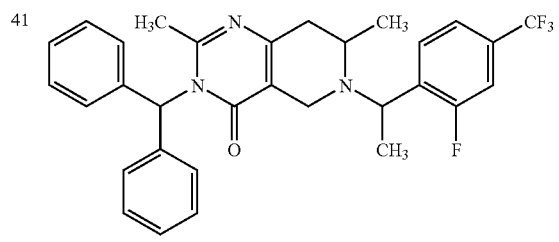
Isomer 2 |
| 42 | 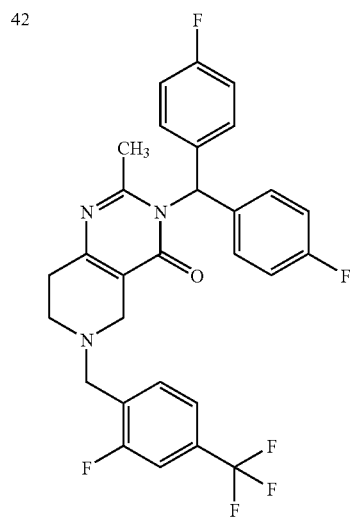 |
| 43 | 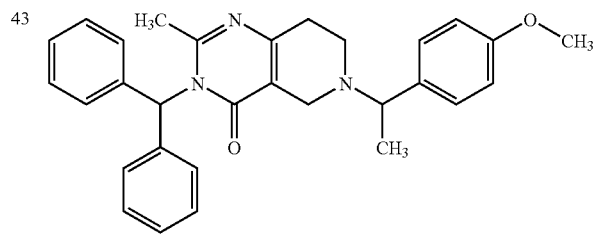 |
| 44 | 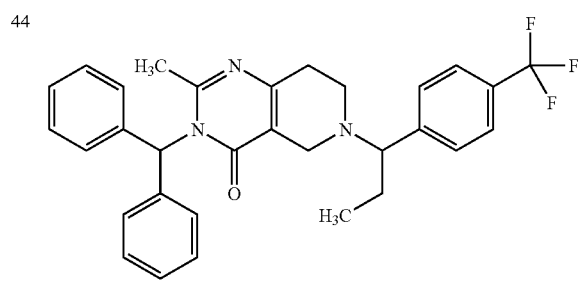 |

-continued
| No. | Structure |
|---|---|
| 45 | 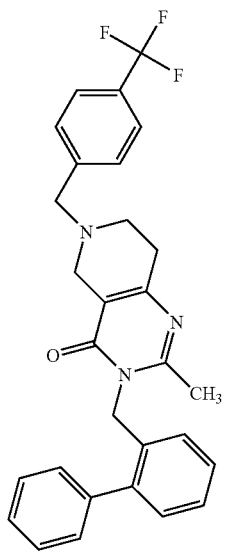 |
| 46 | 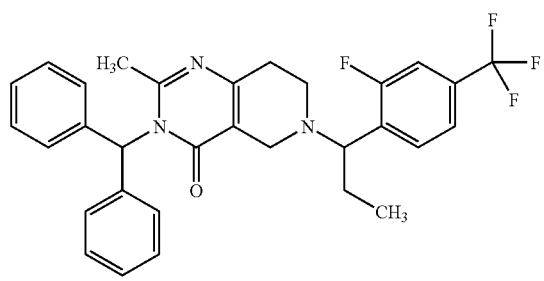 |
| 47 | 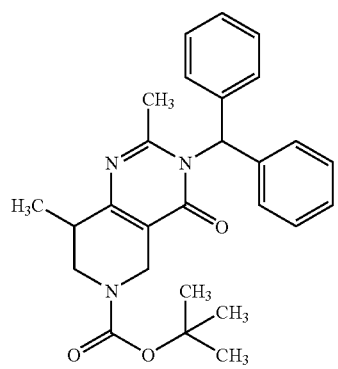 |
| 48 | 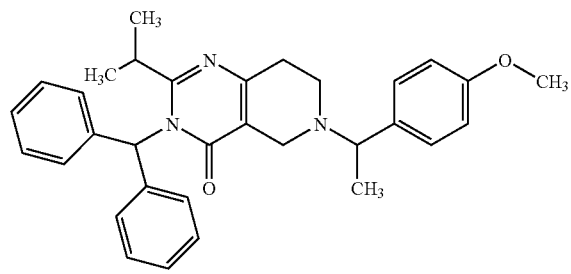 |

-continued
| No. | Structure |
|---|---|
| 49 | 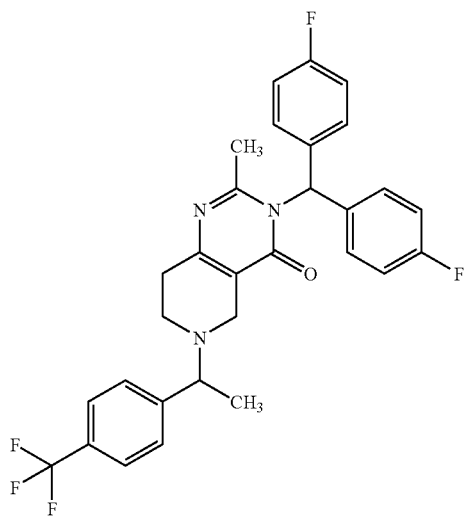 |
| 50 | 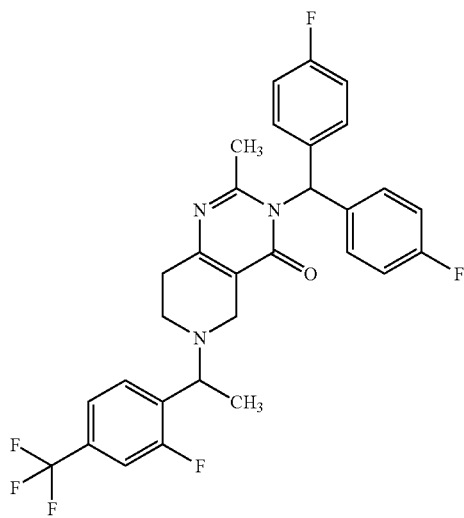 |
| 51 | 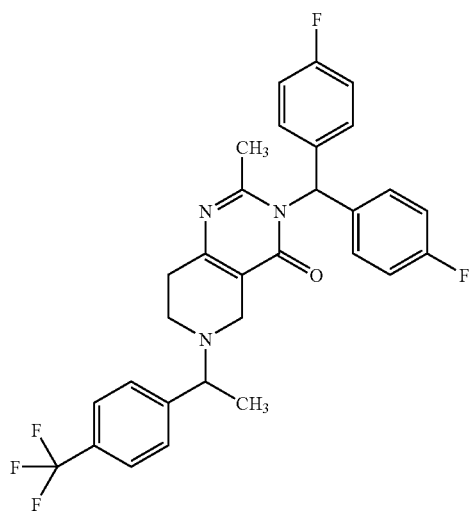 |

| No. | Structure |
|---|---|
| 52 | 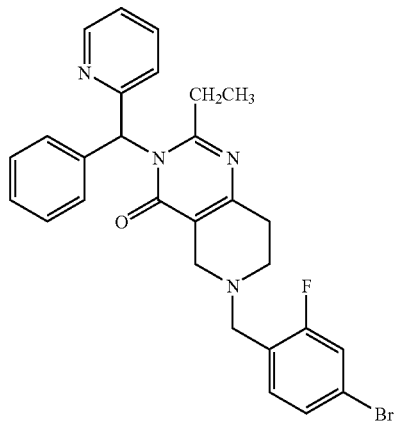 |
| 53 | 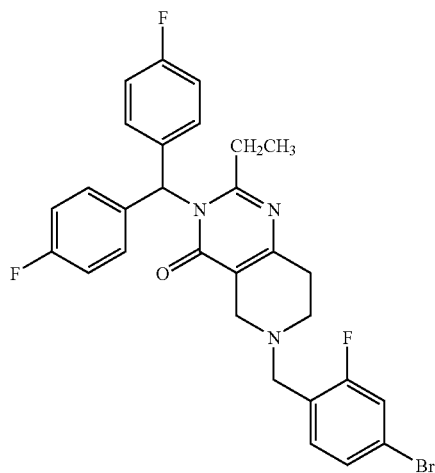 |
| 54 | 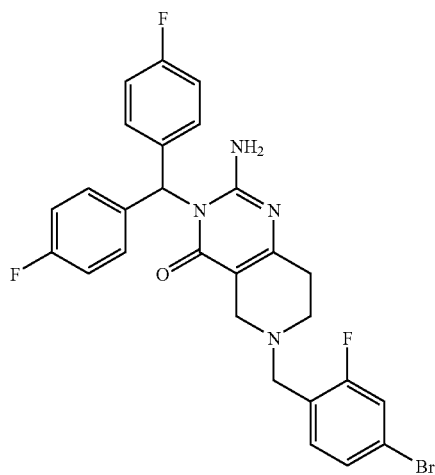 |

-continued
| No. | Structure |
|---|---|
| 55 | 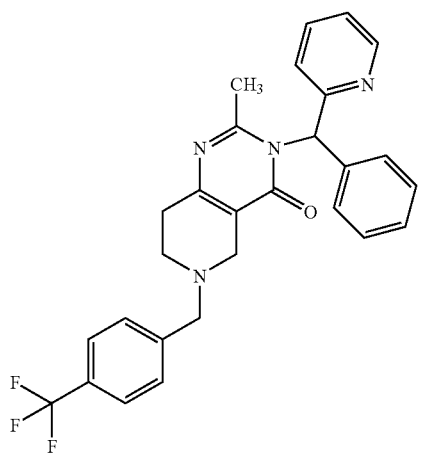 |
| 56 | 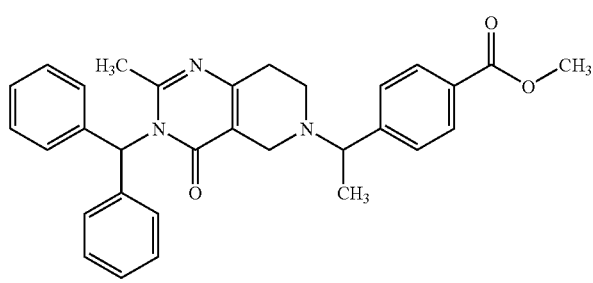 |
| 57 | 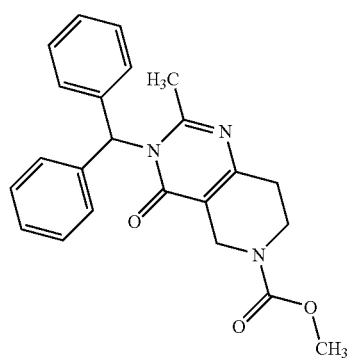 |
| 58 | 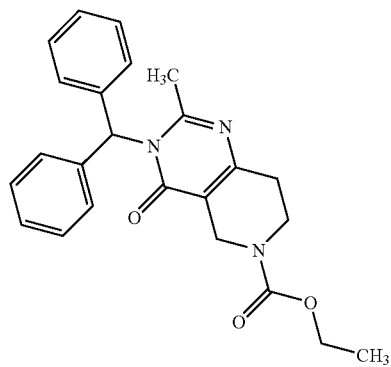 |

-continued
| No. | Structure |
|---|---|
| 59 | 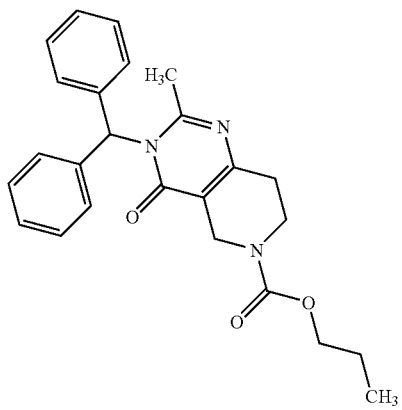 |
| 60 | 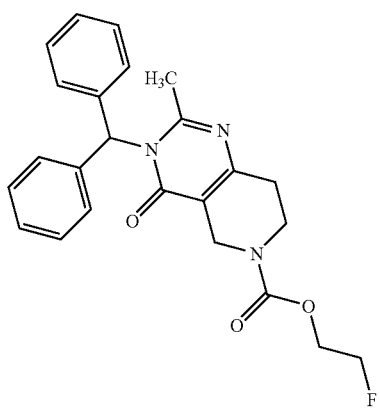 |
| 61 | 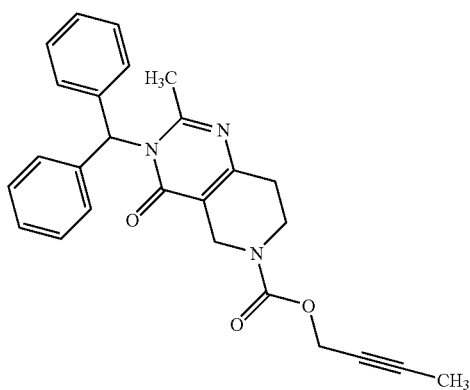 |

-continued
| No. | Structure |
|---|---|
| 62 | 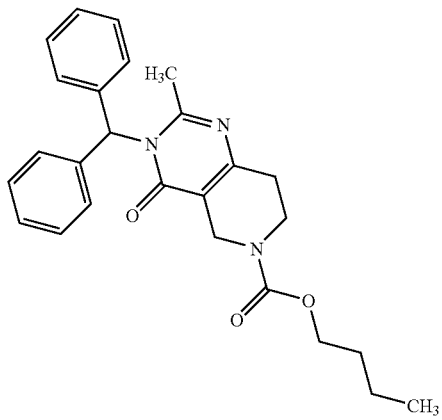 |
| 63 | 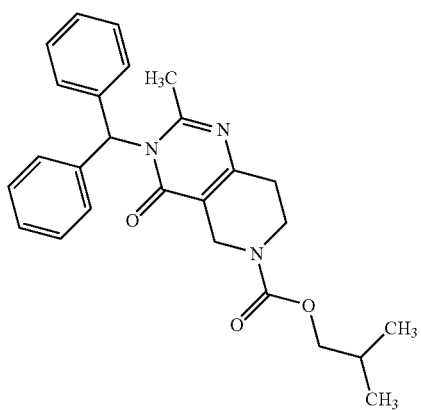 |
| 64 | 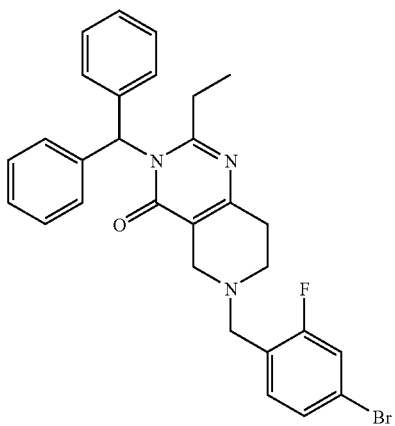 |

| No. | Structure |
|---|---|
| 65 | 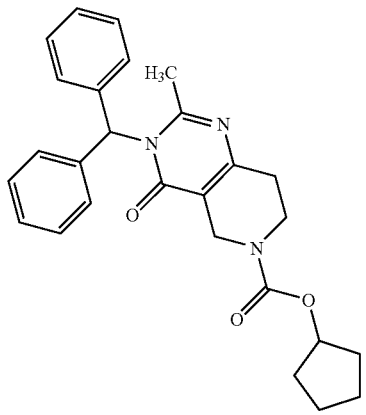 |
| 66 | 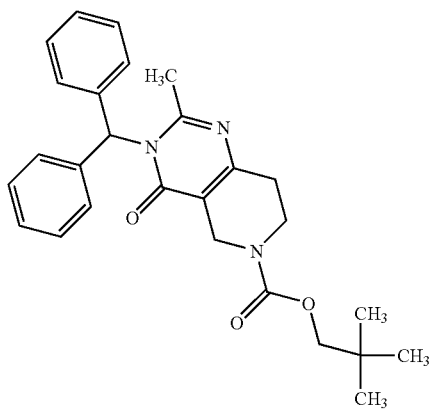 |
| 67 | 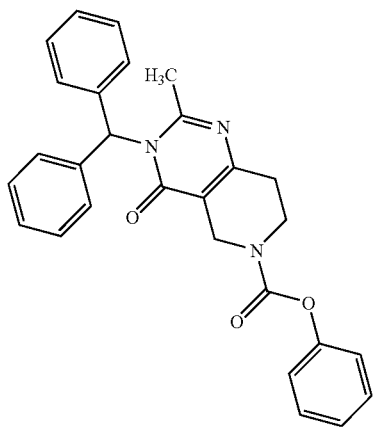 |

-continued
| No. | Structure |
|---|---|
| 68 | 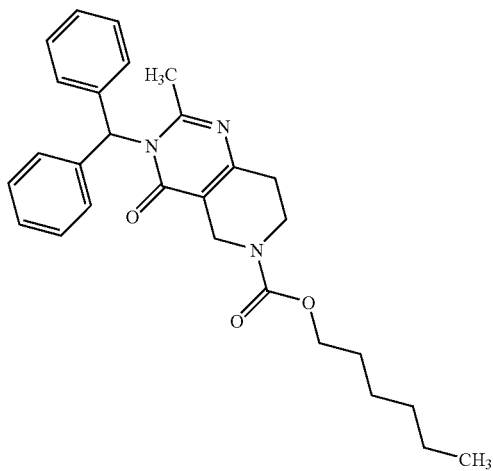 |
| 69 | 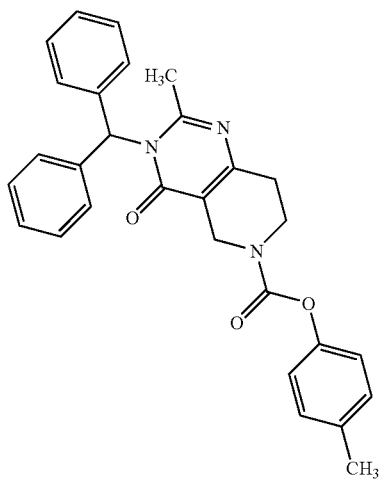 |
| 70 | 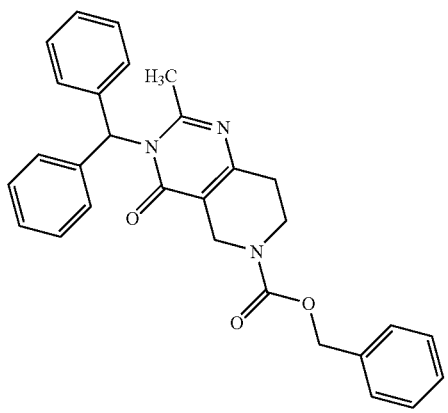 |

| No. | Structure |
|-----|-----------|
| 71 | 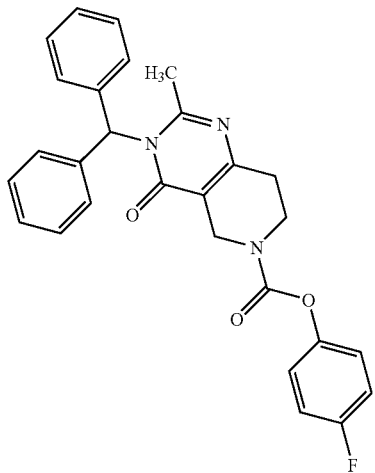 |
| 72 | 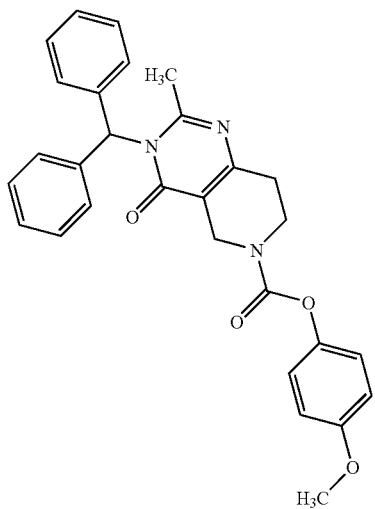 |
| 73 | 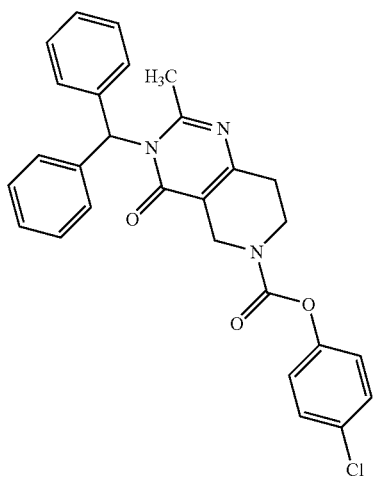 |

| No. | Structure |
|---|---|
| 74 | 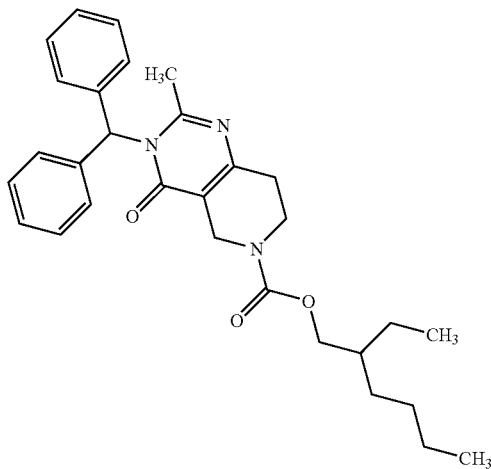 |
| 75 | 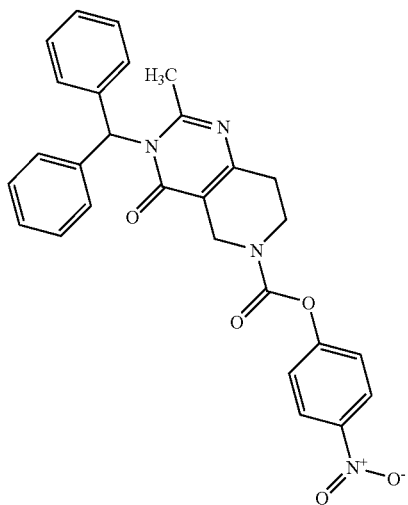 |
| 76 | 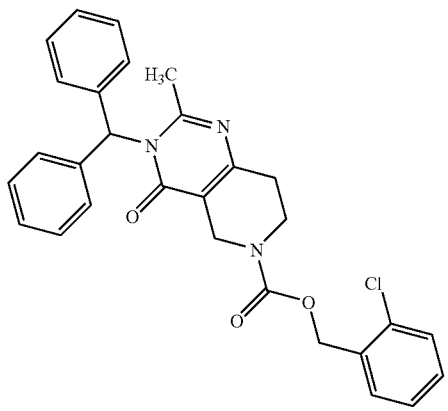 |

| No. | Structure |
|---|---|
| 77 | 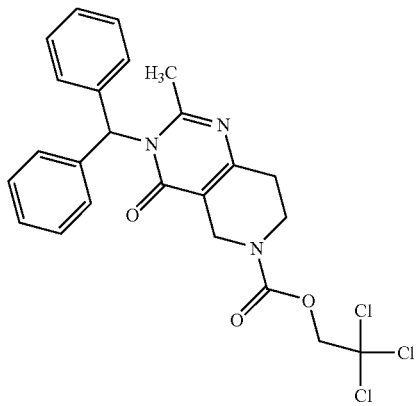 |
| 78 | 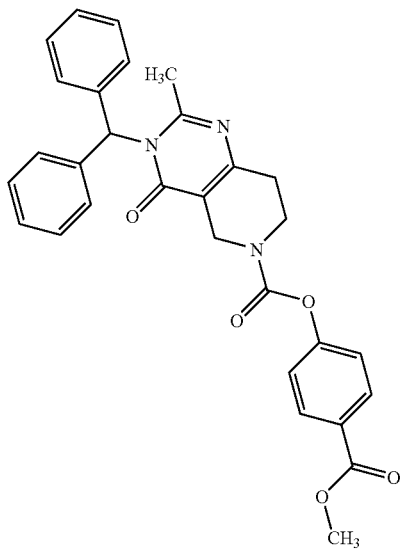 |
| 79 | 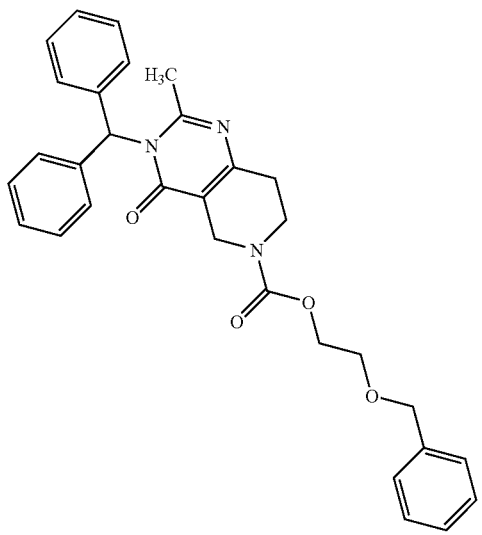 |

| No. | Structure |
|---|---|
| 80 | 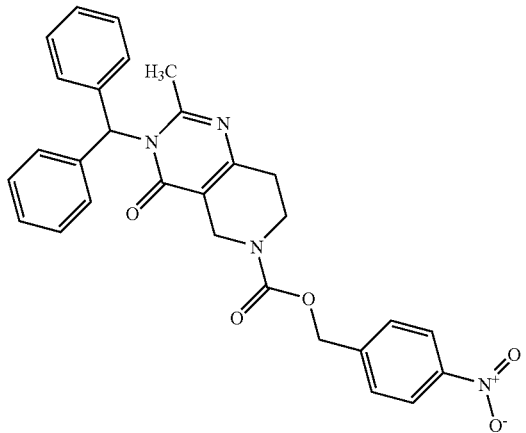 |
| 81 | 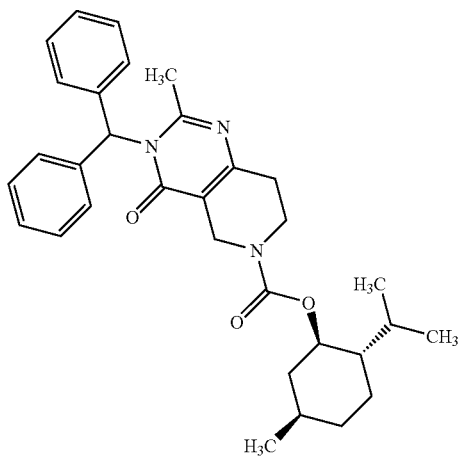 |
| 82 | 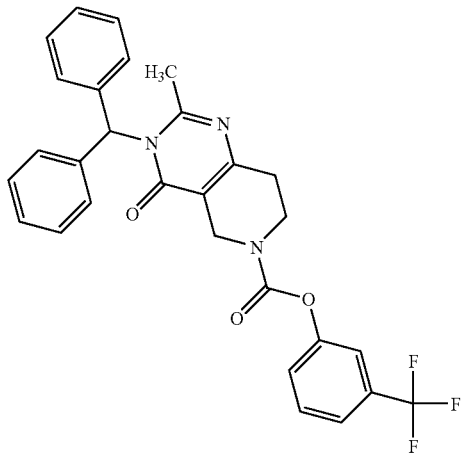 |

| No. | Structure |
|---|---|
| 83 | 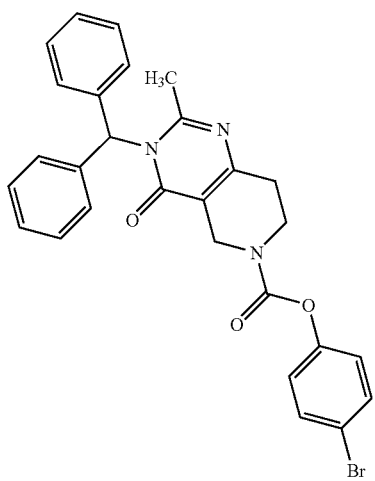 |
| 84 | 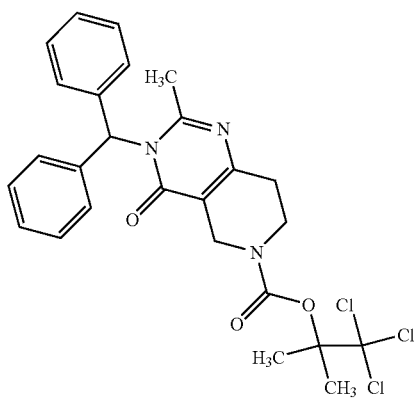 |
| 85 | 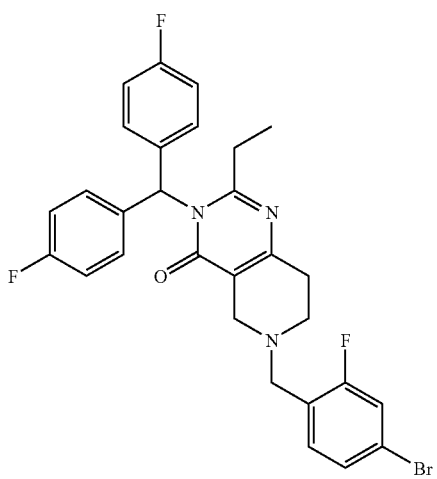 |
| 86 | 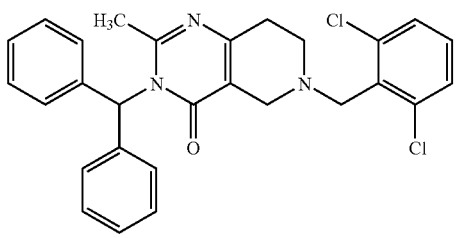 |

-continued
| No. | Structure |
|-----|-----------|
| 87 | 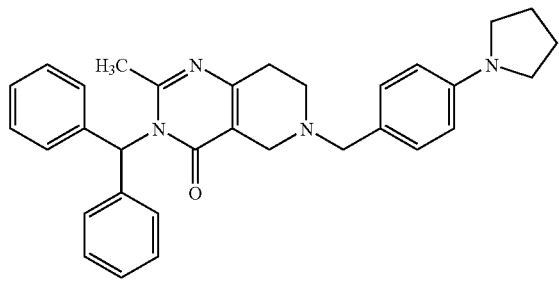 |
| 88 | 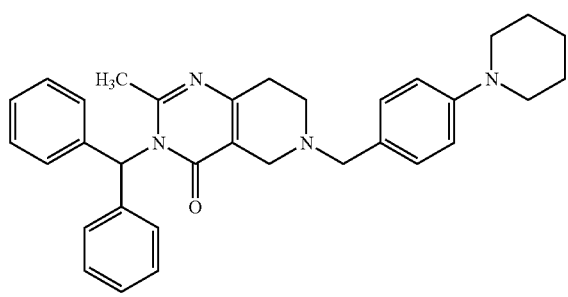 |
| 89 | 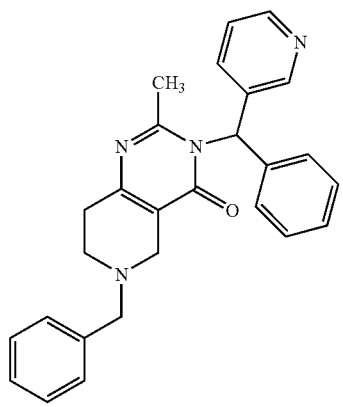 |
| 90 | 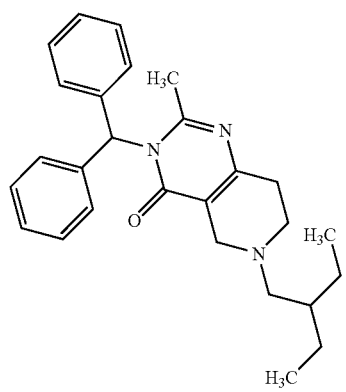 |

| No. | Structure |
|-----|-----------|
| 91 | 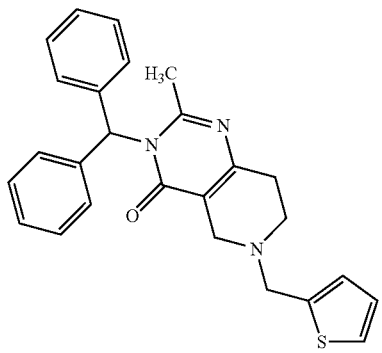 |
| 92 | 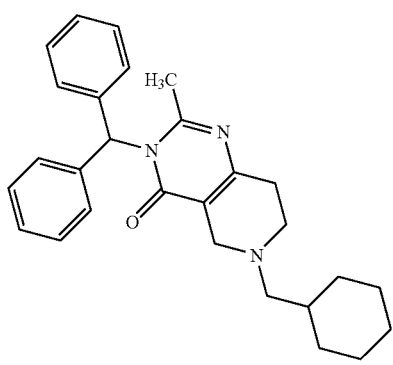 |
| 93 | 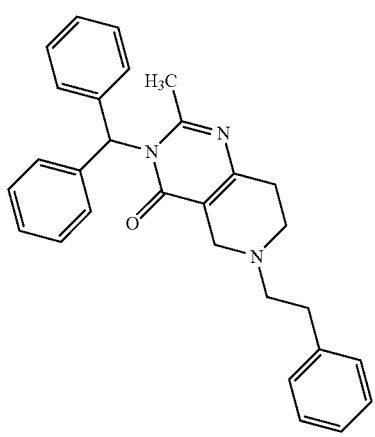 |
| 94 | 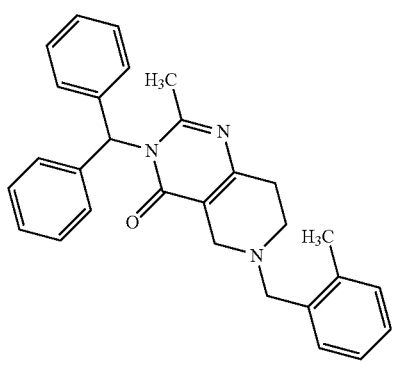 |

| No. | Structure |
|---|---|
| 95 | 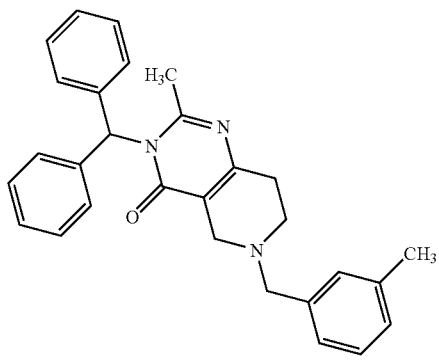 |
| 96 | 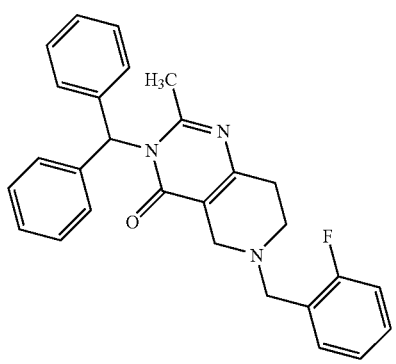 |
| 97 | 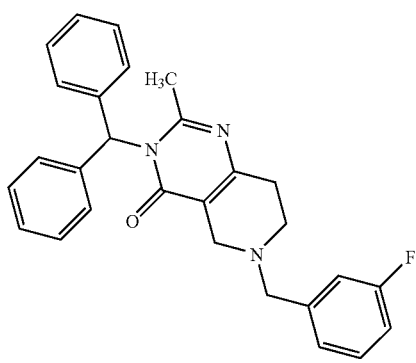 |
| 98 | 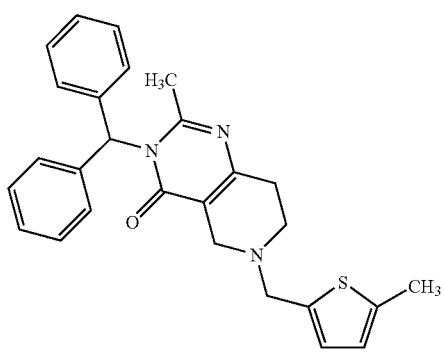 |

| No. | Structure |
|---|---|
| 99 | 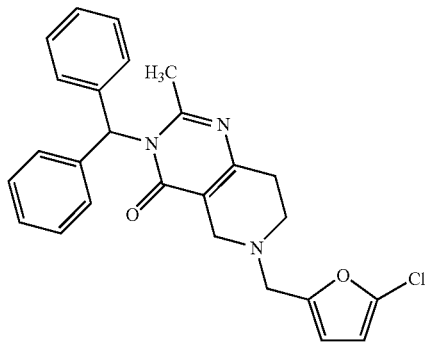 |
| 100 | 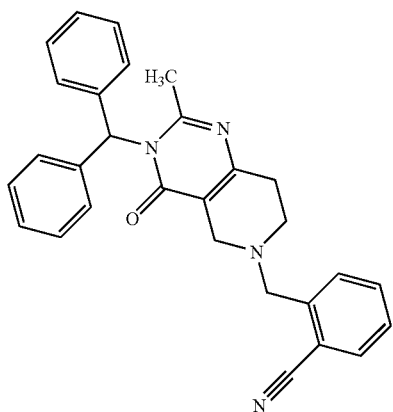 |
| 101 | 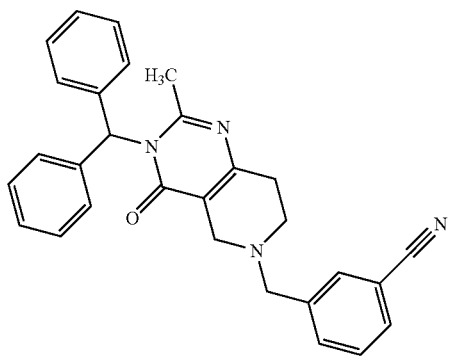 |
| 102 | 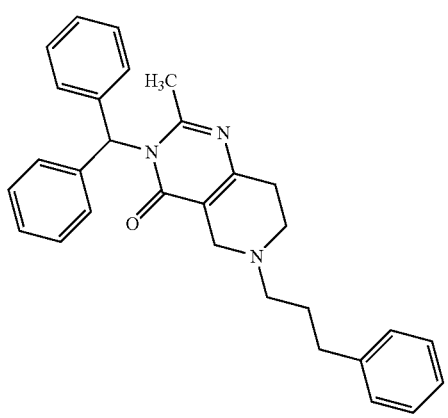 |

| No. | Structure |
|---|---|
| 103 | 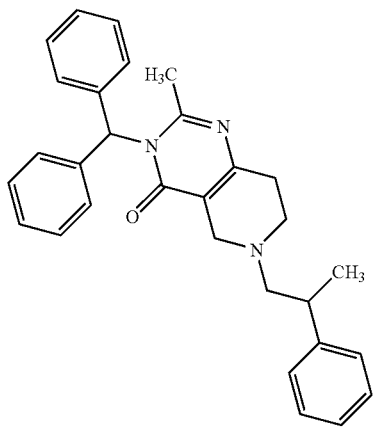 |
| 104 | 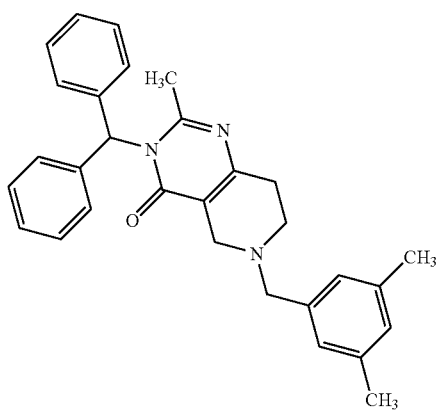 |
| 105 | 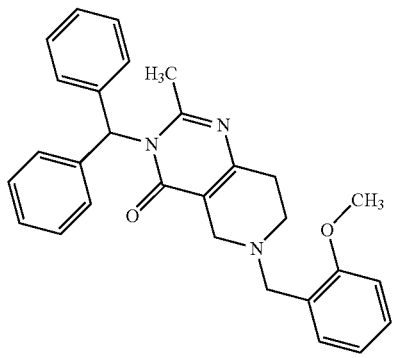 |
| 106 | 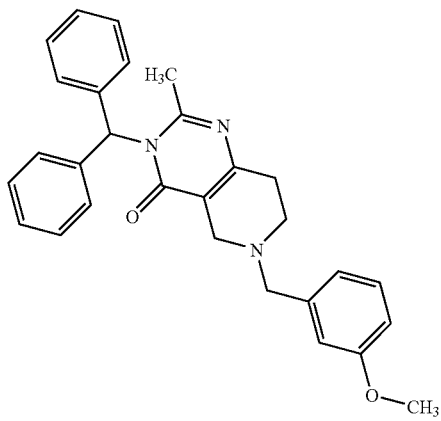 |

| No. | Structure |
|---|---|
| 107 | 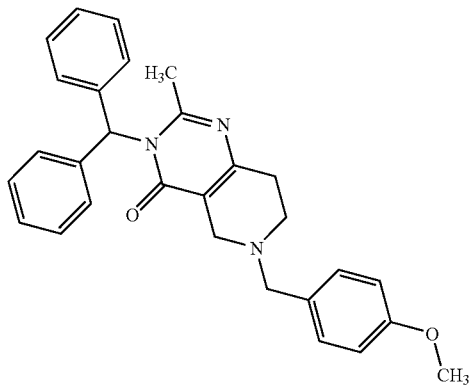 |
| 108 | 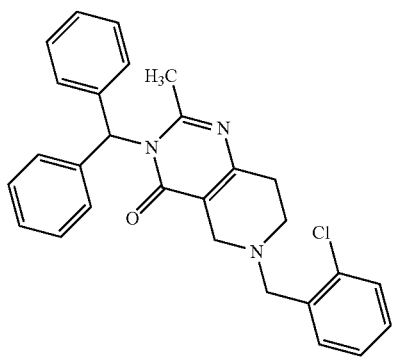 |
| 109 | 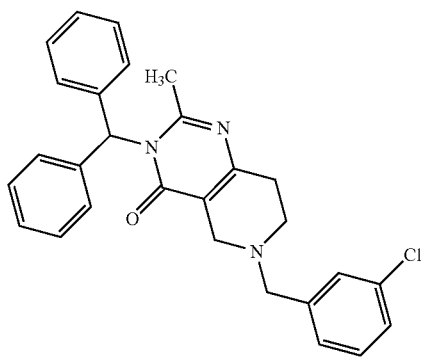 |
| 110 | 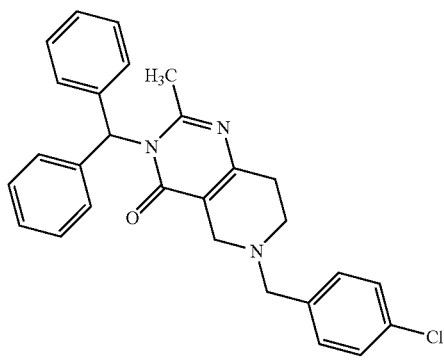 |

-continued
| No. | Structure |
|---|---|
| 111 | 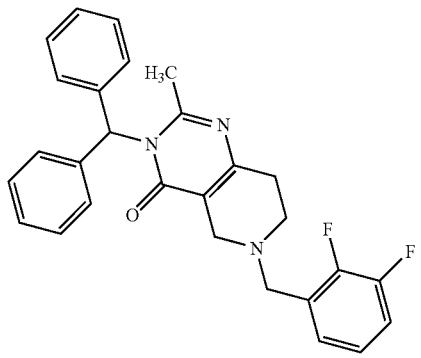 |
| 112 | 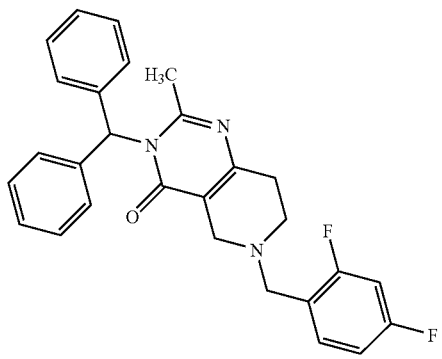 |
| 113 | 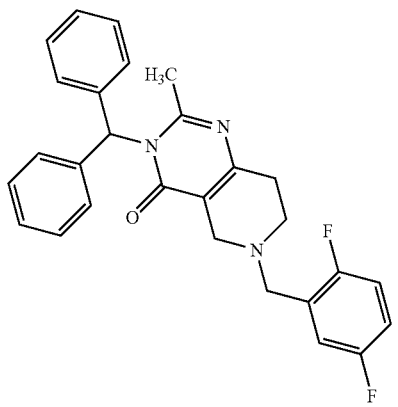 |
| 114 | 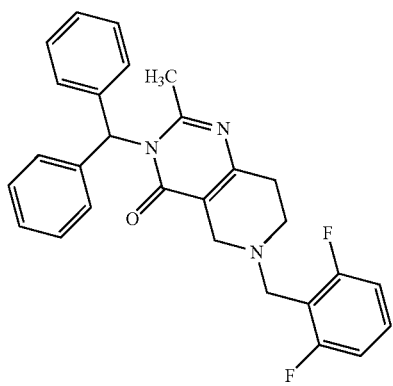 |

| No. | Structure |
|---|---|
| 115 | 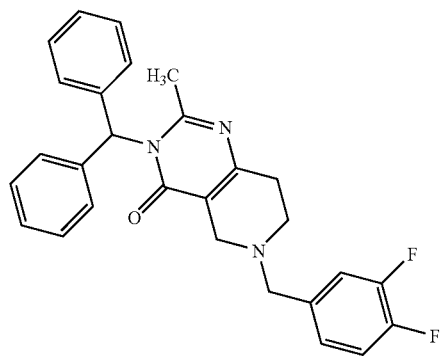 |
| 116 | 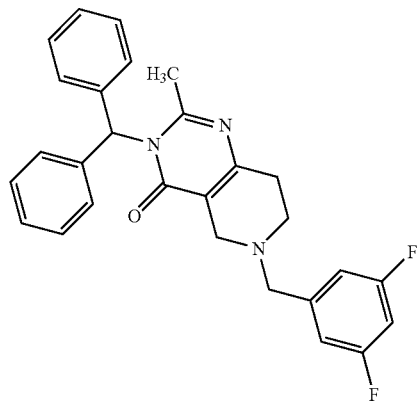 |
| 117 | 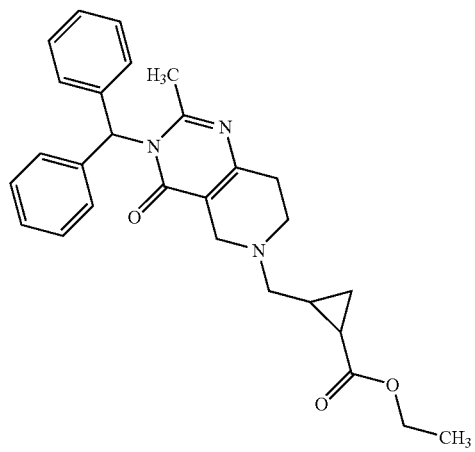 |
| 118 | 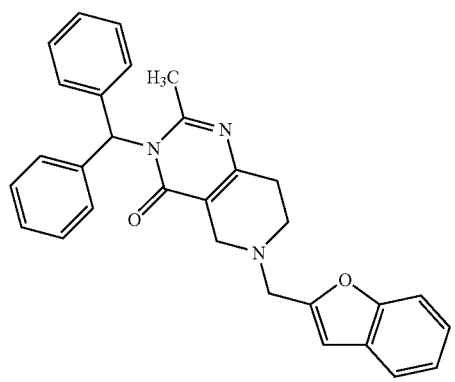 |

| No. | Structure |
|---|---|
| 119 | 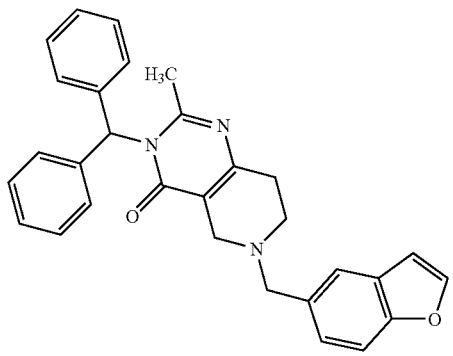 |
| 120 | 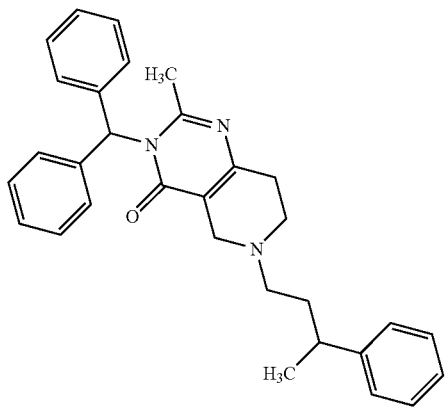 |
| 121 | 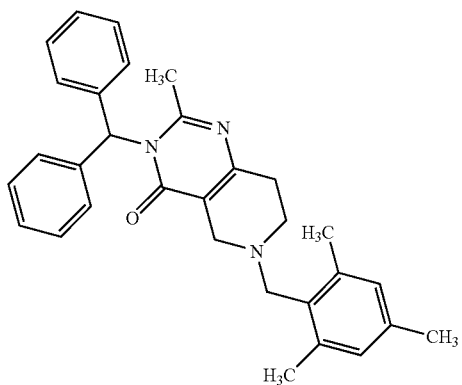 |
| 122 | 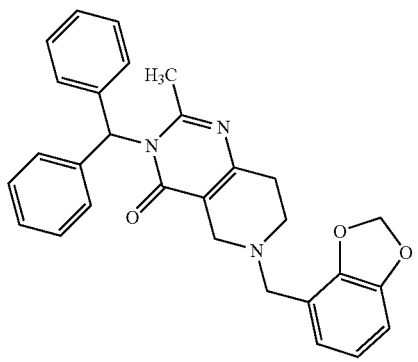 |

| No. | Structure |
|---|---|
| 123 | 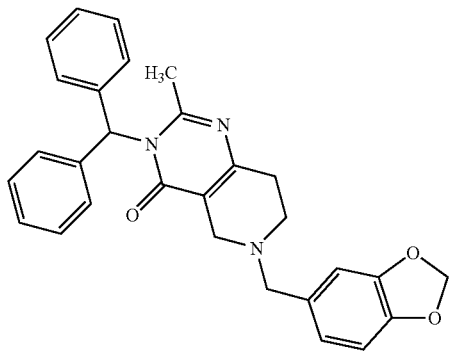 |
| 124 | 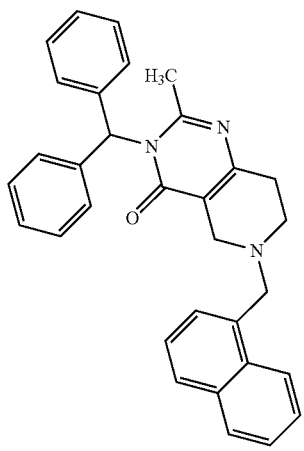 |
| 125 | 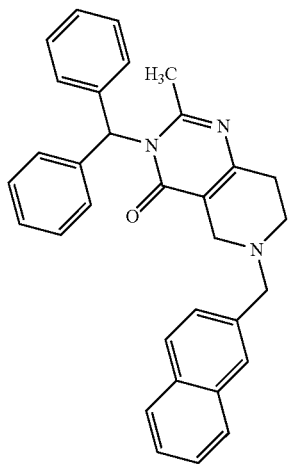 |

-continued
| No. | Structure |
|---|---|
| 126 | 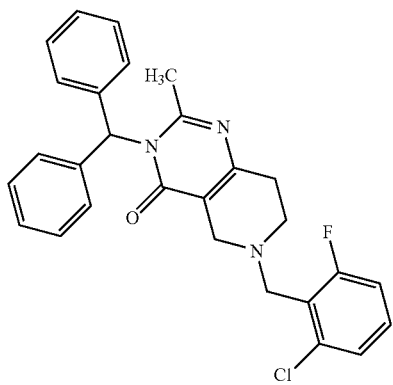 |
| 127 | 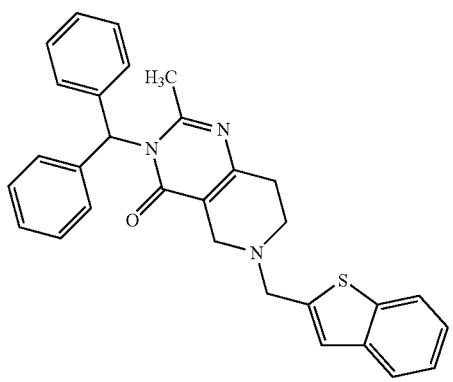 |
| 128 | 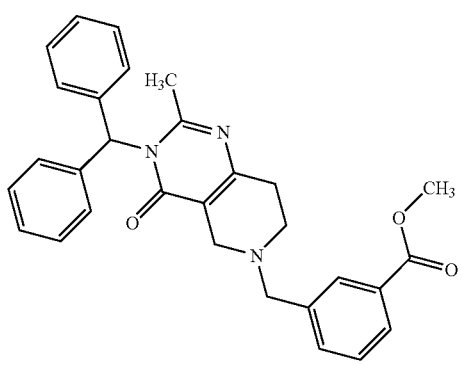 |
| 129 | 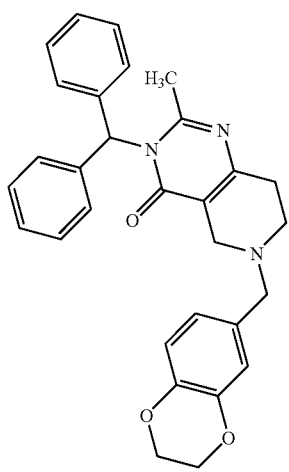 |

| No. | Structure |
|---|---|
| 130 | 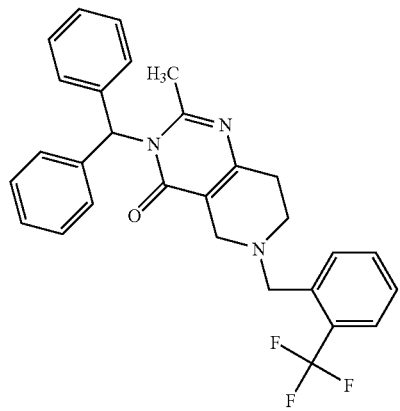 |
| 131 | 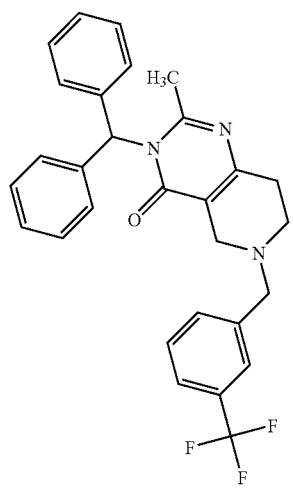 |
| 132 | 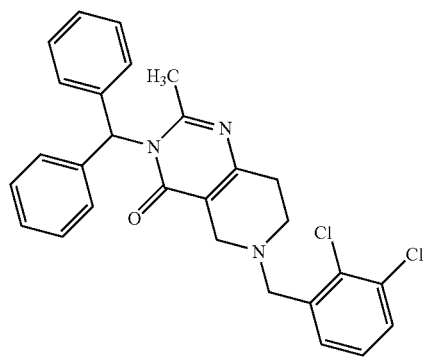 |

| No. | Structure |
|---|---|
| 133 | 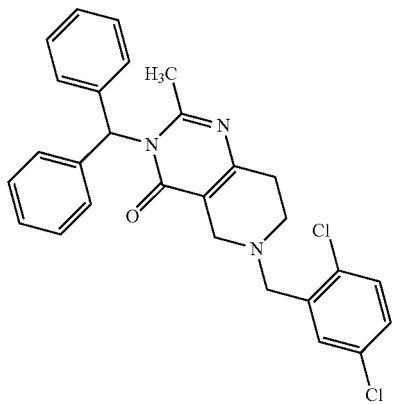 |
| 134 | 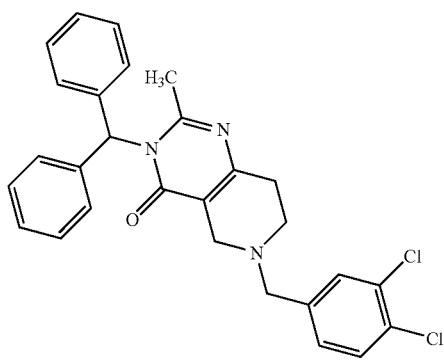 |
| 135 | 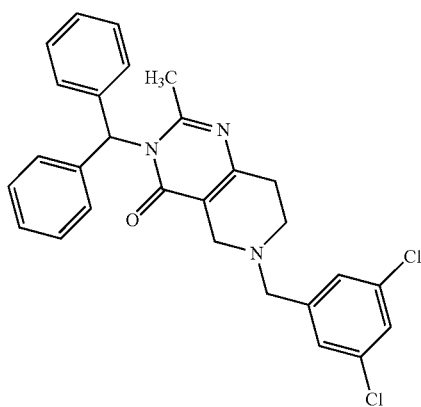 |
| 136 | 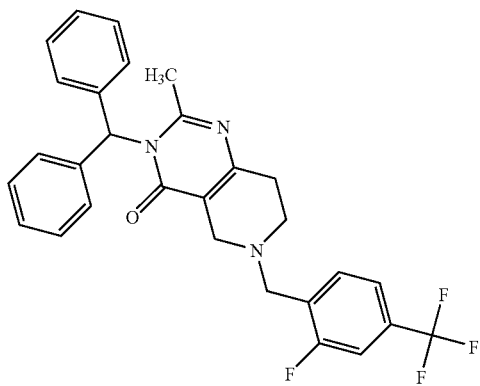 |

-continued
| No. | Structure |
|---|---|
| 137 | 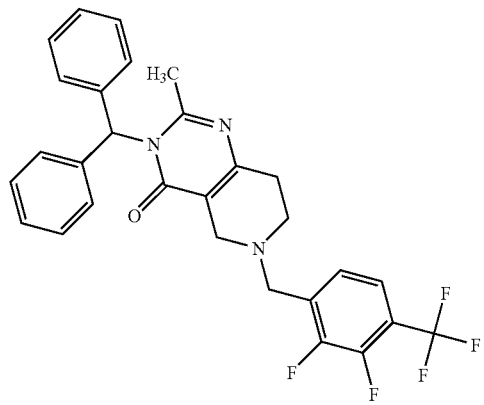 |
| 138 | 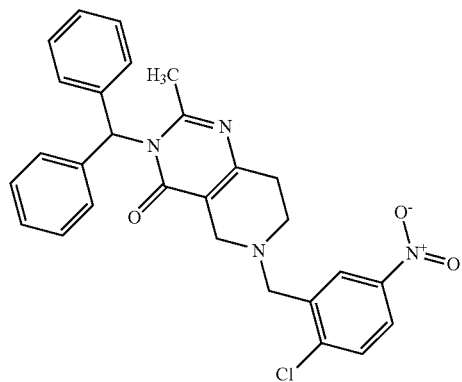 |
| 139 | 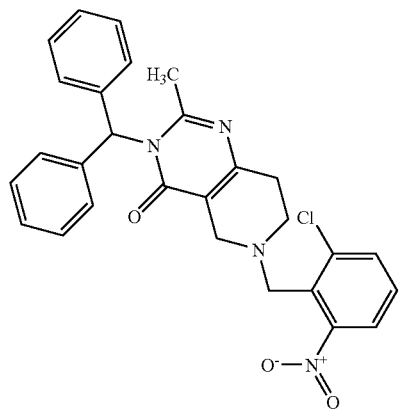 |
| 140 | 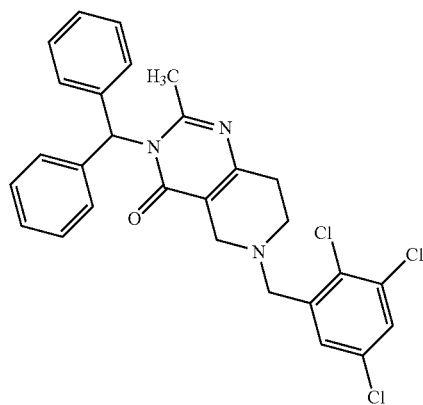 |

| No. | Structure |
|---|---|
| 141 | 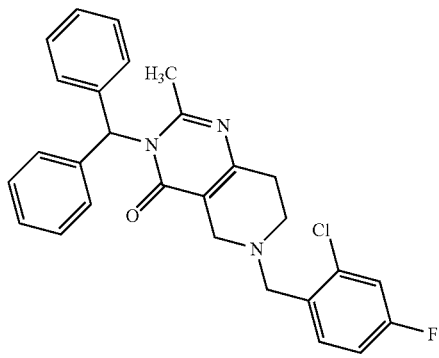 |
| 142 | 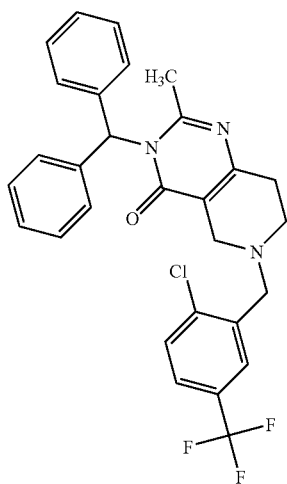 |
| 143 | 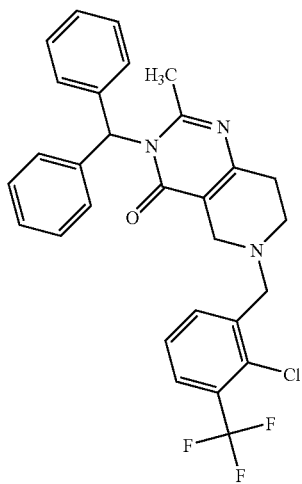 |

| No. | Structure |
|---|---|
| 144 | 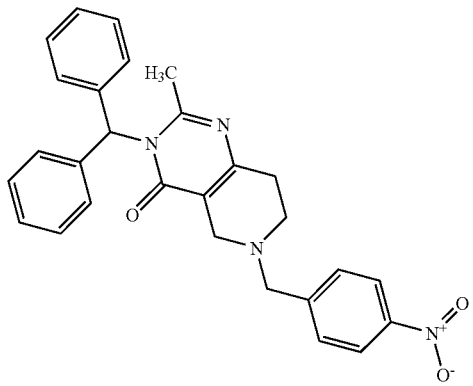 |
| 145 | 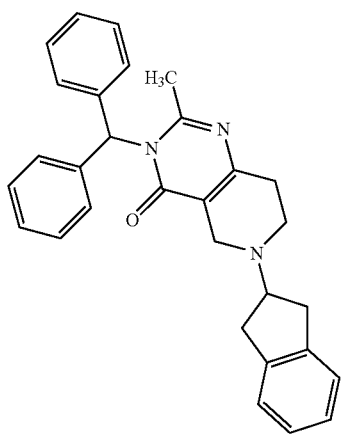 |
| 146 | 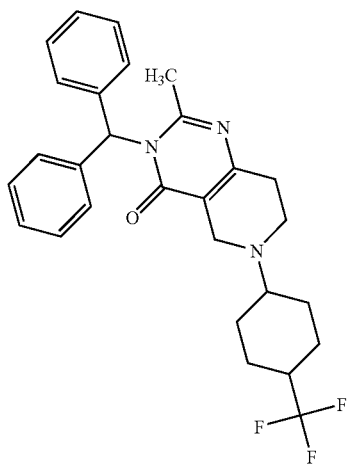 |

| No. | Structure |
|---|---|
| 147 | 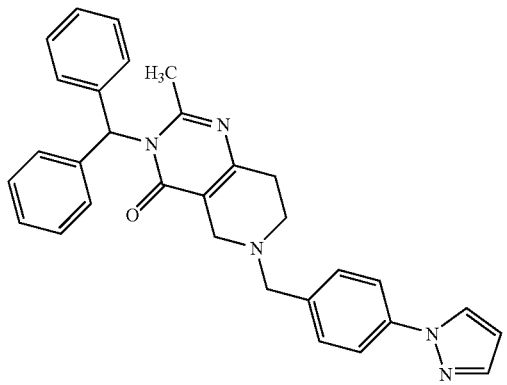 |
| 148 | 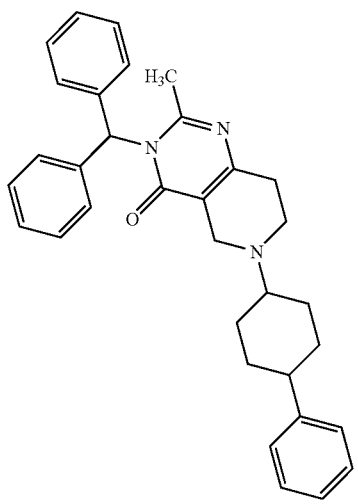 |
| 149 | 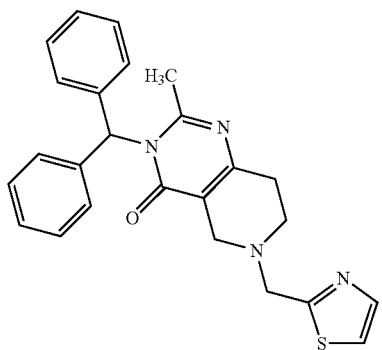 |

| No. | Structure |
|---|---|
| 150 | 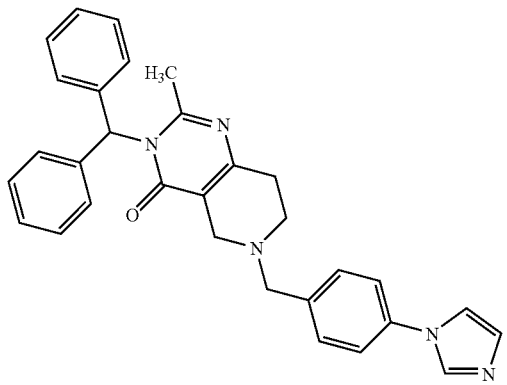 |
| 151 | 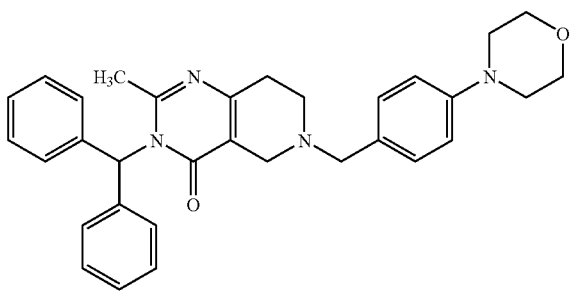 |
| 152 | 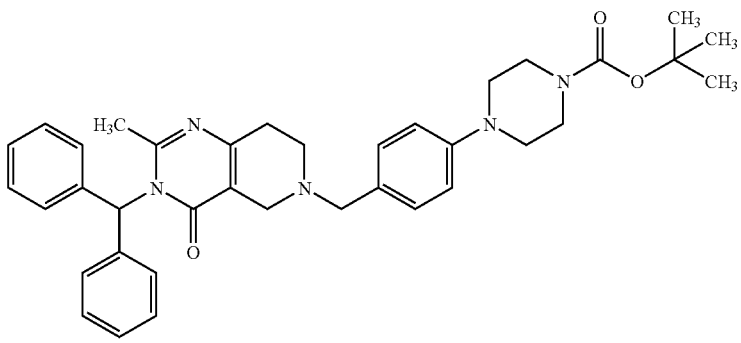 |
| 153 | 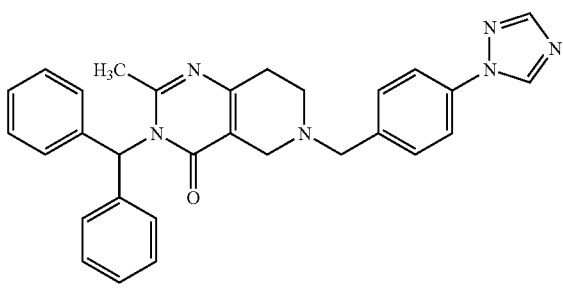 |

| No. | Structure |
|---|---|
| 154 | 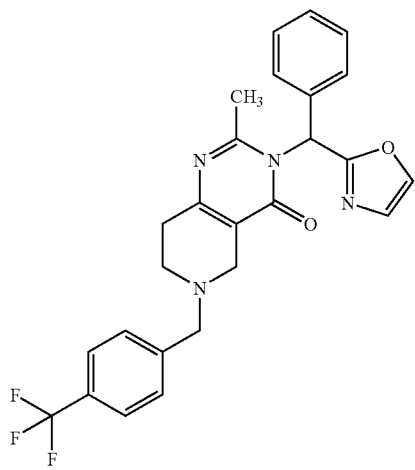 |
| 155 | 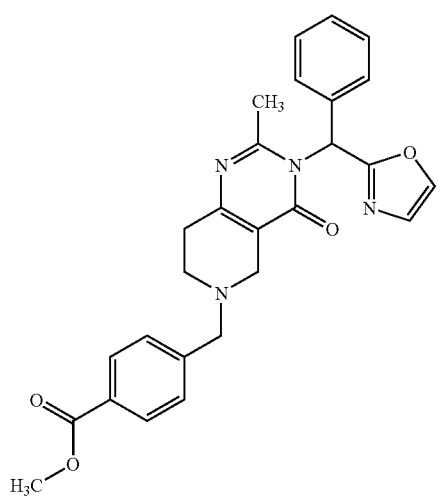 |
| 156 | 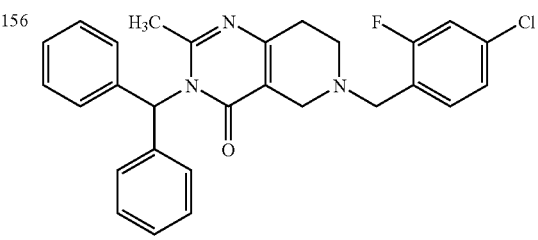 |
| 157 | 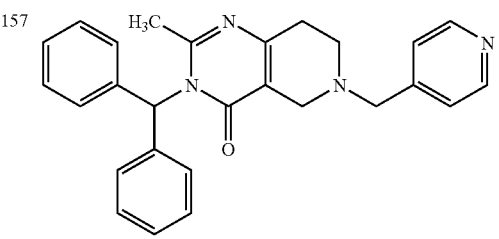 |

| No. | Structure |
|---|---|
| 158 | 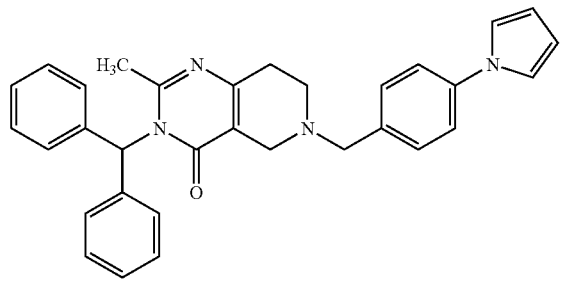 |
| 159 | 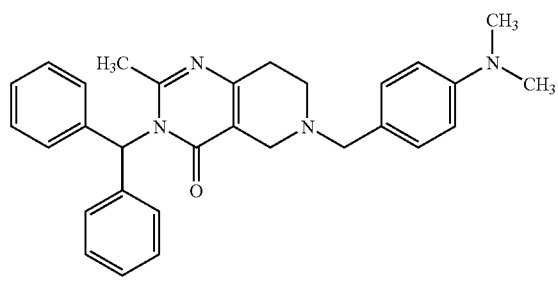 |
| 160 | 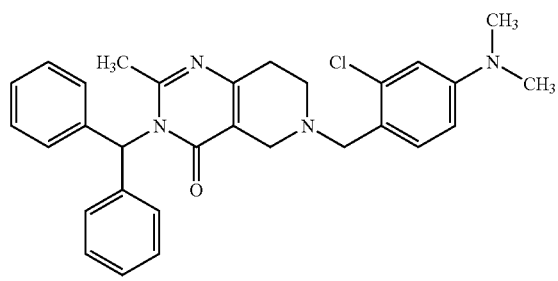 |
| 161 | 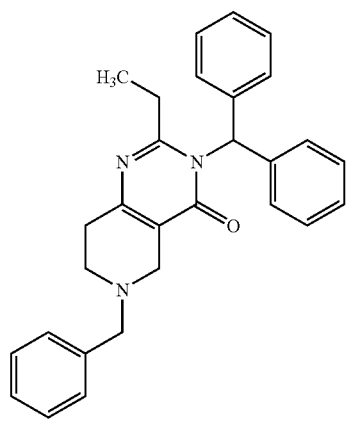 |

| No. | Structure |
|---|---|
| 162 | 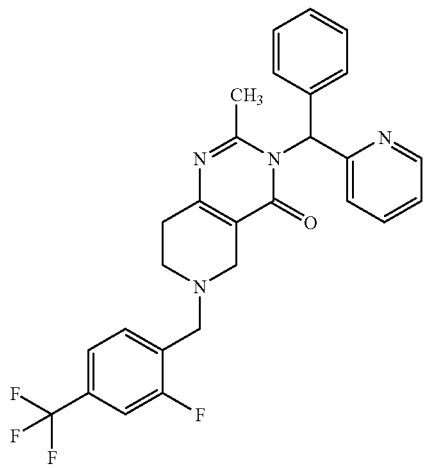 |
| 163 | 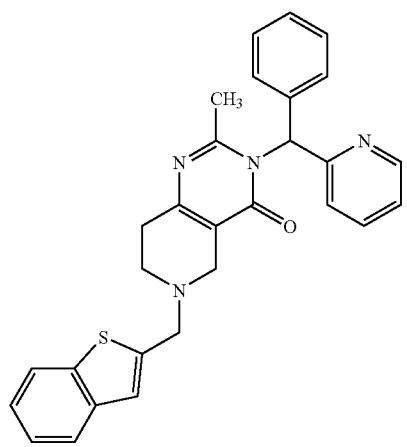 |
| 164 | 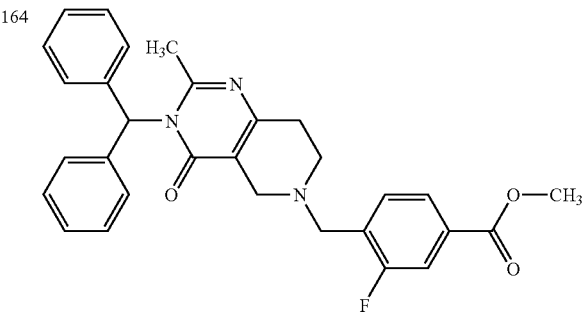 |
| 165 | 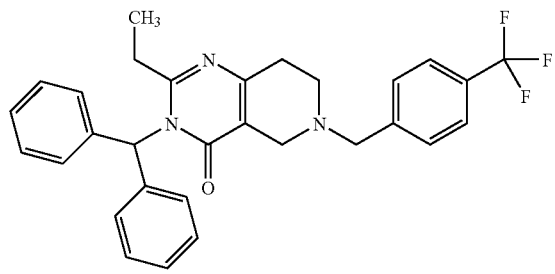 |

-continued
| No. | Structure |
|---|---|
| 166 | 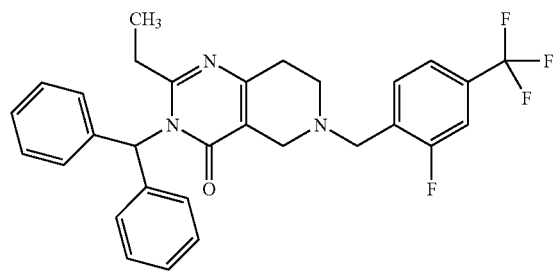 |
| 167 | 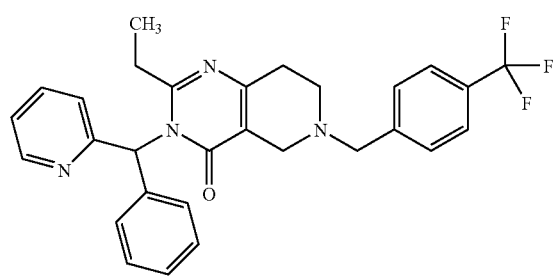 |
| 168 | 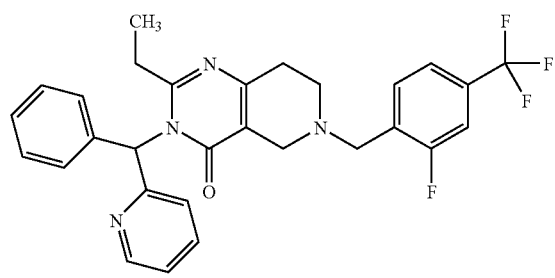 |
| 169 | 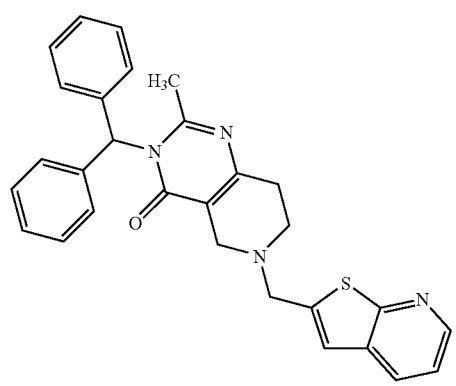 |
| 170 | 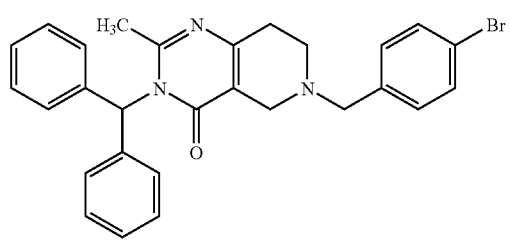 |

| No. | Structure |
|---|---|
| 171 | 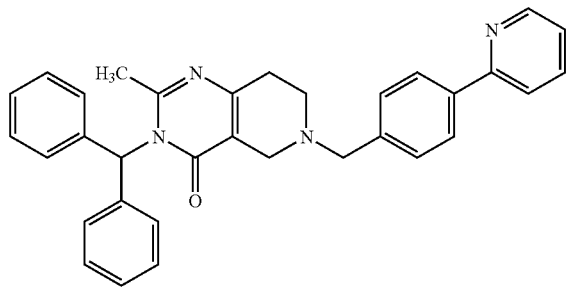 |
| 172 | 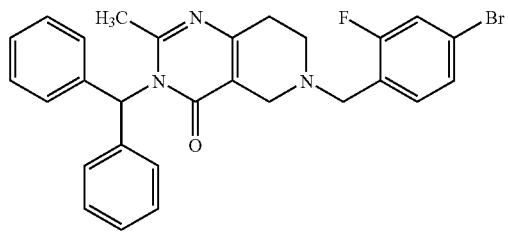 |
| 173 | 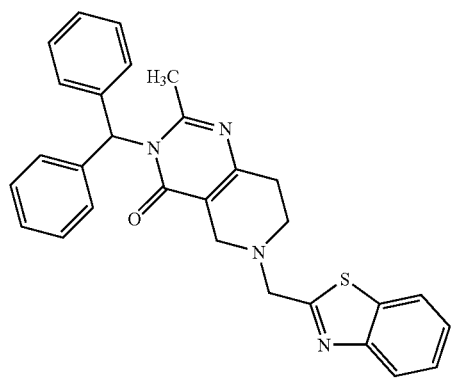 |
| 174 | 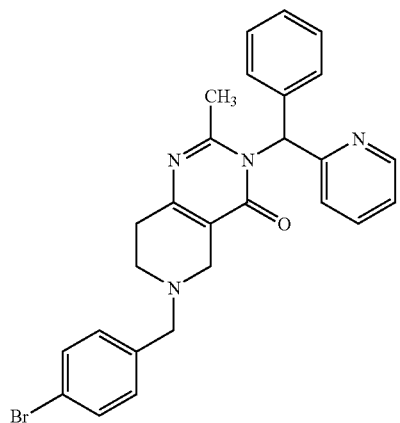 |

| No. | Structure |
|---|---|
| 175 | 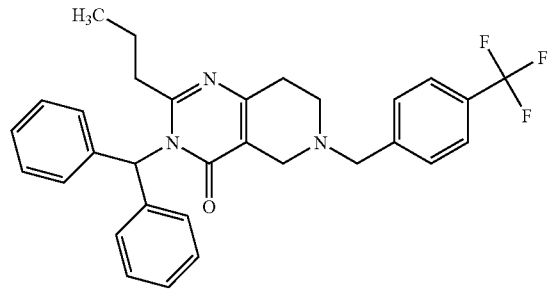 |
| 176 | 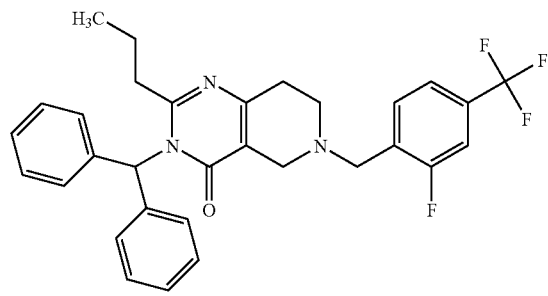 |
| 177 | 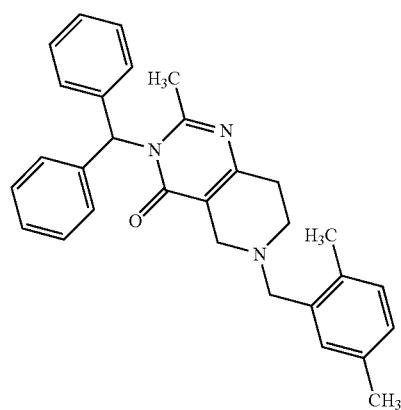 |
| 178 | 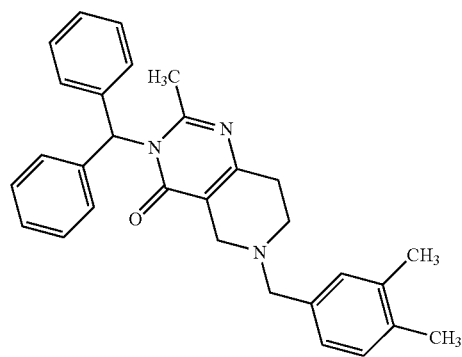 |

| No. | Structure |
|---|---|
| 179 | 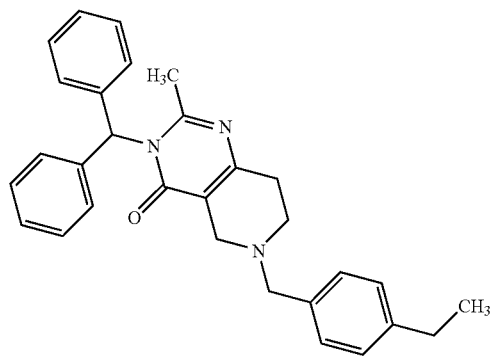 |
| 180 | 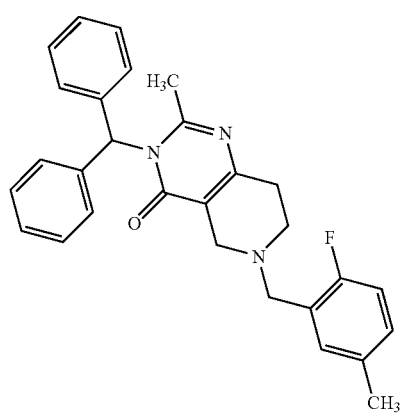 |
| 181 | 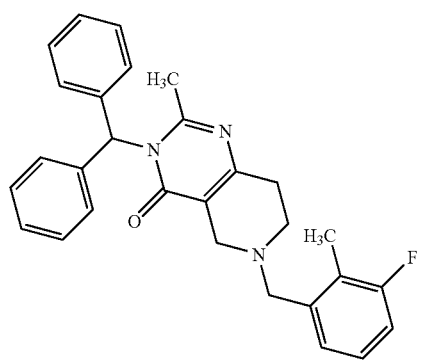 |
| 182 | 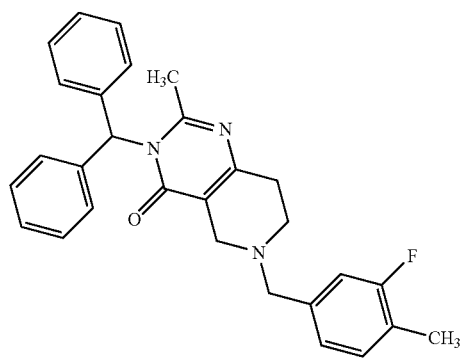 |

| No. | Structure |
|---|---|
| 183 | 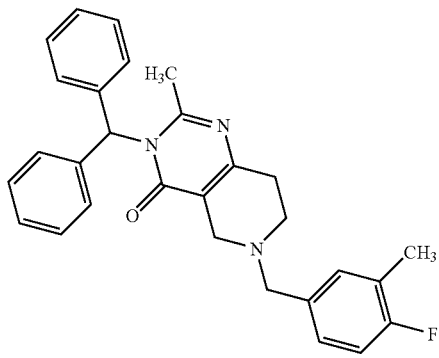 |
| 184 | 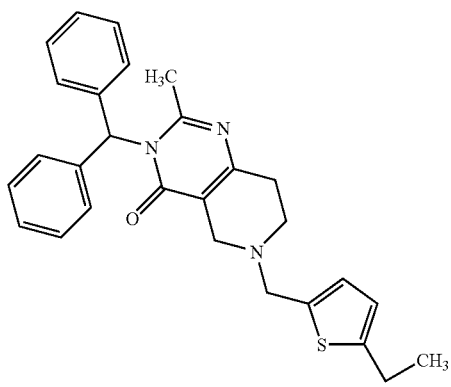 |
| 185 | 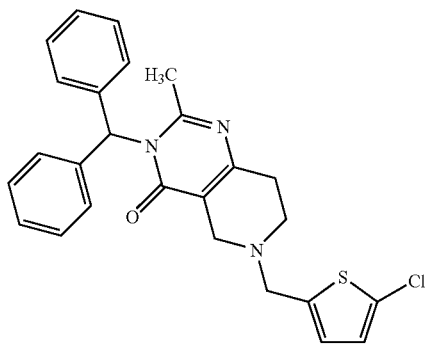 |
| 186 | 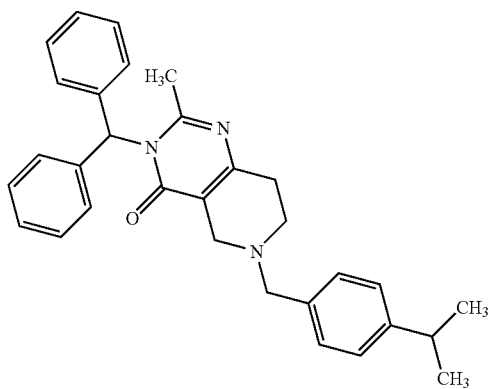 |

| No. | Structure |
|---|---|
| 187 | 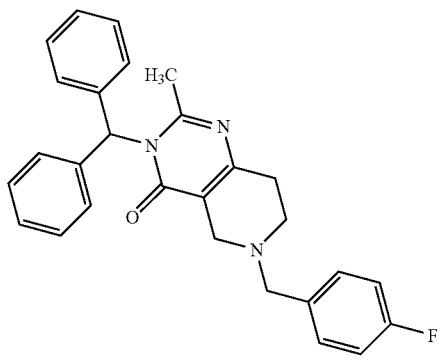 |
| 188 | 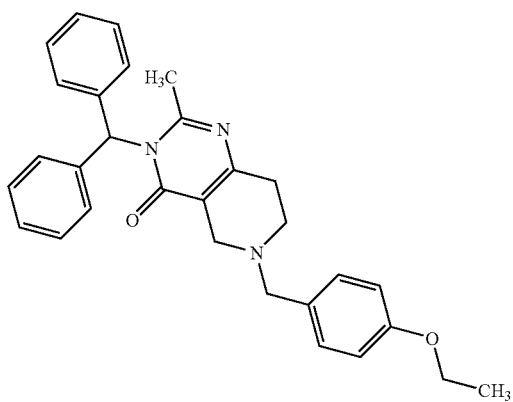 |
| 189 | 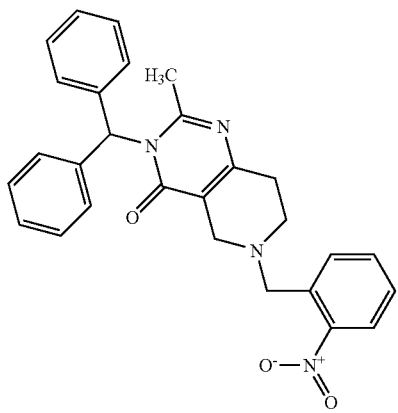 |
| 190 | 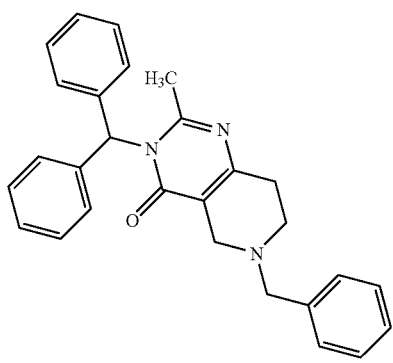 |

| No. | Structure |
|---|---|
| 191 | 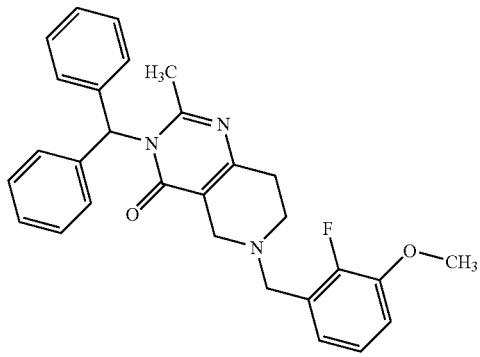 |
| 192 | 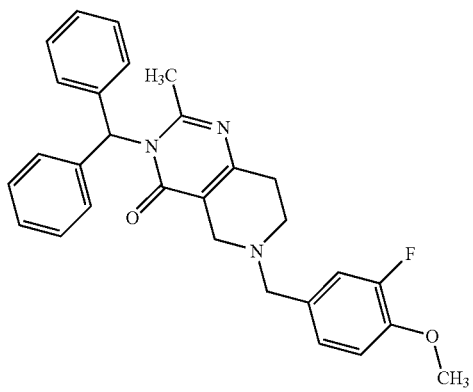 |
| 193 | 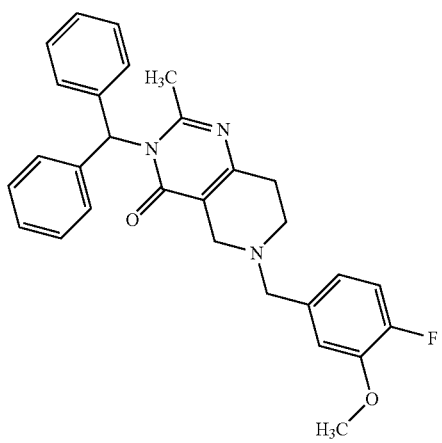 |
| 194 | 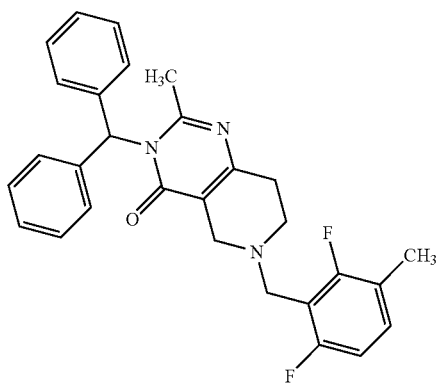 |

US 8,318,751 B2
| No. | Structure |
|---|---|
| 195 | 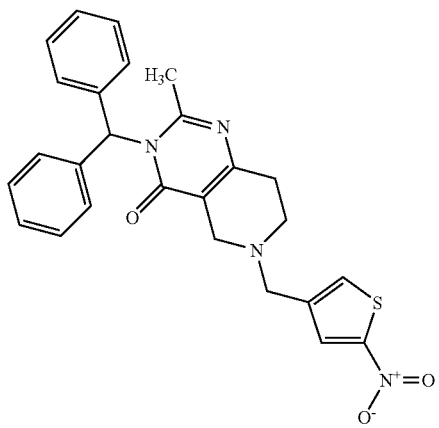 |
| 196 | 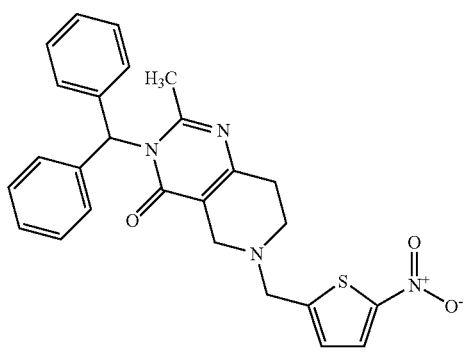 |
| 197 | 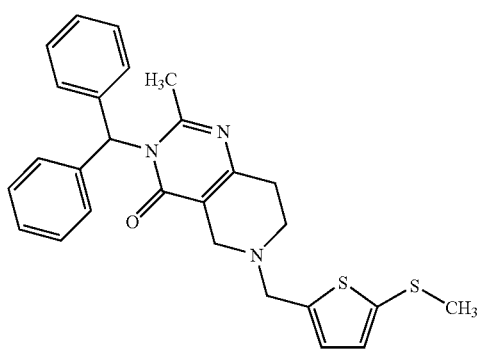 |
| 198 | 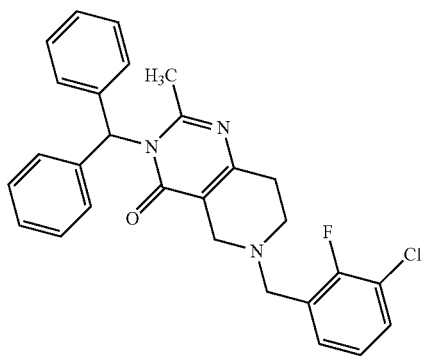 |

| No. | Structure |
|---|---|
| 199 | 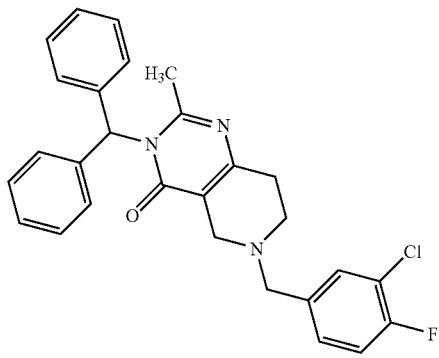 |
| 200 | 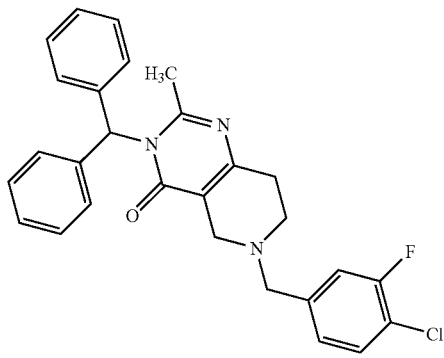 |
| 201 | 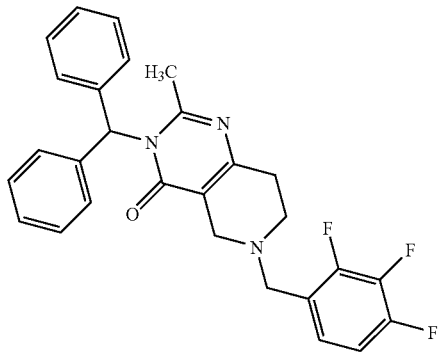 |
| 202 | 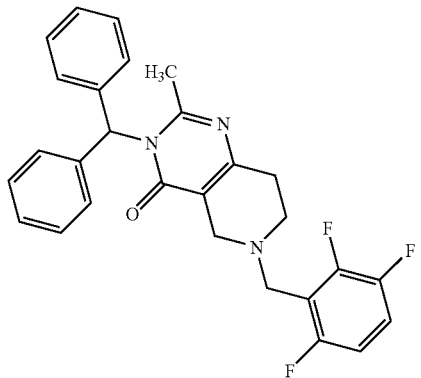 |

| No. | Structure |
|---|---|
| 203 | 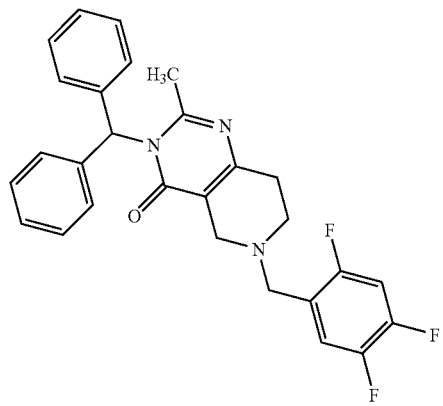 |
| 204 | 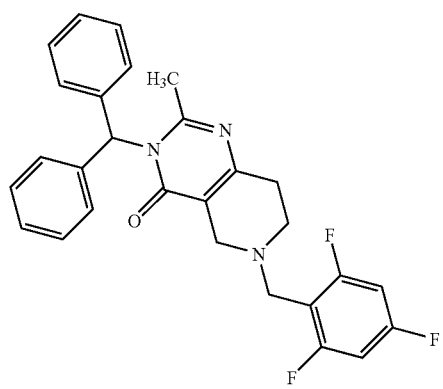 |
| 205 | 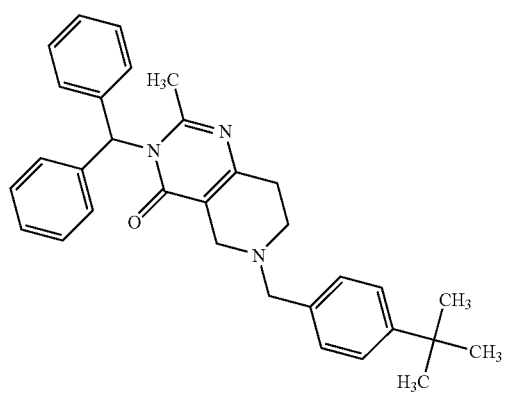 |
| 206 | 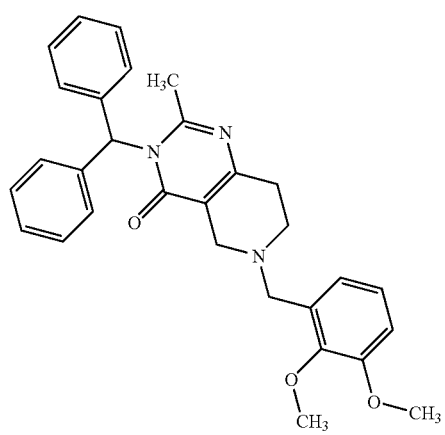 |

| No. | Structure |
|---|---|
| 207 | 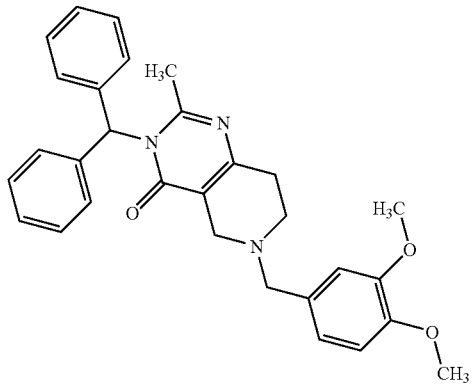 |
| 208 | 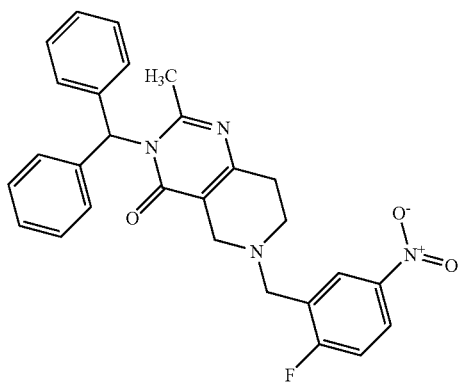 |
| 209 | 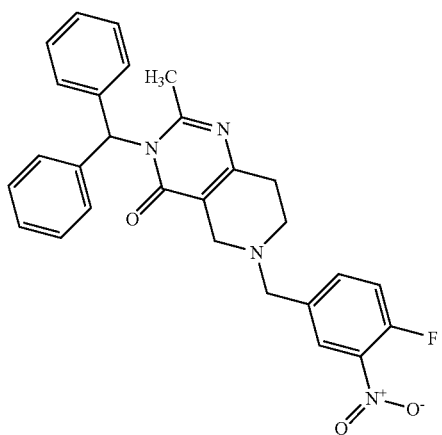 |

-continued
| No. | Structure |
|-----|-----------|
| 210 | 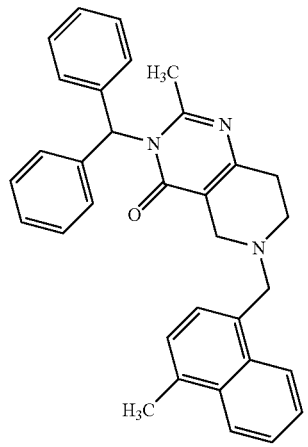 |
| 211 | 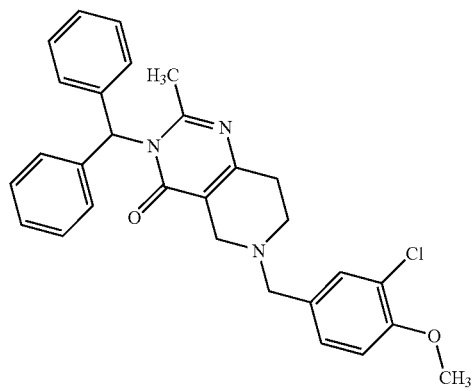 |
| 212 | 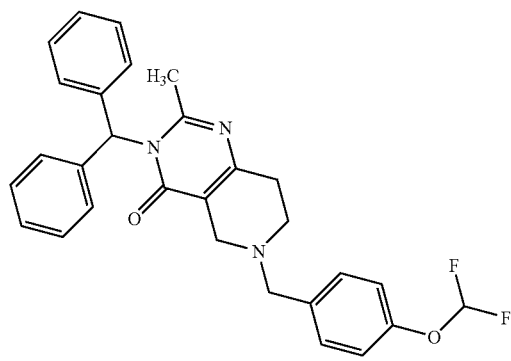 |
| 213 | 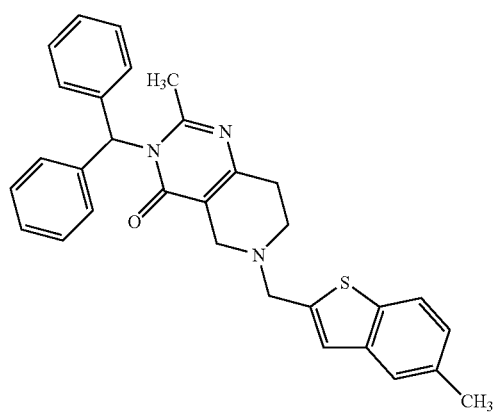 |

| No. | Structure |
|---|---|
| 214 | 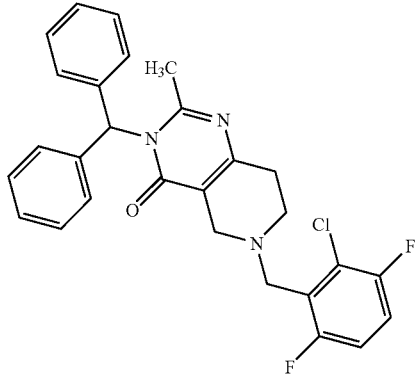 |
| 215 | 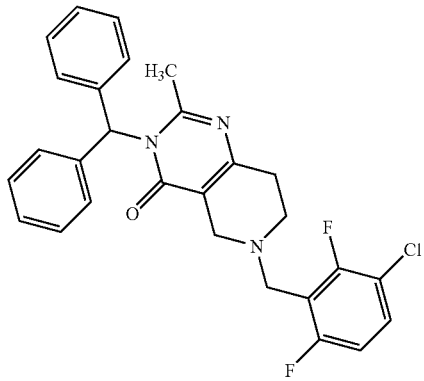 |
| 216 | 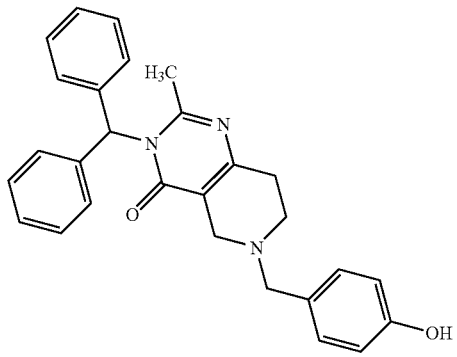 |
| 217 | 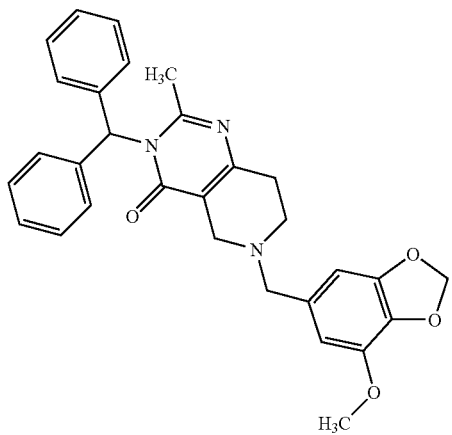 |

| No. | Structure |
|---|---|
| 218 | 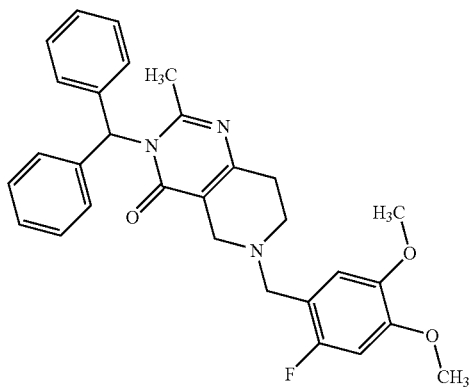 |
| 219 | 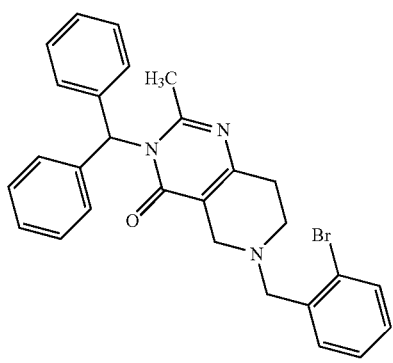 |
| 220 | 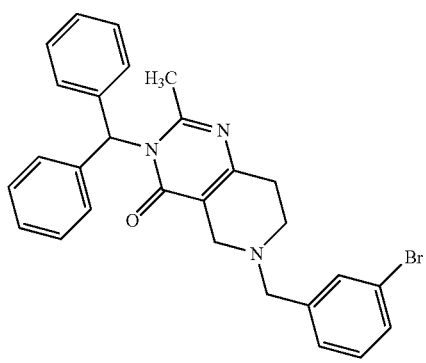 |
| 221 | 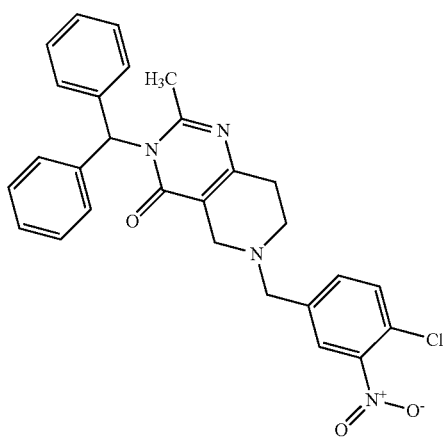 |

| No. | Structure |
|---|---|
| 222 | 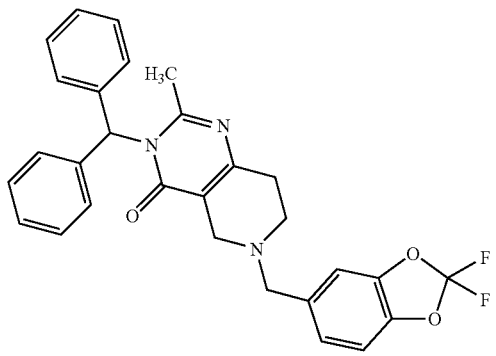 |
| 223 | 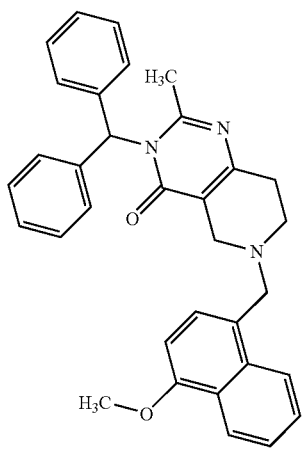 |
| 224 | 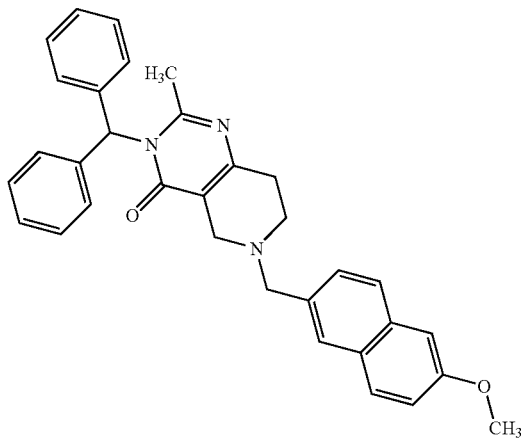 |

| No. | Structure |
|---|---|
| 225 | 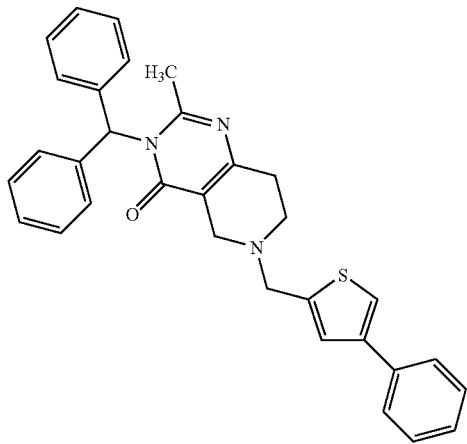 |
| 226 | 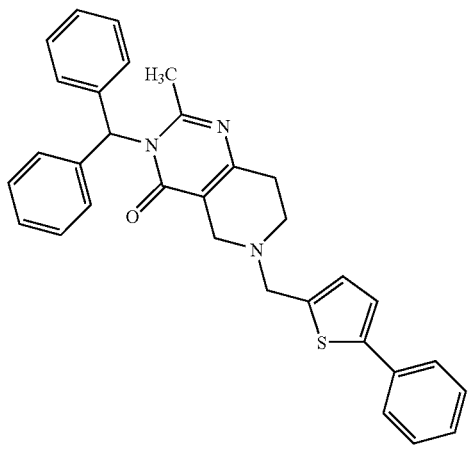 |
| 227 | 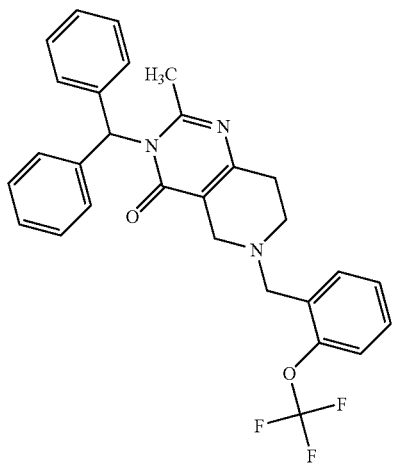 |

-continued
| No. | Structure |
|---|---|
| 228 | 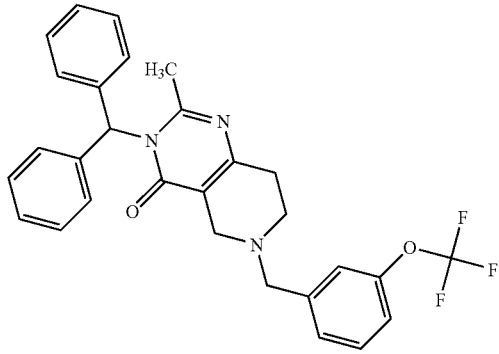 |
| 229 | 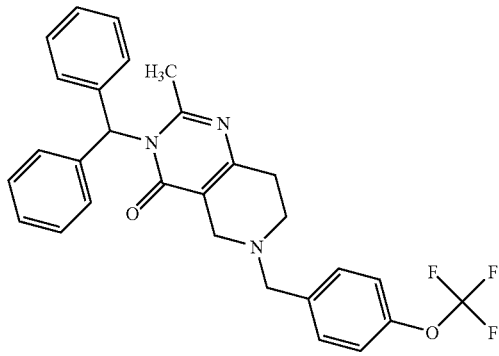 |
| 230 | 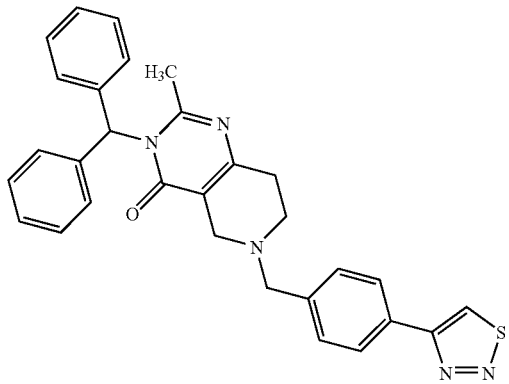 |
| 231 | 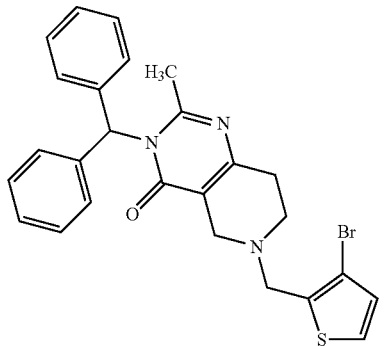 |

| No. | Structure |
|---|---|
| 232 | 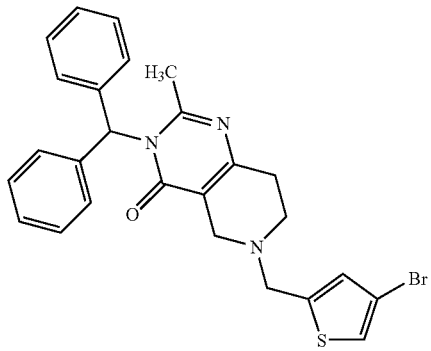 |
| 233 | 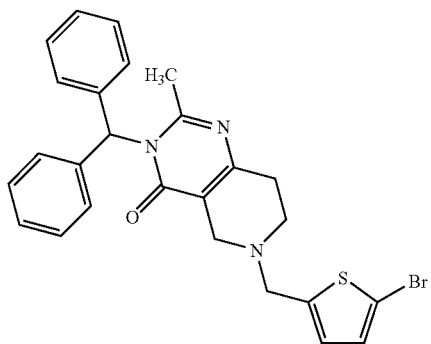 |
| 234 | 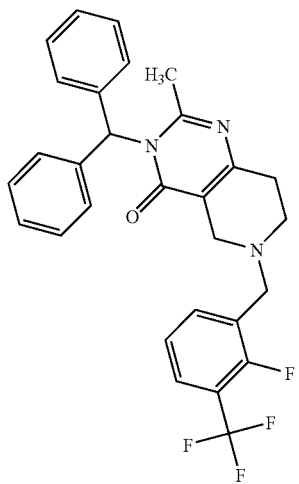 |

| No. | Structure |
|---|---|
| 235 | 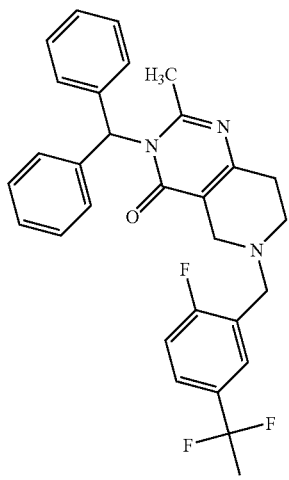 |
| 236 | 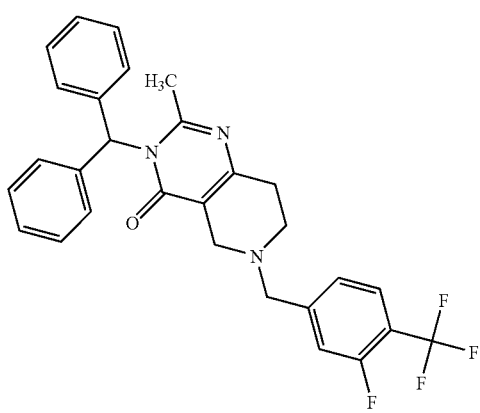 |
| 237 | 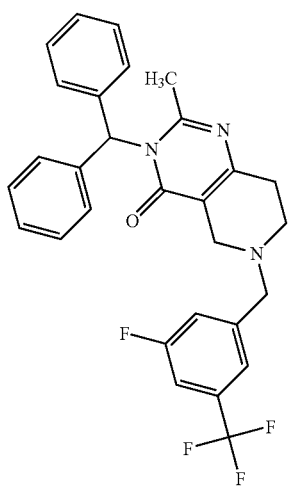 |

| No. | Structure |
|---|---|
| 238 | 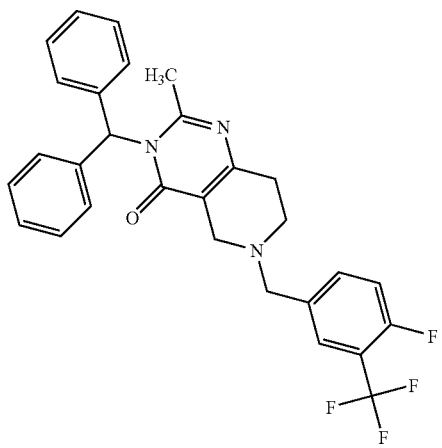 |
| 239 | 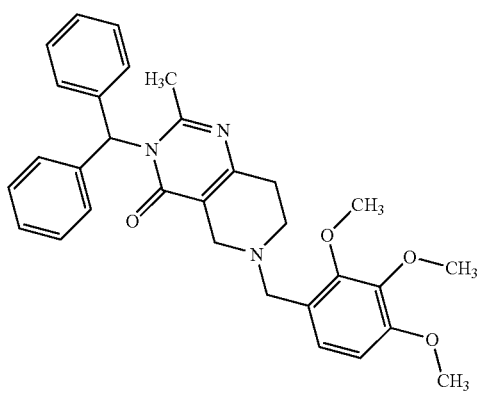 |
| 240 | 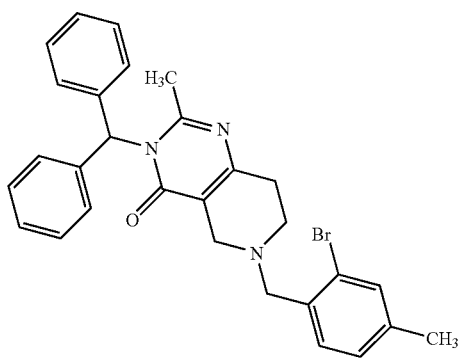 |
| 241 | 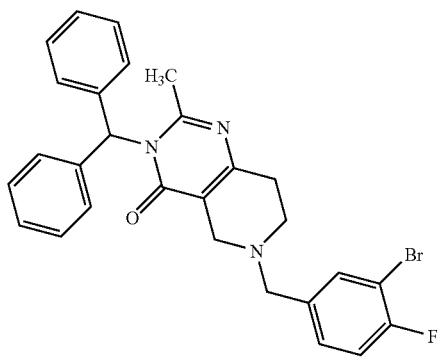 |

| No. | Structure |
|---|---|
| 242 | 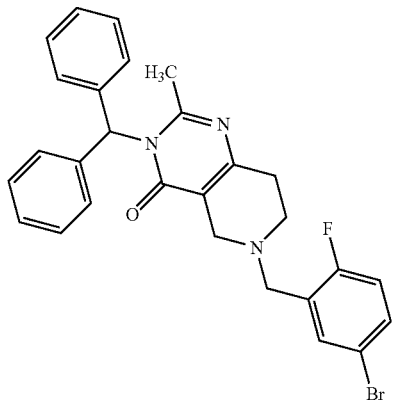 |
| 243 | 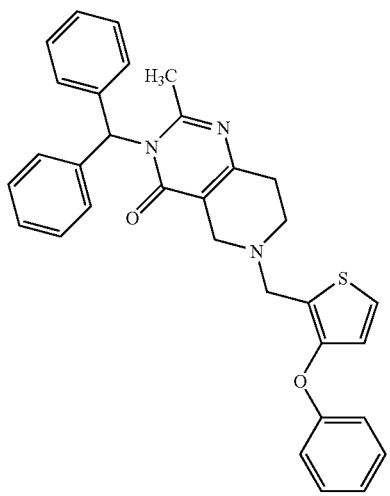 |
| 244 | 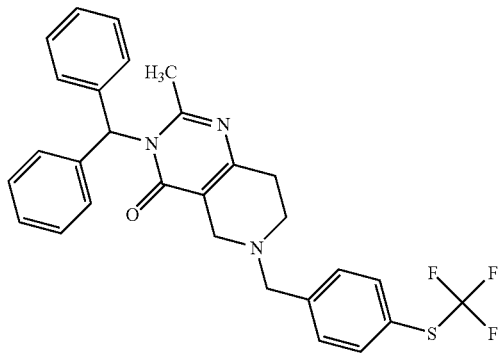 |

| No. | Structure |
|---|---|
| 245 | 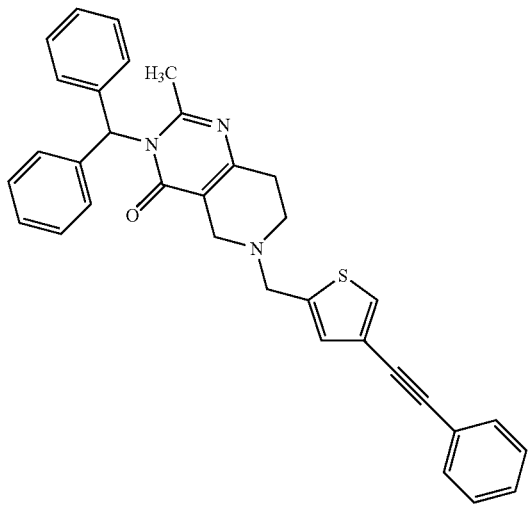 |
| 246 | 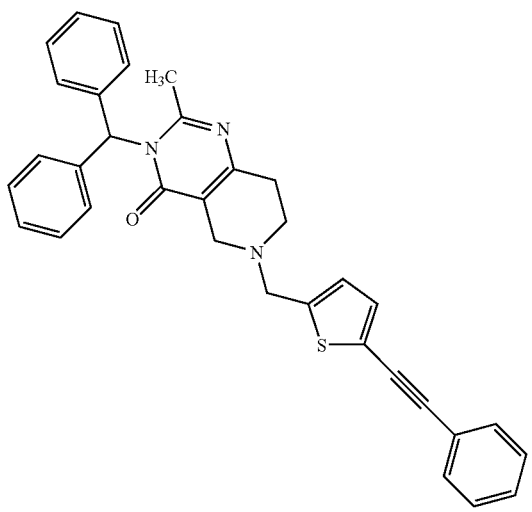 |
| 247 | 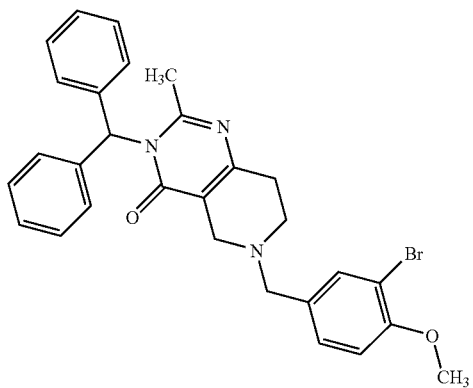 |

| No. | Structure |
|---|---|
| 248 | 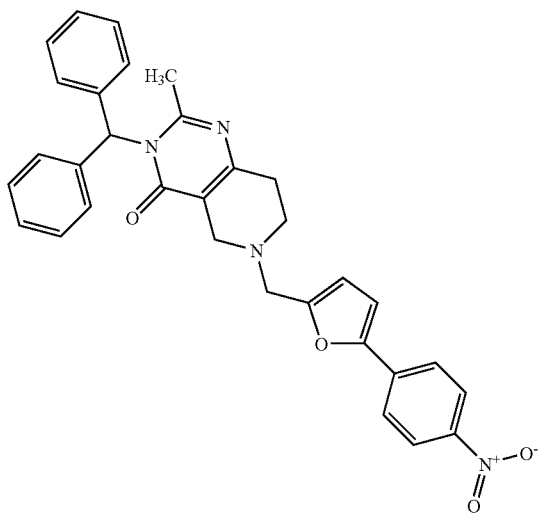 |
| 249 | 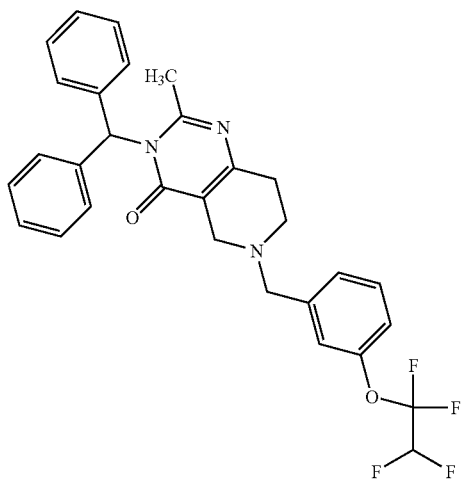 |
| 250 | 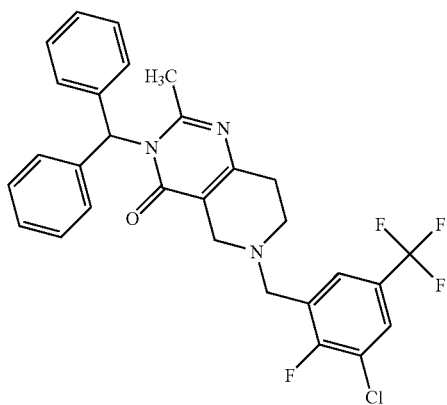 |

| No. | Structure |
|---|---|
| 251 | 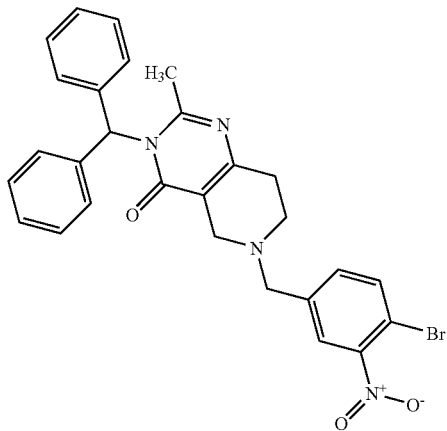 |
| 252 | 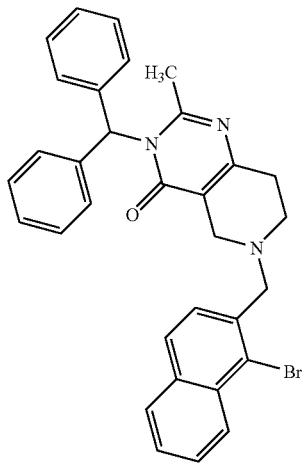 |
| 253 | 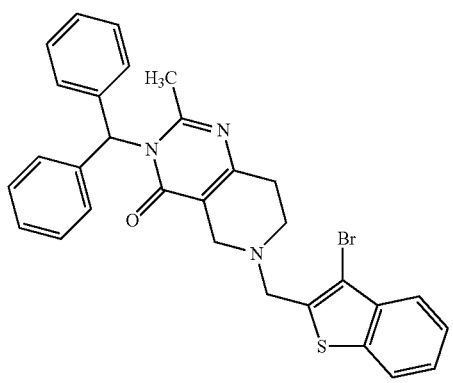 |

| No. | Structure |
|-----|-----------|
| 254 | 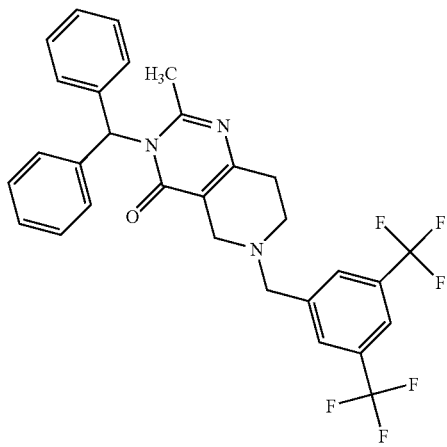 |
| 255 | 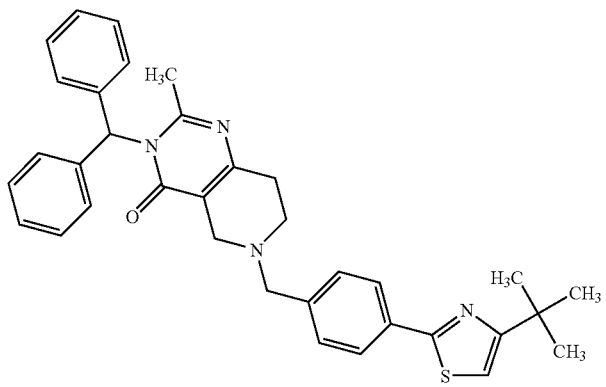 |
| 256 | 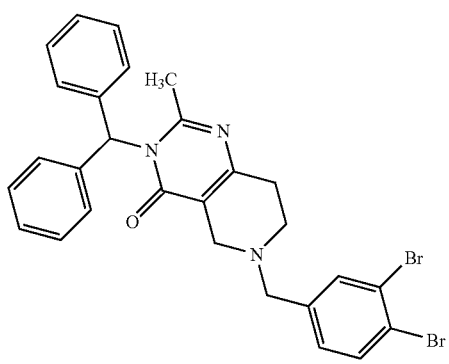 |
| 257 | 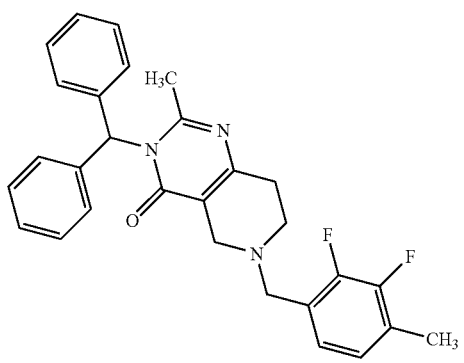 |

| No. | Structure |
|---|---|
| 258 | 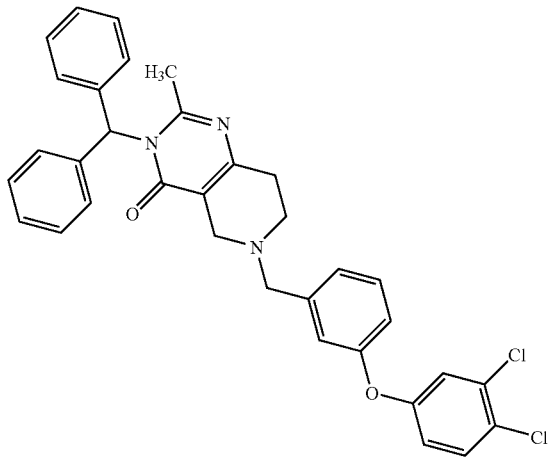 |
| 259 | 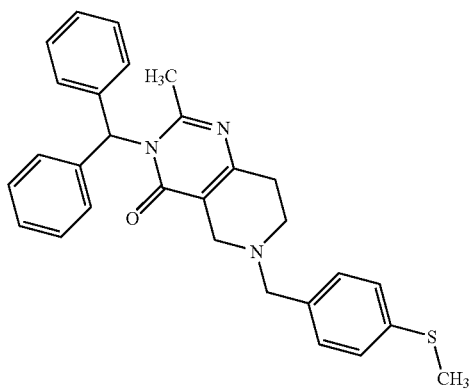 |
| 260 | 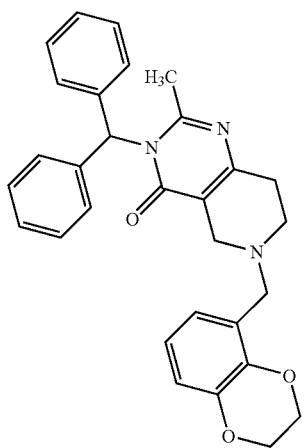 |

| No. | Structure |
|---|---|
| 261 | 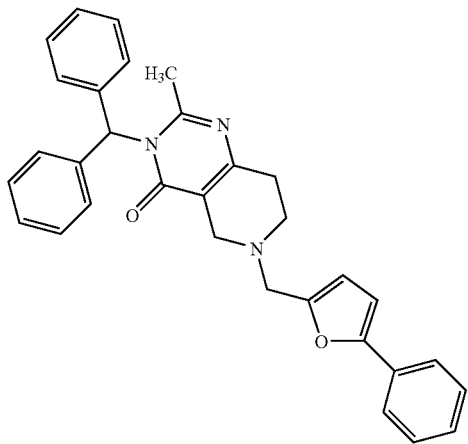 |
| 262 | 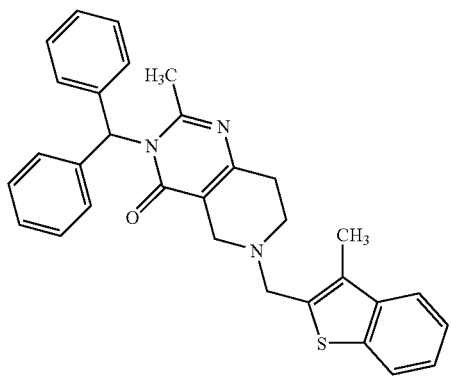 |
| 263 | 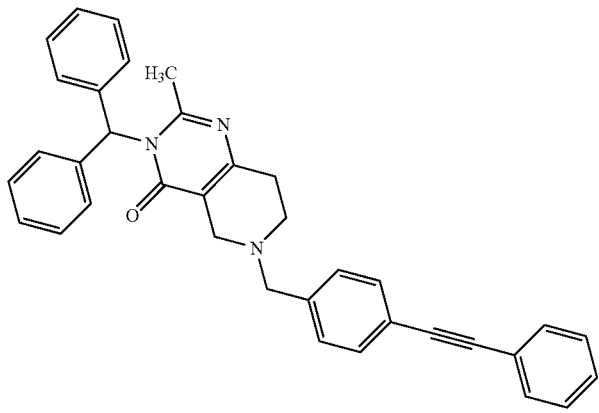 |

| No. | Structure |
|---|---|
| 264 | 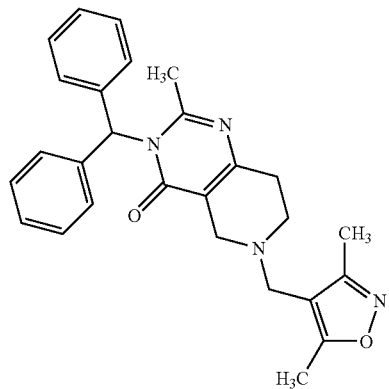 |
| 265 | 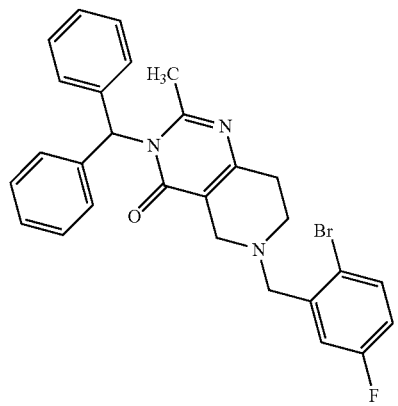 |
| 266 | 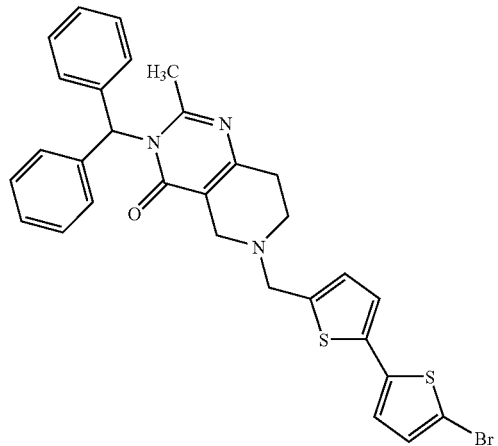 |

-continued
| No. | Structure |
|---|---|
| 267 | 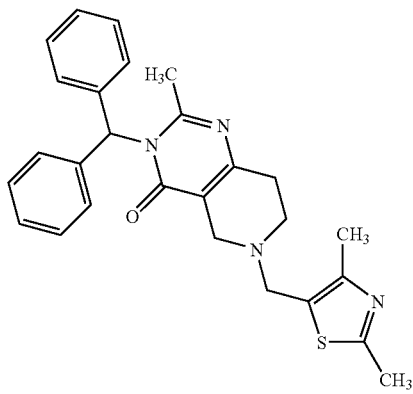 |
| 268 | 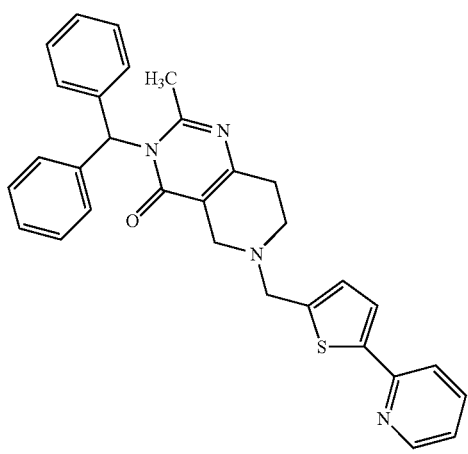 |
| 269 | 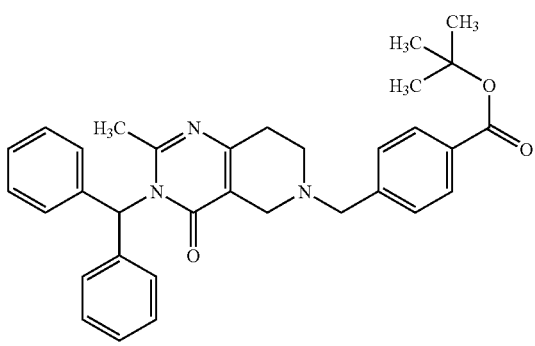 |
| 270 | 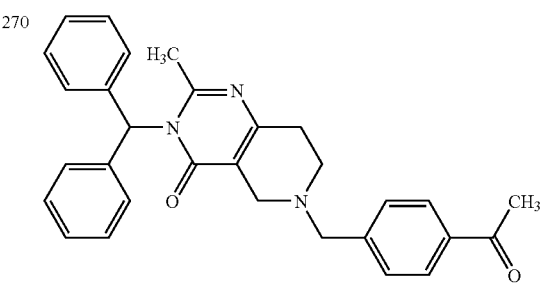 |

| No. | Structure |
|-----|-----------|
| 271 | 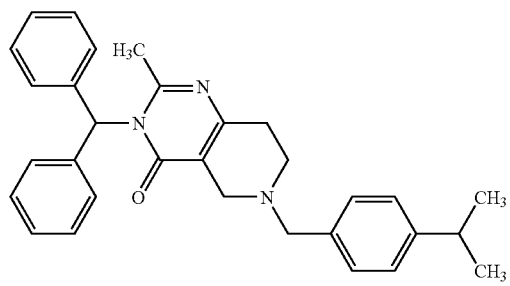 |
| 272 | 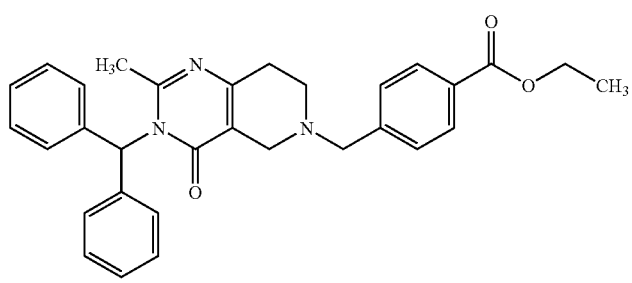 |
| 273 | 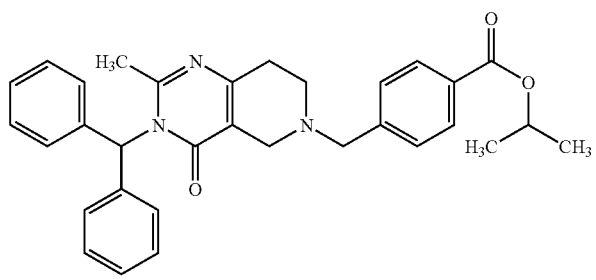 |
| 274 | 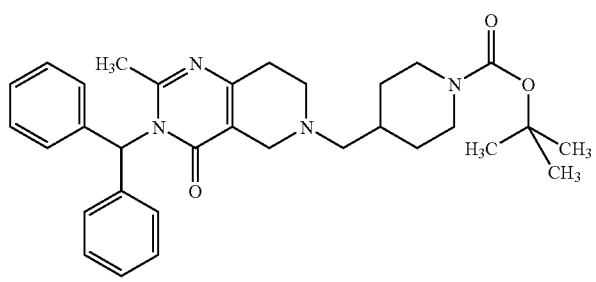 |
| 275 | 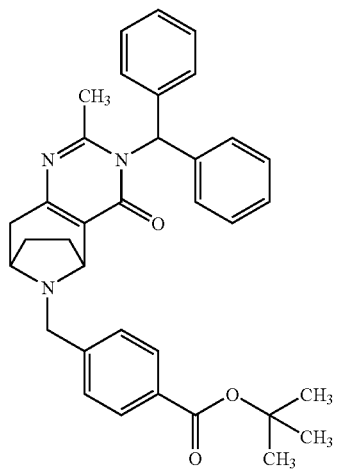 |

| No. | Structure |
|---|---|
| 276 | 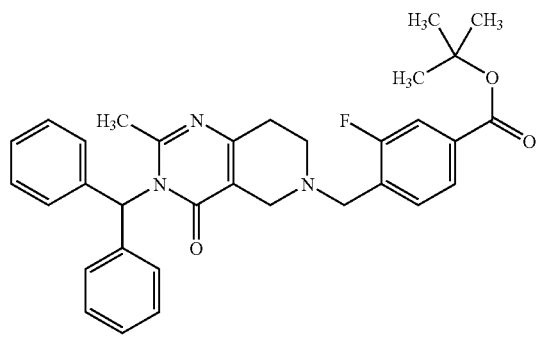 |
| 277 | 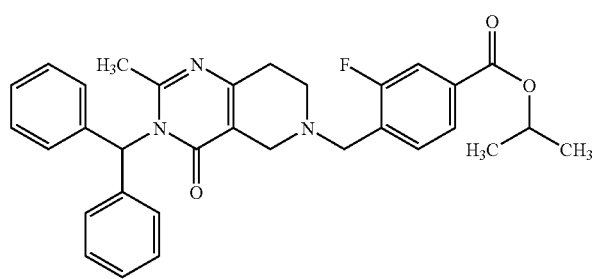 |
| 278 | 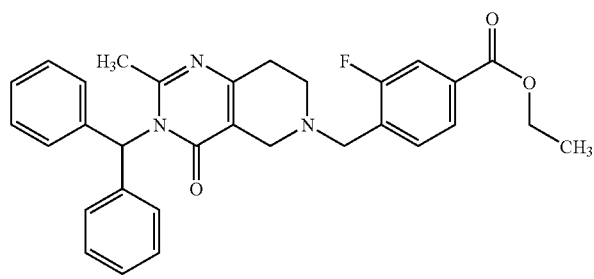 |
| 279 | 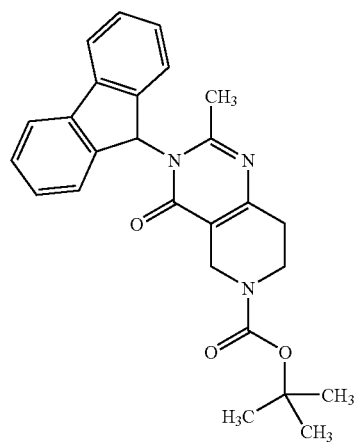 |

-continued
| No. | Structure |
|---|---|
| 280 | 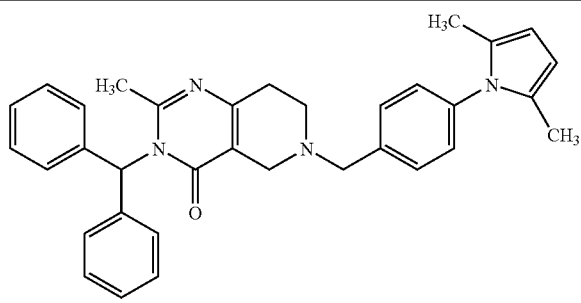 |
| 281 | 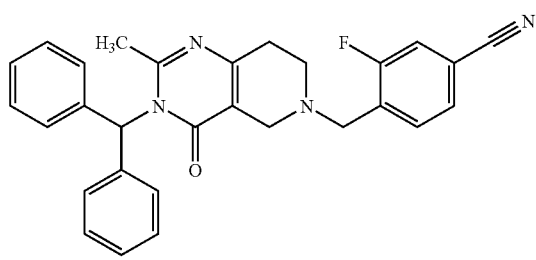 |
| 282 | 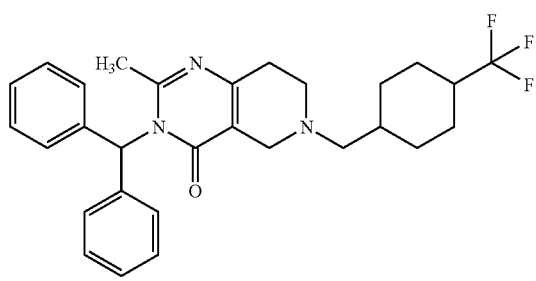 |
| 283 | 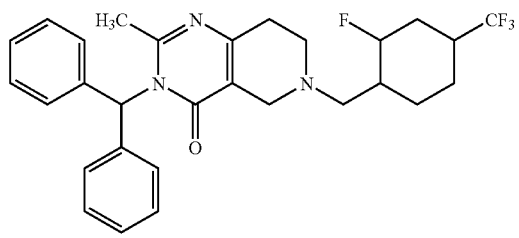 |
| 284 | 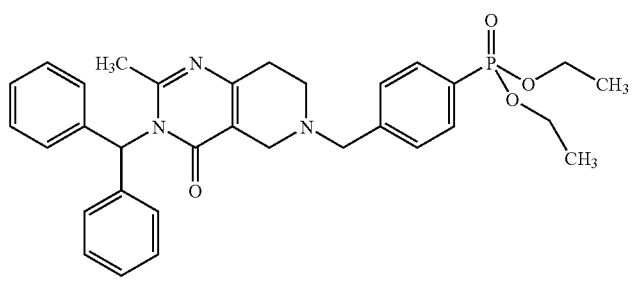 |
| 285 | 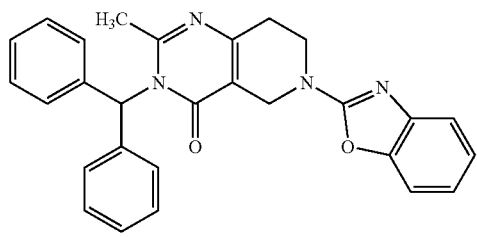 |

| No. | Structure |
|---|---|
| 286 | 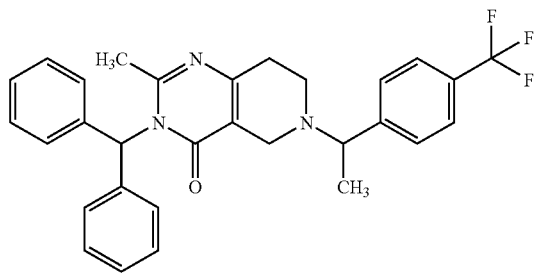 |
| 287 | 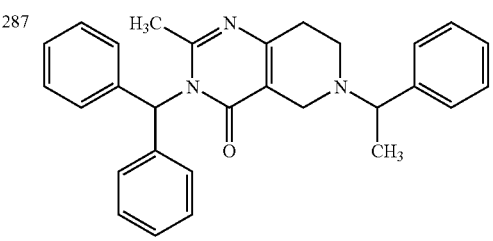 |
| 288 | 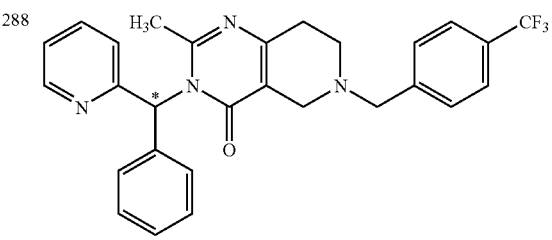
Enantiomer 1 |
| 289 | 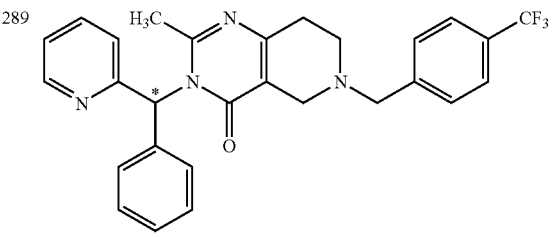
Enantiomer 2 |
| 290 | 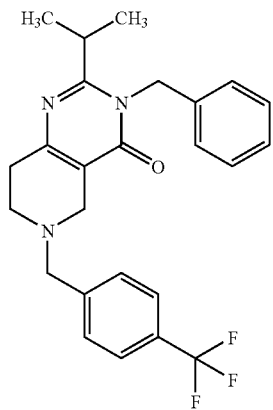 |

-continued
| No. | Structure |
|---|---|
| 291 | 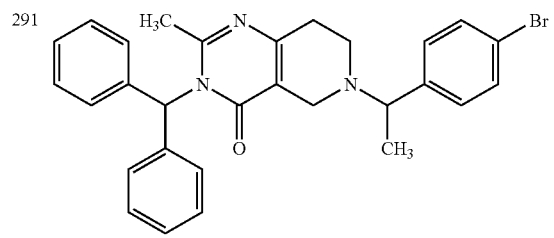 |
| 292 | 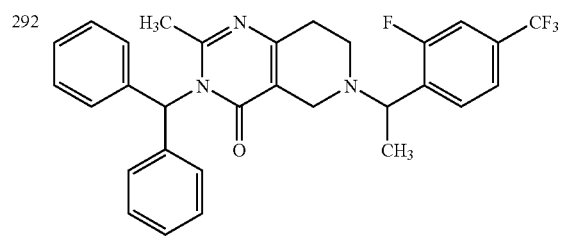 |
| 293 | 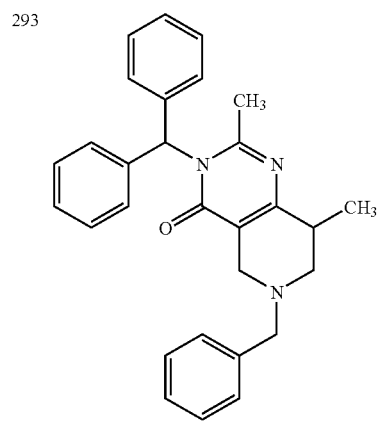 |
| 294 | 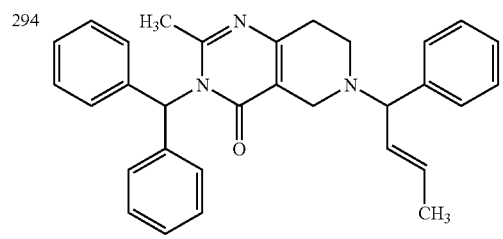 |
| 295 | 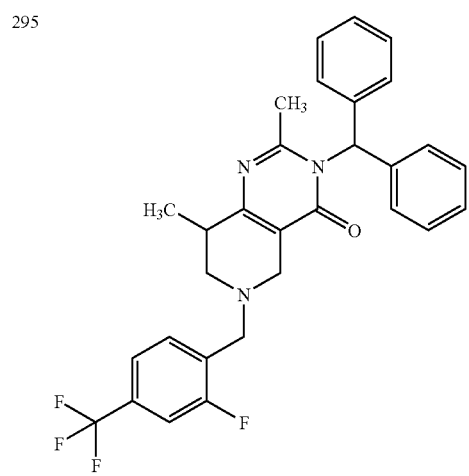 |

-continued
| No. | Structure |
|---|---|
| 296 | 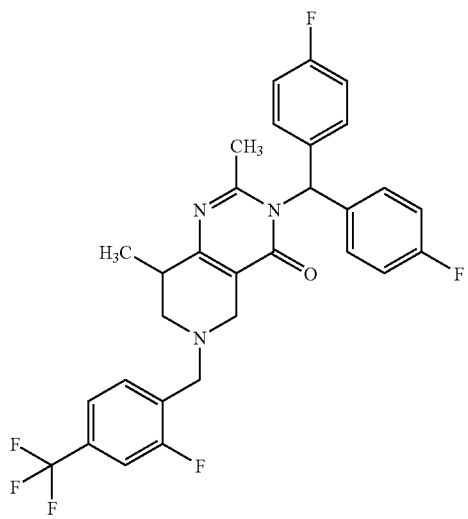 |
| 297 | 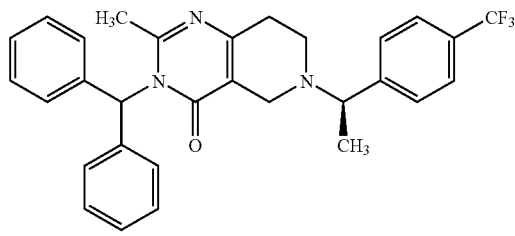 |
| 298 | 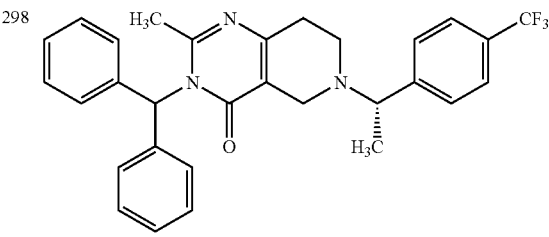 |
| 299 | 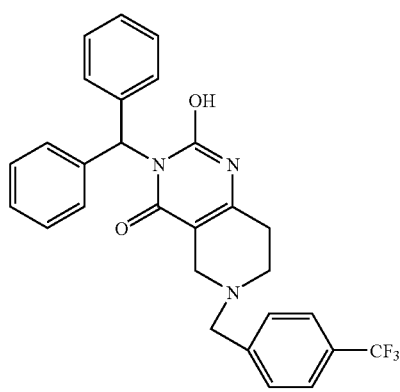 |

-continued
| No. | Structure |
|---|---|
| 300 | 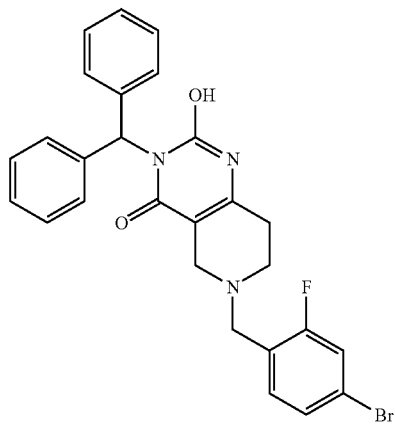 |
| 301 | 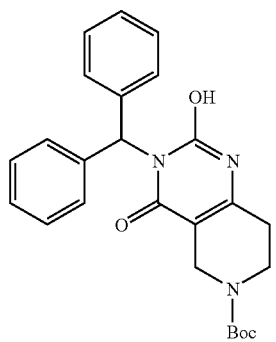 |
| 302 | 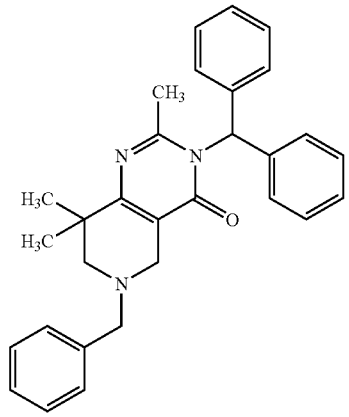 |
| 303 | 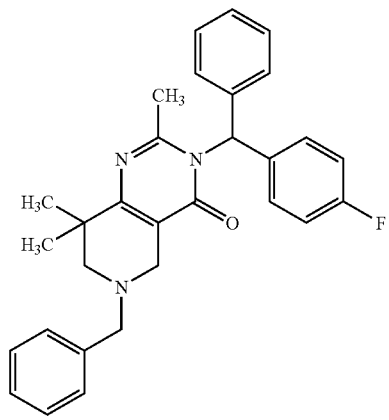 |

| No. | Structure |
|-----|-----------|
| 304 | 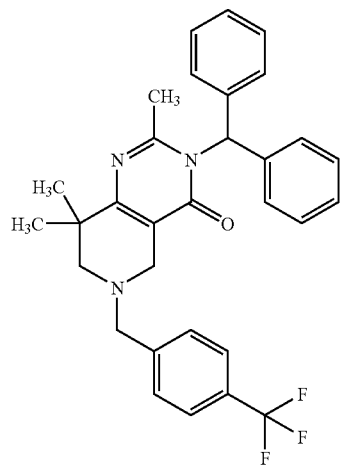 |
| 305 | 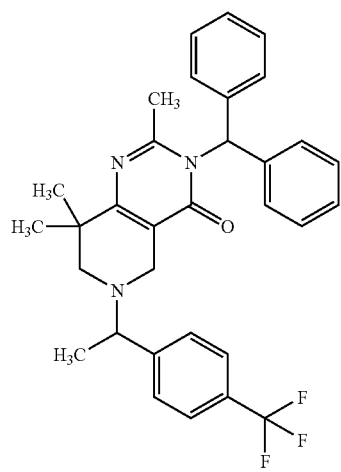 |
| 306 | 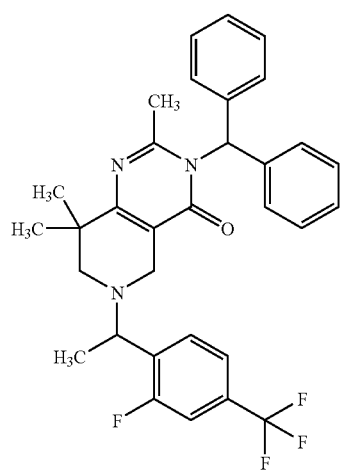 |

| No. | Structure |
|---|---|
| 307 | 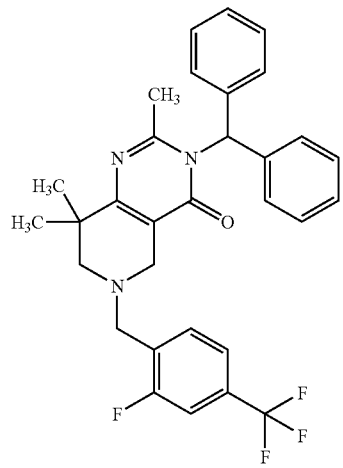 |
| 308 | 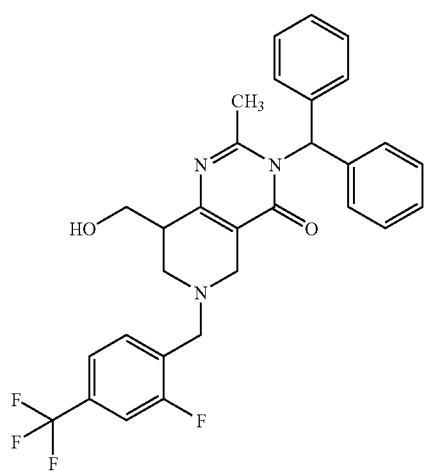 |
| 309 | 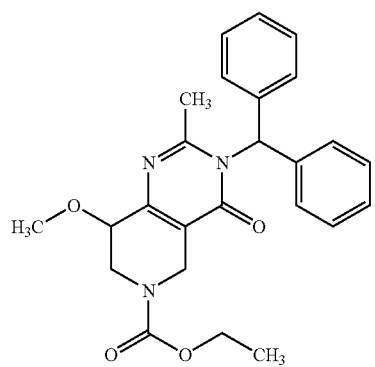 |

-continued
| No. | Structure |
|---|---|
| 310 | 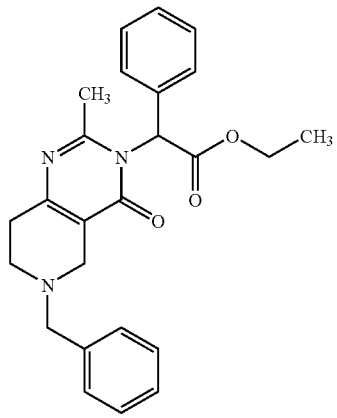 |
| 311 | 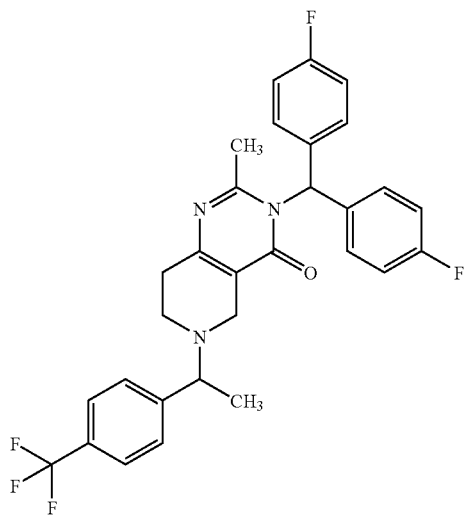<br>Enantiomer 1 |
| 312 | 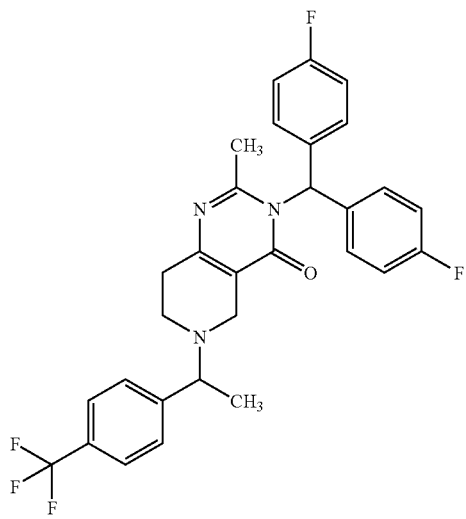<br>Enantiomer 2 |

| No. | Structure |
|---|---|
| 313 | 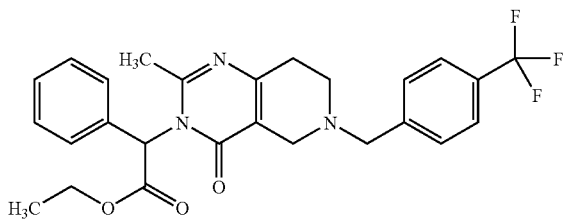 |
| 314 | 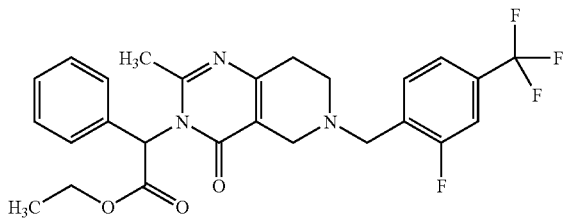 |
| 315 | 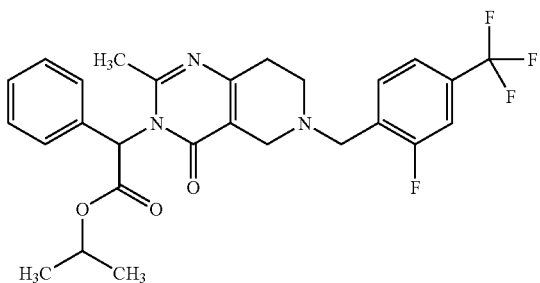 |
| 316 | 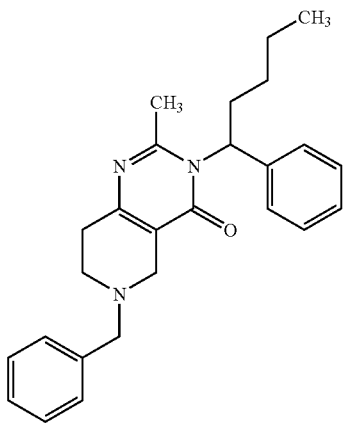 |
| 317 | 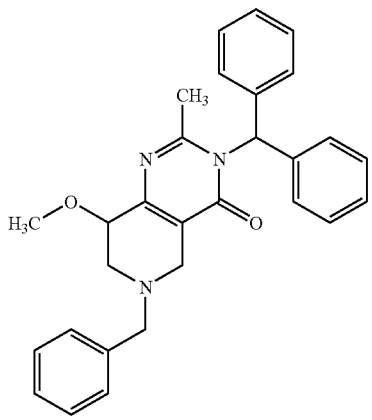 |

-continued
| No. | Structure |
|---|---|
| 318 | 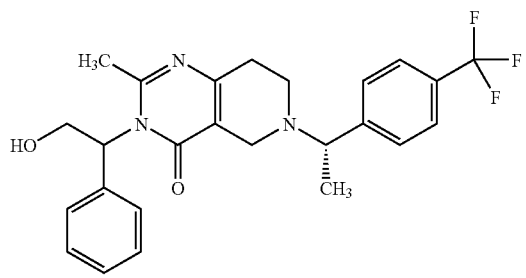 |
| 319 | 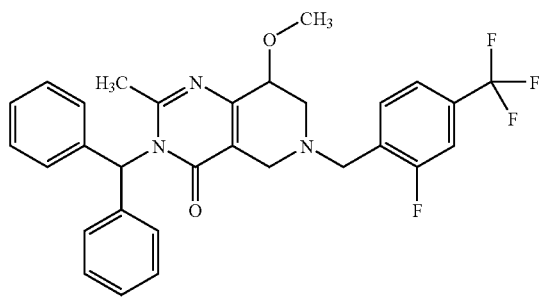 |
| 320 | 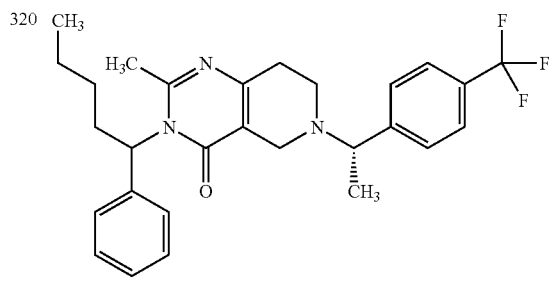 |
| 321 | 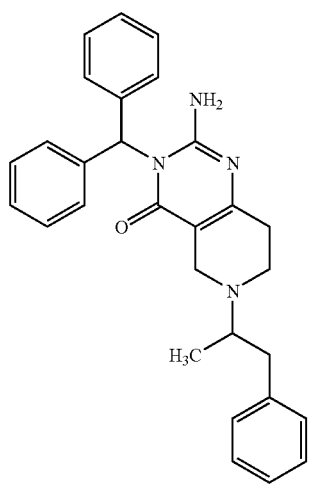 |

| No. | Structure |
|---|---|
| 322 | 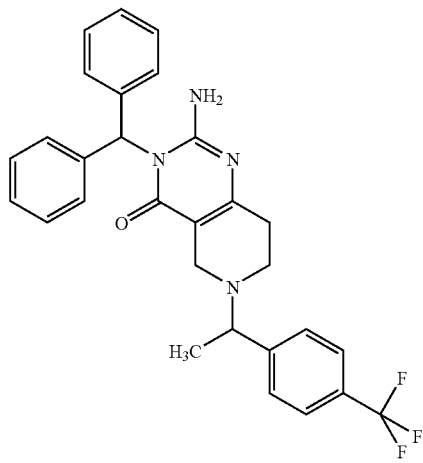 |
| 323 | 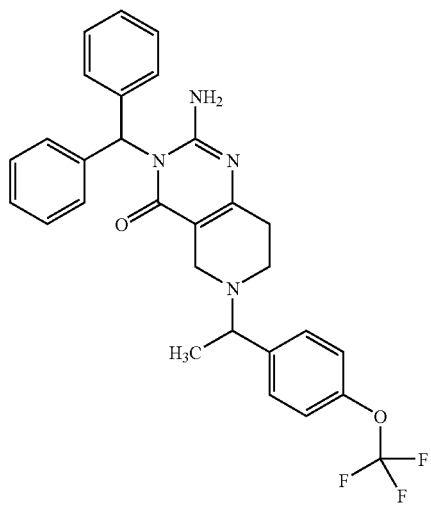 |
| 324 | 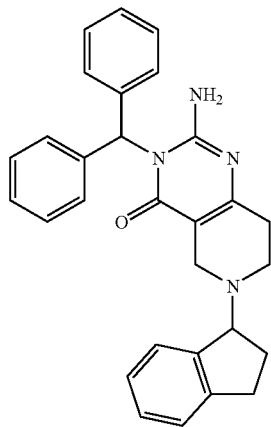 |

| No. | Structure |
|---|---|
| 325 | 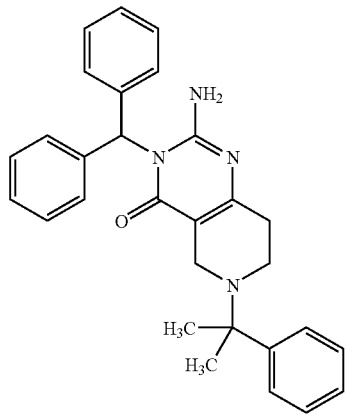 |
| 326 | 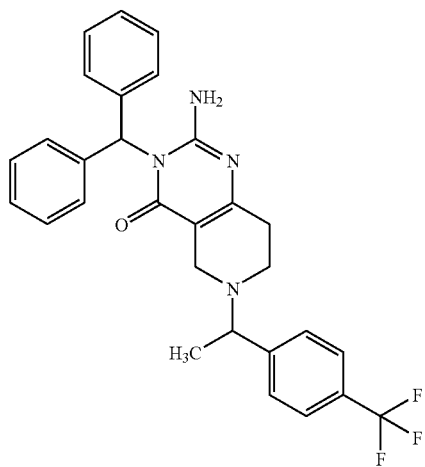<br>Enantiomer 1 |
| 327 | 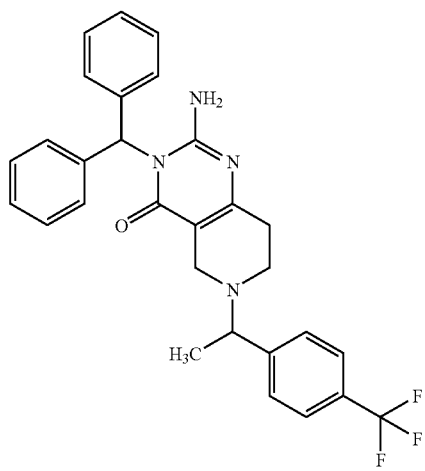<br>Enantiomer 2 |

| No. | Structure |
|---|---|
| 328 | 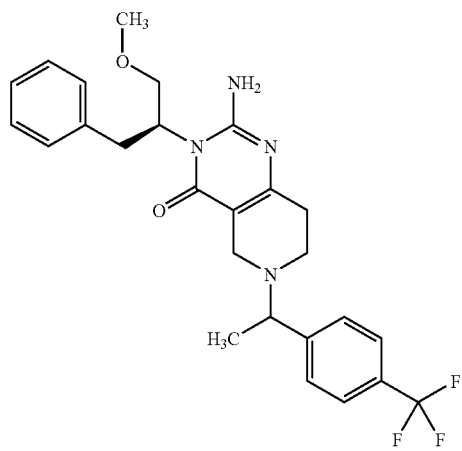 |
| 329 | 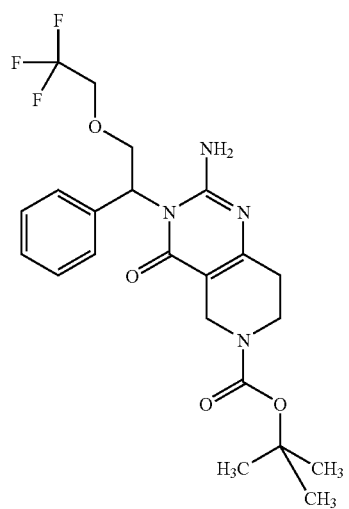 |
| 330 | 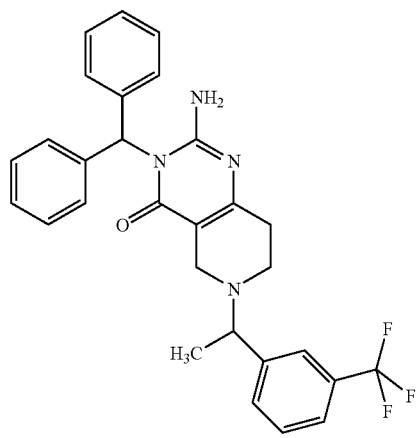 |

| No. | Structure |
|---|---|
| 331 | 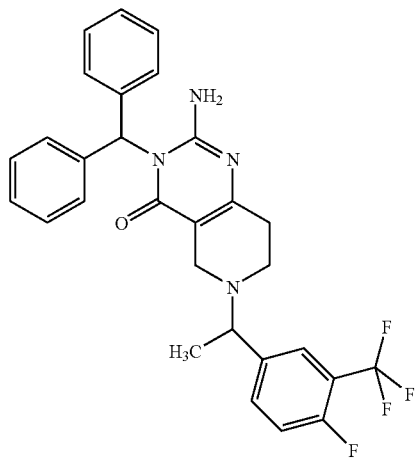 |
| 332 | 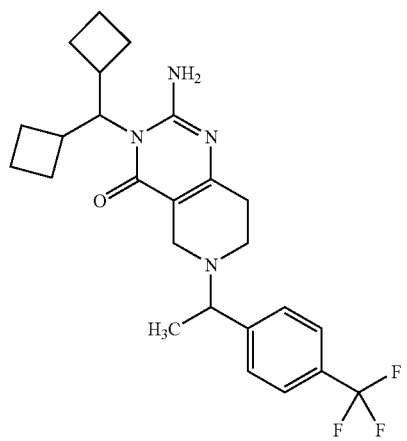 |
| 333 | 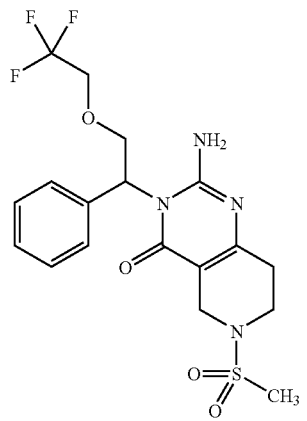 |

| No. | Structure |
|---|---|
| 334 | 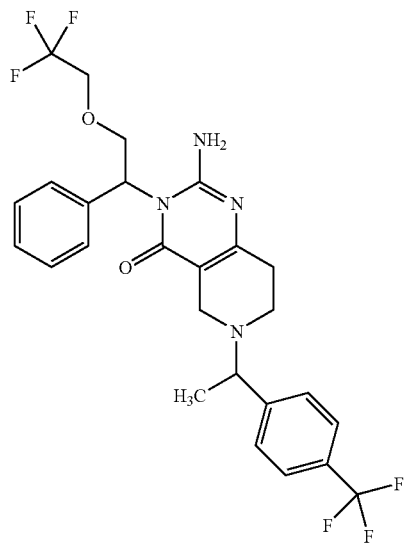 |
| 335 | 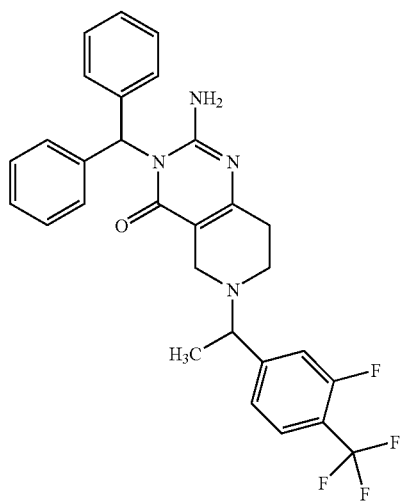 |
| 336 | 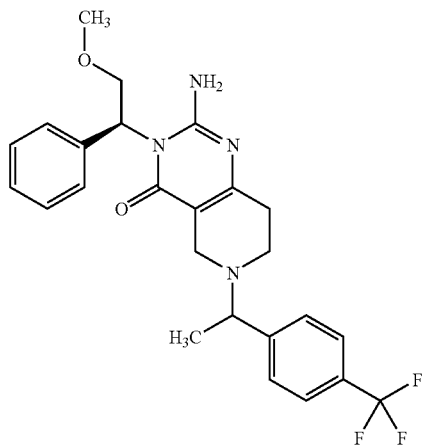 |

| No. | Structure |
|---|---|
| 337 | 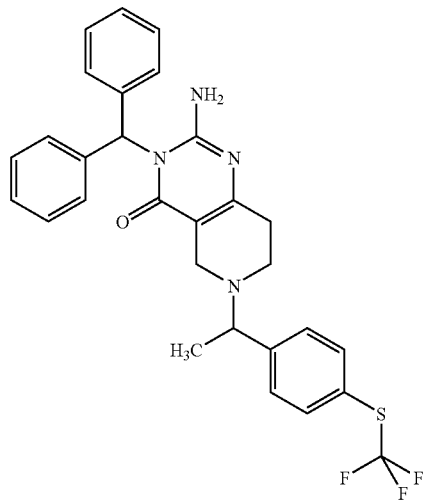 |
| 338 | 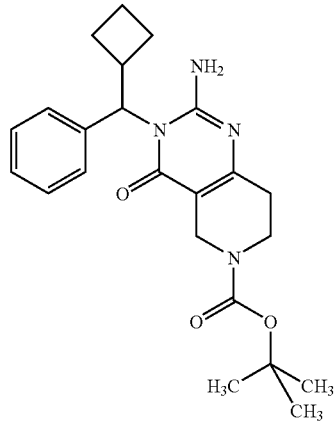 |
| 339 | 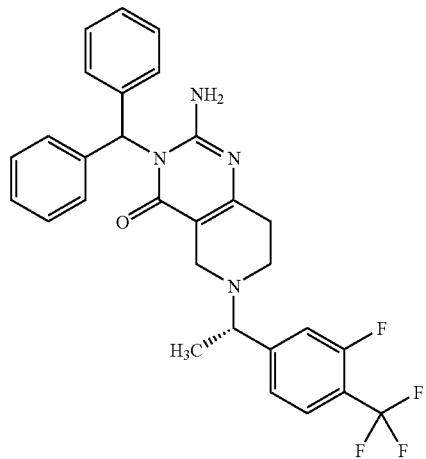 |

| No. | Structure |
|---|---|
| 340 | 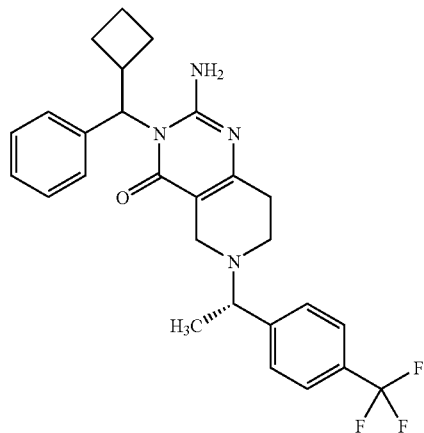 |
| 341 | 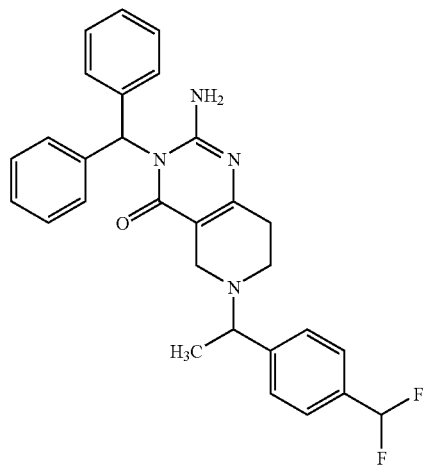 |
| 342 | 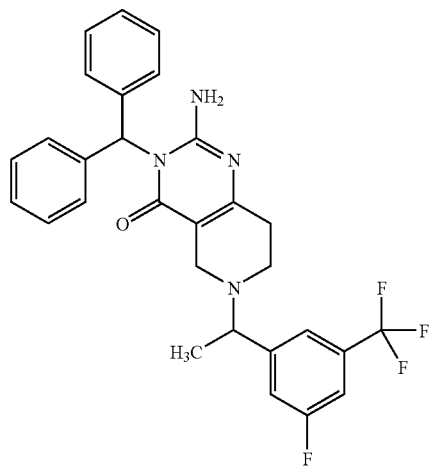 |

| No. | Structure |
|---|---|
| 343 | 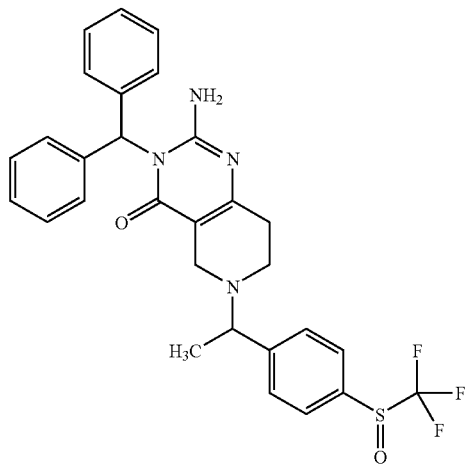 |
| 344 | 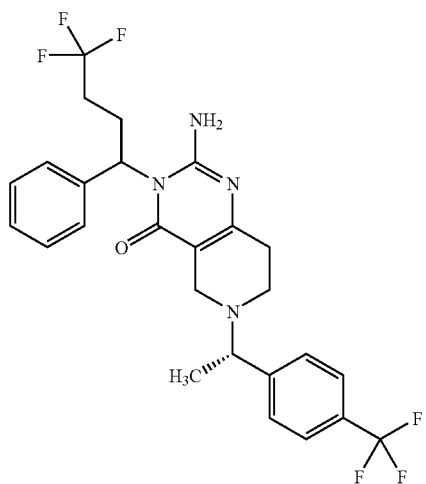 |
| 345 | 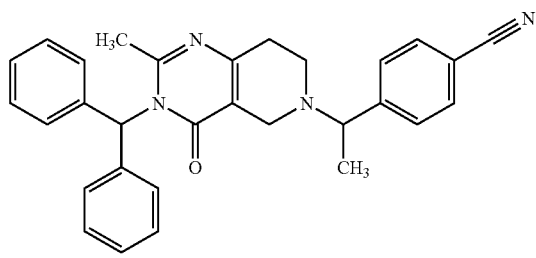 |
| 346 | 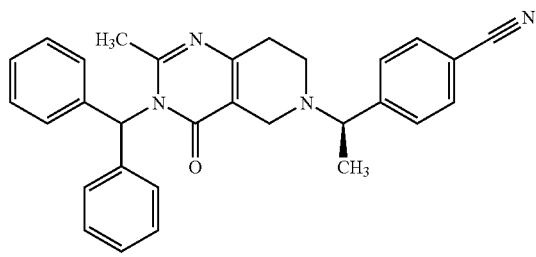 |

| No. | Structure |
|---|---|
| 347 | 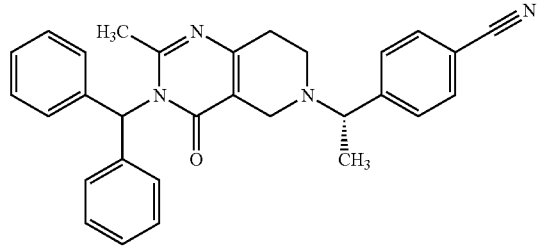 |
| 348 | 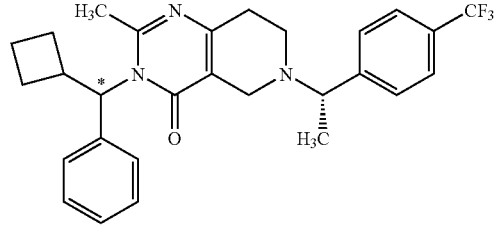
Diastereomer 1 |
| 349 | 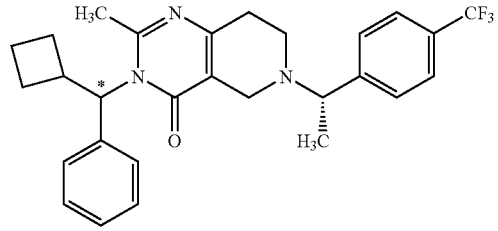
Diastereomer 2 |
| 350 | 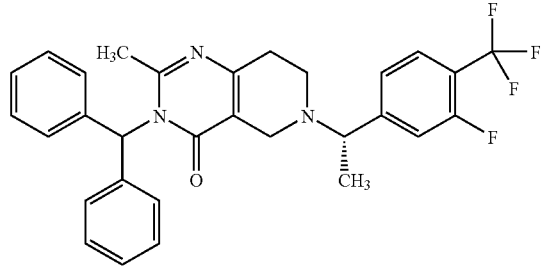 |
| 351 | 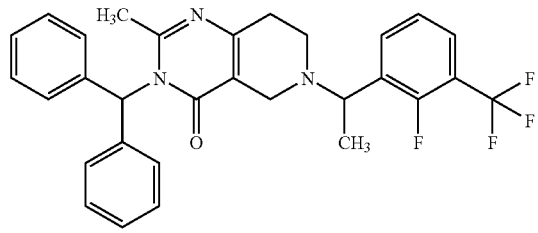 |
| 352 | 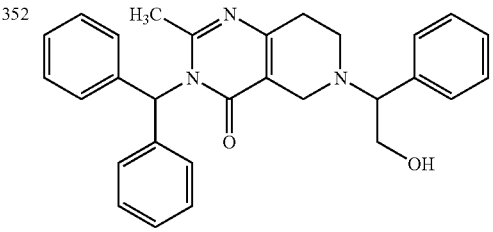 | and pharmaceutically acceptable salts, solvates, esters and prodrugs thereof.

Methods for Making the Compounds of Formula (I)

Methods useful for making the Pyrimidinone Derivatives of Formula (I) are set forth in the Examples below and generalized in Schemes 1-7.

Scheme 1 shows a method useful for making compound C, which is a useful intermediate for making the Pyrimidinone Derivatives.

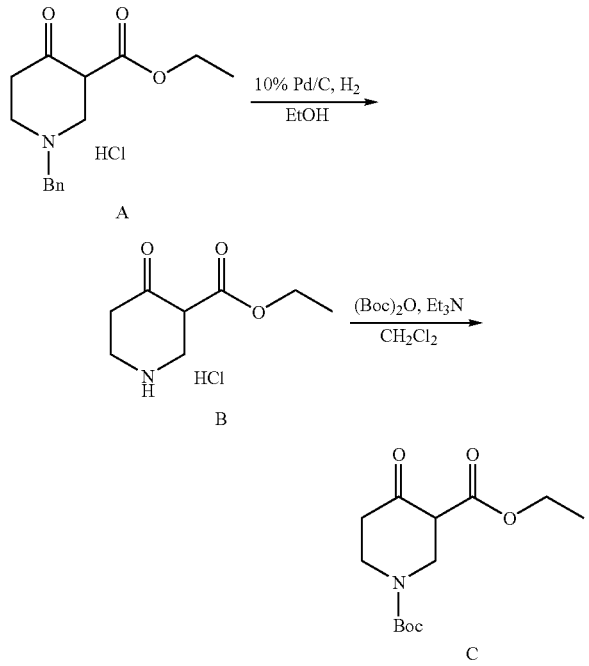

A 4-Oxo-N-benzyl piperidinyl compound of formula A can be deprotected via catalytic hydrogenation using Pd/C to provide the 4-Oxo-piperidinyl compound B. The cyclic amine group of compound B can then be reprotected as its N-t-butyloxycarbonyl (BOC) derivative to provide intermediate compound C using BOC-anhydride and triethylamine.

Scheme 2 shows a method for making the intermediate piperidine hydrochloride compounds of formula H which are useful intermediates for making the Pyrimidinone Derivatives.

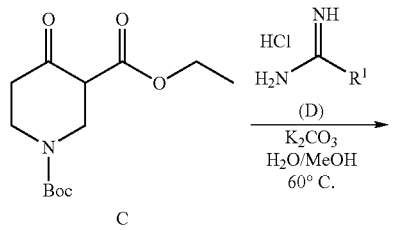

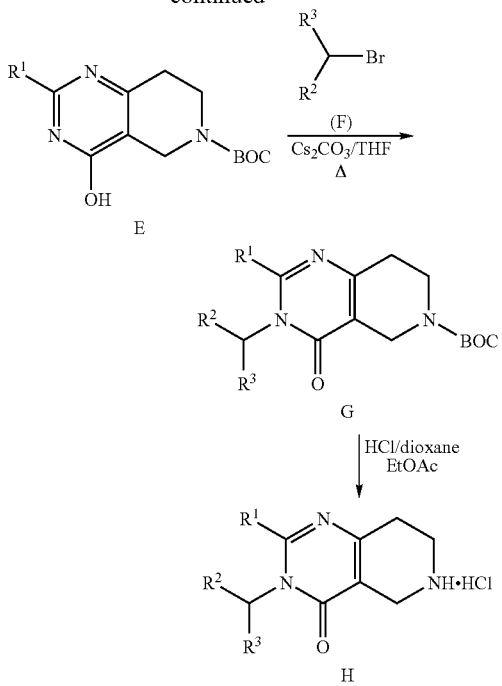

wherein $R^1$, $R^2$ and $R^3$ are defined above for the compounds of formula (I).

Compound C can be reacted with an amidine hydrochloride compound of formula D to provide the pyrido-pyrimidine compounds of formula E, which can then be reacted with a compound of formula F in the presence of a carbonate base to provide the substituted pyrimidinone compounds of formula G. The BOC protecting group of a compound of formula G can then be removed using HCl to provide the piperidine hydrochloride compounds of formula H.

Scheme 3 shows a method for converting intermediate compounds of formula H to the Pyrimidinone Derivatives, wherein $R^4$ is joined via a methylene group.

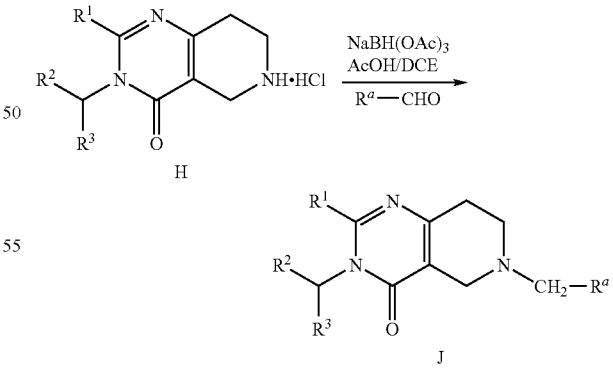

wherein $R^1$, $R^2$ and $R^3$ are defined above for the compounds of formula (I) and $CH_2R^a$ is representative of all $R^4$ substituents, as defined for the compounds of formula (I), that are connected via a methylene group.

The amine hydrochloride compounds of formula H can be reacted with an aldehyde of formula $R^a$—CHO and NaBH (OAc)$_3$ to provide the compounds of formula J, which correspond to the compounds of formula (I) wherein R$^4$ is a substituent that is connected via a methylene group.

Scheme 4 shows a method for converting intermediate compounds of formula H to the Pyrimidinone Derivatives, wherein R$^4$ is joined via a —SO$_2$—group.

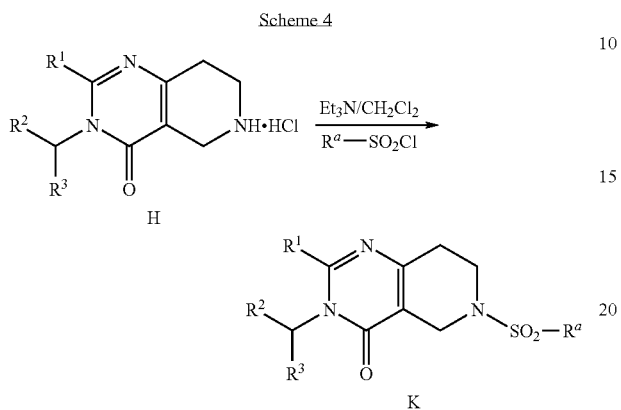

wherein R$^1$, R$^2$ and R$^3$ are defined above for the compounds of formula (I) and —SO$_2$R$^a$ is representative of all R$^4$ substituents, as defined for the compounds of formula (I), that are connected via a —S(O)$_2$—group.

The amine hydrochloride compounds of formula H can be reacted with a sulfonyl chloride of formula R$^a$—SO$_2$Cl in the presence of a non-nucleophilic base, such as Et$_3$N, to provide the compounds of formula K, which correspond to the compounds of formula (I) wherein R$^4$ is a substituent that is connected via a —S(O)$_2$—group.

Scheme 5 shows a method for converting intermediate compounds of formula H to the Pyrimidinone Derivatives, wherein R$^4$ is joined via a —C(O)NH—group.

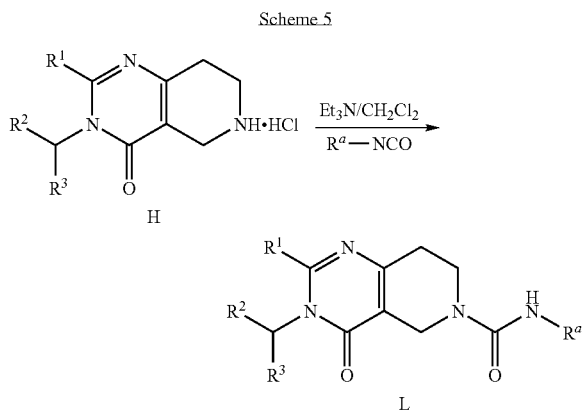

wherein R$^1$, R$^2$ and R$^3$ are defined above for the compounds of formula (I) and —C(O)NHR$^a$ is representative of all R$^4$ substituents, as defined for the compounds of formula (I), that are connected via a —C(O)NH—group.

The amine hydrochloride compounds of formula H can be reacted with an isocyanate of formula R$^a$—NCO, in the presence of a non-nucleophilic base, such as Et$_3$N, to provide the compounds of formula L, which correspond to the compounds of formula (I) wherein R$^4$ is a substituent that is connected via a —C(O)NH—group.

Scheme 6 shows a method for converting intermediate compounds of formula H to the Pyrimidinone Derivatives, wherein R$^4$ is joined via a —C(O)—group.

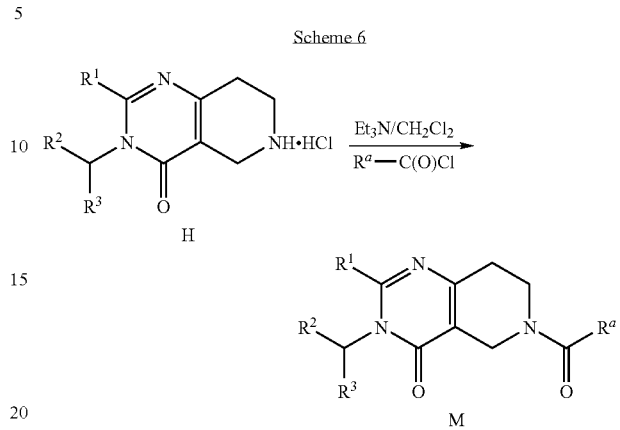

wherein R$^1$, R$^2$ and R$^3$ are defined above for the compounds of formula (I) and —C(O)R$^a$ is representative of all R$^4$ substituents, as defined for the compounds of formula (I), that are connected via a —C(O)—group.

The amine hydrochloride compounds of formula H can be reacted with an acid chloride of formula R$^a$—C(O)Cl or an appropriate mixed anhydride, in the presence of a non-nucleophilic base, such as Et$_3$N, to provide the compounds of formula M, which correspond to the compounds of formula (I) wherein R$^4$ is a substituent that is connected via a —C(O)—group.

Scheme 7 shows a method for converting intermediate compounds of formula H to the Pyrimidinone Derivatives, wherein R$^4$ is joined via a —C(O)O—group.

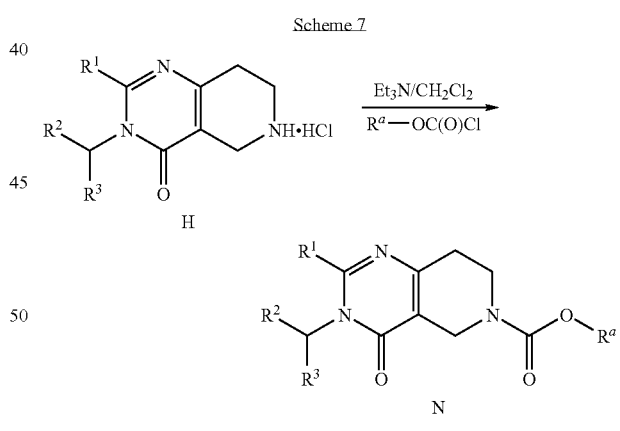

wherein R$^1$, R$^2$ and R$^3$ are defined above for the compounds of formula (I) and —C(O)OR$^a$ is representative of all R$^4$ substituents, as defined for the compounds of formula (I), that are connected via a —C(O)O—group.

The amine hydrochloride compounds of formula H can be reacted with a chloroformate of formula R$^a$—OC(O)Cl, in the presence of a non-nucleophilic base, such as Et$_3$N, to provide the compounds of formula N, which correspond to the compounds of formula (I) wherein R$^4$ is a substituent that is connected via a —C(O)O—group.

The starting materials and reagents depicted in Schemes 1-7 are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art will recognize that the synthesis of the compounds of Formula (I) may require the need for the protection of certain functional groups (i.e., derivatization for the purpose of chemical compatibility with a particular reaction condition). Suitable protecting groups for the various functional groups of the compounds of formula (I) and methods for their installation and removal may be found in Greene et al., Protective Groups in Organic Synthesis, Wiley-Interscience, New York, (1999).

EXAMPLES

The following examples exemplify illustrative examples of compounds of the present invention and are not to be construed as limiting the scope of the disclosure. Alternative mechanistic pathways and analogous structures within the scope of the invention may be apparent to those skilled in the art.

General Methods

Solvents, reagents, and intermediates that are commercially available were used as received. Reagents and intermediates that are not commercially available were prepared in the manner described below. $^1$H NMR spectra were obtained on a Gemini AS-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

Example 1

Preparation of Compound 25

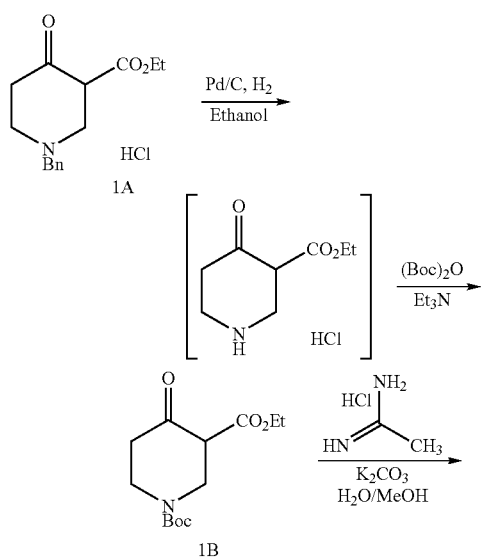

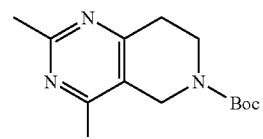

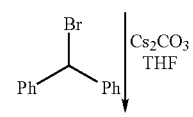

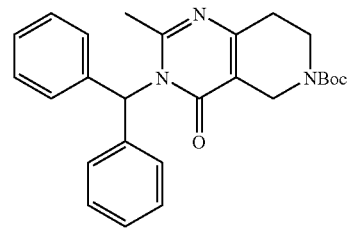

Step 1—Synthesis of Compound 1B

A solution of 1-benzyl-3-carboethoxy-4-piperidone hydrochloride (1A) (10.0 g, 33.6 mmol) in ethanol (800 mL) and Pd/C (1.0 g, 10% w/w) was hydrogenated at 1 atm. for about 15 hours at room temperature. After the reaction was complete, triethylamine (19 mL, 134.3 mmol) and (Boc)$_2$O (8.0 g, 36.9 mmol) were added to the mixture. The resulting solution was stirred at room temperature for 16 hours and the catalyst was removed by filtering through Celite®. The filtrate was concentrated in vacuo, the resulting residue was dissolved in dichloromethane and extracted by washing with water. The organic phase was separated and dried over Na$_2$SO$_4$ and concentrated in vacuo to provide compound 1B (9.1 g, 100%).

Step 2—Synthesis of Compound 1C

To a solution of acetamidine hydrochloride (3.8 g, 40.3 mmol) in water (18 mL) and methanol (70 mL) was added potassium carbonate (7.03 g, 50.9 mmol) and compound 1B (9.1 g, 33.6 mmol). The reaction was stirred at 60° C. for about 15 hours, then cooled to room temperature, neutralized with 1N HCl and extracted with dichloromethane. The combined organic extracts were dried over MgSO$_4$, filtered and triturated with hexanes. The precipitate formed was filtered and collected to provide compound 1C (5.5 g, 61%).

Step 3—Synthesis of Compound 25

To a solution of Compound 1C (5.64 g, 21.3 mmol) in THF (50 mL) was added benzhydryl bromide (5.57 g, 22.4 mmol), followed by Cs$_2$CO$_3$ (10.4 g, 31.9 mmol) and the resulting reaction was heated to reflux and allowed to stir at this temperature for about 15 hours. The reaction mixture was cooled to room temperature and diluted with water. The resulting solution was extracted with EtOAc and the organics were dried over MgSO$_4$, filtered and concentrated in vacuo to

Example 2

Preparation of Compound 1

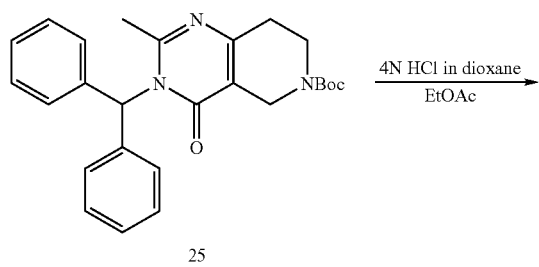

Step 1—Synthesis of the Hydrochloride Salt of Compound 1

To a solution of compound 25 (1.1 g, 2.5 mmol) in EtOAc (11.0 mL) was added 4 N HCl in dioxane (3.0 mL). The solution was stirred at room temperature for about 15 hours. The product precipitated out of solution as a white solid. The suspension was filtered to provide the hydrochloride salt of compound 1 (0.90 g, 98%).

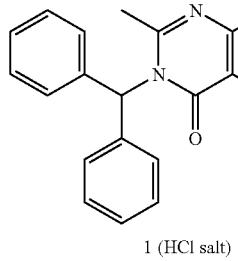

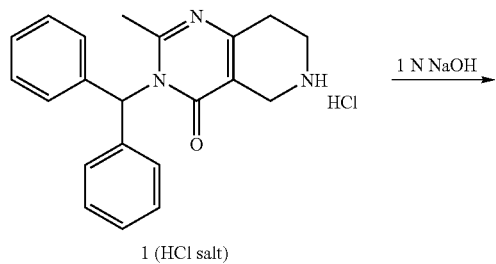

Step 2—Synthesis of Compound 1

The hydrochloride salt of compound 1 (0.25 g, 0.68 mmol) was treated with 1 N NaOH and extracted with dichloromethane several times. The organics were combined, dried over MgSO$_4$, filtered and concentrated in vacuo to provide compound 1 (0.225 g, 100%).

Example 3

Preparation of Compound 4

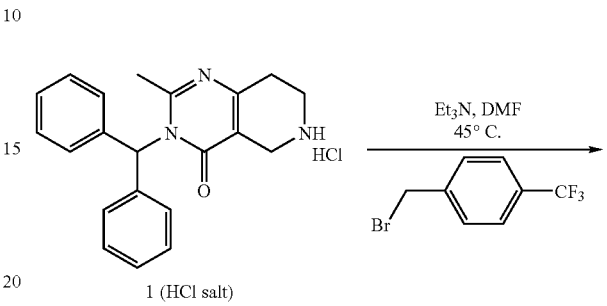

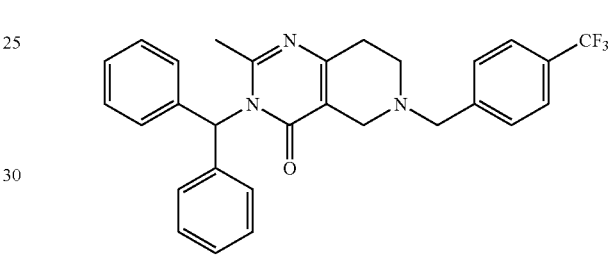

A solution of the hydrochloride salt of compound 1 (0.010 g, 0.027 mmol), p-trifluoromethyl benzyl bromide (0.01 mL, 0.054 mmol) and triethylamine (0.01 mL, 0.081 mmol) in DMF (0.75 mL) was heated to 45° C. in a sealed tube for about 15 hours. The solvent was concentrated in vacuo and EtOAc and water were added to the resulting residue. The resulting solution was extracted with EtOAc (3×) and the combined organics were washed with water, dried over MgSO$_4$, filtered and concentrated in vacuo to provide a crude residue which was purified using preparative layer chromatography (5% MeOH/dichloromethane) to provide compound 4 (0.008 g, 60%).

Example 4

Preparation of Compound 136

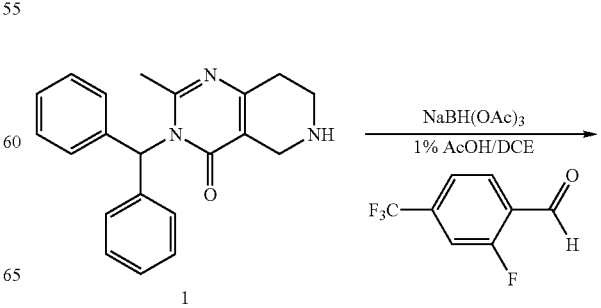

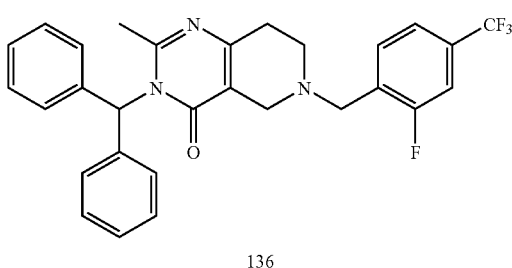

136

Compound 1 (0.058 g, 0.18 mmol) was dissolved in 1% acetic acid in dichloroethane (3.5 mL) and 2-fluoro-4-(trifluoromethyl)benzaldehyde (0.048 g, 0.23 mmol) was added followed by sodium triacetoxyborohydride (0.067 g, 0.32 mmol). The reaction was stirred for about 15 hours at room temperature, then diluted with dichloromethane, washed with NaHCO$_3$, dried over MgSO$_4$, filtered and concentrated in vacuo. The crude residue obtained was purified using preparative layer chromatography (5% MeOH/dichloromethane) to provide compound 136 (0.053 g, 55%).

Example 5

Preparation of Compound 26

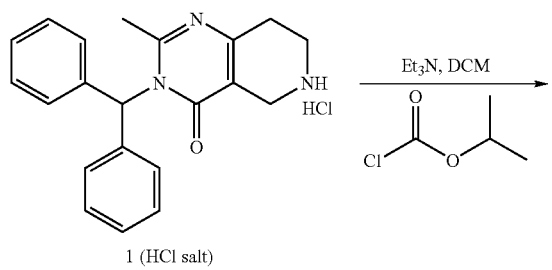

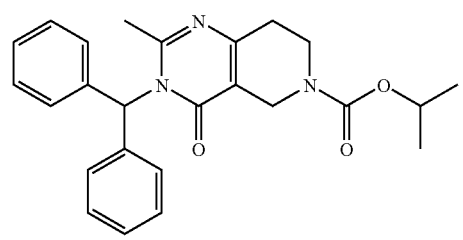

26

To a solution of the hydrochloride salt of compound 1 (0.025 g, 0.068 mmol) and triethylamine (0.03 mL, 0.20 mmol) in dichloromethane (1 mL), was added isopropyl chloroformate (0.08 mL, 0.075 mmol) and the reaction was allowed to stir for about 15 hours at RT. The reaction mixture was quenched with saturated aqueous NH$_4$Cl, then extracted with dichloromethane and concentrated in vacuo. The residue obtained was purified using preparative layer chromatography (5% MeOH/dichloromethane) to provide compound 26 (0.020 g, 71%).

Example 6

Preparation of Compound 271

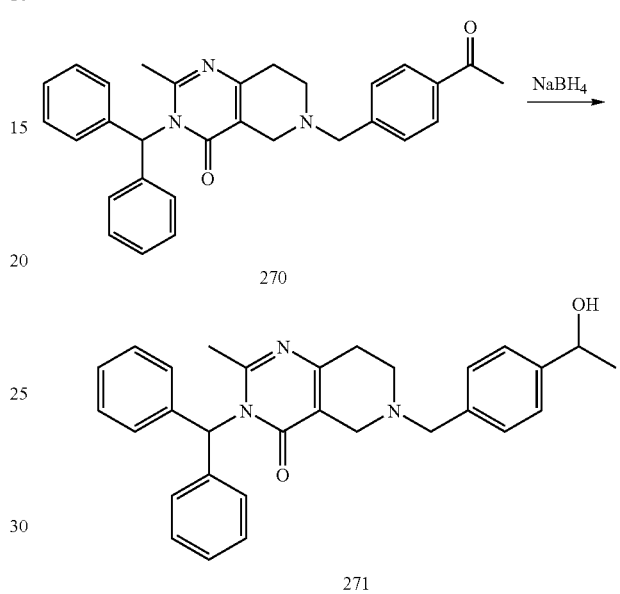

Step 1—Synthesis of Compound 270

Compound 270 was prepared from compound 1 using the method described in Example 4 and substituting 4-acetylbenzaldehyde for 2-fluoro-4-(trifluoromethyl)benzaldehyde.

Step 2—Synthesis of Compound 271

A solution of compound 270 (0.025 g, 0.054 mmol) in MeOH (1 mL) was cooled to 0° C. under N$_2$ and sodium borohydride (0.006 g, 0.16 mmol) was added as a solid. After stirring for 1.5 hours, the reaction mixture was concentrated in vacuo and the residue obtained was diluted with dichloromethane and water. The mixture was extracted with dichloromethane and the combined organics were dried over MgSO$_4$, filtered and concentrated in vacuo to provide a crude residue which was purified using preparative layer chromatography (5% MeOH/dichloromethane) to provide compound 271 (0.018 g, 70%).

Example 7

Preparation of Compound 284

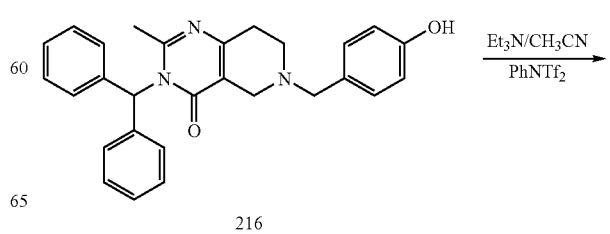

216

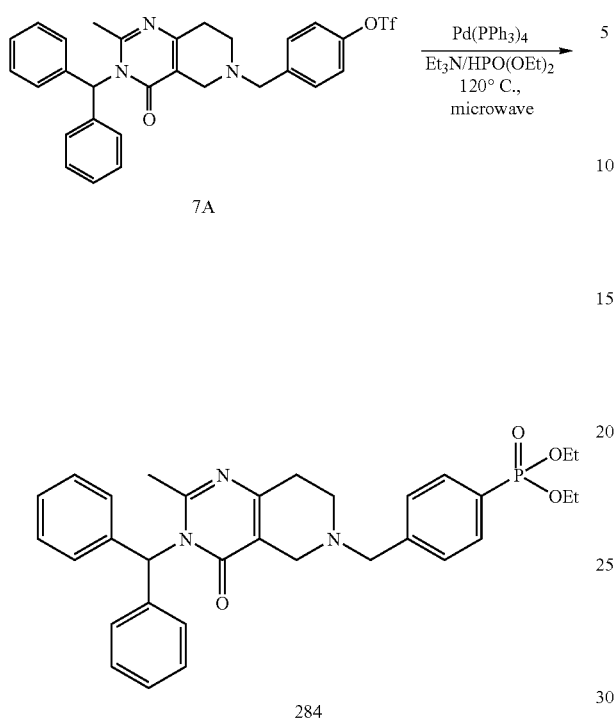

7A

284

Step 1—Synthesis of Compound 216

Compound 216 was prepared from compound 1 using the method described in Example 4 and substituting 4-hydroxybenzaldehyde for 2-fluoro-4-(trifluoromethyl)benzaldehyde.

Step 2—Synthesis of Compound 7A

To a solution of compound 216 (0.080 g, 0.18 mmol) in CH$_3$CN (9 mL) was added triethylamine (0.05 mL) and N-phenyltrifluoromethanesulfonimide (0.121 g, 0.33 mmol). The reaction was allowed to stir at room temperature for about 15 hours and was then diluted with EtOAc and the organic phase was washed sequentially with saturated aqueous NaHCO$_3$ and brine. The organics then were dried over MgSO$_4$, filtered and concentrated in vacuo to provide a crude material which was purified using silica gel column chromatography with 20% acetone/hexanes to provide compound 7A (0.090 g, 88%).

Step 2—Synthesis of Compound 284

To a solution of compound 7A (0.090 g, 0.16 mmol) in triethylamine (2 mL) was added diethyl phosphite (0.03 mL, 0.024 mmol) and tetrakis(triphenyl phosphine)palladium(0) (0.018 g). The reaction was heated to 120° C. and allowed to stir at this temperature for 40 minutes in a microwave oven (Biotage Optimizer microwave run at high absorption). The reaction was then quenched with water, neutralized with 1N HCl and extracted with EtOAc. The combined organics were washed with brine, dried over MgSO$_4$, filtered and concentrated in vacuo to provide a crude material which was purified using preparative layer chromatography (5% MeOH/dichloromethane) to provide compound 284 (0.019 g, 21%).

Example 8

Preparation of Compound 285

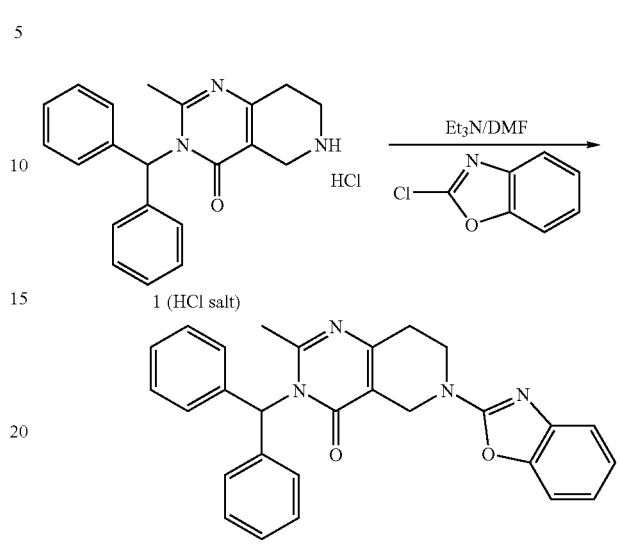

1 (HCl salt)

285

2-Chlorobenzoxazole (0.015 g, 0.100 mmol) was added dropwise to a stirred solution of the hydrochloride salt of compound 1 (0.035 g, 0.095 mmol) in DMF (1.5 mL) and triethylamine (0.05 mL, 0.48 mmol) in a sealed tube. The reaction was heated to 100° C. and allowed to stir at this temperature for about 15 hours. The reaction was cooled to room temperature, quenched with saturated aqueous NH$_4$Cl, then extracted with dichloromethane (3×). The combined organics were dried over MgSO$_4$, filtered and concentrated in vacuo to provide a crude material which was purified using preparative layer chromatography (20% acetone/hexanes) to provide compound 285 (0.011 g, 24%).

Example 9

Preparation of Compound 292

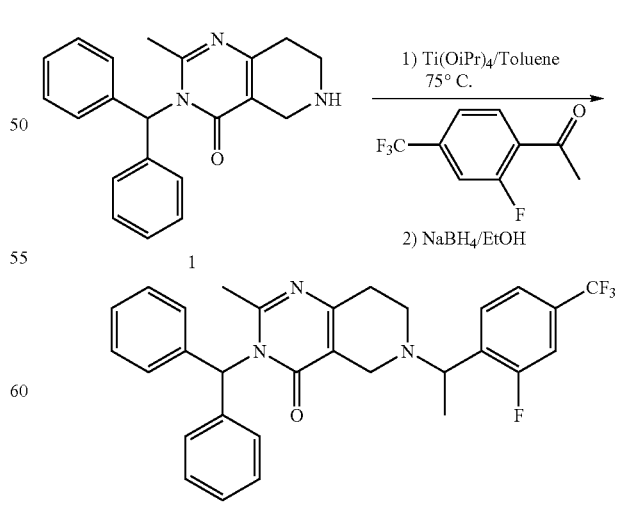

1

292

A mixture of compound 1 (0.037 g, 0.094 mmol), titanium isopropoxide (0.1 mL, 0.27 mmol) and 4'-(trifluoromethyl) acetophenone (0.040 g, 0.21 mmol) was heated to 75° C. and allowed to stir at this temperature for 5.5 hours. The reaction was cooled to room temperature and EtOH (0.6 mL) was added, followed by sodium borohydride (0.028 g, 0.74 mmol) and the resulting reaction was stirred at room temperature. After 2 hours, the reaction was quenched with water and the resulting suspension was filtered and washed with dichloromethane several times. The filtrate was concentrated in vacuo to provide a crude material which was purified using preparative layer chromatography (20% acetone/hexanes) to provide compound 292 (0.005 g, 7%).

Example 10

Preparation of Compound 287

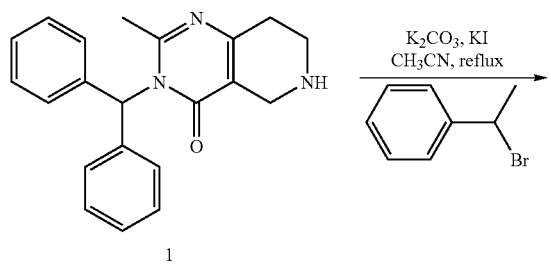

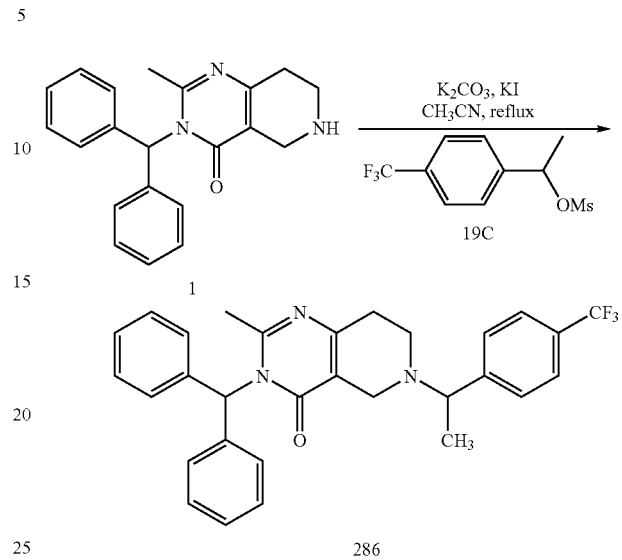

A mixture of compound 1 (0.048 g, 0.15 mmol), 1-bromoethylbenzene (0.04 mL, 0.29 mmol), potassium carbonate (0.046 g, 0.33 mmol) and potassium iodide (0.058 g, 0.35 mmol) in acetonitrile (2.0 mL) was heated to reflux and allowed to stir at this temperature for about 15 hours. The reaction was cooled to room temperature and filtered and the filtrate was concentrated in vacuo. The resulting residue was purified using silica gel flash chromatography (20% acetone/ hexanes) to provide compound 287 (0.041 g, 63%).

Example 11

Preparation of Compound 286

A mixture of compound 1 (0.23 g, 0.68 mmol), compound 19C (0.25 g, 0.91 mmol), potassium carbonate (0.19 g, 1.36 mmol) and potassium iodide (0.24 g, 1.46 mmol) in acetonitrile (29 mL), was heated to reflux and allowed to stir at this temperature for about 15 hours. The reaction was cooled to room temperature and filtered and the filtrate was concentrated in vacuo. The resulting residue was purified using silica gel flash chromatography (20% acetone/hexanes) to provide compound 286 as a racemic mixture (0.113 g, 35%), which was separated into its enantiomers using the method described below in Example 22.

Example 12

Library Procedure for Making Carbamates of Formula 12A

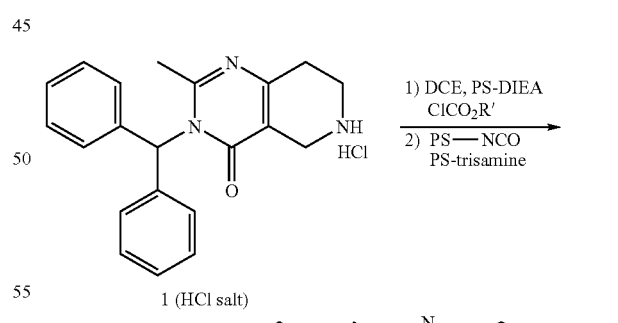

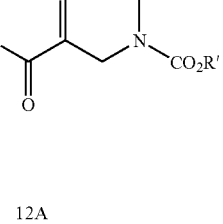

A stock solution was prepared by dissolving the hydrochloride salt of compound 1 (0.280 g, 0.76 mmol) in dichloroethane (35.0 mL). This stock solution (1.0 mL, 0.022 mmol) was then added to 32-wells of a deep well polypropylene microtiter plate and PS-DIEA (3.51 mmol/g, 0.042 g) was then added to each well. 1M stock solutions of various chloroformates (1.0 M in dichloroethane, 2.0 equiv, 0.05 mL) were next added to the wells, which were then sealed and shaken at 25° C. for 20 hours. The reaction mixtures were individually filtered through a polypropylene frit into a second microtiter plate containing PS-isocyanate resin (3 equiv., 0.066 mmol) and PS-trisamine resin (6 equiv., 0.132 mmol). After the top plate was washed with MeCN (0.5 mL/well), the plate was removed, the bottom microtiter plate was sealed and then shaken at 25° C. for 16 hours. The solutions were filtered through a polypropylene frit into a 32-well collection plate. The wells of the top plate were then washed with MeCN (0.5 mL/well), and the plate removed. The resultant solutions in the collection plate were transferred into vials and the solvents removed in vacuo using a SpeedVac to provide the compounds of formula 12A. The resulting samples were evaluated by LCMS and those that were >70% pure were submitted for further analysis.

Example 13

Library Procedure for Making Benzyl Amines of Formula 13A

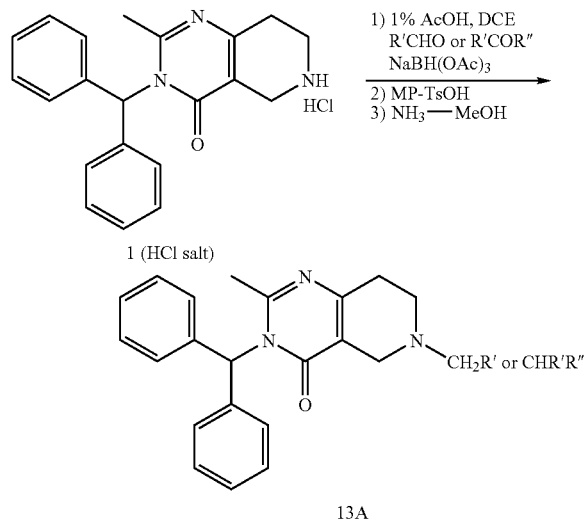

The hydrochloride salt of compound 1 (0.885 g, 2.41 mmol) was neutralized with a tertiary amine resin (diethylaminomethyl polystyrene) and a stock solution made. This stock solution of amine (1 mL, 0.024 mmol) in dichloroethane (1% AcOH) was added to 96-tubes in four Bohdan MiniBlock™ synthesizers (Mettler Toledo Inc., Columbia, Md.). A 1 M stock solution of each of the individual aldehydes (R'CHO) and ketones (R'COR") in dichloroethane (0.120 mL, 0.120 mmol) was then added, followed by sodium triacetoxyborohydride (0.026 g, 0.120 mmol). The MiniBlocks were then sealed and shaken at 25° C. for about 20 hours. Methanol (0.5 mL) was added to each tube and the MiniBlocks shaken for 10 min. Then MP-TsOH resin (~0.15 g) was added to each tube and the blocks were shaken at 25° C. for 2 hours. The tubes were drained and the resin was washed three times each with dichloromethane then MeOH, shaking for 2 min each time, to remove unreacted reagents. Ammonia in MeOH (2N, 1.5 mL) was then added to each tube and the MiniBlocks were shaken at 25° C. for 40 minutes. The MeOH filtrates were collected into 2-dram vials and the resin was washed several times with MeOH (2×0.5 mL). The combined filtrates from each tube were then evaporated to dryness for about 15 hours on a SpeedVac concentrator to provide compounds of formula 13A. The resulting samples were evaluated by LCMS and those that were >70% pure were submitted for further analysis.

Example 14

Preparation of Intermediate 14D

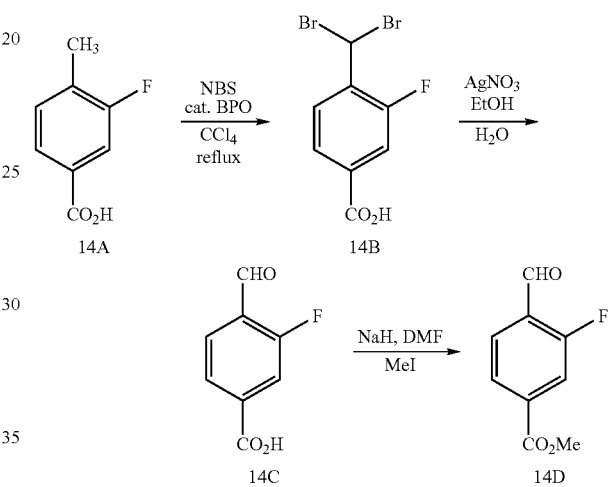

Step 1—Synthesis of Compound 14B

A solution of 3-fluoro-4-methylbenzoic acid 14A (3.00 g, 19.5 mmol), N-bromosuccinimide (8.00 g, 44.8 mmol) and benzoyl peroxide (0.24 g, 1.00 mmol) in carbon tetrachloride (40 mL) was heated to reflux for about 15 hours. The reaction was cooled to room temperature and the solid was filtered off and washed with carbon tetrachloride. The filtrate and washings were combined and concentrated in vacuo to provide compound 14B (6.0 g, 100%).

Step 2—Synthesis of Compound 14C

Compound 14B (6.0 g, 19.5 mmol) was dissolved in EtOH (50 mL) and the resulting solution was heated to 50° C. Silver nitrate (6.8 g, 39.9 mmol) in hot water (11 mL) was added dropwise to the warmed solution over 5 minutes. The reaction was allowed to stir at 50° C. for 50 minutes, then cooled to room temperature. The reaction mixture was poured onto 1 N HCl (25 mL) and the solid was filtered and washed with ethanol. The filtrate was concentrated in vacuo to about 30 mL and extracted with EtOAc several times. The organics were washed with brine, dried over MgSO$_4$, filtered, then concentrated in vacuo to provide compound 14C (3.0 g, 92%).

Step 3—Synthesis of Compound 14D

To a solution of compound 14C (0.25 g, 1.49 mmol) in DMF (4.5 mL) was added sodium hydride (60% in oil, 0.069 g, 1.73 mmol). The reaction was placed under N$_2$, stirred for 30 minutes, then iodomethane (0.11 mL, 1.74 mmol) was added and reaction was stirred at room temperature for about 15 hours. The reaction mixture was then poured onto 1N HCl

Example 15

Preparation of Compound 15B

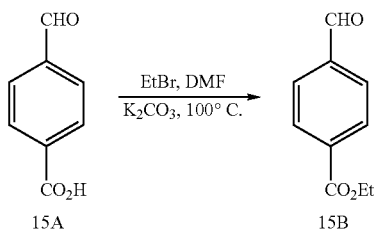

A mixture of 4-carboxybenzaldehyde (15A) (0.255 g, 1.69 mmol), bromoethane (0.25 mL, 3.33 mmol) and potassium carbonate (0.446 g, 3.23 mmol) in DMF (2.5 mL) was heated to 100° C. in a sealed tube and allowed to stir at this temperature for about 15 hours. The reaction was cooled to room temperature and the solvent removed in vacuo. Ether was added to the residue and the organics were washed sequentially with dilute NaOH, water and brine, then dried over MgSO$_4$, filtered and concentrated in vacuo to provide compound 15B (0.290 g, 98%) which was used without further purification.

Example 16

Preparation of Compound 16A

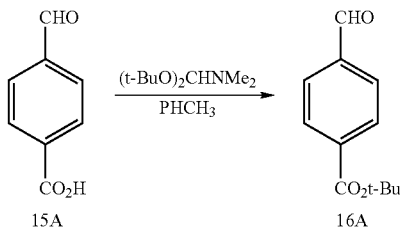

A solution of 4-carboxybenzaldehyde (15A) (0.35 g, 2.1 mmol) in toluene (9 mL) was heated to reflux and N,N-dimethylformamide di-tert-butyl-acetal (3.8 mL, 16.0 mmol) was added over 25 minutes. After the addition was complete, the reaction was stirred at reflux for an additional hour then cooled to room temperature. The reaction mixture was washed sequentially with water, 5% aqueous NaHCO$_3$, and brine. The organic phase was separated, dried over MgSO$_4$, filtered and concentrated in vacuo to provide compound 16A, which was used without further purification (0.37 g, 45%).

Example 17

Preparation of Compound 17A

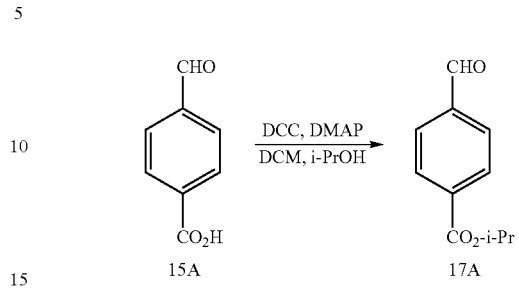

To a 0° C. solution of 4-carboxybenzaldehyde (15A) (0.21 g, 1.4 mmol), 2-propanol (0.4 mL, 5.3 mmol) and N,N-dimethylaminopyridine (0.16 g, 1.3 mmol) in dichloromethane (2.5 mL) was added a solution of N,N'-dicyclohexylcarbodiimide (0.55 g, 2.7 mmol) in dichloromethane (1 mL), which was also at 0° C. The reaction was allowed to warmed to room temperature and was then stirred under N$_2$ for about 15 hours. The reaction mixture was filtered through Celite® and washed with EtOAc. The filtrate was concentrated in vacuo to provide a crude material which was purified using preparative layer chromatography (15% EtOAc/Hexanes) to provide compound 17A (0.1 g, 74%).

Example 18

Preparation of Compound 18C

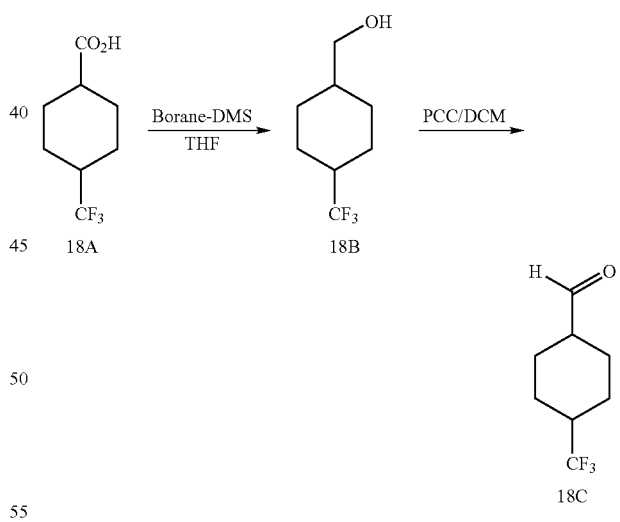

Step 1—Synthesis of Compound 18B

To a 0° C. solution of 4-(trifluoromethyl)cyclohexanecarboxylic acid 18A (0.25 g, 1.3 mmol) in THF (2.5 mL) was added dropwise borane-dimethyl sulfide complex (0.55 mL, 5.2 mmol) and the reaction was allowed to warm to room temperature. The reaction was then stirred for 96 hours, MeOH was added, and the resulting solution was heated to reflux and allowed to stir at this temperature for 3 hours. The reaction mixture was concentrated in vacuo and to the resulting residue was added ice water. The resulting solution was extracted with EtOAc (3×) and the combined organics were washed with 1 N HCl, then brine, dried over MgSO₄, filtered and concentrated in vacuo to provide compound 18B (0.20 g, 86%) which was used without further purification.

Step 2—Synthesis of Compound 18C

To a solution of compound 18B (0.20 g, 1.06 mmol) in dichloromethane (5 mL) was added PCC (0.46 g, 2.11 mmol) and the resulting reaction was allowed to stir at room temperature for 20 hours. The reaction was then filtered through florisil and washed with ether. The filtrate was concentrated in vacuo to compound 18C (0.14 g, 72%) which was used without further purification.

Example 19

Preparation of Compound 19C

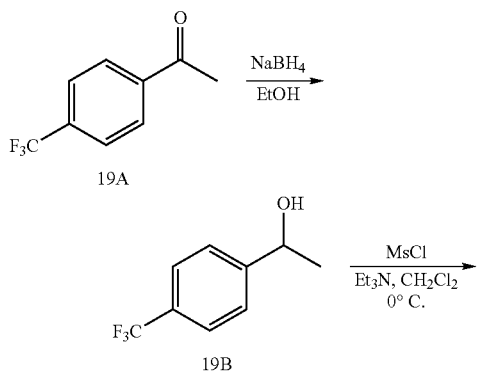

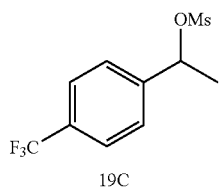

Step 1—Synthesis of Compound 19B

4'-(Trifluoromethyl)acetophenone (19A) (0.507 g, 2.69 mmol) was dissolved in ethanol (27 mL) and to the resulting solution was added sodium borohydride (0.120 g, 3.17 mmol). The reaction was stirred at room temperature for about 15 hours and was then concentrated in vacuo to provide a residue which was dissolved in dichloromethane. The organic phase was washed with water several times, dried over MgSO₄, filtered and concentrated in vacuo to provide compound 19B (0.359 g, 71%), which was used without further purification.

Step 2—Synthesis of Compound 19C

To a 0° C. solution of compound 19B (0.329 g, 1.73 mmol) in dichloromethane (4 mL) was added triethylamine (0.48 mL, 3.46 mmol), followed by mesyl chloride (0.17 mL, 2.25 mmol). The reaction was stirred for 30 minutes, and then quenched with water. The reaction mixture was extracted with dichloromethane and the organics were washed sequentially with water, 1 N HCl, sat'd NaHCO₃ and brine, then dried over MgSO₄, filtered and concentrated in vacuo to provide compound 19C (0.460 g, 99%) which was used without further purification.

Example 20

Preparation of Compounds 297 and 298

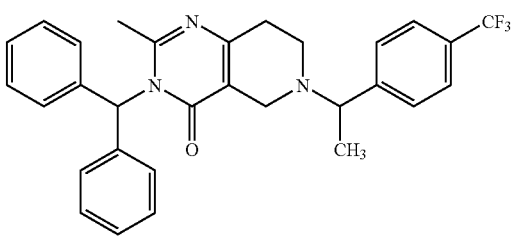

286 chiral separation

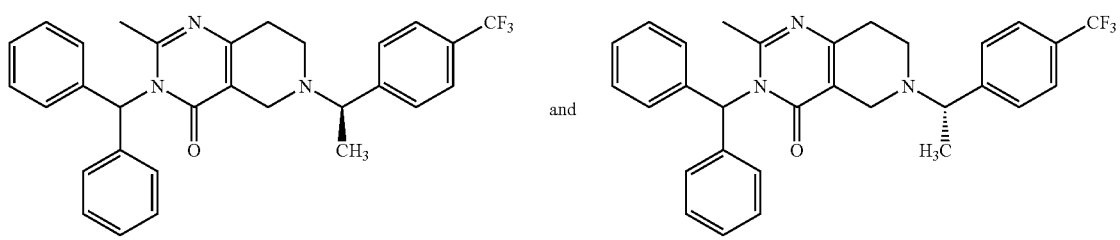

Compound 286 (90 mg) was dissolved in a mixture of hexanes/isopropanol (95/5) and injected onto a Chiralpak AD preparative HPLC column (5 cm×50 cm) and eluted with 2.5% isopropanol in hexanes at 50 mL/min. Detection was at 254 nm. 27 mg of compound 297 (isomer 1, retention time=42.8 minutes) and 24 mg of compound 298 (isomer 2, retention time=49.1 minutes) were obtained.

Example 21

Preparation of Intermediate Compound 21B

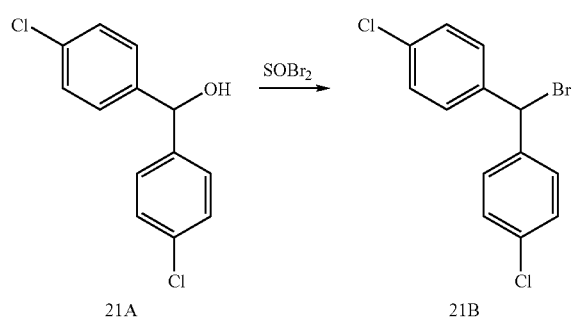

To a solution of bis-(4-chloro-phenyl)-methanol (21A, 2.53 g, 10 mmol) in dichloromethane (50 mL) was added thionyl bromide (1.2 mL, 15 mmol) at 0° C. The ice-bath was removed after 30 min. and the reaction was stirred at room temperature for 4 hours after which the solvent was removed in vacuo. The crude oil obtained was diluted with dichloromethane and washed several times with saturated aqueous sodium bicarbonate solution. The combined organic fractions were dried (MgSO$_4$), filtered and concentrated in vacuo to provide compound 21B, which was used without further purification.

Example 22

Preparation of Compound 10

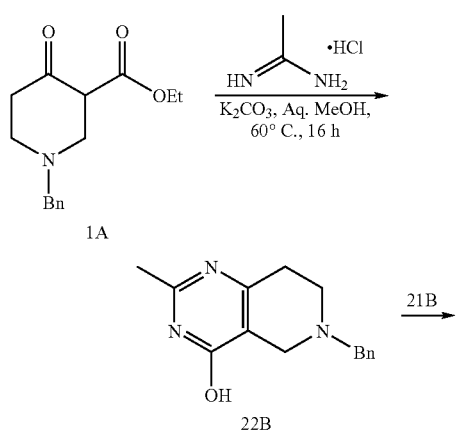

-continued

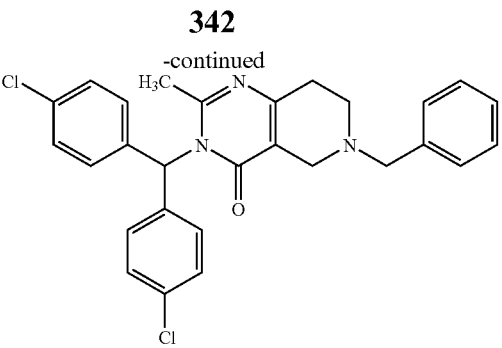

Step 1—Synthesis of Compound 22B

To a solution of 1A (10.0 g, 33.6 mmol) in 20 mL methanol were added acetamidine hydrochloride (3.8 g, 40.3 mmol), potassium carbonate (6.96 g, 50.4 mmol), and water (75 mL). The reaction was stirred at 60° C. for 16 h after which it was neutralized with 1N HCl and then extracted with dichloromethane. The organic fraction was dried (magnesium sulfate), filtered, and concentrated in vacuo. The crude product was treated with hexane and the resulting white solid was filtered to provide 22B (5.3 g, 55% yield).

Step 2—Synthesis of Compound 10

Compound 10 was prepared by reacting compound 21B with compound 22B according to the method described in Example 1, Step 3.

Example 23

Preparation of Compound 23B

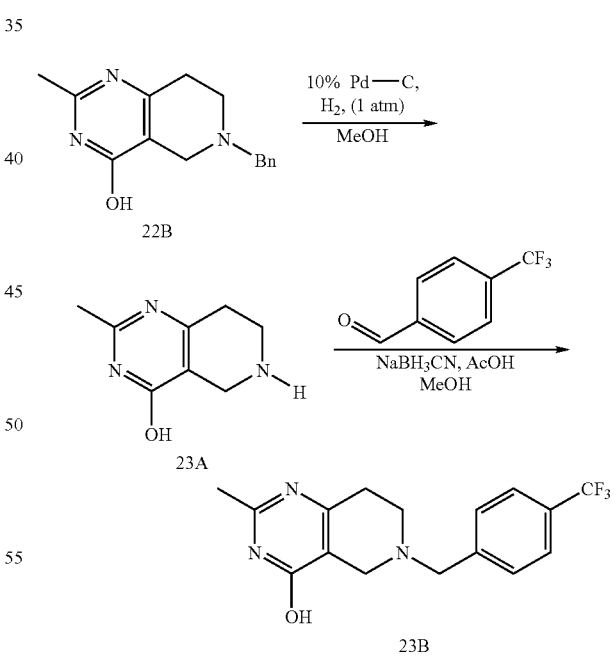

Step 1—Synthesis of Compound 23A

To a solution of compound 22B (1.0 g, 3.92 mmol) in a 1:1 mixture of ethanol and methanol (100 mL) was added 10% Pd/C. The reaction was hydrogenated at 1 atm for 16 h after which it was filtered through celite. The filtrate was concentrated in vacuo to provide compound 23A which was used without further purification.

Step 2—Synthesis of Compound 23B

To a solution of compound 23A (0.32 g, 1.95 mmol) in 15 mL methanol were added 4-(trifluoromethyl)benzaldehyde (0.51 g, 2.93 mmol), acetic acid (0.2 mL), and sodium cyanoborohydride (0.18 g, 2.93 mmol) and the reaction was stirred for 3 h at room temperature. After removing the solvent in vacuo, the crude product was diluted with ethyl acetate and washed with water. The organic fraction was dried (magnesium sulfate), filtered, and concentrated in vacuo and the residue obtained was purified using column chromatography (5% methanol in dichloromethane) to provide compound 23B (0.46 g, 74% yield).

Example 24

Preparation of Compound 24A

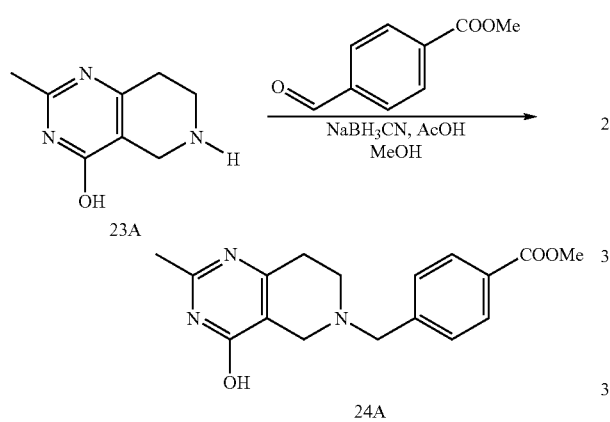

Compound 24A was prepared using the method described in Example 23, Step 2 and substituting 4-formylbenzoic acid methyl ester for 4-(trifluoromethyl)benzaldehyde.

Example 25

Preparation of Intermediate Compound 25B

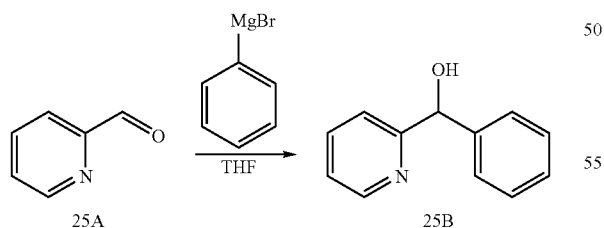

To a 0° C. solution of pyridine-2-carboxaldehyde (25A, 1.07 g, 10 mmol) in 50 mL dry THF was added phenylmagnesium bromide (3M in ether, 5 mL, 15 mmol). The reaction was allowed to warm up to room temperature, then was stirred for 3 hours. The reaction mixture was diluted with ethyl acetate and quenched with saturated ammonium chloride solution. The organic layer was separated, washed with water and brine, dried over MgSO$_4$, filtered and concentrated in vacuo. The resulting residue was purified using column chromatography (50% ethyl acetate in hexane) to provide compound 25B (75%).

Example 26

Preparation f Compounds 288 and 289

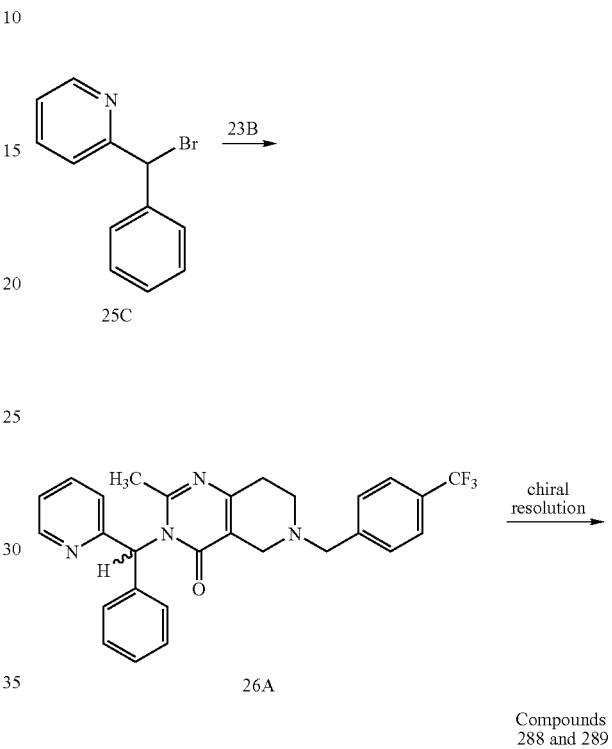

Compound 26A was prepared by reacting compound 23B with compound 25C (prepared from compound 25B using the method described in Example 21) according to the method described in Example 1, Step 3.

Resolution of compound 26A using a Chiralpak OD column (eluent 12% isopropyl alcohol in hexanes) provided compounds 288 and 289.

Example 27

Preparation of Compound 165

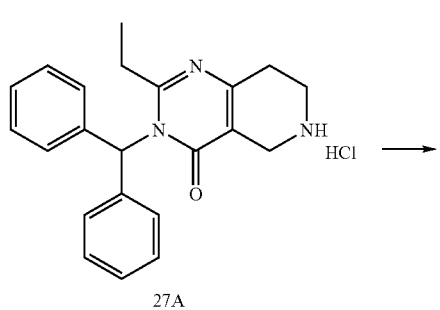

-continued

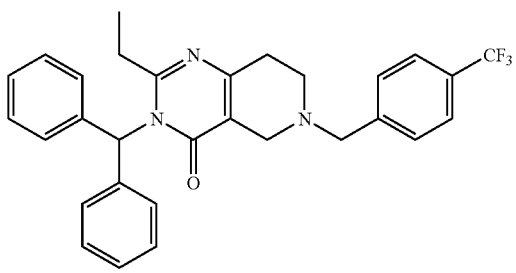

165

Step 1—Synthesis of Compound 27A
Compound 27A was prepared using the method set forth in Example 1 and Example 2, Step 1, and by substituting propionamidine hydrochloride for acetamidine hydrochloride in Example 1, Step 2.

Step 2—Synthesis of Compound 165
Compound 165 was synthesized from compound 27A and 4-trifluoromethylbenzaldehyde using the method described in Example 4.

Example 28

Preparation of Compound 166

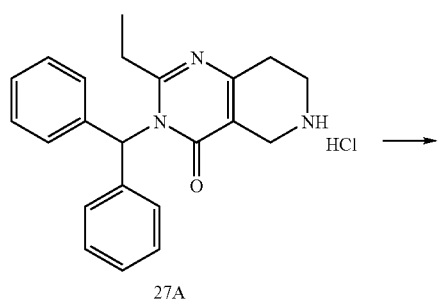

27A

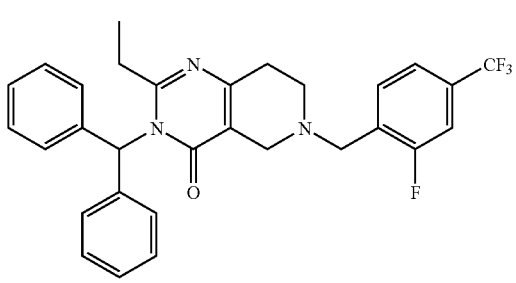

166

Compound 166 was synthesized from compound 27A using the method described in Example 3 and substituting 4-trifluoromethyl-2-fluorobenzylbromide for p-trifluoromethyl benzyl bromide.

Example 29

Preparation of Compound 29A

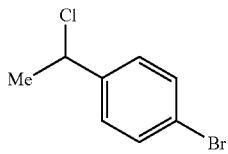

29A

To a solution of 4'-bromoacetophenone (0.60 g, 3.0 mmol) in THF (15 mL) was added NaBH$_4$ (0.15 g, 4.5 mmol). The resulting reaction was heated to 40° C. and allowed to stir at this temperature for 1 hour, cooled to room temperature, then partitioned with ether and 1N NaHCO$_3$. The organic phase was separated, dried over MgSO$_4$ and concentrated in vacuo. The yellow oil residue obtained (0.30 g, 1.5 mmol) was combined with SOCl$_2$ (0.33 mL, 4.5 mmol) and one drop of DMF. The resulting reaction was heated to 40° C. and allowed to stir at this temperature for 1 hour, cooled to room temperature, then triturated with ether. The suspension formed was filtered and the filtrate concentrated in vacuo to provide compound 29A as a colorless oil.

Example 30

Preparation of Compound 30A

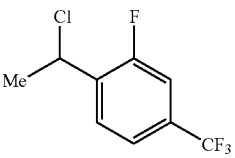

30A

Using the method described in Example 29, and substituting 2'-fluoro-4'-(trifluoromethyl)acetophenone for 4'-bromoacetophenone, compound 30A was obtained as a yellow oil.

Example 31

Preparation of Compound 301

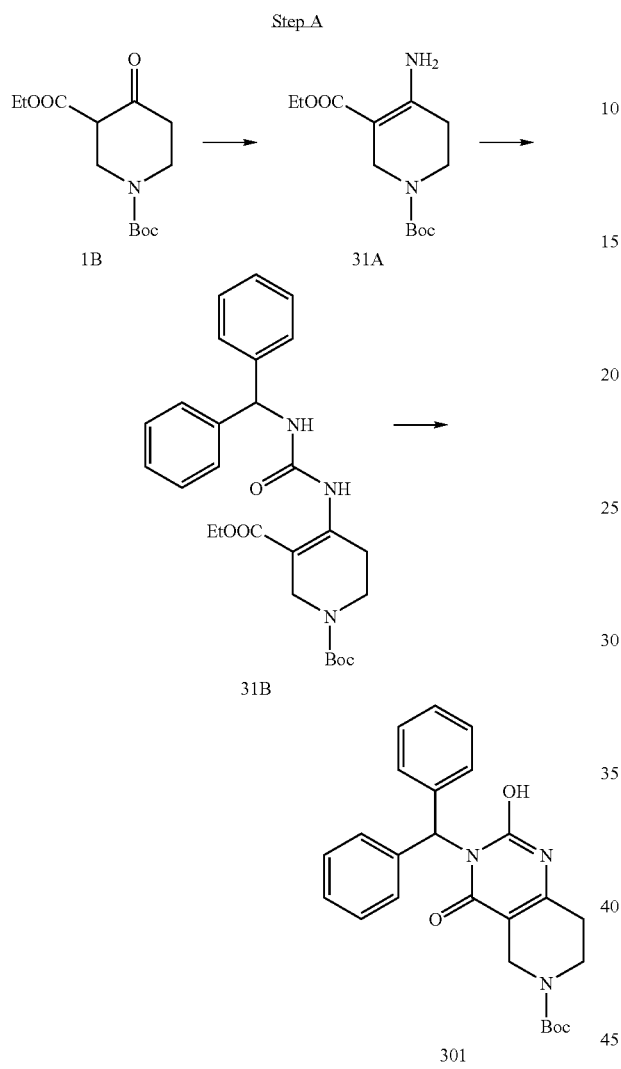

—Synthesis of Compound 31A

To a solution of compound 1B (0.81 g, 3.0 mmol) in EtOH (5 mL) was added 28% ammonia (2.0 mL, 30 mmol). The resulting reaction was allowed to stir for 18 hours and was then concentrated in vacuo. The resulting residue was partitioned with EtOAc and water and the organic phase was collected, washed with brine, dried ($MgSO_4$), and concentrated in vacuo to provide compound 31A as a yellow oil.

Step B—Synthesis of Compound 31B

Compound 31A (0.27 g, 1.0 mmol), diphenylmethyl isocyanate (1.19 g, 4.0 mmol), and $Et_3N$ (0.05 mL, 0.5 mmol) were taken up in toluene (5 mL) in a sealed tube. The resulting reaction was heated to 100° C. and allowed to stir at this temperature for 18 hours, then filtered. The filtrate was concentrated in vacuo and the resulting residue was purified using preparative layer chromatography to provide compound 31B as a white solid.

Step C—Synthesis of Compound 301

To a solution of NaH (60% in oil, 0.019 g, 0.50 mmol) in EtOH was added compound 31B (0.12 g, 0.25 mmol). The resulting reaction was heated to 50° C. and allowed to stir at this temperature for 2 hours. The reaction mixture was cooled to room temperature, then neutralized with 4M HCl in dioxane. The neutral solution was concentrated in vacuo and the residue obtained was purified using preparative layer chromatography to provide compound 301 as a white solid.

Example 32

Preparation of Compound 300

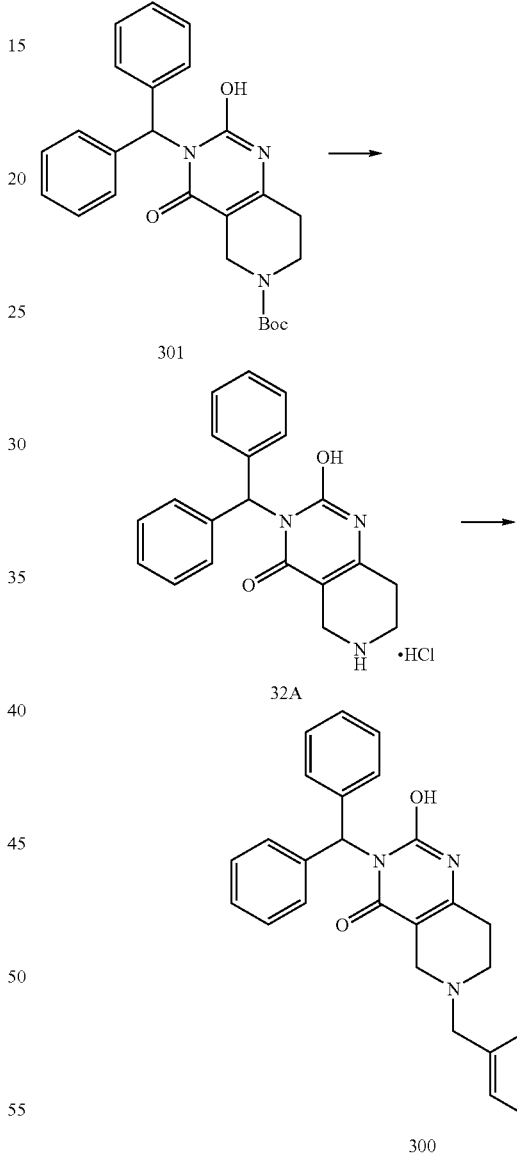

Step A—Synthesis of Compound 32A

To a solution of compound 301 (0.60 g, 1.4 mmol) in dichloromethane (2.0 mL) was added 4.0M HCl in dioxane (10 ml, 40 mmol). The resulting reaction was allowed to stir for 3 hours, then concentrated in vacuo to provide compound 32A as a yellow solid.

Step B—Synthesis of Compound 300

Compound 32A (0.060 g, 0.16 mmol), DIPEA (0.12 mL, 0.6 mmol) and 4-bromo-2-fluorobenzyl bromide (0.043 g, 0.16 mmol) were taken up in DMF (1.00 mL). The resulting reaction was heated to 90° C. and allowed to stir at this temperature for 18 hours. The reaction mixture was then cooled to room temperature, concentrated in vacuo, and the residue obtained was purified using preparative layer chromatography to provide compound 300 a yellow solid.

Example 33

Preparation of Compound 28

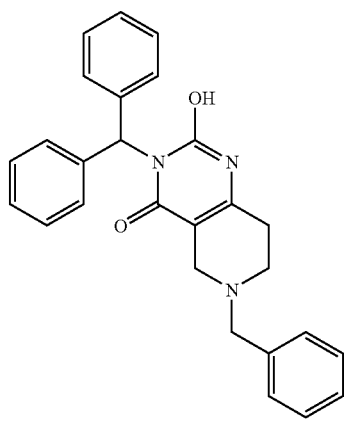

28

Using the method described in Example 32, Step B, and substituting benzyl bromide for 4-bromo-2-fluorobenzyl bromide, compound 28 was prepared.

Example 34

Preparation of Compound 29

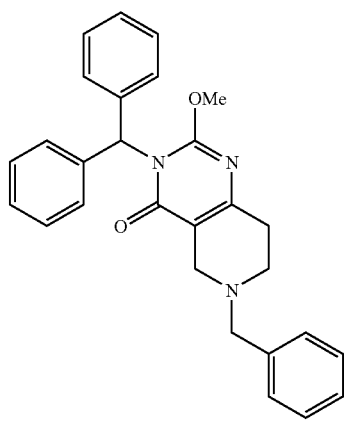

29

Using the method described in Example 35, Step C, and substituting compound 28 for compound 35B, compound 29 was provided as a colorless film.

Example 35

Preparation of Compound 31

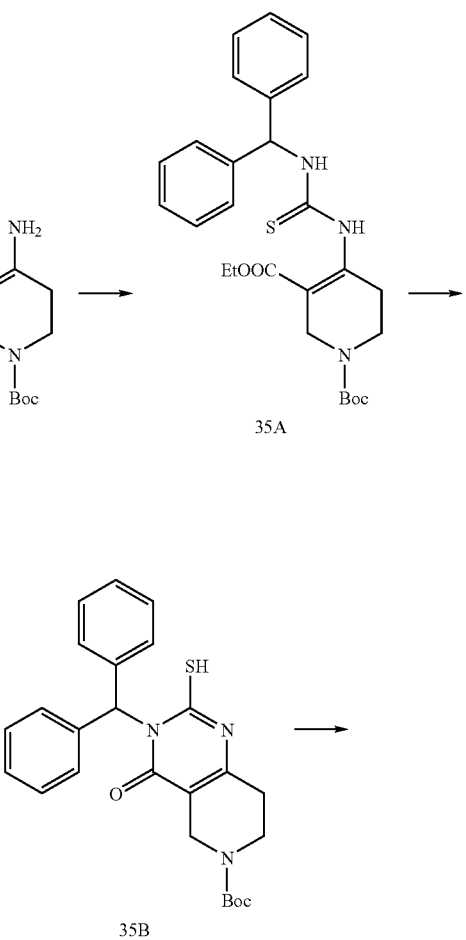

-continued

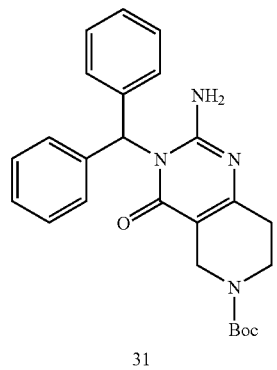

31

Step A—Synthesis of Compound 35A

To a 0° C. solution of compound 31A (2.50 g, 9.3 mmol) in dichloromethane (30 mL) was added NMM (1.1 mL, 10 mmol), then thiophosgene (0.92 ml, 12 mmol). The resulting reaction was allowed to stir at 0° C. for 3 hours, then concentrated in vacuo. The resulting residue was diluted with ether (30 mL), and the resulting solution was filtered and concentrated in vacuo. The residue obtained was diluted with acetonitrile (40 mL) and to the resulting solution was added benzhydrylamine (2.4 mL, 13 mmol). The resulting solution was heated to reflux and allowed to stir at this temperature for 1 hour, then cooled to room temperature and filtered. The collected solid was dried under vacuum to provide compound 35A as a white solid.

Step B—Synthesis of Compound 35B

To a solution of compound 35A (0.50 g, 1.0 mmol) in dioxane (30 mL) was added NaO-tBu (0.15 g, 1.5 mmol). The reaction was heated to 60° C. and allowed to stir at this temperature for 45 minutes, then cooled to room temperature and neutralized with acetic acid. The resulting solution was extracted with EtOAc and the organic phase was washed with 1N NaHCO₃, then brine, then dried (MgSO₄) and concentrated in vacuo. The residue obtained was purified using preparative layer chromatography to provide compound 35B as a yellow solid.

Step C—Synthesis of Compound 35C

To a solution of compound 35B (0.43 g, 0.96 mmol) in THF (4.0 mL) was added K₂CO₃ (0.16 g, 1.1 mmol), followed by iodomethane (0.04 mL, 1.1 mmol). The resulting reaction was allowed to stir for 18 hours, filtered, then concentrated in vacuo to provide compound 35C as a yellow solid.

Step D—Synthesis of Compound 31

To a solution of compound 35C (0.20 g, 0.43 mmol) and K₂CO₃ (0.12 g, 0.9 mmol) in dichloromethane (5.0 mL) was added mCPBA (70%, 0.15 g, 0.9 mmol). The resulting reaction was allowed to stir for 2 hours, then was concentrated in vacuo. The white solid residue obtained was diluted with 2.0M NH₃/isopropanol (4.0 mL, 8.0 mmol). And the resulting reaction was placed in a sealed tube, heated to 80° C. and allowed to remain at this temperature for 8 hours. The reaction mixture was then cooled to room temperature and concentrated in vacuo to provide a crude residue which was purified using preparative layer chromatography to provide compound 31 as a white solid.

Example 36

Preparation of Compound 32

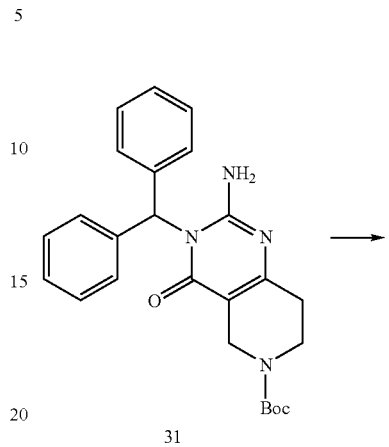

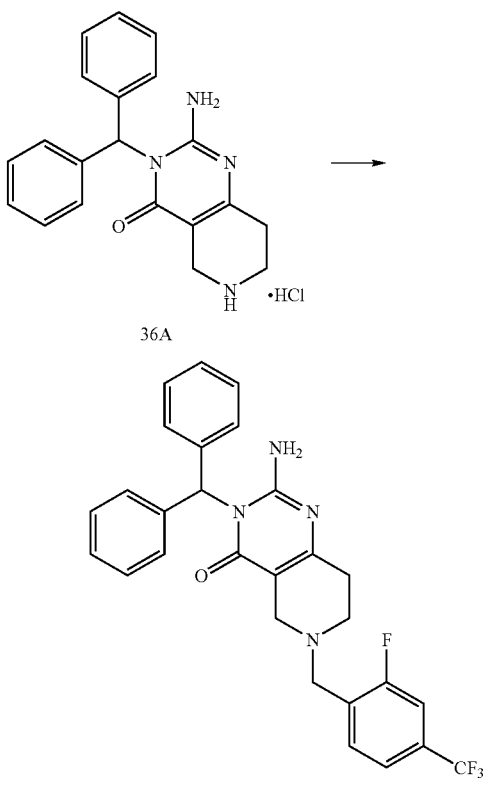

Step A—Synthesis of Compound 36A

Using the method described in Example 32, Step A, compound 31 was converted to compound 36A.

Step B—Synthesis of Compound 32

To a solution of compound 36A (0.035 g, 0.010 mmol) in dichloromethane (2.0 mL) was added 2-fluoro-4-trifluoromethylbenzaldehyde (0.024 g, 0.12 mmol), Et₃N (0.026 mL, 0.2 mmol) and Na(OAc)₃BH (0.10 g, 0.49 mmol). The resulting reaction was allowed to stir for 3 hours, then was concentrated in vacuo and the residue obtained was purified using preparative layer chromatography to provide compound 32 as a yellow solid.

Example 37

Preparation of Compound 34

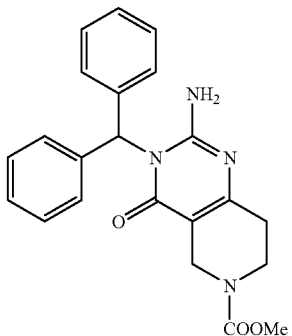

34

Using the method described in Example 5 and substituting methyl chloroformate for isopropyl chloroformate, compound 36A was converted to compound 34. The crude product obtained was purified using preparative layer chromatography to provide compound 34 as a white solid.

Example 38

Preparation of Compound 35

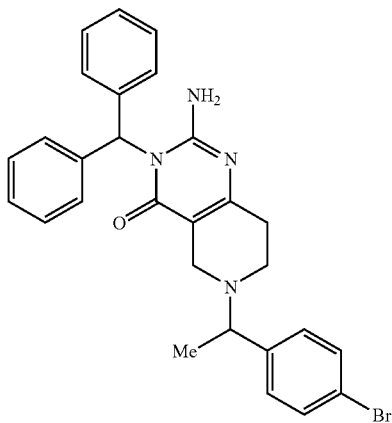

35

To a solution of compound 36A (0.050 g, 0.15 mmol) in acetonitrile (4.0 mL) was added $K_2CO_3$ (0.03 g, 0.2 mmol), KI (0.01 g, 0.6 mmol) and 4-(1-chloroethyl)bromobenzene (0.05 g, 0.2 mmol). The resulting reaction was heated to 80° C. and allowed to stir at this temperature for 18 hours, then was concentrated in vacuo. The residue obtained was purified using preparative layer chromatography to provide compound 35 as a white solid.

Example 39

Preparation of Compound 36

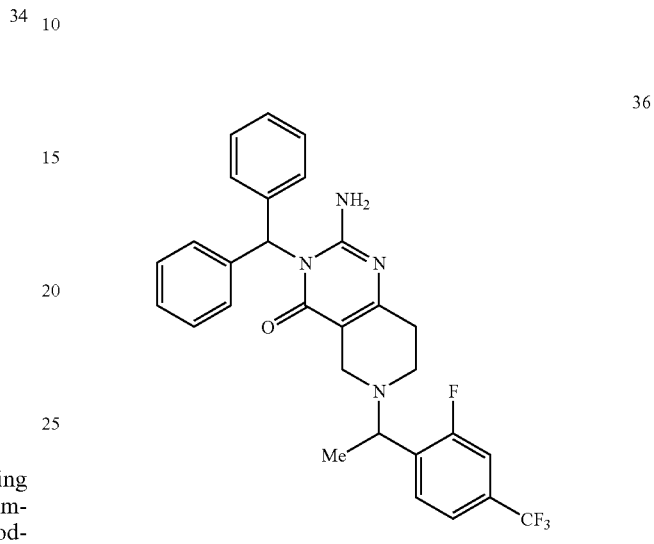

36

Using the method described in Example 38 and substituting 4-(1-chloroethyl)-3-fluoro-trifluoromethylbenzene for 4-(1-chloroethyl)bromobenzene, compound 36 was prepared as a white solid.

Example 40

Preparation of Compound 40A

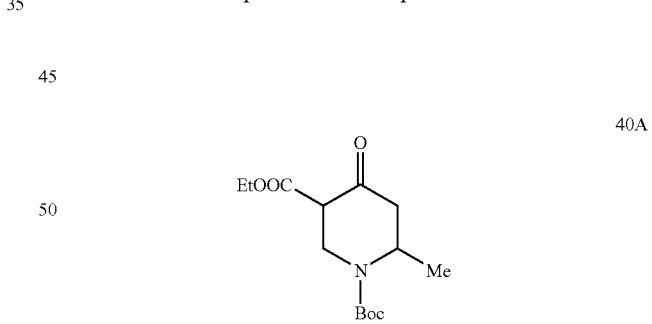

40A

Combine ethyl 3-(N-Boc-N-(2-ethoxycarbonylethyl) amino)butyrate (9.8 g, 42 mmol) with sodium (0.82 g, 36 mmol) and ethanol (0.10 mL) in p-xylene (40 mL). The reaction was heated to 138° C. and allowed to stir at this temperature, then cooled to room temperature and diluted with ice water, and the resulting solution was acidified using HOAc. Extract with ether, dry over $MgSO_4$, concentrate, and chromatograph on silica to obtain the keto-ester as a yellow oil.

Example 41

Preparation of Compounds 40 and 41

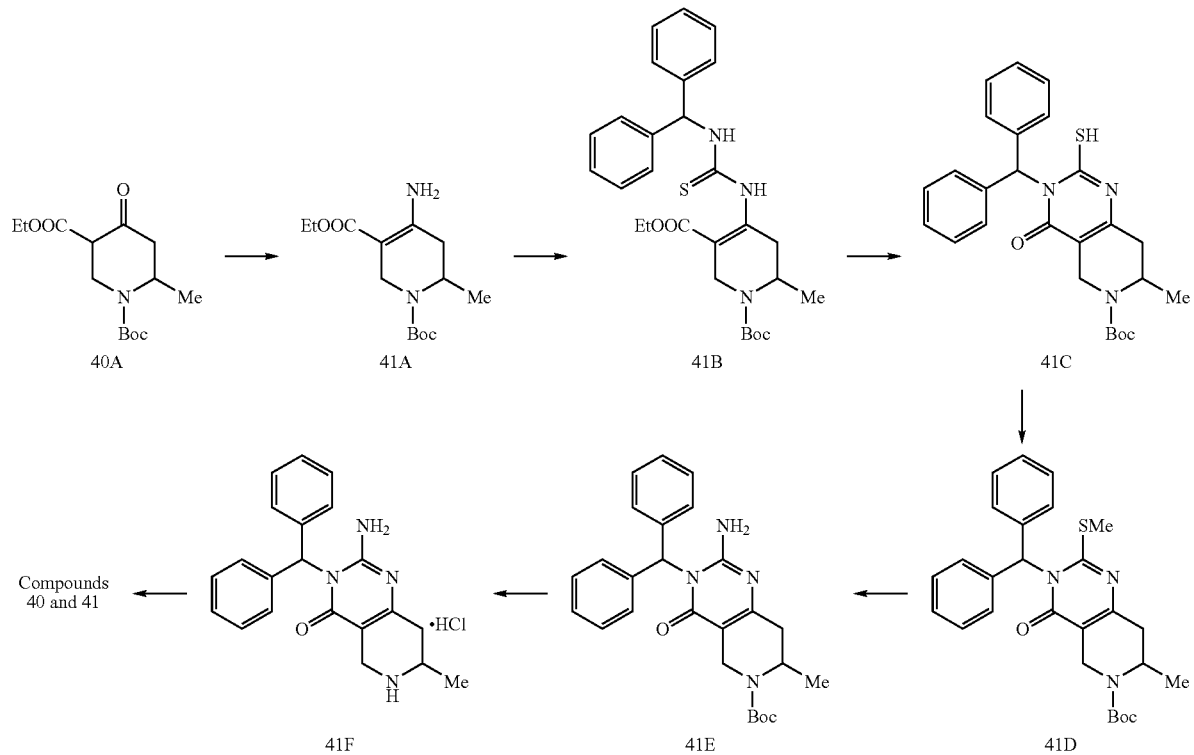

Step A—Synthesis of Compound 41A
Using the method described in Example 31, Step A, compound 40A was converted to compound 41A.
Step B—Synthesis of Compound 41B
Using the method described in Example 35, Step A, compound 41A was converted to compound 41B.
Step C—Synthesis of Compound 41C
Using the method described in Example 35, Step B, compound 41B was converted to compound 41C.
Step D—Synthesis of Compound 41D
Using the method described in Example 35, Step C, compound 41C was converted to compound 41D.
Step E—Synthesis of Compound 41E
Using the method described in Example 35, Step D, compound 41D was converted to compound 41E.

Step F—Synthesis of Compound 41F
Using the method described in Example 32, Step A, compound 41E was converted to compound 41F.
Step G—Synthesis of Compounds 40 and 41
Using the method described in Example 39, step A, compound 41F was converted to a mixture of diastereomeric compounds 40 and 41, which were separated using preparative layer chromatography to provide individual diastereomeric compounds 40 and 41, each as a yellow solid.

Example 42

Preparation of Compounds 302, 303, 304, 305, 306, and 307

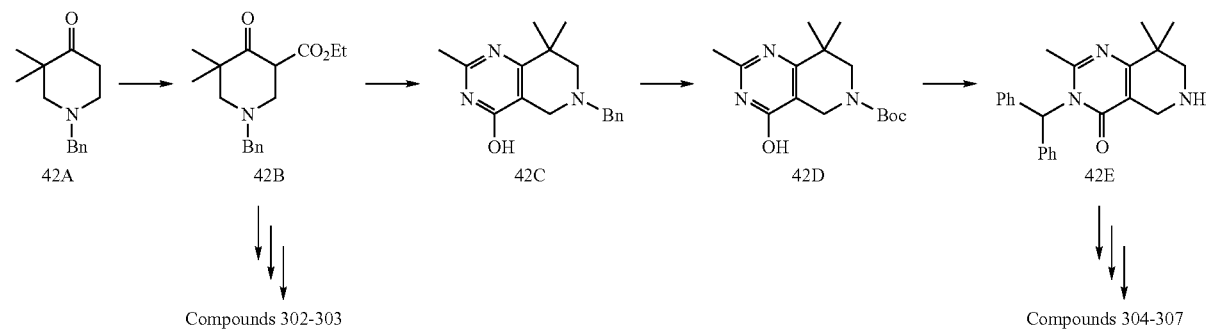

Step A—Synthesis of Compound 42A

To a suspension of 60% NaH (1.27 g, 31.70 mmol) in THF (40 mL) at −5° C. was added N-benzyl-4-piperidone (3.0 g, 15.85 mmol). After stirring the resulting solution for 1 h, iodomethane (1.98 mL, 31.70 mmol) was added dropwise while maintaining a bath temperature of 0° C. The reaction was stirred at 0° C. for 1 hour and then at room temperature for 3 hours, after which time it was quenched with saturated aqueous ammonium chloride solution and extracted with ethyl acetate. The organic phase was dried over $MgSO_4$ and concentrated in vacuo to provide a crude yellow oil which was purified using flash column chromatography on silica gel (20% EtOAc in hexanes) to provide 1.7 g of compound 42A as a yellow oil.

Step B—Synthesis of Compounds 42B, 302 and 303

To a solution of compound 42A (1.0 g, 4.61 mmol) in THF (40 mL) at 0° C. was added LHMDS (5.76 mL, 1M in THF, 5.76 mmol). After stirring for 40 minutes, the reaction was cooled to −78° C. and HMPA (0.81 mL, 4.61 mmol) was added, followed by $CNCO_2Et$ (0.58 mmol, 5.76 mmol). The reaction was allowed to stir at −78° C. for 30 minutes, then the reaction mixture was warmed to 0° C. and stirred for 2 hours at this temperature. The reaction was then quenched with saturated aqueous ammonium chloride and extracted with ethyl acetate. The combined organic phase was dried and concentrated in vacuo to provide compound 42B. Compounds 302 and 303 were synthesized from compound 42B (via compound 42C) using the methods described in Example 1.

Step C—Synthesis of Compounds 42E, 304, 305, 306 and 307

To a solution of compound 42C (0.36 g, 1.27 mmol) in 5 mL MeOH and 0.15 mL acetic acid was added 10% Pd—C (50 mg). The resulting solution was then hydrogenated at 1 atmospheric pressure for 16 hours. The reaction mixture was then treated with triethylamine (1.25 mL, 8.91 mmol) and di-tert-butyl dicarbonate (540 mg, 2.5 mmol), allowed to stir for an additional 3 hours, then filtered through celite. The filtrate was washed with saturated aqueous ammonium chloride and concentrated in vacuo to provide a crude yellow oil, which was purified using flash, column chromatography on silica gel (5% MeOH in dichloromethane) to provide 0.27 g of compound 42D. N-alkylation of compound 42D with benzhydryl bromide followed by BOC deprotection as described in Examples 1 and 2 provided compound 42E.

Compounds 304 and 307 were prepared from compound 42E via reductive amination with the corresponding aldehydes using the method described in Example 4.

Compounds 305 and 306 were prepared via N-alkylation of compound 42E with the corresponding mesylates using the method described in Example 11.

Example 43

Preparation of Compound 308

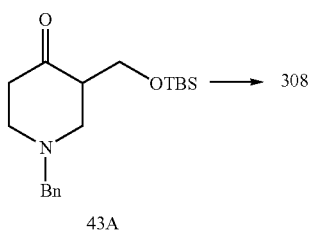

Compound 308 was synthesized from compound 43A (prepared as described in McCombie et al., Bioorg. Med. Chem. Lett. 2005, 15, 1375) using the method described in example 42 for the preparation of compound 307.

Example 44

Preparation of Compound 309

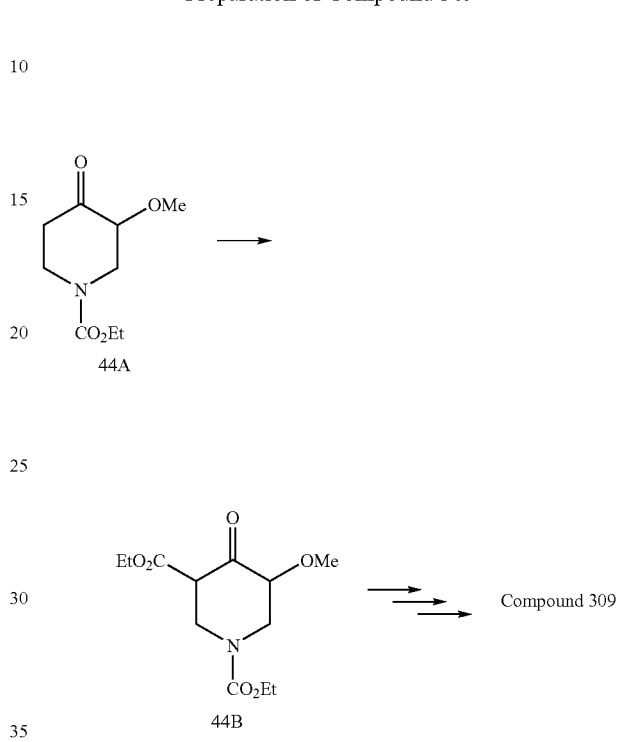

Compound 44B was synthesized starting from commercially available compound 44A using the method described in Example 42 for the synthesis of compound 42B. Compound 309 was synthesized from compound 44B using the method described in Example 1.

Example 45

Preparation of Compound 315

To a solution of compound 314 (35 mg, 0.069 mmol) in 0.5 mL ethanol and 0.5 mL THF was added lithium hydroxide (15 mg, 0.35 mmol) and the resulting reaction was allowed to stir at room temperature for 20 hours. 10% aqueous $KHSO_4$ was then added to the reaction mixture and the resulting solution was extracted with ethyl acetate. The organic phase was dried over $MgSO_4$, filtered and concentrated in vacuo to provide a crude residue, which was diluted with 3 mL DMF and to the resulting solution was added 22 mg HOBT and 0.05 mL isopropanol followed by 30 mg EDCI. The resulting reaction was allowed to stir for 20 hours, then quenched with water and extracted with ethyl acetate and the organic phase was dried over $MgSO_4$, filtered and concentrated in vacuo. The crude residue obtained was purified using flash column chromatography (20% acetone in hexanes) to provide compound 315.

Example 46

Preparation of Compound 317

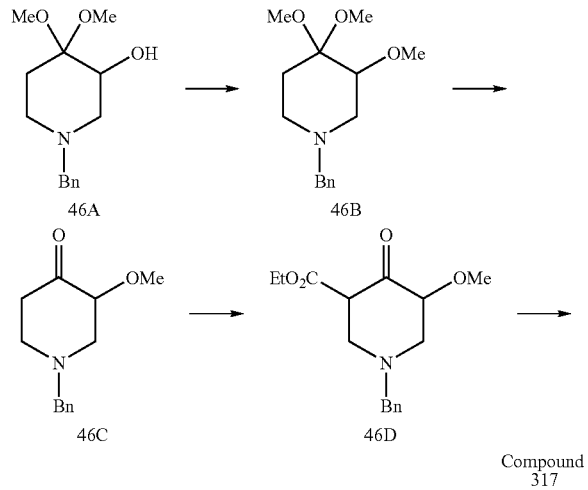

Compound 317

Step A—Synthesis of Compound 46B

Compound 46A was synthesized as described in the U.S. Pat. No. 4,994,471, 1991. Methylation of the hydroxy group of compound 46A using NaH and iodomethane as described in Example 14, Step D, provided compound 46B.

Step B—Synthesis of Compound 46D

To a solution of compound 46B (0.5 g, 1.89 mmol) in acetone (20 mL) and water (1 mL) was added p-TsOH.H$_2$O (0.9 g, 4.72 mmol). The resulting reaction was heated to reflux and allowed to stir at this temperature for 6 hours after which it was cooled, basified with 1N NaOH and extracted with ether and the combined organic fractions were concentrated in vacuo. The crude product obtained was purified using flash column chromatography (50% ethyl acetate in hexanes) resulted in the ketone 46C (80% yield). Compound 46C was converted to compound 46D using the method described in Example 42 for the synthesis of 42B.

Step C—Synthesis of Compound 317

Compound 317 was synthesized from compound 46D using the methods described in Example 1.

Example 47

Preparation of Compound 318

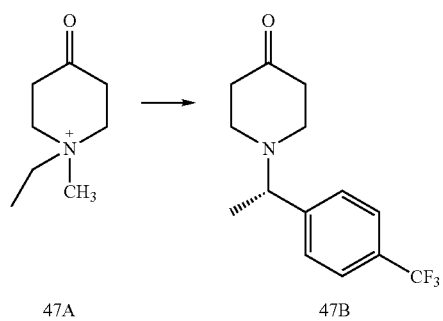

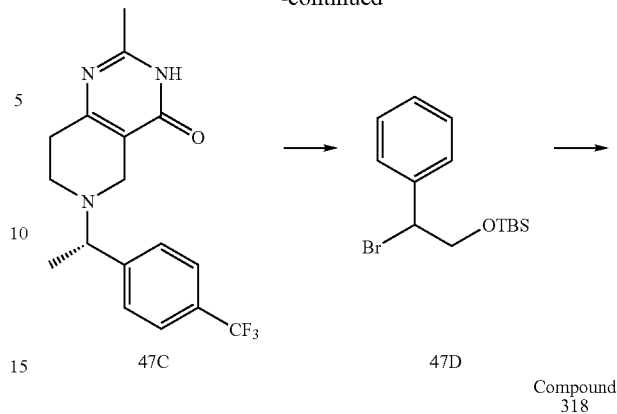

Compound 318

Step A—Synthesis of Compound 47B

To a solution of N-ethyl-4-piperidone (0.76 g, 6.0 mmol) in 6 mL acetone was added dropwise iodomethane. The reaction was stirred at ambient temperature for 5 h after which it was cooled to 0° C. and stirred for an additional 30 minutes. The resulting yellow suspension was filtered and the solid was washed with 10 mL hexanes and 3 mL acetone. The yellow solid was dried under high vacuum and stored in freezer for 20 h before using it for the next step.

To a solution of (S)-1-[4-(trifluoromethyl)phenyl]ethylamine (0.89 g, 4.68 mmol) in 10 mL ethanol was added a solution of K$_2$CO$_3$ (1.36 g, 9.88 mmol) in 1.5 mL water. The solution was heated to 90° C. and then a solution of compound 47A (1.4 g, 5.2 mmol) in 5 mL water was added over 10 minutes. The reaction was stirred at 90° C. for 2 hours, then cooled to room temperature and concentrated in vacuo to provide a crude residue which was diluted with dichloromethane and the organic layer was washed with water and brine, then dried over MgSO$_4$, filtered and concentrated in vacuo. The resulting residue was purified using flash column chromatography on silica gel (30% ethyl acetate in hexane) to provide 1.05 g of compound 47B as a yellowish solid.

Step B—Synthesis of Compound 47C

Compound 47B was converted to compound 47C using the method described in Example 42. Compound 47C was N-alkylated using the method described in Example 1.

Step C—Synthesis of Compound 47C

N-alkylation of 47C with 47D (prepared using the method described in Tetrahedron 1999, 55, 10155) followed by TBS deprotection using TBAF/THF, provided compound 318.

Example 48

Preparation of Compound 319

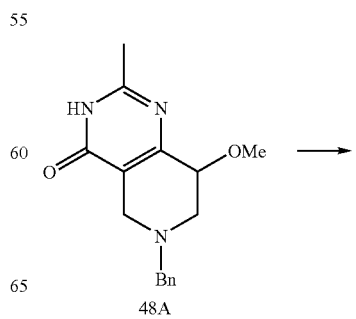

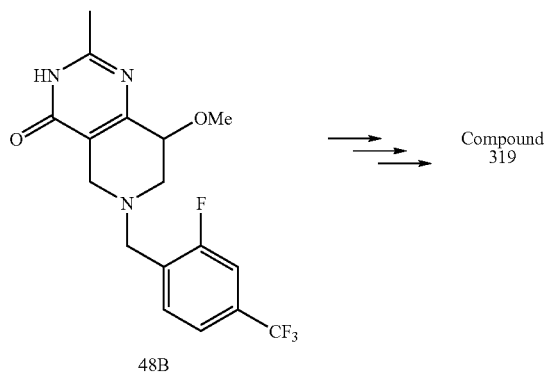

48B

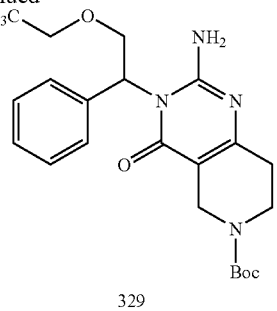

329

Step A—Synthesis of Compound 48B

To a solution of compound 48A (90 mg, 0.32 mmol) in 7 mL MeOH was added ammonium formate (200 mg, 3.2 mmol) and Pd(OH)₂ (70 mg). The resulting reaction was heated to reflux and allowed to stir at this temperature for 2 hours, then cooled to room temperature and filtered through celite. The filtrate was concentrated in vacuo and the crude residue obtained was diluted with 10 mL dichloromethane and to the resulting solution was added o-fluoro-p-trifluoromethylbenzaldehyde (0.19 g, 0.96 mmol), sodium triacetoxyborohydride (0.2 g, 0.96 mmol), and acetic acid (0.06 ml, 0.96 mmol). The resulting reaction was allowed to stir for 16 hours and was then concentrated in vacuo and the crude residue obtained was purified using preparative TLC (20% acetone in hexanes) to provide compound 48B.

Step B—Synthesis of Compound 319

Compound 48B was converted to compound 319 using the methods described in Example 1.

Example 49

Preparation of Compound 129

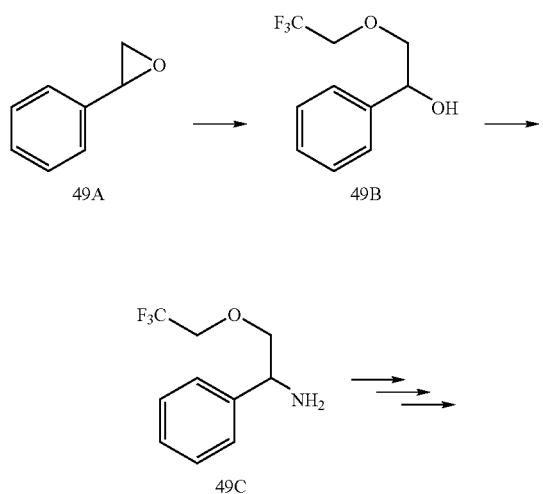

Step A—Synthesis of Compound 49B

To a solution of compound 49A (3.74 g, 26 mmol) in DMF (40 mL) was added trifluoroethanol (20.6 g, 206 mmol) and NaO-tBu (0.60 g, 6.2 mmol). The resulting reaction was heated to 100° C. and allowed to stir at this temperature for 18 hours, then cooled to room temperature and partitioned with ether and water. The ether layer was dried over MgSO₄, filtered and concentrated in vacuo to provide compound 49B as a yellow oil.

Step B—Synthesis of Compound 49C

To a solution of compound 49B (2.54 g, 11.5 mmol) in CH₂Cl₂ (20 mL) at 0° C. were added MsCl (1.58 g, 13.8 mmol) and Et₃N (1.40 g, 13.8 mmol), and the resulting reaction was allowed to stir at 0° C. for 1 hour. The reaction was partitioned with ether and water, and the ether layer was dried over MgSO₄, filtered and concentrated in vacuo. The resulting oily residue was diluted with 2N NH₃ in i-PrOH and the resulting solution was placed in a sealed tube which was placed in an 80° C. bath and allowed to stand for 18 hours. The reaction mixture was cooled to room temperature, concentrated in vacuo, partitioned with ether and water, and extracted with 1N HCl. The extract was basified, extracted with ether, and the ether phase was dried over MgSO₄, filtered and concentrated in vacuo to provide compound 49C as a yellow oil.

Step C—Synthesis of Compound 329

Compound 49C was converted to compound 329 using the method described in Example 35.

Example 50

Preparation of Compound 336

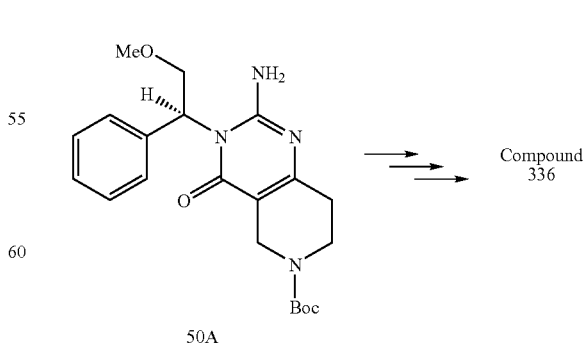

50A (S)-1-Amino-1-phenyl-2-methoxyethane was converted to Compound 50A using the method described in Example 35.

Compound 50A was then converted to compound 336 using the method described in Example 38.

Example 51

Preparation of Compound 344

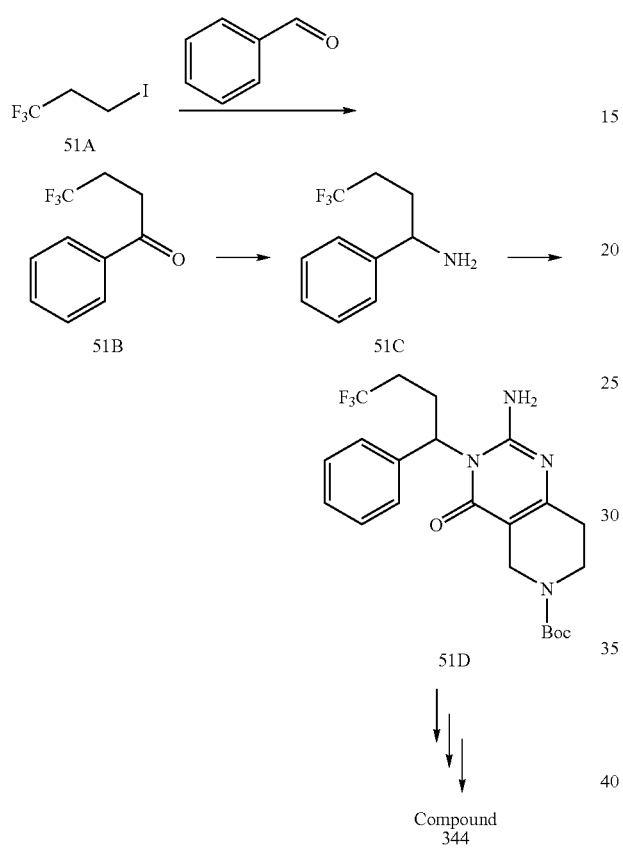

Step A—Synthesis of Compound 51B

Compound 51A (5.00 g, 22.3 mmol) was added to dropwise to Mg turnings (0.70 g, 29 mmol) and catalytic iodine in ether (30 mL). The mixture was stirred 1 h, cooled to 0° C., and treated with benzaldehyde (2.08 g, 20.0 mmol). After 1 h, satd. NH$_4$Cl (100 mL) was added. The mixture was extracted with Et$_2$O, dried (MgSO$_4$), and concentrated to leave the crude alcohol. This material in CH$_2$Cl$_2$ (40 mL) was treated with PCC (12.0 g, 55 mmol), stirred 4 h, treated with hexane (30 mL), filtered, the hexane layer separated and concentrated to give 51B as a yellow solid.

Step B—Synthesis of Compound 51C

Compound 51B (2.8 g, 14 mmol) was combined with formic acid (20 mL) and formamide (50 mL). The mixture was heated at 150° C. for 4 h., allowed to cool, extracted with Et$_2$O, dried (MgSO$_4$), and concentrated. The residue was heated at reflux with conc. HCl (30 mL) for 1 h. and concentrated. The residue was partition between ether and water, the aqueous basified with NaOH., extracted with ether, dried (MgSO$_4$) and concentrated in vacuo to provide compound 51C as a colorless oil.

Step C—Synthesis of Compound 344

Compound 51C was converted to 51D using the method described in Example 35. Compound 51D was converted to compound 344 using the method described in Example 11.

Example 52

Preparation of Compound 325

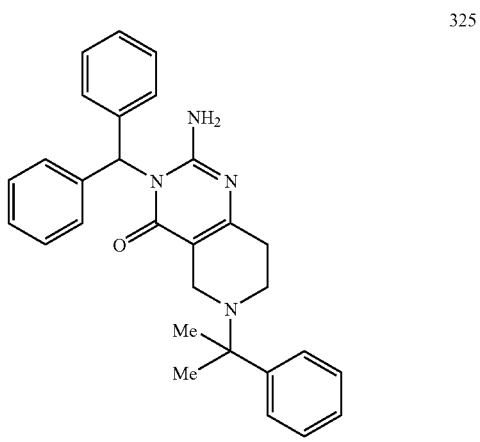

Compound 36A (0.40 g, 1.1 mmol, prepared as described in Example 36) was suspended in water (3 mL) and acetone (2.0 equiv.) and the resulting solution was cooled to 0° C. and KCN (2.0 equiv.) was added. The mixture was allowed to warm to room temperature, stirred for 1 hour, then diluted with DMF (2 mL), and stirred for an additional 18 hours. Water (15 mL) was added to the reaction mixture and the resulting suspended solid was collected and washed with water. The solid was then taken up in THF (2 mL), treated with PhMgBr (3.0 eq in ether) and the resulting reaction was allowed to stir for 72 hours. The reaction mixture was then diluted with saturated NH$_4$Cl and extracted with EtOAc. The organic phase was dried over MgSO$_4$, filtered and concentrated in vacuo to provide compound 325 as a white solid.

Example 53

Preparation of Compounds 348 and 349

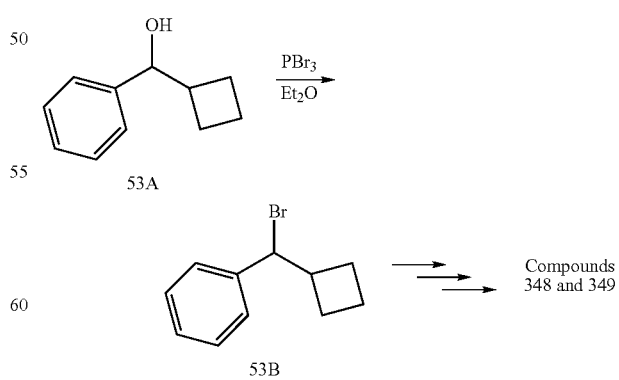

Step A—Synthesis of Compound 53B

To a solution of 1-cyclobutyl-1-phenyl methanol 53A (4.1 g, 25.27 mmol, commercially available) in ether (45.0 mL)

was added pyridine (1.0 mL) and the resulting solution was cooled to −10° C. and allowed to stir at this temperature for 15 minutes. PBr$_3$ (3.18 mL, 33.87 mmol) was then added dropwise to the reaction mixture and the resulting reaction was allowed to stir for 1 hour at 0° C. The reaction mixture was then poured over ice and extracted with ether. The organic phase was sequentially washed with saturated NaHCO$_3$ and brine, dried over K$_2$CO$_3$ and concentrated in vacuo and to provide compound 53B (~3.5 g crude), which was used without further purification.

Step B—Synthesis of Compounds 348 and 349

Compounds 348 and 349 were synthesized from compound 53B using the methods described in Examples 11 and 20, respectively.

Example 54

Preparation of Compound 352

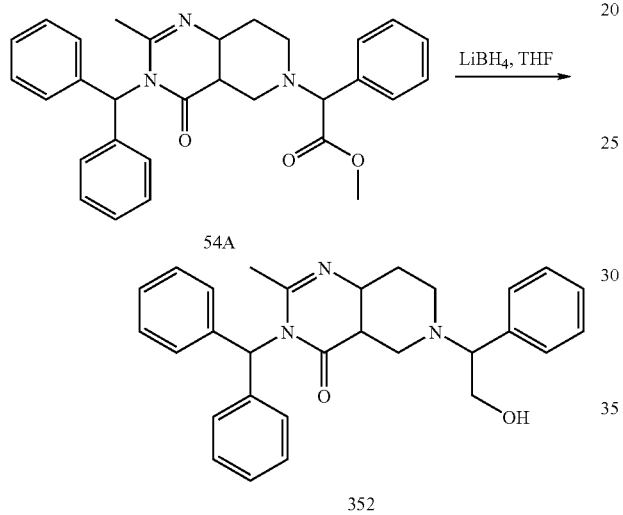

Lithium borohydride (10 mg, 0.22 mmol) was added to a solution of 54A (30 mg, 0.060 mmol, prepared using the method described in Example 10) in THF (2 mL) and the resulting reaction was allowed to stir at room temperature for 20 hours. The reaction was then quenched with water and extracted with EtOAc. The organic phase was collected, dried over MgSO$_4$, filtered and concentrated in vacuo to provide a crude residue which was purified using preparative thin-layer chromatography (5% MeOH/CH$_2$Cl$_2$) to provide compound 352 (8 mg, 30% yield).

Example 55

Preparation of Compounds 321, 322, 323, 324

Convert compound 36A to compound 321 employing 2-bromo-1-phenylpropane according to the method of Example 36. Similarly, with 1-chloro-1-(4-trifluoromethylphenyl)ethane obtain compound 322. With 1-chloro-1-(4-trifluoromethoxyphenyl)ethane obtain compound 323, and with 1-chloroindane obtain compound 324.

Example 56

Preparation of Compounds 330 and 331

Employ the method of Example 19, Step 2, to convert 1-(4-fluoro-3-trifluoromethylphenyl)ethanol to the mesylate and then the method of Example 36 to obtain compound 331. Similarly convert 1-(3-trifluoromethylphenyl)ethanol to the corresponding trifluoromethanesulfonate and then to compound 330.

Example 57

Preparation of Compounds 335, 337, 339, 341 and 342

Employ the method of Example 19 to convert 1-(3-fluoro-4-trifluoromethylphenyl)ethanone to the alcohol mesylate and then the method of Example 36 to obtain compound 337. Similarly, convert 4-(trifluoromethylthio)benzaldehyde into 1-(4-trifluoromethylthiophenyl)ethanol by addition of MeMgBr in ether and then the method of Example 56 to obtain compound 335. By the same methods convert 3-fluoro-5-(trifluoromethyl)benzaldehyde into compound 342.

Following the method for compound 337, but employing (S)-CBS reducing agent, furnished compound 339.

The method for compound 337 was employed to convert 1-(4-difluoromethylphenyl)ethanone (obtained from 4-(difluoromethyl)bromobenzene and 1-ethoxyvinyltributylstannane by Stille reaction) to compound 341.

Example 58

Preparation of Compound 343

1-(4-Trifluoromethylthiophenyl)ethanol (0.096 g, 0.43 mmol) of Example 57 was oxidized with mCPBA (70%, 0.128 g, 0.52 mmol) in CH$_2$Cl$_2$ (2 mL) for 18 h. The concentrated mixture was purified by PLC to obtain the sulfoxide as a yellow oil, and the method of Example 36 provided compound 343.

Example 59

Preparation of Compounds 326 and 327

Compound 322 was resolved on a Chiralcel AD column (10% isopropanol in cyclohexane), eluting compound 326, then compound 327.

Example 60

Preparation of Compounds 333 and 334

Compound 329 was deprotected according to Example 2. Reaction of this amine with 1-(4-trifluoromethylphenyl)ethanol according to Example 19, Step 2 (but without purification of the mesylate), then the method of Example 36, provided compounds 333 and 334.

Example 61

Preparation of Compounds 328

(S)-2-Amino-1-methoxy-3-phenylpropane was converted to Compound 328 using the method described in Example 50.

Example 62

Preparation of Compound 332

1-Aminodicyclobutylmethane was converted to Compound 332 using the method of Example 50.

Example 63

Preparation of Compound 338

1-Amino-1-phenylcyclobutylmethane was converted to Compound 338 using the method of Example 35.

Example 64

Preparation of Compound 340

Employing the method for Compound 337 in Example 57, compound 338 was converted to compound 340.

Example 65

LCMS Data for Selected Compounds

LCMS data for selected Pyrimidinone Derivatives is provided below in Table 1, wherein the compound numbers correspond to the compound numbering set forth in the above specification.

TABLE 1

LCMS Data For Selected Pyrimidinone Derivatives

| Compound | LCMS [M + 1] |
|---|---|
| 22 | 518 |
| 23 | 450 |
| 24 | 508 |
| 25 | 432 |
| 26 | 418 |
| 27 | 447 |
| 28 | 423 |
| 29 | 437 |
| 30 | 605 |
| 31 | 432 |
| 32 | 508 |
| 33 | NA |
| 34 | 390 |
| 35 | 515 |
| 36 | 522 |
| 37 | 521 |
| 38 | 521 |
| 39 | 467 |
| 40 | 536 |
| 41 | 536 |
| 42 | 543 |
| 43 | 465 |
| 44 | 517 |
| 45 | 535 |
| 46 | 445 |
| 47 | 447 |
| 49 | 539 |
| 50 | 557 |
| 51 | 517 |
| 56 | 493 |
| 57 | 390 |
| 58 | 404 |
| 59 | 418 |
| 60 | 422 |
| 61 | 428 |
| 62 | 432 |
| 63 | 432 |
| 64 | NA |
| 65 | 444 |
| 66 | 446 |
| 67 | 452 |
| 68 | 460 |
| 69 | 466 |
| 70 | 466 |
| 71 | 470 |
| 72 | 482 |
| 73 | 486 |
| 74 | 488 |
| 75 | 497 |
| 76 | 500 |
| 77 | 506 |
| 78 | 510 |
| 79 | 510 |
| 80 | 511 |
| 81 | 514 |
| 82 | 520 |
| 83 | 530 |
| 84 | 534 |
| 85 | NA |
| 86 | 490 |
| 87 | 491 |
| 88 | 505 |
| 89 | 423 |
| 90 | 416 |
| 91 | 428 |
| 92 | 428 |
| 93 | 436 |
| 94 | 436 |
| 95 | 436 |
| 96 | 440 |
| 97 | 440 |
| 98 | 442 |
| 99 | 446 |
| 100 | 447 |
| 101 | 447 |
| 102 | 450 |
| 103 | 450 |
| 104 | 450 |
| 105 | 452 |
| 106 | 452 |
| 107 | 452 |
| 108 | 456 |
| 109 | 456 |
| 110 | 456 |
| 111 | 458 |
| 112 | 458 |
| 113 | 458 |
| 114 | 458 |
| 115 | 458 |
| 116 | 458 |
| 117 | 458 |
| 118 | 462 |
| 119 | 462 |
| 120 | 464 |
| 121 | 464 |
| 122 | 466 |
| 123 | 466 |
| 124 | 472 |
| 125 | 472 |
| 126 | 474 |
| 127 | 478 |
| 128 | 480 |
| 129 | 480 |
| 130 | 490 |
| 131 | 490 |
| 132 | 490 |
| 133 | 490 |
| 134 | 490 |
| 135 | 490 |
| 136 | 508 |
| 137 | 526 |
| 138 | 501 |
| 139 | 501 |

TABLE 1-continued

LCMS Data For Selected Pyrimidinone Derivatives

| Compound | LCMS [M + 1] |
|---|---|
| 140 | 524 |
| 141 | 474 |
| 142 | 524 |
| 143 | 524 |
| 144 | 467 |
| 145 | 448 |
| 146 | 488 |
| 147 | 490 |
| 148 | 429 |
| 149 | 488 |
| 150 | 488 |
| 151 | 507 |
| 152 | 606 |
| 153 | 489 |
| 154 | 481 |
| 155 | 471 |
| 156 | 474 |
| 157 | 423 |
| 158 | 487 |
| 159 | 465 |
| 160 | 499 |
| 161 | 436 |
| 162 | 509 |
| 163 | 479 |
| 164 | 498 |
| 165 | 504 |
| 166 | 522 |
| 167 | 505 |
| 168 | 523 |
| 169 | 479 |
| 170 | 500 |
| 171 | 499 |
| 172 | 518 |
| 173 | 479 |
| 174 | 501 |
| 175 | 518 |
| 176 | 536 |
| 177 | 450 |
| 178 | 450 |
| 179 | 450 |
| 180 | 454 |
| 181 | 454 |
| 182 | 454 |
| 183 | 454 |
| 184 | 456 |
| 185 | 462 |
| 186 | 464 |
| 187 | 465 |
| 188 | 466 |
| 189 | 467 |
| 190 | 467 |
| 191 | 470 |
| 192 | 470 |
| 193 | 470 |
| 194 | 472 |
| 195 | 473 |
| 196 | 473 |
| 197 | 474 |
| 198 | 474 |
| 199 | 474 |
| 200 | 474 |
| 201 | 476 |
| 202 | 476 |
| 203 | 476 |
| 204 | 476 |
| 205 | 478 |
| 206 | 482 |
| 207 | 482 |
| 208 | 485 |
| 209 | 485 |
| 210 | 486 |
| 211 | 486 |
| 212 | 488 |
| 213 | 492 |
| 214 | 492 |
| 215 | 492 |
| 216 | 438 |
| 217 | 496 |
| 218 | 500 |
| 219 | 500 |
| 220 | 500 |
| 221 | 501 |
| 222 | 502 |
| 223 | 502 |
| 224 | 502 |
| 225 | 504 |
| 226 | 504 |
| 227 | 506 |
| 228 | 506 |
| 229 | 506 |
| 230 | 506 |
| 231 | 506 |
| 232 | 506 |
| 233 | 506 |
| 234 | 508 |
| 235 | 508 |
| 236 | 508 |
| 237 | 508 |
| 238 | 508 |
| 239 | 512 |
| 240 | 514 |
| 241 | 518 |
| 242 | 518 |
| 243 | 520 |
| 244 | 522 |
| 245 | 528 |
| 246 | 528 |
| 247 | 530 |
| 248 | 533 |
| 249 | 538 |
| 250 | 542 |
| 251 | 545 |
| 252 | 550 |
| 253 | 556 |
| 254 | 558 |
| 255 | 561 |
| 256 | 578 |
| 257 | 471 |
| 258 | 582 |
| 259 | 468 |
| 260 | 480 |
| 261 | 488 |
| 262 | 492 |
| 263 | 522 |
| 264 | 441 |
| 265 | 518 |
| 266 | 588 |
| 267 | 457 |
| 268 | 505 |
| 269 | 522 |
| 270 | 464 |
| 271 | 466 |
| 272 | 494 |
| 273 | 508 |
| 274 | 529 |
| 275 | 548 |
| 276 | 540 |
| 277 | 526 |
| 278 | 512 |
| 279 | 430 |
| 280 | 515 |
| 281 | 465 |
| 282 | 496 |
| 283 | 496 |
| 284 | 558 |
| 285 | 449 |
| 286 | 504 |
| 287 | 436 |
| 288 | 491 |
| 289 | 491 |

TABLE 1-continued

LCMS Data For Selected Pyrimidinone Derivatives

| Compound | LCMS [M + 1] |
|---|---|
| 290 | 442 |
| 291 | 514 |
| 292 | 522 |
| 293 | 436 |
| 294 | 462 |
| 295 | 522 |
| 296 | 558 |
| 297 | 504 |
| 298 | 504 |
| 302 | 450 |
| 303 | 468 |
| 304 | 518 |
| 305 | 532 |
| 306 | 550 |
| 307 | 536 |
| 308 | 538 |
| 309 | 434 |
| 310 | 418 |
| 311 | 540 |
| 312 | 540 |
| 313 | 486 |
| 314 | 504 |
| 315 | 518 |
| 316 | 402 |
| 317 | 452 |
| 318 | 458 |
| 319 | 538 |
| 320 | 484 |
| 321 | 451 |
| 322 | 505 |
| 323 | 521 |
| 324 | 449 |
| 325 | 451 |
| 326 | 505 |
| 327 | 505 |
| 328 | 487 |
| 329 | 469 |
| 330 | 505 |
| 331 | 523 |
| 332 | 461 |
| 333 | 447 |
| 334 | 541 |
| 335 | 523 |
| 336 | 473 |
| 337 | 537 |
| 338 | 411 |
| 339 | 523 |
| 340 | 483 |
| 341 | 487 |
| 342 | 523 |
| 343 | 553 |
| 344 | 525 |
| 345 | 461 |
| 346 | 461 |
| 347 | 461 |
| 348 | 482 |
| 349 | 482 |
| 350 | 522 |
| 351 | 522 |
| 352 | 452 |

Example 56 cAMP Assay

The ability of illustrative compounds of the present invention to activate GPR119 and stimulate increases in cAMP levels can be determined using the LANCE™ cAMP kit (Perkin Elmer). HEK293 cells expressing human GPR119 are maintained in culture flasks at 37° C./5% $CO_2$ in DMEM containing 10% fetal bovine serum, 100 U/ml Pen/Strep, and 0.5 mg/ml geneticin. The media is changed to Optimem and cells are incubated for about 15 hours at 37° C./5% $CO_2$. The Optimem is then aspirated and the cells are removed from the flasks using room temperature Hank's balanced saline solution (HBSS). The cells are then pelleted using centrifugation (1300 rpm, 7 minutes, room temperature), then resuspended in stimulation buffer (HBSS, 0.1% BSA, 5 mM HEPES, 15 μM RO-20) at $2.5 \times 10^6$ cells/mL Alexa Fluor 647-anti cAMP antibody (1:100) is then added to the cell suspension and incubated for 30 minutes. Representative compound(s) of formula (I) (6 μl at 2× concentration) in stimulation buffer containing 2% DMSO are then added to white 384 well Matrix plates. Cell suspension mix (6 μl) is added to each well and incubated with the compound of formula (I) for 30 minutes. A cAMP standard curve is also created in each assay according to the kit protocol. Standard concentrations of cAMP in stimulation buffer (6 μl) are added to white 384 well plates. Subsequently, 6 μl of 1:100 anti-cAMP antibody is then added to each well. Following the 30-minute incubation period, 12 μl of detection mix (included in kit) is added to all wells and incubated for 2-3 hours at room temperature. Fluorescence can be detected on the plates using an Envision instrument. The level of cAMP in each well can then determined by extrapolation from the cAMP standard curve.

Using this assay, $EC_{50}$ values for various illustrative Pyrimidinone Derivatives of the present invention were calculated and range from about 50 nM to about 14000 nM.

Example 57

Effects of Selected Compounds in Oral Glucose Tolerance Test

Male C57Bl/6NCrl mice (6-8 week old) are fasted overnight and randomly dosed with either vehicle (20% hydroxypropyl-β-cyclodextrin) or a representative compound of the invention (at 3, 10 or 30 mg/kg) via oral gavage (n=8 mice/group). Glucose is administered to the animals 30 minutes post-dosing (3 g/kg p.o.). Blood glucose is measured prior to administration of test compound and glucose, and at 20 minutes after glucose administration using a hand-held glucometer (Ascensia Elite, Bayer).

Using the above method, illustrative Pyrimidinone Derivatives of the present invention were evaluated and the results indicate that the Pyrimidinone Derivatives of the present invention are useful in reducing blood glucose levels in response to glucose challenge.

Example 58

Effects of Compounds of the Invention in an Animal Model of Diabetes

Four week old male C57Bl/6NCrl mice can be used to generate a nongenetic model of type 2 diabetes mellitus as previously described (*Metabolism* 47(6): 663-668, 1998). Briefly, mice are made insulin-resistant by high fat feeding (60% of kcal as fat) and hyperglycemia is induced using a low dose of streptozotocin (100 mg/kg i.p.). Eight weeks after streptozotocin administration, mice are placed into one of 4 groups (n=13/gp) receiving the following treatments: vehicle (20% hydroxypropyl-β-cyclodextrin p.o.), a compound of the invention (30 mg/kg p.o.), glipizide (20 mg/kg p.o.) or exendin-4 (10 ug/kg i.p.). Mice are dosed once daily for 13 consecutive days, and blood glucose can measured daily using a hand held glucometer (Ascensia Elite, Bayer).

Uses of the Pyrimidinone Derivatives

The Pyrimidinone Derivatives are useful in human and veterinary medicine for treating or preventing a Condition in a patient. In accordance with the invention, the Pyrimidinone Derivatives can be administered to a patient in need of treatment or prevention of a Condition.

Treatment of Obesity and Obesity-Related Disorders

The Pyrimidinone Derivatives can be useful for treating obesity or an obesity-related disorder in a patient. Accordingly, in one embodiment, the invention provides methods for treating obesity or an obesity-related disorder in a patient, wherein the method comprises administering to the patient an effective amount of one or more Pyrimidinone Derivatives, or a pharmaceutically acceptable salt, solvate, ester or prodrug thereof.

Treatment of Diabetes

The Pyrimidinone Derivatives can be useful for treating diabetes in a patient. Accordingly, in one embodiment, the present invention provides a method for treating diabetes in a patient, comprising administering to the patient an effective amount of one or more Pyrimidinone Derivatives.

Examples of diabetes treatable or preventable using the Pyrimidinone Derivatives include, but are not limited to, type I diabetes (insulin-dependent diabetes mellitus), type II diabetes (non-insulin dependent diabetes mellitus), idiopathic type I diabetes (Type 1b), latent autoimmune diabetes in adults, early-onset type 2 diabetes (EOD), youth-onset atypical diabetes (YOAD), maturity onset diabetes of the young (MODY), malnutrition-related diabetes, gestational diabetes, autoimmune diabetes, insulinopathies, diabetes due to pancreatic disease, diabetes associated with other endocrine diseases (such as Cushing's Syndrome, acromegaly, pheochromocytoma, glucagonoma, primary aldosteronism or somatostatinoma), type A insulin resistance syndrome, type B insulin resistance syndrome, lipatrophic diabetes and diabetes induced by β-cell toxins.

Treatment of a Diabetic Complication

The Pyrimidinone Derivatives can be useful for treating a diabetic complication in a patient. Accordingly, in one embodiment, the present invention provides a method for treating a diabetic complication in a patient, comprising administering to the patient an effective amount of one or more Pyrimidinone Derivatives.

Examples of diabetic complications treatable or preventable using the Pyrimidinone Derivatives include, but are not limited to, diabetic cataract, glaucoma, retinopathy, aneuropathy (such as diabetic neuropathy, polyneuropathy, mononeuropathy, autonomic neuropathy, microaluminuria and progressive diabetic neuropathyl), nephropathy, gangrene of the feet, immune-complex vasculitis, systemic lupsus erythematosus (SLE), atherosclerotic coronary arterial disease, peripheral arterial disease, nonketotic hyperglycemic-hyperosmolar coma, foot ulcers, joint problems, a skin or mucous membrane complication (such as an infection, a shin spot, a candidal infection or necrobiosis lipoidica diabeticorumobesity), hyperlipidemia, cataract, hypertension, syndrome of insulin resistance, coronary artery disease, a fungal infection, a bacterial infection, and cardiomyopathy.

Treatment of a Metabolic Disorder

The Pyrimidinone Derivatives can be useful for treating a metabolic disorder in a patient. Accordingly, in one embodiment, the invention provides methods for treating a metabolic disorder in a patient, wherein the method comprises administering to the patient an effective amount of one or more Pyrimidinone Derivatives, or a pharmaceutically acceptable salt, solvate, ester or prodrug thereof.

Examples of metabolic disorders treatable include, but are not limited to, metabolic syndrome (also known as "Syndrome X"), impaired glucose tolerance, impaired fasting glucose, hypercholesterolemia, hyperlipidemia, hypertriglyceridemia, low HDL levels, hypertension, phenylketonuria, postprandial lipidemia, a glycogen-storage disease, Gaucher's Disease, Tay-Sachs Disease, Niemann-Pick Disease, ketosis and acidosis.

In one embodiment, the metabolic disorder is hypercholesterolemia.

In another embodiment, the metabolic disorder is hyperlipidemia.

In another embodiment, the metabolic disorder is hypertriglyceridemia.

In still another embodiment, the metabolic disorder is metabolic syndrome.

In a further embodiment, the metabolic disorder is low HDL levels.

Treatment of a Cardiovascular Disease

The Pyrimidinone Derivatives can be useful for treating a cardiovascular disease in a patient. Accordingly, in one embodiment, the invention provides methods for treating a cardiovascular disease in a patient, wherein the method comprises administering to the patient an effective amount of one or more Pyrimidinone Derivatives, or a pharmaceutically acceptable salt, solvate, ester or prodrug thereof.

Examples of cardiovascular diseases treatable or preventable using the present methods include, but are not limited to, atherosclerosis, congestive heart failure, circulatory shock, coronary artery disease, left ventricular hypertrophy, angina pectoris, cardiomyopathy, myocardial infarction and a cardiac arrhythmia.

In one embodiment, the cardiovascular disease is atherosclerosis.

In another embodiment, the cardiovascular disease is congestive heart failure.

Combination Therapy

In one embodiment, the present invention provides methods for treating a Condition in a patient, the method comprising administering to the patient one or more Pyrimidinone Derivatives, or a pharmaceutically acceptable salt, solvate, ester or prodrug thereof and at least one additional therapeutic agent that is not a Pyrimidinone Derivative, wherein the amounts administered are together effective to treat or prevent a Condition.

Non-limiting examples of additional therapeutic agents useful in the present methods for treating or preventing a Condition include, anti-obesity agents, antidiabetic agents, any agent useful for treating metabolic syndrome, any agent useful for treating a cardiovascular disease, cholesterol biosynthesis inhibitors, cholesterol absorption inhibitors, bile acid sequestrants, probucol derivatives, IBAT inhibitors, nicotinic acid receptor (NAR) agonists, ACAT inhibitors, cholesteryl ester transfer proten (CETP) inhibitors, low-density lipoprotein (LDL) activators, fish oil, water-soluble fibers, plant sterols, plant stanols, fatty acid esters of plant stanols, or any combination of two or more of these additional therapeutic agents.

Non-limiting examples of anti-obesity agents useful in the present methods for treating a Condition include CB1 antagonists or inverse agonists such as rimonabant, neuropeptide Y antagonists, MCR4 agonists, MCH receptor antagonists, histamine $H_3$ receptor antagonists or inverse agonists, metabolic rate enhancers, nutrient absorption inhibitors, leptin, appetite suppressants and lipase inhibitors.

Non-limiting examples of appetite suppressant agents useful in the present methods for treating or preventing a Condition include cannabinoid receptor 1 ($CB_1$) antagonists or inverse agonists (e.g., rimonabant); Neuropeptide Y (NPY1, NPY2, NPY4 and NPY5) antagonists; metabotropic glutamate subtype 5 receptor (mGluR5) antagonists (e.g., 2-methyl-6-(phenylethynyl)-pyridine and 3[(2-methyl-1,4-thiazol-4-yl)ethynyl]pyridine); melanin-concentrating hormone receptor (MCH1R and MCH2R) antagonists; melanocortin receptor agonists (e.g., Melanotan-II and Mc4r agonists); serotonin uptake inhibitors (e.g., dexfenfluramine and fluoxetine); serotonin (5HT) transport inhibitors (e.g., paroxetine, fluoxetine, fenfluramine, fluvoxamine, sertaline and imipramine); norepinephrine (NE) transporter inhibitors (e.g., desipramine, talsupram and nomifensine); ghrelin antagonists; leptin or derivatives thereof; opioid antagonists (e.g., nalmefene, 3-methoxynaltrexone, naloxone and nalterxone); orexin antagonists; bombesin receptor subtype 3 (BRS3) agonists; Cholecystokinin-A (CCK-A) agonists; ciliary neurotrophic factor (CNTF) or derivatives thereof (e.g., butabindide and axokine); monoamine reuptake inhibitors (e.g., sibutramine); glucagon-like peptide 1 (GLP-1) agonists; topiramate; and phytopharm compound 57.

Non-limiting examples of metabolic rate enhancers useful in the present methods for treating or preventing a Condition include acetyl-CoA carboxylase-2 (ACC2) inhibitors; beta adrenergic receptor 3 (β3) agonists; diacylglycerol acyltransferase inhibitors (DGAT1 and DGAT2); fatty acid synthase (FAS) inhibitors (e.g., Cerulenin); phosphodiesterase (PDE) inhibitors (e.g., theophylline, pentoxifylline, zaprinast, sildenafil, amrinone, milrinone, cilostamide, rolipram and cilomilast); thyroid hormone β agonists; uncoupling protein activators (UCP-1, 2 or 3) (e.g., phytanic acid, 4-[(E)-2-(5,6,7,8-tetramethyl-2-naphthalenyl)-1-propenyl]benzoic acid and retinoic acid); acyl-estrogens (e.g., oleoyl-estrone); glucocorticoid antagonists; 11-beta hydroxy steroid dehydrogenase type 1 (11β HSD-1) inhibitors; melanocortin-3 receptor (Mc3r) agonists; and stearoyl-CoA desaturase-1 (SCD-1) compounds.

Non-limiting examples of nutrient absorption inhibitors useful in the present methods for treating or preventing a Condition include lipase inhibitors (e.g., orlistat, lipstatin, tetrahydrolipstatin, teasaponin and diethylumbelliferyl phosphate); fatty acid transporter inhibitors; dicarboxylate transporter inhibitors; glucose transporter inhibitors; and phosphate transporter inhibitors.

Non-limiting examples of cholesterol biosynthesis inhibitors useful in the present methods for treating or preventing a Condition include HMG-CoA reductase inhibitors, squalene synthase inhibitors, squalene epoxidase inhibitors, and mixtures thereof.

Non-limiting examples of cholesterol absorption inhibitors useful in the present methods for treating or preventing a Condition include ezetimibe. In one embodiment, the cholesterol absorption inhibitor is ezetimibe.

HMG-CoA reductase inhibitors useful in the present methods for treating or preventing a Condition include, but are not limited to, statins such as lovastatin, pravastatin, fluvastatin, simvastatin, atorvastatin, cerivastatin, CI-981, resuvastatin, rivastatin, pitavastatin, rosuvastatin or L-659,699 ((E,E)-11-[3'R-(hydroxy-methyl)-4'-oxo-2'R-oxetanyl]-3,5,7R-trimethyl-2,4-undecadienoic acid).

Squalene synthesis inhibitors useful in the present methods for treating or preventing a Condition include, but are not limited to, squalene synthetase inhibitors; squalestatin 1; and squalene epoxidase inhibitors, such as NB-598 ((E)-N-ethyl-N-(6,6-dimethyl-2-hepten-4-ynyl)-3-[(3,3'-bithiophen-5-yl)methoxy]benzene-methanamine hydrochloride).

Bile acid sequestrants useful in the present methods for treating or preventing a Condition include, but are not limited to, cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly (allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl) alkylamines and poliglusam, insoluble quaternized polystyrenes, saponins and mixtures thereof. Suitable inorganic cholesterol sequestrants include bismuth salicylate plus montmorillonite clay, aluminum hydroxide and calcium carbonate antacids.

Probucol derivatives useful in the present methods for treating or preventing a Condition include, but are not limited to, AGI-1067 and others disclosed in U.S. Pat. Nos. 6,121,319 and 6,147,250.

IBAT inhibitors useful in the present methods for treating or preventing a Condition include, but are not limited to, benzothiepines such as therapeutic compounds comprising a 2,3,4,5-tetrahydro-1-benzothiepine 1,1-dioxide structure such as are disclosed in International Publication No. WO 00/38727.

Nicotinic acid receptor agonists useful in the present methods for treating or preventing a Condition include, but are not limited to, those having a pyridine-3-carboxylate structure or a pyrazine-2-carboxylate structure, including acid forms, salts, esters, zwitterions and tautomers, where available. Other examples of nicotinic acid receptor agonists useful in the present methods include nicotinic acid, niceritrol, nicofuranose and acipimox. An example of a suitable nicotinic acid product is NIASPAN® (niacin extended-release tablets) which are available from Kos Pharmaceuticals, Inc. (Cranbury, N.J.). Further nicotinic acid receptor agonists useful in the present methods for treating or preventing a Condition include, but are not limited to, the compounds disclosed in U.S. Patent Publication Nos. 2006/0264489 and 2007/0066630, and U.S. patent application Ser. No. 11/771,538, each of which is incorporated herein by reference.

ACAT inhibitors useful in the present methods for treating or preventing a Condition include, but are not limited to, avasimibe, HL-004, lecimibide and CL-277082 (N-(2,4-difluorophenyl)-N-[[4-(2,2-dimethylpropyl)phenyl]-methyl]-N-heptylurea). See P. Chang et al., "Current, New and Future Treatments in Dyslipidaemia and Atherosclerosis", *Drugs* 2000 July; 60(1); 55-93, which is incorporated by reference herein.

CETP inhibitors useful in the present methods for treating or preventing a Condition include, but are not limited to, those disclosed in International Publication No. WO 00/38721 and U.S. Pat. No. 6,147,090, which are incorporated herein by reference.

LDL-receptor activators useful in the present methods for treating or preventing a Condition include, but are not limited to, include HOE-402, an imidazolidinyl-pyrimidine derivative that directly stimulates LDL receptor activity. See M. Huettinger et al., "Hypolipidemic activity of HOE-402 is Mediated by Stimulation of the LDL Receptor Pathway", *Arterioscler. Thromb.* 1993; 13:1005-12.

Natural water-soluble fibers useful in the present methods for treating or preventing a Condition include, but are not limited to, psyllium, guar, oat and pectin.

Fatty acid esters of plant stanols useful in the present methods for treating or preventing a Condition include, but are not limited to, the sitostanol ester used in BENECOL® margarine.

Non-limiting examples of antidiabetic agents useful in the present methods for treating a Condition include insulin sensitizers, β-glucosidase inhibitors, DPP-IV inhibitors, insulin secretagogues, hepatic glucose output lowering compounds, antihypertensive agents, sodium glucose uptake transporter 2 (SGLT-2) inhibitors, insulin and insulin-containing compositions, and anti-obesity agents as set forth above.

In one embodiment, the antidiabetic agent is an insulin secretagogue. In one embodiment, the insulin secretagogue is a sulfonylurea.

Non-limiting examples of sulfonylureas useful in the present methods include glipizide, tolbutamide, glyburide, glimepiride, chlorpropamide, acetohexamide, gliamilide, gliclazide, gliquidone, glibenclamide and tolazamide.

In another embodiment, the insulin secretagogue is a meglitinide.

Non-limiting examples of meglitinides useful in the present methods for treating a Condition include repaglinide, mitiglinide, and nateglinide.

In still another embodiment, the insulin secretagogue is GLP-1 or a GLP-1 mimetic.

Non-limiting examples of GLP-1 mimetics useful in the present methods include Byetta-Exanatide, Liraglutinide, CJC-1131 (ConjuChem, Exanatide-LAR (Amylin), BIM-51077 (Ipsen/LaRoche), ZP-10 (Zealand Pharmaceuticals), and compounds disclosed in International Publication No. WO 00/07617.

Other non-limiting examples of insulin secretagogues useful in the present methods include exendin, GIP and secretin.

In another embodiment, the antidiabetic agent is an insulin sensitizer.

Non-limiting examples of insulin sensitizers useful in the present methods include PPAR activators or agonists, such as troglitazone, rosiglitazone, pioglitazone and englitazone; biguanidines such as metformin and phenformin; PTP-1B inhibitors; and glucokinase activators.

In another embodiment, the antidiabetic agent is a β-Glucosidase inhibitor.

Non-limiting examples of β-Glucosidase inhibitors useful the present methods include miglitol, acarbose, and voglibose.

In another embodiment, the antidiabetic agent is an hepatic glucose output lowering agent.

Non-limiting examples of hepatic glucose output lowering agents useful in the present methods include Glucophage and Glucophage XR.

In yet another embodiment, the antidiabetic agent is insulin, including all formulations of insulin, such as long acting and short acting forms of insulin.

Non-limiting examples of orally administrable insulin and insulin containing compositions include AL-401 from Autoimmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

In another embodiment, the antidiabetic agent is a DPP-IV inhibitor.

Non-limiting examples of DPP-IV inhibitors useful in the present methods include sitagliptin, saxagliptin (Januvia™, Merck), denagliptin, vildagliptin (Galvus™, Novartis), alogliptin, alogliptin benzoate, ABT-279 and ABT-341 (Abbott), ALS-2-0426 (Alantos), ARI-2243 (Arisaph), BI-A and BI-B (Boehringer Ingelheim), SYR-322 (Takeda), MP-513 (Mitsubishi), DP-893 (Pfizer), RO-0730699 (Roche) or a combination of sitagliptin/metformin HCl (Janumet™, Merck).

In a further embodiment, the antidiabetic agent is a SGLT-2 inhibitor.

Non-limiting examples of SGLT-2 inhibitors useful in the present methods include dapagliflozin and sergliflozin, AVE2268 (Sanofi-Aventis) and T-1095 (Tanabe Seiyaku).

Non-limiting examples of antihypertensive agents useful in the present methods for treating a Condition include β-blockers and calcium channel blockers (for example diltiazem, verapamil, nifedipine, amlopidine, and mybefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), renin inhibitors and endothelin receptor antagonists (for example sitaxsentan).

In one embodiment, the antidiabetic agent is an agent that slows or blocks the breakdown of starches and certain sugars.

Non-limiting examples of antidiabetic agents that slow or block the breakdown of starches and certain sugars and are suitable for use in the compositions and methods of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in International Publication No. WO 00/07617.

Other specific additional therapeutic agents useful in the present methods for treating or preventing a Condition include, but are not limited to, rimonabant, 2-methyl-6-(phenylethynyl)-pyridine, 3[(2-methyl-1,4-thiazol-4-yl)ethynyl]pyridine, Melanotan-II, dexfenfluramine, fluoxetine, paroxetine, fenfluramine, fluvoxamine, sertaline, imipramine, desipramine, talsupram, nomifensine, leptin, nalmefene, 3-methoxynaltrexone, naloxone, nalterxone, butabindide, axokine, sibutramine, topiramate, phytopharm compound 57, Cerulenin, theophylline, pentoxifylline, zaprinast, sildenafil, amrinone, milrinone, cilostamide, rolipram, cilomilast, phytanic acid, 4-[(E)-2-(5,6,7,8-tetramethyl-2-naphthalenyl)-1-propenyl]benzoic acid, retinoic acid, oleoyl-estrone, orlistat, lipstatin, tetrahydrolipstatin, teasaponin and diethylumbelliferyl phosphate.

In one embodiment, the present combination therapies for treating or preventing diabetes comprise administering a compound of formula (I), an antidiabetic agent and/or an antiobesity agent.

In another embodiment, the present combination therapies for treating or preventing diabetes comprise administering a compound of formula (I) and an antidiabetic agent.

In another embodiment, the present combination therapies for treating or preventing diabetes comprise administering a compound of formula (I) and an anti-obesity agent.

In one embodiment, the present combination therapies for treating or preventing obesity comprise administering a compound of formula (I), an antidiabetic agent and/or an antiobesity agent.

In another embodiment, the present combination therapies for treating or preventing obesity comprise administering a compound of formula (I) and an antidiabetic agent.

In another embodiment, the present combination therapies for treating or preventing obesity comprise administering a compound of formula (I) and an anti-obesity agent.

In one embodiment, the present combination therapies for treating or preventing metabolic syndrome comprise administering a compound of formula (I) and one or more additional therapeutic agents selected from: anti-obesity agents, antidiabetic agents, any agent useful for treating metabolic syndrome, any agent useful for treating a cardiovascular disease, cholesterol biosynthesis inhibitors, sterol absorption inhibitors, bile acid sequestrants, procubol derivatives, IBAT inhibitors, nicotinic acid receptor (NAR) agonists, ACAT inhibitors, cholesteryl ester transfer proten (CETP) inhibitors, low-density lipoprotein (LDL) activators, fish oil, water-soluble fibers, plant sterols, plant stanols and fatty acid esters of plant stanols.

In one embodiment, the additional therapeutic agent is a cholesterol biosynthesis inhibitor. In another embodiment, the cholesterol biosynthesis inhibitor is a squalene synthetase inhibitor. In another embodiment, the cholesterol biosynthesis inhibitor is a squalene epoxidase inhibitor. In still another embodiment, the cholesterol biosynthesis inhibitor is an HMG-CoA reductase inhibitor. In another embodiment, the HMG-CoA reductase inhibitor is a statin. In yet another embodiment, the statin is lovastatin, pravastatin, simvastatin or atorvastatin.

In one embodiment, the additional therapeutic agent is a cholesterol absorption inhibitor. In another embodiment, the cholesterol absorption inhibitor is ezetimibe.

In one embodiment, the additional therapeutic agent comprises a cholesterol absorption inhibitor and a cholesterol biosynthesis inhibitor. In another embodiment, the additional therapeutic agent comprises a cholesterol absorption inhibitor and a statin. In another embodiment, the additional therapeutic agent comprises ezetimibe and a statin. In another embodiment, the additional therapeutic agent comprises ezetimibe and simvastatin.

In one embodiment, the present combination therapies for treating or preventing metabolic syndrome comprise administering a compound of formula (I), an antidiabetic agent and/or an antiobesity agent.

In another embodiment, the present combination therapies for treating or preventing metabolic syndrome comprise administering a compound of formula (I) and an antidiabetic agent.

In another embodiment, the present combination therapies for treating or preventing metabolic syndrome comprise administering a compound of formula (I) and an anti-obesity agent.

In one embodiment, the present combination therapies for treating or preventing a cardiovascular disease comprise administering one or more compounds of formula (I), and an additional agent useful for treating or preventing a cardiovascular disease.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more Pyrimidinone Derivatives are administered during a time when the additional therapeutic agent(s) exert their prophylactic or therapeutic effect, or vice versa.

In another embodiment, the one or more Pyrimidinone Derivatives and the additional therapeutic agent(s) are administered in doses commonly employed when such agents are used as monotherapy for treating a Condition.

In another embodiment, the one or more Pyrimidinone Derivatives and the additional therapeutic agent(s) are administered in doses lower than the doses commonly employed when such agents are used as monotherapy for treating a Condition.

In still another embodiment, the one or more Pyrimidinone Derivatives and the additional therapeutic agent(s) act synergistically and are administered in doses lower than the doses commonly employed when such agents are used as monotherapy for treating a Condition.

In one embodiment, the one or more Pyrimidinone Derivatives and the additional therapeutic agent(s) are present in the same composition. In one embodiment, this composition is suitable for oral administration. In another embodiment, this composition is suitable for intravenous administration.

The one or more Pyrimidinone Derivatives and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more Pyrimidinone Derivatives and the additional therapeutic agent(s) may inhibit the resistance of a Condition to these agents.

In one embodiment, when the patient is treated for diabetes or a diabetic complication, the additional therapeutic agent is an antidiabetic agent which is not a Pyrimidinone Derivative. In another embodiment, the additional therapeutic agent is an agent useful for reducing any potential side effect of a Pyrimidinone Derivative. Such potential side effects include, but are not limited to, nausea, vomiting, headache, fever, lethargy, muscle aches, diarrhea, general pain, and pain at an injection site.

In one embodiment, the additional therapeutic agent is used at its known therapeutically effective dose. In another embodiment, the additional therapeutic agent is used at its normally prescribed dosage. In another embodiment, the additional therapeutic agent is used at less than its normally prescribed dosage or its known therapeutically effective dose.

The doses and dosage regimen of the other agents used in the combination therapies of the present invention for the treatment or prevention of a Condition can be determined by the attending clinician, taking into consideration the approved doses and dosage regimen in the package insert; the age, sex and general health of the patient; and the type and severity of the viral infection or related disease or disorder. When administered in combination, the Pyrimidinone Derivative(s) and the other agent(s) for treating diseases or conditions listed above can be administered simultaneously or sequentially. This particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the one or more Pyrimidinone Derivatives and the additional therapeutic agent(s) can when administered as combination therapy, range from about 0.1 to about 2000 mg per day, although variations will necessarily occur depending on the target of the therapy, the patient and the route of administration. In one embodiment, the dosage is from about 0.2 to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

Compositions and Administration

In one embodiment, the invention provides compositions comprising an effective amount of one or more compounds of formula (I) or a pharmaceutically acceptable salt, solvate, ester or prodrug thereof, and a pharmaceutically acceptable carrier.

For preparing pharmaceutical compositions from the compounds of formula (I), inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In one embodiment, the Pyrimidinone Derivative is administered orally.

In one embodiment, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation is from about 0.1 to about 2000 mg. Variations will necessarily occur depending on the target of the therapy, the patient and the route of administration. In one embodiment, the unit dose dosage is from about 0.2 to about 1000 mg. In another embodiment, the unit dose dosage is from about 1 to about 500 mg. In another embodiment, the unit dose dosage is from about 1 to about 100 mg/day. In still another embodiment, the unit dose dosage is from about 1 to about 50 mg. In yet another embodiment, the unit dose dosage is from about 1 to about 10 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When the invention comprises a combination of one or more Pyrimidinone Derivatives and an additional therapeutic agent, the two active components may be co-administered simultaneously or sequentially, or a single pharmaceutical composition comprising one or more Pyrimidinone Derivatives and an additional therapeutic agent in a pharmaceutically acceptable carrier can be administered. The components of the combination can be administered individually or together in any conventional dosage form such as capsule, tablet, powder, cachet, suspension, solution, suppository, nasal spray, etc. The dosage of the additional therapeutic agent can be determined from published material, and may range from about 1 to about 1000 mg per dose. In one embodiment, when used in combination, the dosage levels of the individual components are lower than the recommended individual dosages because of the advantageous effect of the combination.

In one embodiment, the components of a combination therapy regime are to be administered simultaneously, they can be administered in a single composition with a pharmaceutically acceptable carrier.

In another embodiment, when the components of a combination therapy regime are to be administered separately or sequentially, they can be administered in separate compositions, each containing a pharmaceutically acceptable carrier.

The components of the combination therapy can be administered individually or together in any conventional dosage form such as capsule, tablet, powder, cachet, suspension, solution, suppository, nasal spray, etc.

Kits

In one aspect, the present invention provides a kit comprising an effective amount of one or more Compounds of Formula (I), or a pharmaceutically acceptable salt or solvate of the compound and a pharmaceutically acceptable carrier, vehicle or diluent.

In another aspect the present invention provides a kit comprising an amount of one or more Pyrimidinone Derivatives, or a pharmaceutically acceptable salt or solvate of the compound and an amount of at least one additional therapeutic agent listed above, wherein the combined amounts are effective for treating or preventing diabetes, a diabetic complication impaired glucose tolerance or impaired fasting glucose in a patient.

When the components of a combination therapy regime are to be administered in more than one composition, they can be provided in a kit comprising in a single package, one or more containers, each comprising one or more Pyrimidinone Derivatives in a pharmaceutically acceptable carrier, and a separate container comprising an additional therapeutic agent in a pharmaceutically acceptable carrier, with the active components of each composition being present in amounts such that the combination is therapeutically effective.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound having the formula:

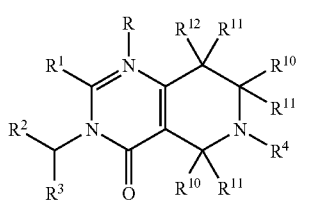

(I)

or a pharmaceutically acceptable salt thereof, wherein:
R is absent or R is oxygen, such that when R is oxygen, this is understood to represent the N-oxide form of the nitrogen atom to which R is attached;
$R^1$ is —H, alkyl, haloalkyl, —N($R^9$)$_2$, —S$R^9$, —S(O)$_q$N($R^6$)$_2$, —S(O)$_p$$R^7$, —O$R^9$, -(alkylene)$_n$-aryl, -(alkylene)$_n$-cycloalkyl, -(alkylene)$_n$-cycloalkenyl, -(alkylene)$_n$-heterocycloalkyl, -(alkylene)$_n$-heteroaryl, -(alkylene)$_n$-heterocycloalkenyl, —C(O)-aryl, —C(O)-alkyl, -alkylene-O-aryl, -alkylene-O-alkyl or -C(O)NH$_2$, wherein any aryl, cycloalkyl, cycloalkenyl, heterocycloalkyl, heterocycloalkenyl or heteroaryl group can be optionally substituted with up to 3 substituents, which can be the same or different, and are selected from alkyl, haloalkyl, hydroxyalkyl, aryl, halo, —OH, —O-haloalkyl, —O-alkyl, -alkylene-O-alkyl, —S(O)$_p$$R^7$, —CN, —N($R^6$)$_2$, —C(O)$R^5$, —C(O)O$R^5$, —C(O)N($R^6$)$_2$, —NHC(O)$R^5$, —NHS(O)$_q$$R^7$ and —S(O)$_q$N($R^6$)$_2$;
$R^2$ is alkyl, haloalkyl, -(alkylene)$_n$-aryl, -(alkylene)$_n$-cycloalkyl, -(alkylene)$_n$-cycloalkenyl, -(alkylene)$_n$-heterocycloalkyl, -(alkylene)$_n$-heteroaryl, -(alkylene)$_n$-heterocycloalkenyl, —C(O)-aryl, —C(O)-alkyl, -alkylene-O-haloalkyl, -alkylene-O-aryl, -alkylene-O-alkyl, —C(O)O$R^5$, or —C(O)N($R^6$)$_2$, wherein any aryl, cycloalkyl, cycloalkenyl, heterocycloalkyl, heterocycloalkenyl or heteroaryl group can be optionally substituted with up to 3 substituents, which can be the same or different, and are selected from alkyl, haloalkyl, hydroxyalkyl, aryl, halo, —OH, —O-haloalkyl, —O-alkyl, -alkylene-O-alkyl, —S(O)$_p$$R^7$, —CN, —N($R^6$)$_2$, —C(O)$R^5$, —C(O)O$R^5$, —C(O)N($R^6$)$_2$, —NHC(O)$R^5$, —NHS(O)$_q$$R^7$ and —S(O)$_q$N($R^6$)$_2$, or $R^2$ and $R^3$ and the carbon atom to which they are both attached, combine to form an aryl, cycloalkyl, cycloalkenyl, heterocycloalkyl, heterocycloalkenyl or heteroaryl group, wherein any of these groups is unsubstituted or substituted with up to 3 substituents, which can be the same or different, and which are selected from alkyl, haloalkyl, hydroxyalkyl, halo, —OH, —O-haloalkyl, —O-alkyl, —O-aryl, -alkylene-O-alkyl, —CN, —N($R^6$)$_2$, —C(O)$R^5$, —C(O)O$R^5$, —C(O)N($R^6$)$_2$, —NHC(O)$R^5$, —NHS(O)$_q$$R^7$, —S(O)$_p$$R^7$ and —S(O)$_q$N($R^6$)$_2$;
$R^3$ is alkyl, -(alkylene)$_n$-aryl, -(alkylene)$_n$-cycloalkyl, -(alkylene)$_n$-cycloalkenyl, -(alkylene)$_n$-heterocycloalkyl, -(alkylene)$_n$-heteroaryl, -(alkylene)$_n$-heterocycloalkenyl, —C(O)-aryl, —C(O)-alkyl, -alkylene-O-aryl, -alkylene-O-alkyl, —C(O)O$R^5$, or —C(O)N($R^6$)$_2$, wherein any aryl, cycloalkyl, cycloalkenyl, heterocycloalkyl, heterocycloalkenyl or heteroaryl group can be optionally substituted with up to 3 substituents, which can be the same or different, and are selected from alkyl, haloalkyl, hydroxyalkyl, aryl, halo, —OH, —O-haloalkyl, —O-alkyl, -alkylene-O-alkyl, —S(O)$_p$$R^7$, —CN, —N($R^6$)$_2$, —C(O)$R^5$, —C(O)O$R^5$, —C(O)N($R^6$)$_2$, —NHC(O)$R^5$, —NHS(O)$_q$$R^7$ and —S(O)$_q$N($R^6$)$_2$, or $R^2$ and $R^3$ and the carbon atom to which they are both attached, combine to form an aryl, cycloalkyl, cycloalkenyl, heterocycloalkyl, heterocycloalkenyl or heteroaryl group, wherein any of these groups is unsubstituted or substituted with up to 3 substituents, which can be the same or different, and which are selected from alkyl, haloalkyl, hydroxyalkyl, halo, —OH, —O-haloalkyl, —O-alkyl, —O-aryl, -alkylene-O-alkyl, —CN, —N($R^6$)$_2$, —C(O)$R^5$, —C(O)O$R^5$, —C(O)N($R^6$)$_2$, —NHC(O)$R^5$, —NHS(O)$_q$$R^7$, —S(O)$_p$$R^7$ and —S(O)$_q$N($R^6$)$_2$;
$R^4$ is H, alkyl, —C(O)$R^5$, —S(O)$_q$$R^7$, -alkylene-O-alkyl, -alkylene-O-aryl, -alkylene-S-alkyl, -alkylene-S-aryl, -alkylene-NH-alkyl, -alkylene-NH-aryl, -alkylene-NC(O)O-alkyl, —C(O)O$R^5$, —C(O)N($R^6$)$_2$, —C(O)NH—O$R^8$, -(alkylene)$_n$-aryl, -(alkylene)$_n$-cycloalkyl, -(alkylene)$_n$-cycloalkenyl, -(alkylene)$_n$-heterocycloalkyl, -(alkylene)$_n$-heterocycloalkenyl or -(alkylene)$_n$-heteroaryl, wherein any aryl, cycloalkyl, cycloalkenyl, heterocycloalkyl, heterocycloalkenyl or heteroaryl group that is part of an $R^4$ group can be unsubstituted or substituted with up to 3 substituents, which can be the same or different, and are selected from: alkyl, aryl, heterocycloalkyl, heteroaryl, -alkylene-O-alkylene-Si(alkyl)$_3$, —NH$_2$, —NH-alkyl, —N(alkyl)$_2$, —OH, -hydroxyalkyl, -alkynylene-aryl, —S(O)$_p$$R^7$, —O-alkyl, —O-aryl, —C(O)O-alkyl, —C(O)O-haloalkyl, halo, —NO$_2$, —CN, heteroaryl, haloalkyl, —O-haloalkyl, —S-haloalkyl, —S(O)-haloalkyl and -(alkynylene)$_n$-aryl, and wherein a cycloalkyl group that is part of an $R^4$ group can be fused with a benzene ring, and wherein an alkylene group can be optionally substituted with a group selected from: alkyl, cycloalkyl, aryl, heterocycloalkyl or heteroaryl;

R⁵ is alkyl, alkenyl, alkynyl, haloalkyl, -alkylene-O-aryl, -alkylene-S-aryl, -alkylene-N(R⁸)C(O)O-alkyl, -(alkylene)$_n$-aryl, -(alkylene)$_n$-cycloalkyl, -(alkylene)$_n$-cycloalkenyl, -(alkylene)$_n$-heterocycloalkyl, -(alkylene)$_n$-heterocycloalkenyl or -(alkylene)$_n$-heteroaryl, wherein any aryl, cycloalkyl, cycloalkenyl, heterocycloalkyl, heterocycloalkenyl or heteroaryl group can be unsubstituted or substituted with up to 4 substituents, which can be the same or different, and are selected from alkyl, haloalkyl, hydroxyalkyl, halo, —OH, —O-haloalkyl, —O-alkyl, —O-aryl, —S-haloalkyl, -alkylene-O-alkyl, —CN, —N(R⁹)₂, —C(O)H, —C(O)R⁹, —C(O)OR⁹, —C(O)N(R⁹)₂, —NHC(O)R⁹, —NHS(O)$_q$R⁹, —S(O)$_p$R⁹ and —S(O)$_q$N(R⁹)₂;

each occurrence of R⁶ is independently H, alkyl, -(alkylene)$_n$-aryl, -(alkylene)$_n$-cycloalkyl, -(alkylene)$_n$-cycloalkenyl, -(alkylene)$_n$-heterocycloalkyl, -(alkylene)$_n$-heterocycloalkenyl or -(alkylene)$_n$-heteroaryl, wherein any of the above groups, excluding H, can be unsubstituted or substituted with from 1 to 3 substituents, which can be the same or different, and which are selected from alkyl, haloalkyl, hydroxyalkyl, halo, —OH, —O-haloalkyl, —O-alkyl, —O-aryl, -alkylene-O-alkyl, —CN, —N(R⁹)₂, —C(O)H, —C(O)R⁹, —C(O)OR⁹, —C(O)N(R⁹)₂, —NHC(O)R⁹, —NHS(O)$_q$R⁹, —S(O)$_p$R⁹ and —S(O)$_q$N(R⁹)₂;

each occurrence of R⁷ is independently alkyl, aryl, heterocycloalkyl, heteroaryl or cycloalkyl, any of which can be unsubstituted or substituted with from 1 to 3 substituents, which can be the same or different, and which are selected from alkyl, haloalkyl, hydroxyalkyl, halo, —OH, —O-haloalkyl, —O-alkyl, -O-aryl, -alkylene-O-alkyl, —CN, —N(R⁹)₂, —C(O)H, —C(O)R⁹, —C(O)OR⁹, —C(O)N(R⁹)₂, —NHC(O)R⁹, —NHS(O)$_q$R⁹, —S(O)$_p$R⁹ and —S(O)$_q$N(R⁹)₂;

each occurrence of R⁸ is independently H or alkyl;

each occurrence of R⁹ is independently H, alkyl, -(alkylene)$_n$-aryl, heterocycloalkyl, heteroaryl or cycloalkyl;

each occurrence of R¹⁰ is independently H, alkyl, -(alkylene)$_n$-aryl, heterocycloalkyl, heteroaryl or cycloalkyl;

each occurrence of R¹¹ is independently H, alkyl, -(alkylene)$_n$-aryl, heterocycloalkyl, heteroaryl or cycloalkyl, or any R¹⁰ and R¹¹, together with the carbon atoms to which they are attached, can join to form a 3- to 7-membered fused or spirocyclic ring, or a 4- to 7-membered bridged ring;

R¹² is H, alkyl, -(alkylene)$_n$-aryl, heterocycloalkyl, heteroaryl, cycloalkyl, alkoxy or hydroxyalkyl;

each occurrence of n is independently 0 or 1;

each occurrence of p is independently 0, 1 or 2; and each occurrence of q is independently 1 or 2, such that the compound of formula (I) is not a compound having the formula (II):

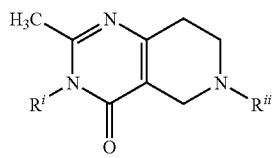

(II)

wherein R$^i$ and R$^{ii}$ are defined in the above specification.

2. The compound of claim 1, wherein R¹ is alkyl or —N(R⁹)₂.

3. The compound of claim 2, wherein R¹ is methyl.

4. The compound of claim 2, wherein R¹ is —NH₂.

5. The compound of claim 1, wherein R² is aryl, heteroaryl or cycloalkyl and R³ is aryl, heteroaryl or cycloalkyl.

6. The compound of claim 5, wherein R² is phenyl, 4-fluorophenyl or pyridyl, and R³ is phenyl, 4-fluorophenyl or pyridyl.

7. The compound of claim 6, wherein R² and R³ are each phenyl.

8. The compound of claim 6, wherein R² is phenyl and R³ is pyridyl.

9. The compound of claim 6, wherein R² and R³ are each 4-fluorophenyl.

10. The compound of claim 6, wherein R² is phenyl and R³ is 4-fluorophenyl.

11. The compound of claim 5, wherein R⁴ is -alkylene-aryl.

12. The compound of claim 11, wherein R⁴ is —CH₂-aryl or —CH(CH₃)—aryl.

13. The compound of claim 12, wherein R⁴ is —CH₂-phenyl or —CH(CH₃)-phenyl, wherein the phenyl group can be optionally substituted with up to 3 substituents, which may be the same or different, and are selected from halo, haloalkyl, heteroaryl, —C(O)O-alkyl, —S-haloalkyl or —NO₂.

14. The compound of claim 13, wherein R⁴ is:

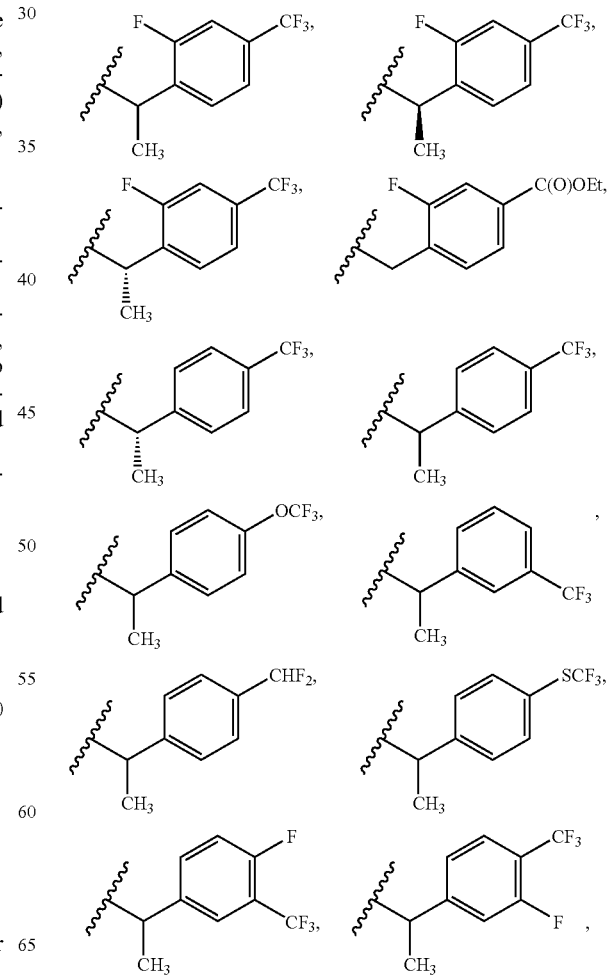

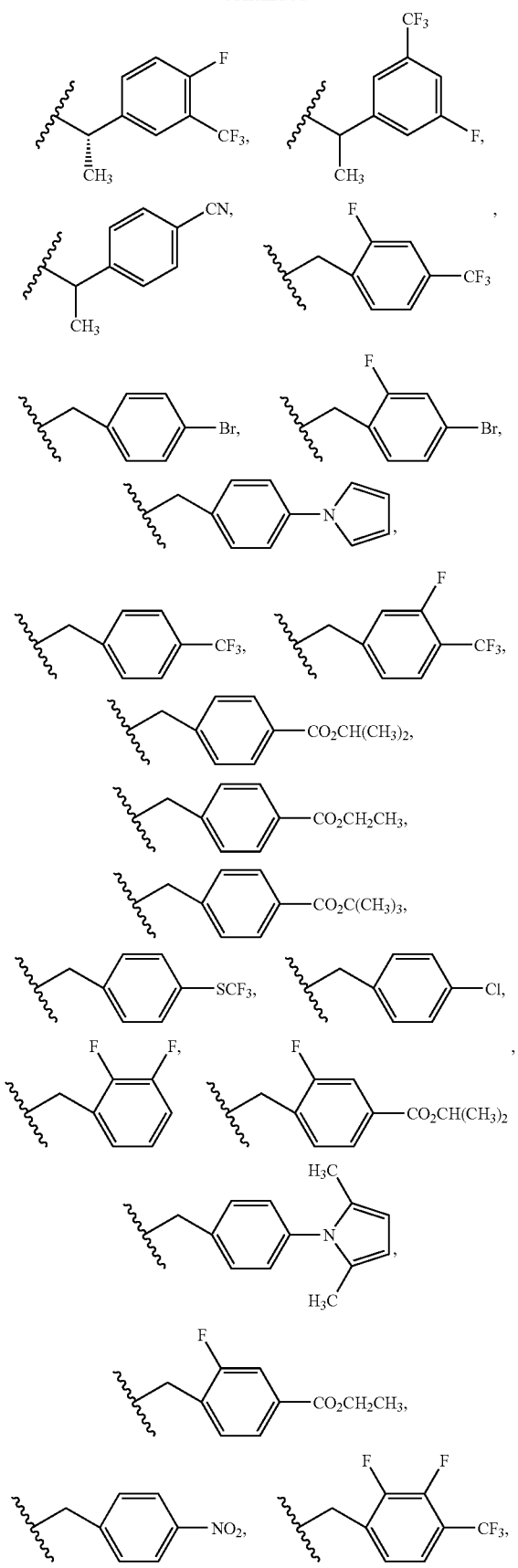
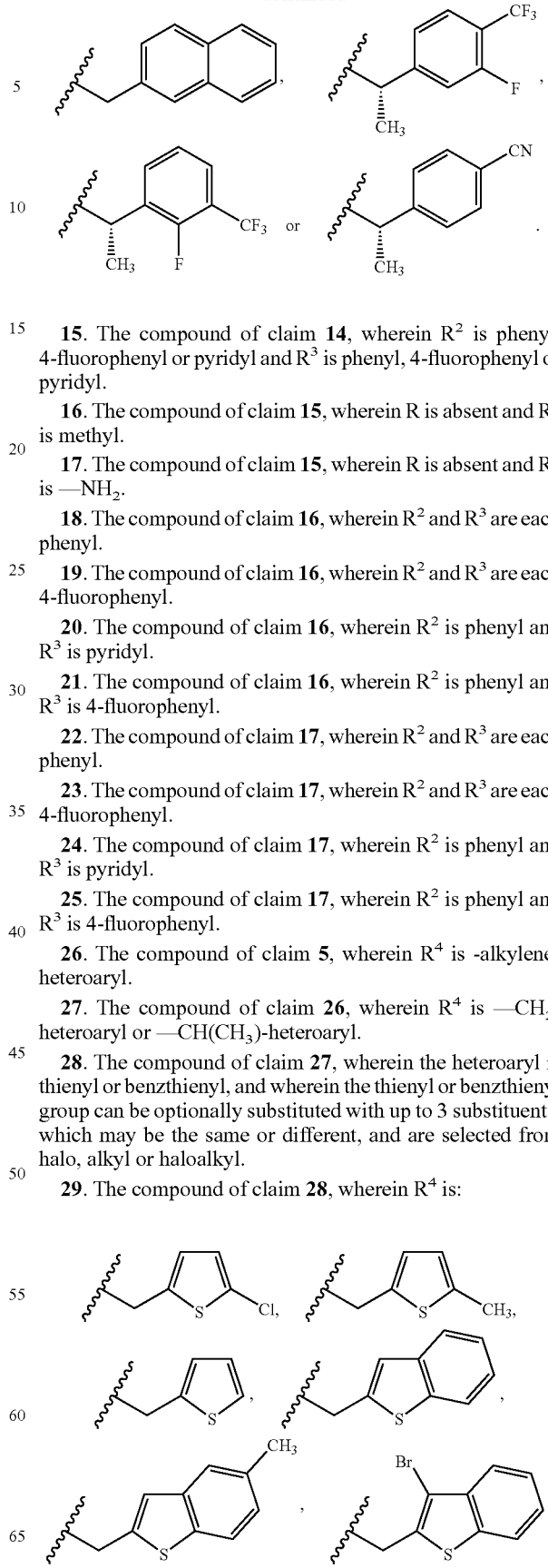

15. The compound of claim 14, wherein $R^2$ is phenyl, 4-fluorophenyl or pyridyl and $R^3$ is phenyl, 4-fluorophenyl or pyridyl.

16. The compound of claim 15, wherein R is absent and $R^1$ is methyl.

17. The compound of claim 15, wherein R is absent and $R^1$ is —$NH_2$.

18. The compound of claim 16, wherein $R^2$ and $R^3$ are each phenyl.

19. The compound of claim 16, wherein $R^2$ and $R^3$ are each 4-fluorophenyl.

20. The compound of claim 16, wherein $R^2$ is phenyl and $R^3$ is pyridyl.

21. The compound of claim 16, wherein $R^2$ is phenyl and $R^3$ is 4-fluorophenyl.

22. The compound of claim 17, wherein $R^2$ and $R^3$ are each phenyl.

23. The compound of claim 17, wherein $R^2$ and $R^3$ are each 4-fluorophenyl.

24. The compound of claim 17, wherein $R^2$ is phenyl and $R^3$ is pyridyl.

25. The compound of claim 17, wherein $R^2$ is phenyl and $R^3$ is 4-fluorophenyl.

26. The compound of claim 5, wherein $R^4$ is -alkylene-heteroaryl.

27. The compound of claim 26, wherein $R^4$ is —$CH_2$-heteroaryl or —$CH(CH_3)$-heteroaryl.

28. The compound of claim 27, wherein the heteroaryl is thienyl or benzthienyl, and wherein the thienyl or benzthienyl group can be optionally substituted with up to 3 substituents, which may be the same or different, and are selected from halo, alkyl or haloalkyl.

29. The compound of claim 28, wherein $R^4$ is:

-continued

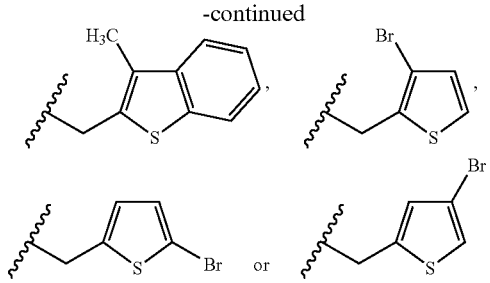

30. The compound of claim 29, wherein R² is phenyl, 4-fluorophenyl or pyridyl and R³ is phenyl, 4-fluorophenyl or pyridyl.

31. The compound of claim 29, wherein R² and R³ are each phenyl.

32. The compound of claim 29, wherein R² and R³ are each 4-fluorophenyl.

33. The compound of claim 29, wherein R² is phenyl and R³ is pyridyl.

34. The compound of claim 30, wherein R² and R³ are each phenyl.

35. The compound of claim 30, wherein R² and R³ are each 4-fluorophenyl.

36. The compound of claim 30, wherein R² is phenyl and R³ is pyridyl.

37. The compound of claim 30, wherein R² is phenyl and R³ is 4-fluorophenyl.

38. A compound having the structure:

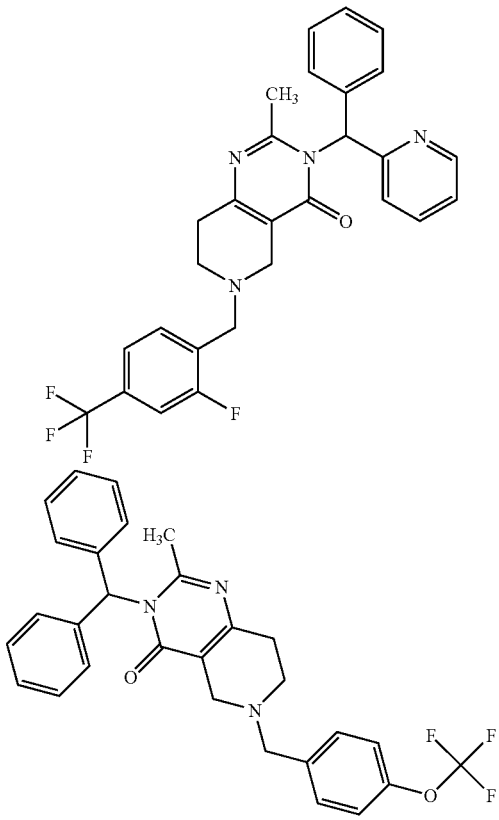

-continued

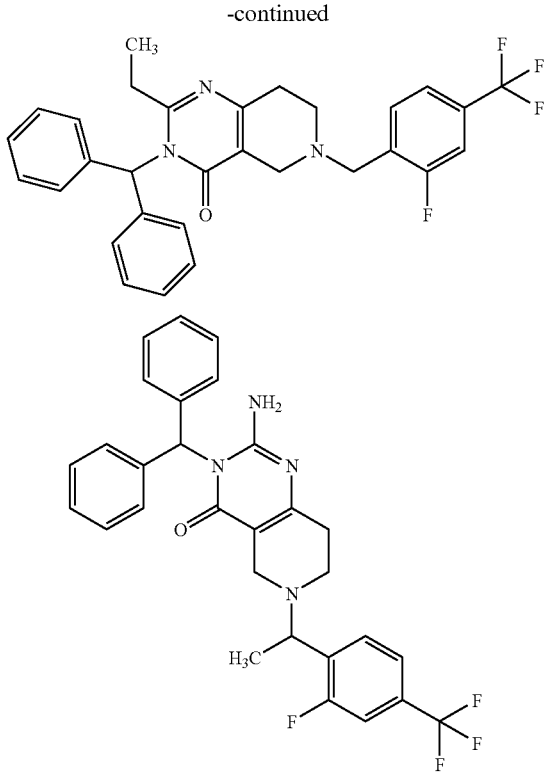

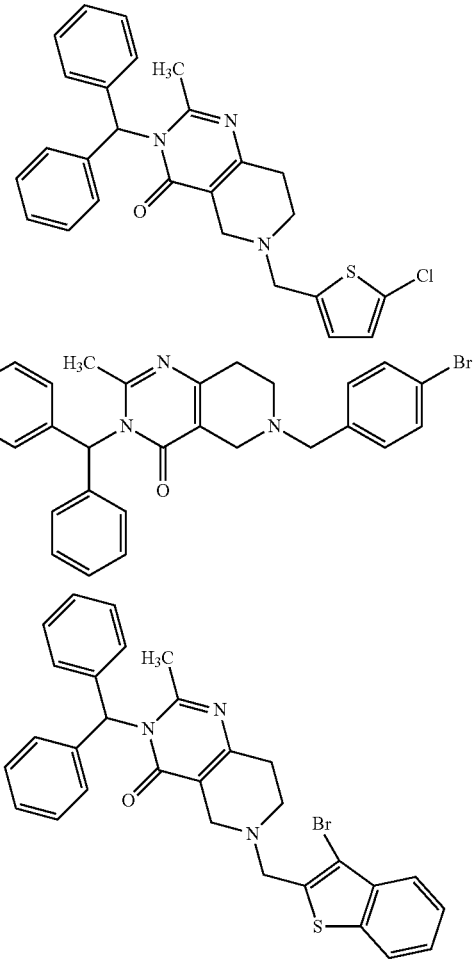

391
-continued
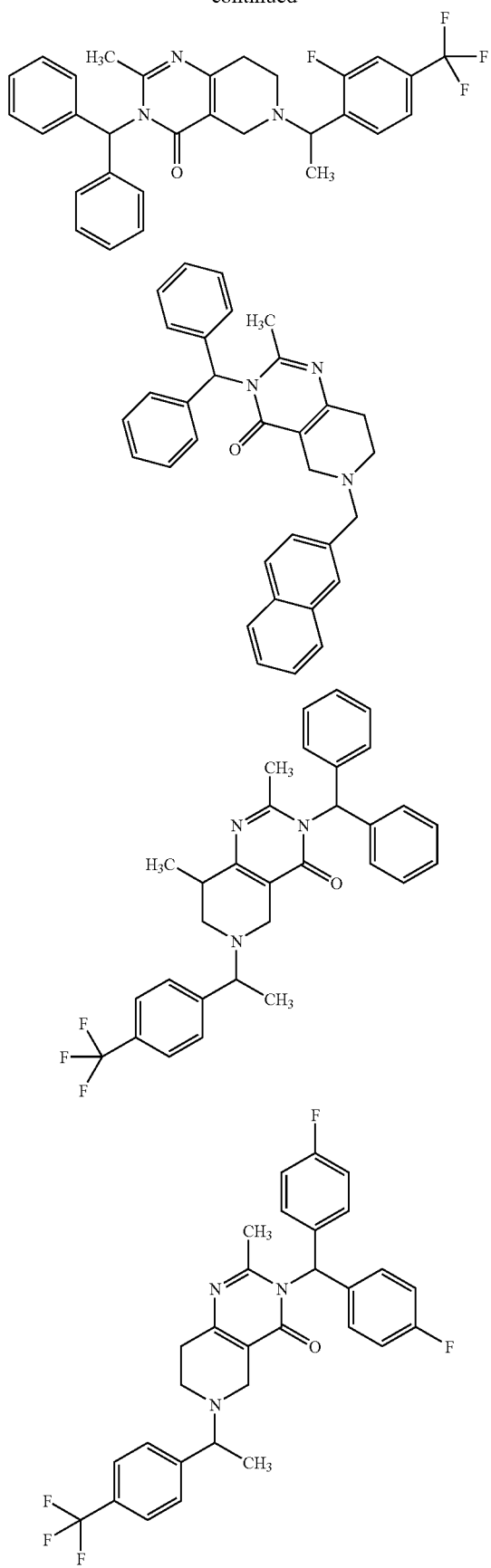
392
-continued
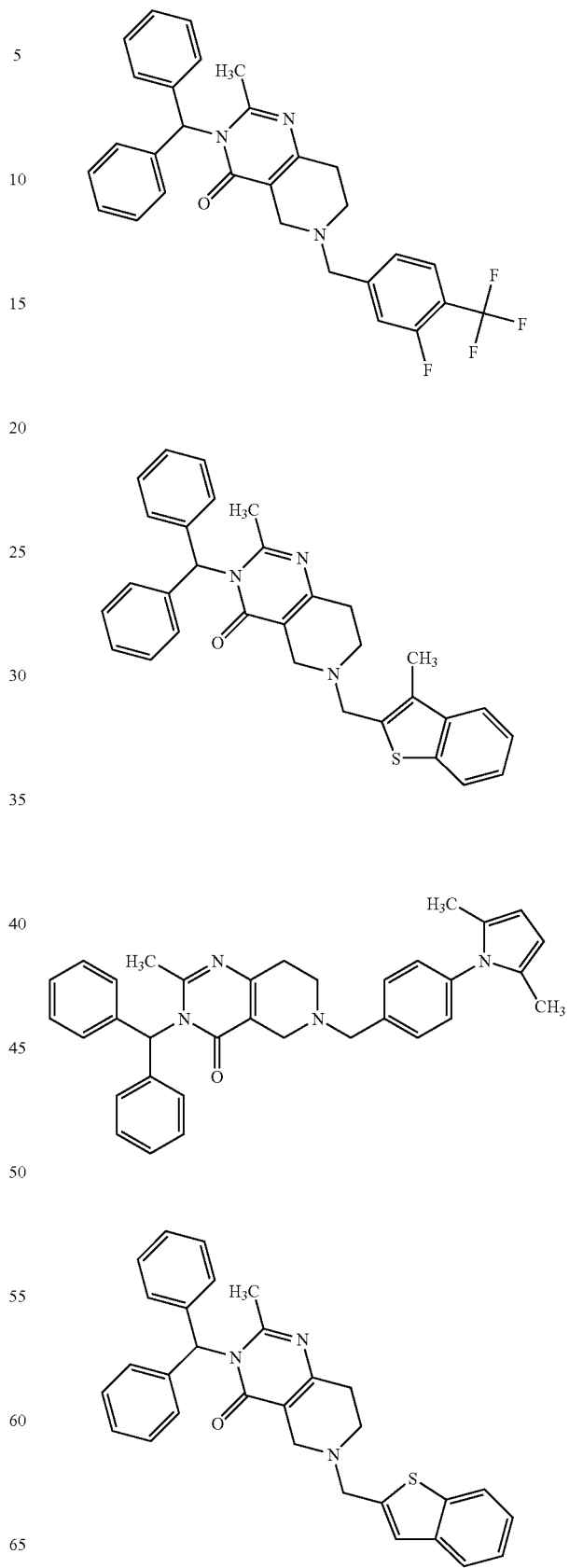

393
-continued
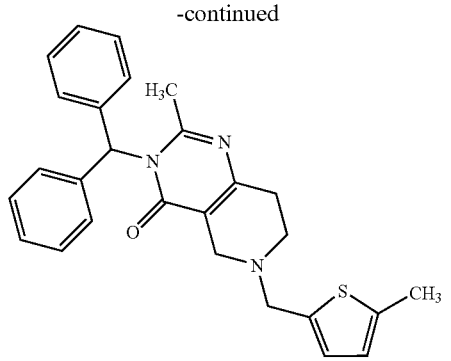
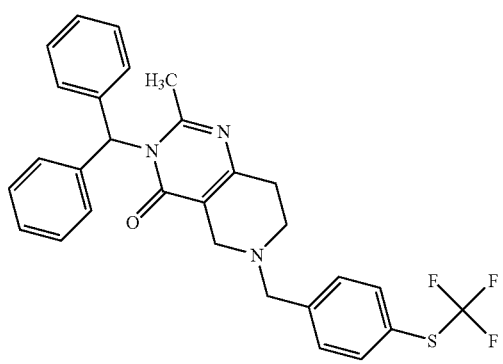
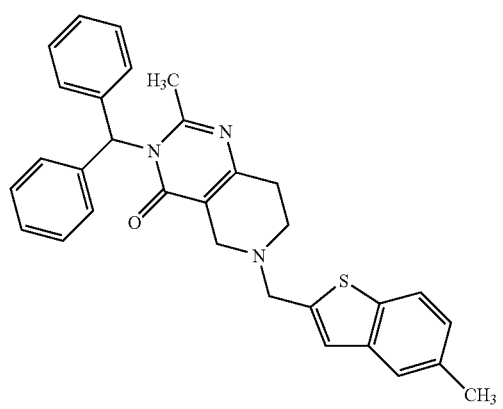
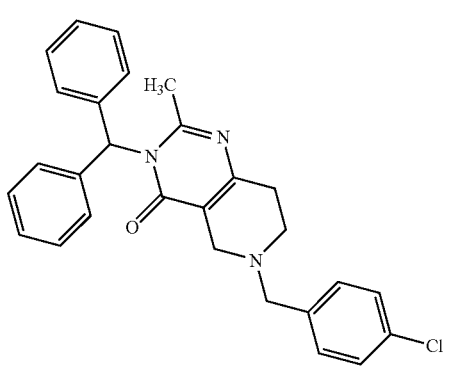
394
-continued
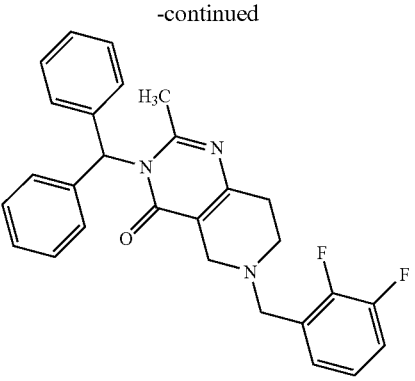
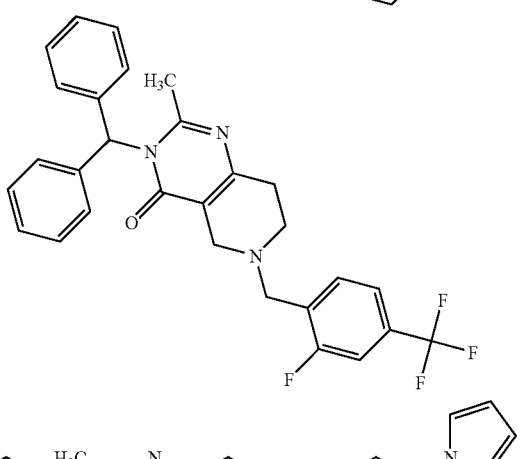
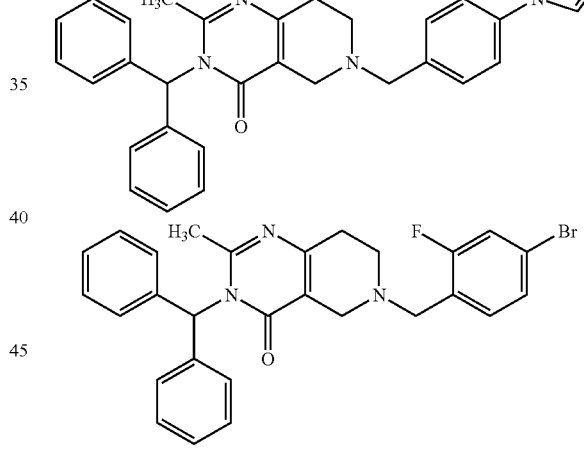
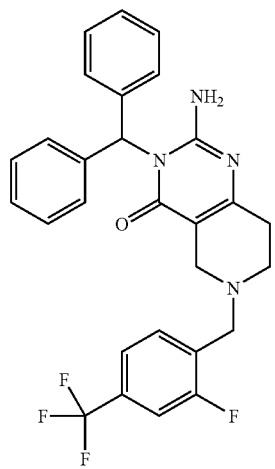

395
-continued
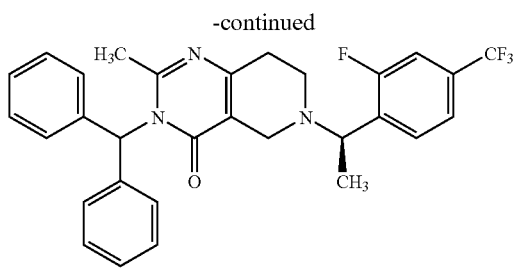
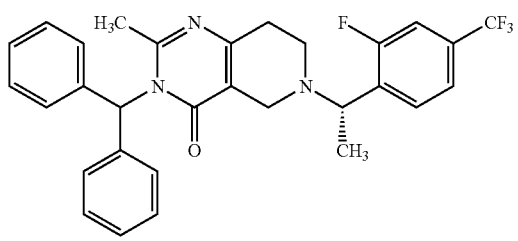
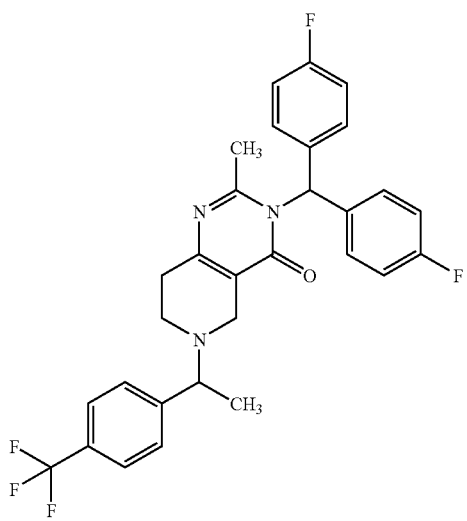
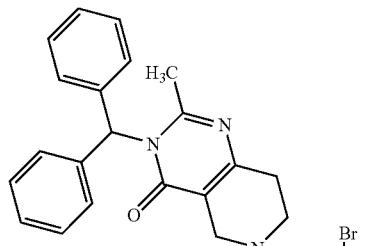
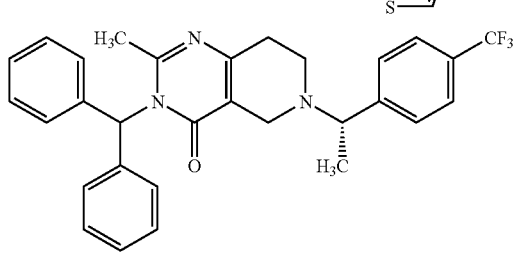
396
-continued
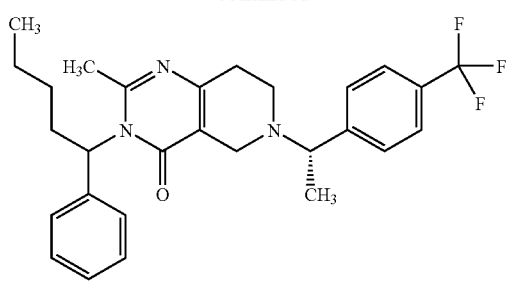
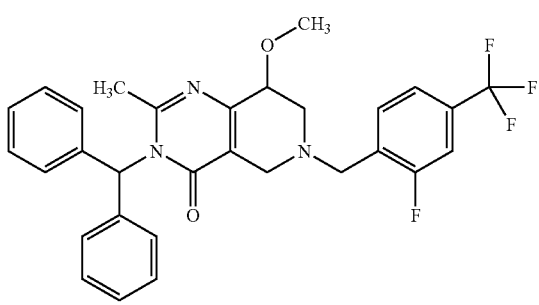
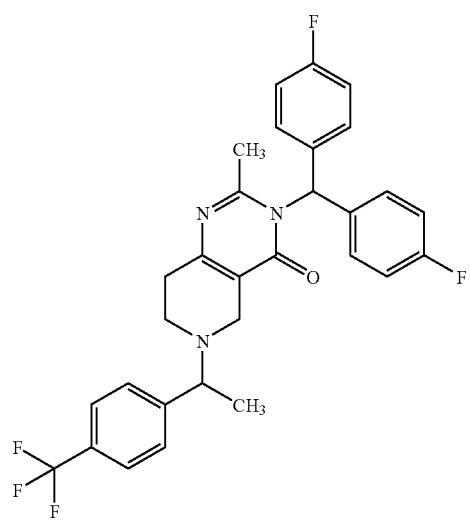
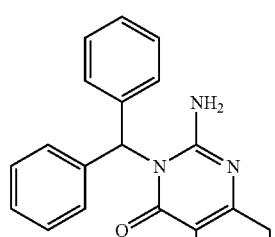
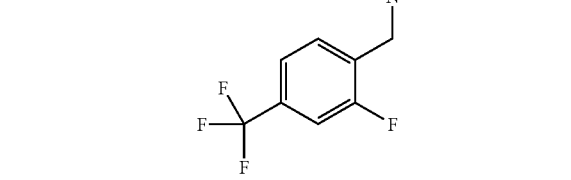

397
-continued
398
-continued
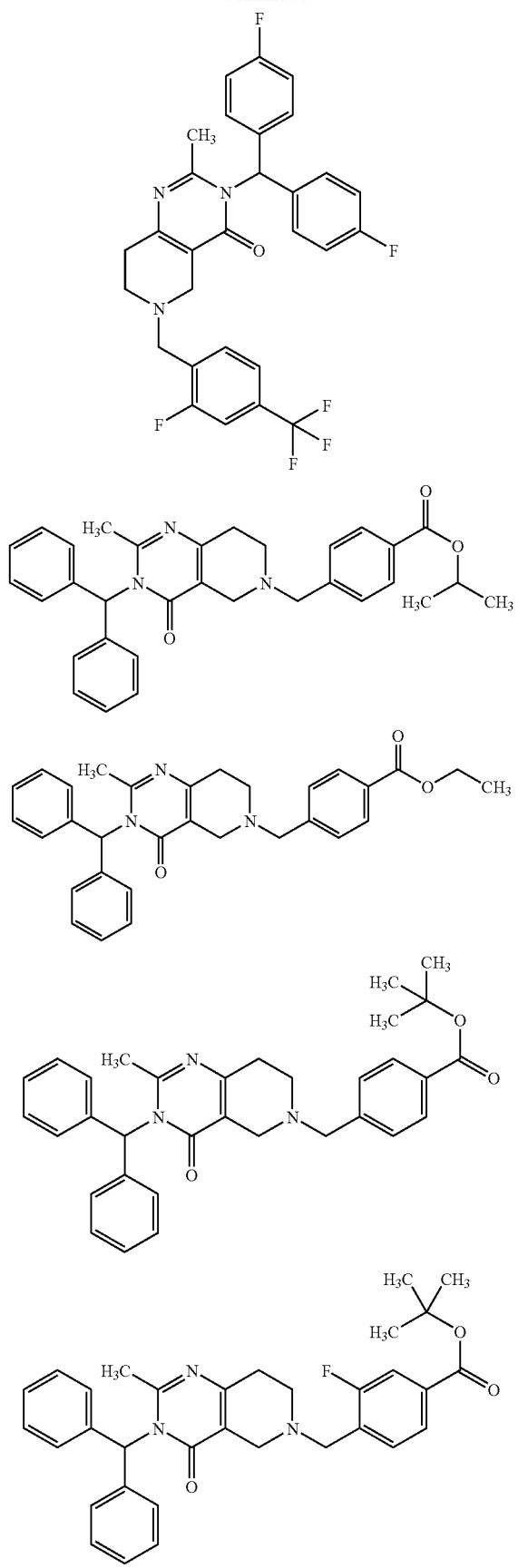
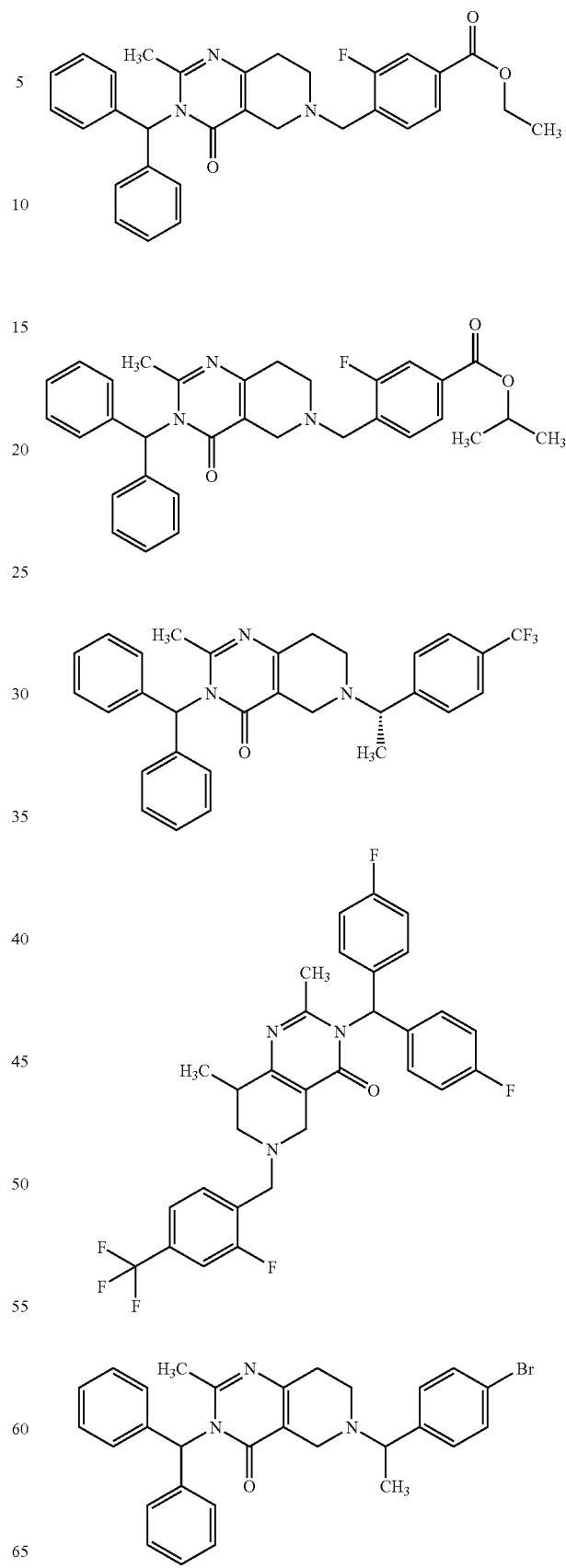

399
-continued
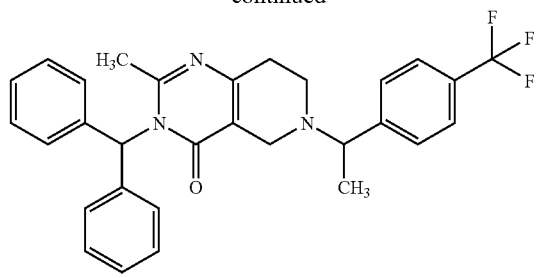
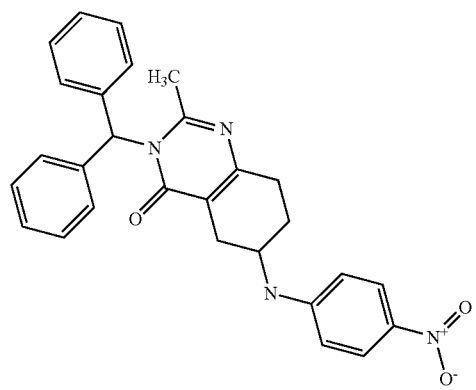
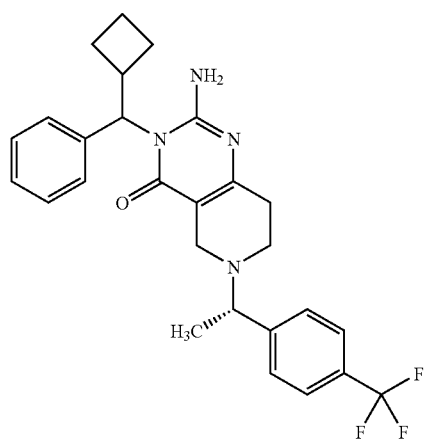
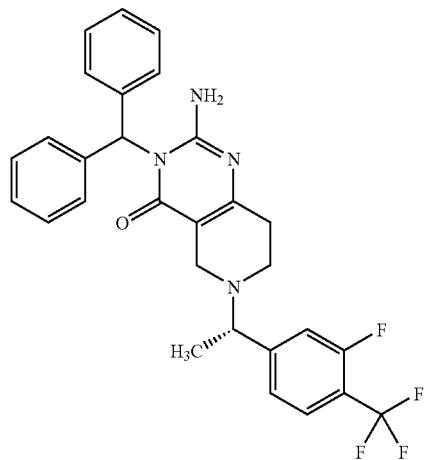
400
-continued
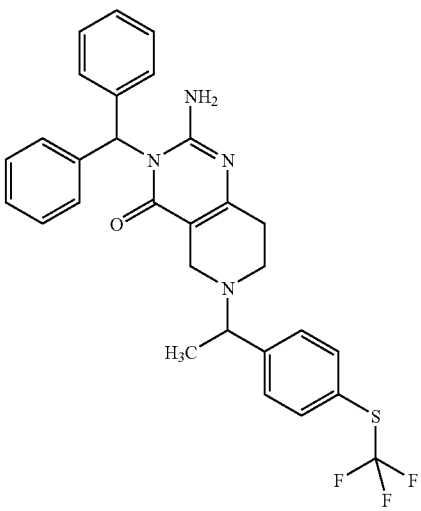
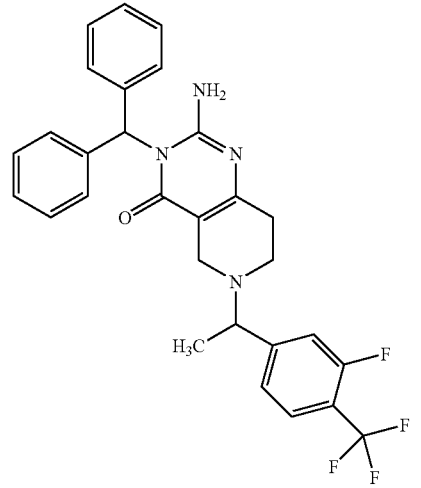
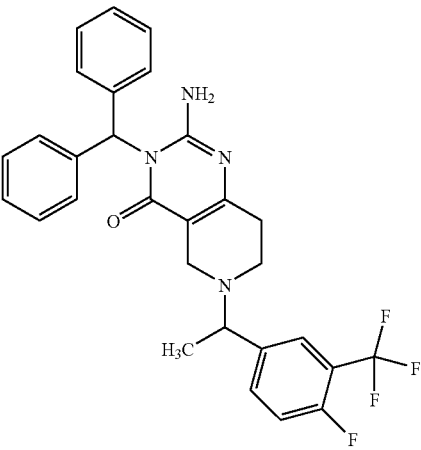

401
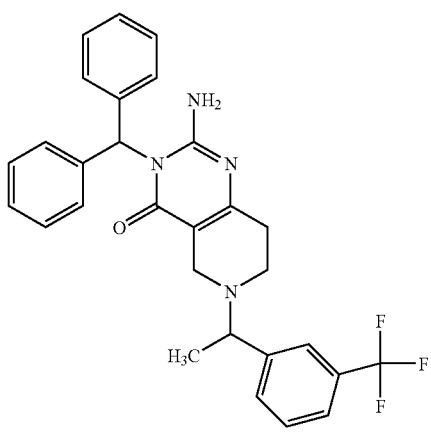
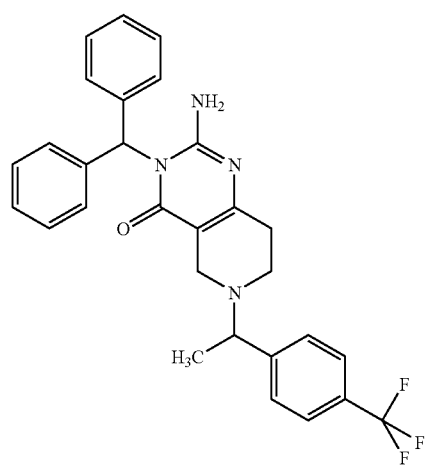
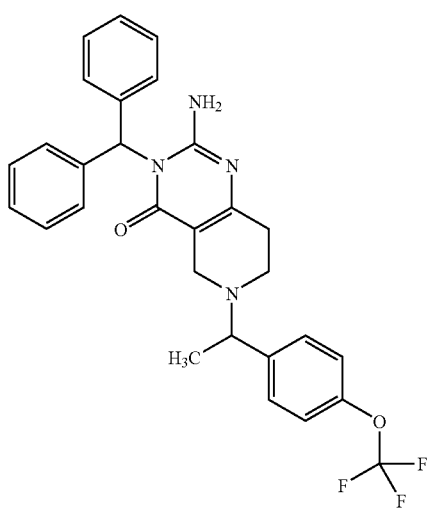
402
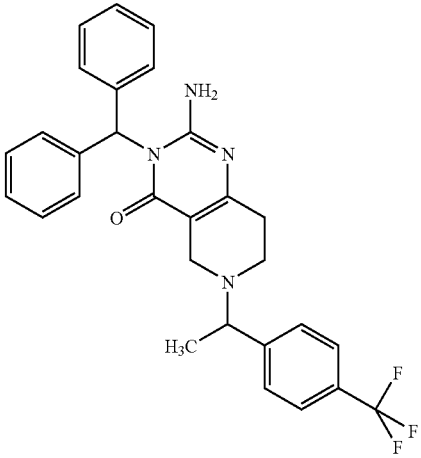
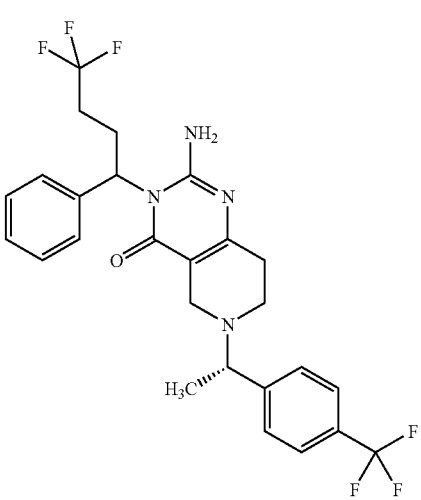
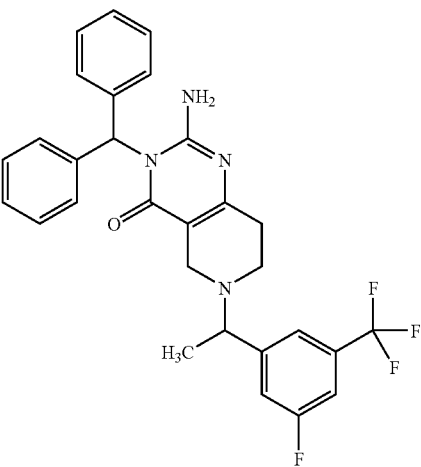

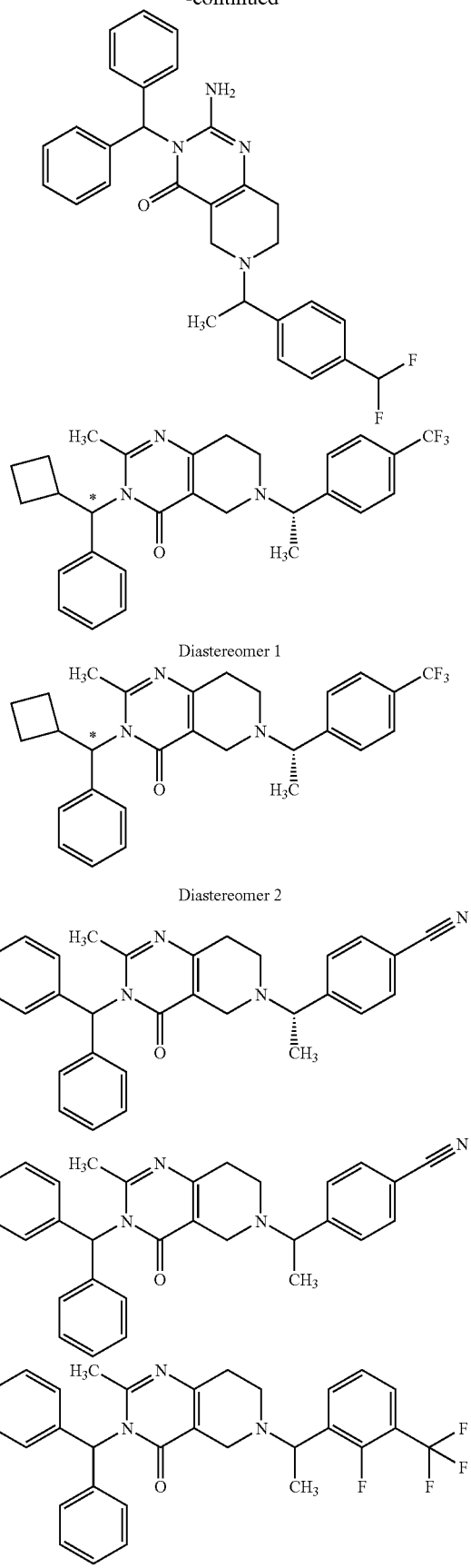

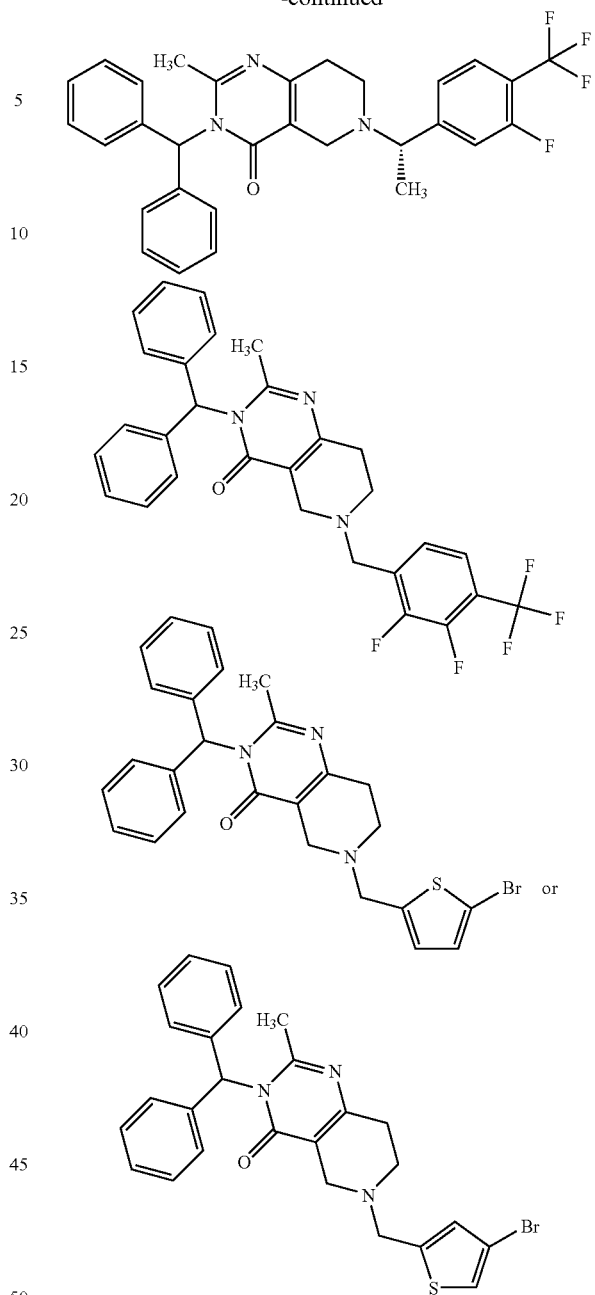

or a pharmaceutically acceptable salt thereof.

39. A pharmaceutical composition comprising one or more compounds of claim 1 or a pharmaceutically acceptable salt thereof, and at least one pharmaceutically acceptable carrier.

40. The composition of claim 39, further comprising at least one antidiabetic agent and/or at least one antiobesity agent that is different from the compounds of claim 1.

41. The composition of claim 40, comprising at least one antidiabetic agent that is different from the compounds of claim 1.

42. The composition of claim 40, comprising at least one antiobesity agent that is different from the compounds of claim 1.

* * * * *